(12) United States Patent
Lai et al.

(10) Patent No.: US 12,162,926 B2
(45) Date of Patent: Dec. 10, 2024

(54) MULTI-SPECIFIC ANTIBODIES FOR CROSS-NEUTRALIZATION OF MULTIPLE FILOVIRUS GLYCOPROTEINS

(71) Applicant: Albert Einstein College of Medicine, Bronx, NY (US)

(72) Inventors: Jonathan R. Lai, Dobbs Ferry, NY (US); Julia Frei, Bronx, NY (US); Elisabeth Nyakatura, New York, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 299 days.

(21) Appl. No.: 17/487,690

(22) Filed: Sep. 28, 2021

(65) Prior Publication Data

US 2022/0218824 A1     Jul. 14, 2022

Related U.S. Application Data

(60) Division of application No. 16/548,309, filed on Aug. 22, 2019, now Pat. No. 11,135,292, which is a division of application No. 15/404,662, filed on Jan. 12, 2017, now Pat. No. 10,391,171, which is a continuation-in-part of application No. PCT/US2015/057499, filed on Oct. 27, 2015.

(60) Provisional application No. 62/131,472, filed on Mar. 11, 2015, provisional application No. 62/069,516, filed on Oct. 28, 2014.

(51) Int. Cl.
*C07K 16/10* (2006.01)
*A61K 39/42* (2006.01)

(52) U.S. Cl.
CPC .............. *C07K 16/10* (2013.01); *A61K 39/42* (2013.01); *C07K 2317/24* (2013.01); *C07K 2317/31* (2013.01); *C07K 2317/622* (2013.01); *C07K 2317/64* (2013.01); *C07K 2317/76* (2013.01)

(58) Field of Classification Search
None
See application file for complete search history.

(56) References Cited

U.S. PATENT DOCUMENTS

| | | |
|---|---|---|
| 9,346,875 B2 | 5/2016 | Lai et al. |
| 10,081,669 B2 | 9/2018 | Lai et al. |
| 10,391,171 B2 | 8/2019 | Lai et al. |
| 10,875,907 B2 | 12/2020 | Lai et al. |
| 11,135,292 B2 | 10/2021 | Lai et al. |
| 2004/0234519 A1 | 11/2004 | Tso et al. |
| 2007/0298042 A1 | 12/2007 | Hart et al. |
| 2010/0045289 A1 | 2/2010 | Chopra et al. |
| 2012/0164153 A1 | 6/2012 | Dye et al. |
| 2014/0035654 A1 | 2/2014 | Jiang et al. |
| 2014/0356354 A1* | 12/2014 | Lai .................. C07K 16/10 536/23.53 |
| 2019/0374640 A1 | 12/2019 | Lai et al. |
| 2021/0292394 A1 | 9/2021 | Lai et al. |

FOREIGN PATENT DOCUMENTS

| | | | |
|---|---|---|---|
| WO | WO-2011071574 A2 | 6/2011 | |
| WO | WO-2016179212 A1 * | 11/2016 | .............. A61K 39/00 |

OTHER PUBLICATIONS

Wu et al., Nat. Biotechnol., 2007, 25:1290-1297 (Year: 2007).*
Casset et al., "A peptide mimetic of an anti-CD4 monoclonal antibody by rational design," Biochem Biophys Res Commun, 307(1):198-205 (2003).
Chen et al., "Synthetic antibodies with a human framework that protect mice from lethal sudan ebolavirus challenge," ACS Chemical Biology, 9: 2263-2273 (2014).
De Pascalis et al., "Grafting of 'Abbreviated' Complementarity-Determining Residues Essential for Ligand Contact to Engineer a Less Immunogenic Humanized Monoclonal Antibody," J Immunol, 169:3076-3084 (2002).
Dong et al., "A stable IgG-like bispecific antibody targeting the epidermal growth factor receptor and the type 1 insulin-like growth factor receptor demonstrates superior anti-tumor activity," mAbs, 3(3): 273-288 (2011).
Dong al., "Stable IgG-like Bispecific Antibodies Directed toward the Type 1 Insulin-like Growth Factor Receptor Demonstrate Enhanced Ligand Blockade and Anti-tumor Activity," J Biol Chem, 286(6): 4703-4717 (2011).
International Preliminary Report on Patentability for International Application No. PCT/US2015/043927 dated Feb. 21, 2017.
International Search Report and Written Opinion for International Application No. PCT/US2015/043927 dated Feb. 25, 2016.
Lee et al., "Structure of the Ebola virus glycoprotein bound to a human survivor antibody," Nature, 454(7201): 177-183 (2008).
MacCallum et al., "Antibody-antigen Interactions: Contact Analysis and Binding Site Topography," J Mol Biol, 262:732-745 (1996).
Marvin et al., "Recombinant approaches to IgG-like bispecific antibodies," Acta Pharmacol Sin, 26(6): 649-658 (2005).
Rudikoff et al., "Single amino acid substitution altering antigen-binding specificity," PNAS, 79:1979-1983 (1982).

* cited by examiner

*Primary Examiner* — Stacy B Chen
(74) *Attorney, Agent, or Firm* — Foley Hoag LLP

(57) ABSTRACT

Methods for treating and for preventing filovirus infections are disclosed, as well as compositions therefor.

19 Claims, 11 Drawing Sheets
Specification includes a Sequence Listing.

A Survival Following EBOV Challenge

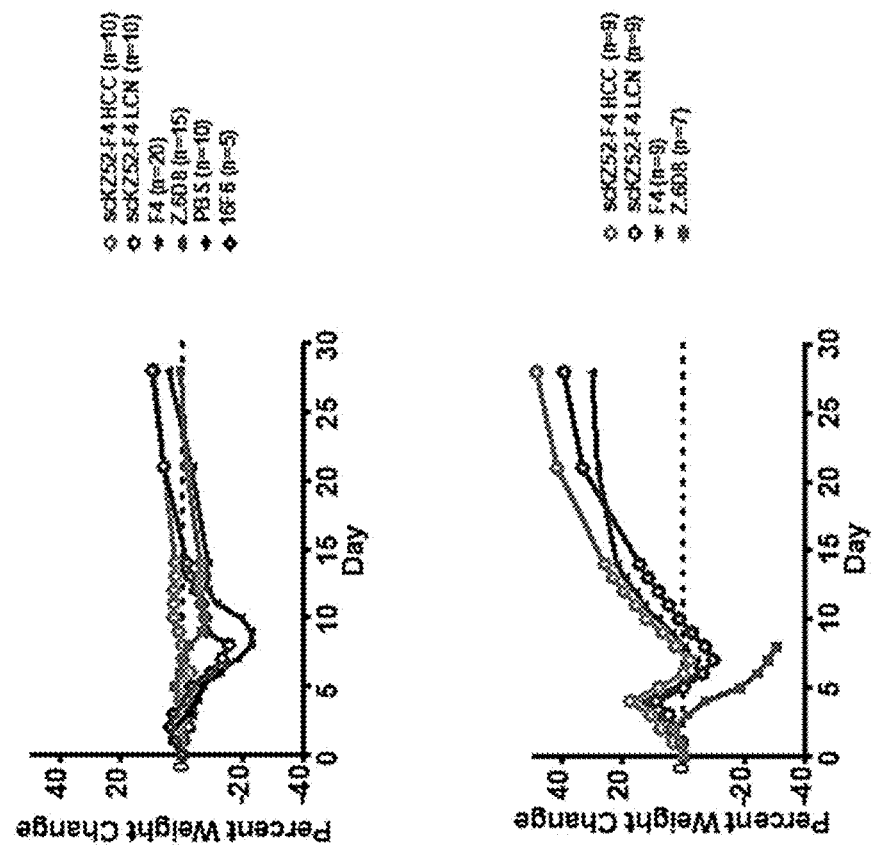
Fig. 10A
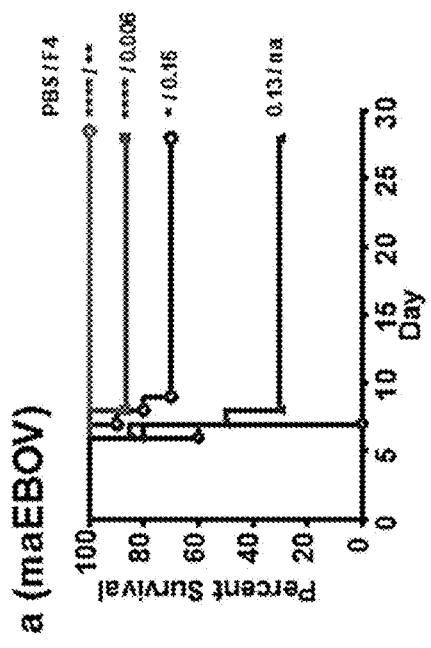
Fig. 10B
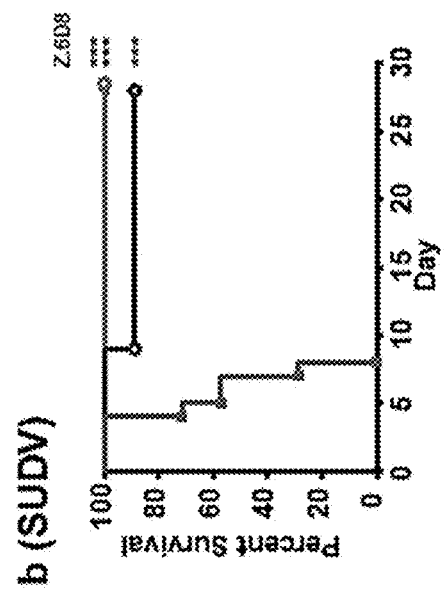

SEQUENCE LISTING

```
<160> NUMBER OF SEQ ID NOS: 72

<210> SEQ ID NO 1
<211> LENGTH: 723
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<223> OTHER INFORMATION: fusion sequence

<400> SEQUENCE: 1

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
    210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Ser Glu Val Gln Leu
            260                 265                 270

Val Glu Ser Gly Gly Gly Leu Val Gln Pro Gly Gly Ser Leu Arg Leu
        275                 280                 285
```

```
Ser Cys Ala Ala Ser Gly Phe Ala Phe Asn Tyr Tyr Asp Ile His Trp
    290                 295                 300

Val Arg Gln Ala Pro Gly Lys Gly Leu Glu Trp Val Ala Tyr Ile Asn
305                 310                 315                 320

Pro Gly Gly Gly Asn Thr Tyr Tyr Ala Asp Ser Val Lys Gly Arg Phe
                325                 330                 335

Thr Ile Ser Ala Asp Thr Ser Lys Asn Thr Ala Tyr Leu Gln Met Asn
            340                 345                 350

Ser Leu Arg Ala Glu Asp Thr Ala Val Tyr Tyr Cys Ala Arg Gln Leu
        355                 360                 365

Tyr Gly Asn Ser Phe Met Asp Tyr Trp Gly Gln Gly Thr Leu Val Thr
    370                 375                 380

Val Ser Ser Ala Ser Thr Lys Gly Pro Ser Val Phe Pro Leu Ala Pro
385                 390                 395                 400

Ser Ser Lys Ser Thr Ser Gly Gly Thr Ala Ala Leu Gly Cys Leu Val
                405                 410                 415

Lys Asp Tyr Phe Pro Glu Pro Val Thr Val Ser Trp Asn Ser Gly Ala
            420                 425                 430

Leu Thr Ser Gly Val His Thr Phe Pro Ala Val Leu Gln Ser Ser Gly
        435                 440                 445

Leu Tyr Ser Leu Ser Ser Val Val Thr Val Pro Ser Ser Ser Leu Gly
    450                 455                 460

Thr Gln Thr Tyr Ile Cys Asn Val Asn His Lys Pro Ser Asn Thr Lys
465                 470                 475                 480

Val Asp Lys Lys Val Glu Pro Lys Ser Cys Asp Lys Thr His Thr Cys
                485                 490                 495

Asp Lys Thr His Thr Cys Pro Cys Pro Ala Pro Glu Leu Leu Gly
            500                 505                 510

Arg Pro Ser Val Phe Leu Phe Pro Pro Lys Pro Lys Asp Thr Leu Met
        515                 520                 525

Ile Ser Arg Thr Pro Glu Val Thr Cys Val Val Val Asp Val Ser His
    530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
            580                 585                 590

Lys Glu Tyr Lys Cys Lys Val Ser Asn Lys Ala Leu Pro Ala Pro Ile
        595                 600                 605

Glu Lys Thr Ile Ser Lys Ala Lys Gly Gln Pro Arg Glu Pro Gln Val
    610                 615                 620

Tyr Thr Leu Pro Pro Ser Arg Glu Glu Met Thr Lys Asn Gln Val Ser
625                 630                 635                 640

Leu Thr Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
        675                 680                 685

Asp Lys Ser Arg Trp Gln Gln Gly Asn Val Phe Ser Cys Ser Val Met
    690                 695                 700
```

His Glu Ala Leu His Asn His Tyr Thr Gln Lys Ser Leu Ser Leu Ser
705                 710                 715                 720

Pro Gly Lys

<210> SEQ ID NO 2
<211> LENGTH: 1161
<212> TYPE: DNA
<213> ORGANISM: Artificial Sequence
<220> FEATURE:
<223> OTHER INFORMATION: Description of Artificial Sequence:
      Synthetic polynucleotide
<220> FEATURE:
<223> OTHER INFORMATION: fusion sequence

<400> SEQUENCE: 2
gaagtgcagt tactggaaag cggcggcggc ctggttaaac ctggcggtag tctgcgtctg      60
agttgcgccg ccagcggttt caccctgatc aactaccgca tgaactgggt gcgtcaggca     120
ccgggtaaag gcctggagtg ggtgagcagc attagcagca gcagcagcta tattcactac     180
gccgacagcg tgaaaggccg ctttaccatc agccgcgaca atgccgagaa cagtctgtat     240
ctgcagatga acagcctaag gcgcgaagat acagccgtgt actactgtgt gcgcgaaggc     300
cctcgcgcaa ccggctatag catggcagac gtgtttgata tctggggtca gggcaccatg     360
gttacagtta gcagtggtgg tggtggtagt ggtggcggtg gtagcggtgg tggtggcagt     420
gaactggtga tgacccagag cccggatagc ttagccgtga gtctgggcga aagggcgacc     480
attaactgca aaagcagcca gagcgtgctg tacagcagca acaacaagag ctacctggca     540
tggtatcagc aaaaaccggg tcagcctccg aaactgctga tctattgggc aagcacccgc     600
gaaagtggtg ttccggatcg cttcagcggt agtggcagcg gtaccgattt caccctgacc     660
atcagcagtc tgcaggccga ggacgttgca gtgtattact gtcagcagta ctacagcgcc     720
ccgctgacct ttggcggcgg caccaaagtt gaaattaagg gcggcagtgc aggcagcgcc     780
ggtagtgccg gtagtggtgg tagcgaagtt cagctggttg aaagtggcgg cggtctggtg     840
cagcctggtg gtagtctgcg tctgagttgt gccgccagcg gctttgcctt caattactat     900
gacattcatt gggttcgcca ggccccgggt aaaggtctgg aatgggttgc atatatcaac     960
ccgggtggcg gtaacaccta ctatgccgac agcgttaagg gtcgcttcac catcagcgca    1020
gataccagca aaaacaccgc ctacctgcag atgaatagcc tgcgtgcaga agataccgcc    1080
gtttactact gtgcccgcca gctgtacggc aatagcttca tggactattg gggccagggc    1140
accttagtta ccgtgagcag c                                               1161

<210> SEQ ID NO 3
<211> LENGTH: 493
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<223> OTHER INFORMATION: fusion sequence

<400> SEQUENCE: 3

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

```
Ser Ser Ile Ser Ser Ser Ser Tyr Ile His Tyr Ala Asp Ser Val
         50                  55                  60
Lys Gly Arg Phe Thr Ile Ser Arg Asp Asn Ala Glu Asn Ser Leu Tyr
 65                  70                  75                  80
Leu Gln Met Asn Ser Leu Arg Ala Glu Asp Thr Ala Val Tyr Tyr Cys
                 85                  90                  95
Val Arg Glu Gly Pro Arg Ala Thr Gly Tyr Ser Met Ala Asp Val Phe
                100                 105                 110
Asp Ile Trp Gly Gln Gly Thr Met Val Thr Val Ser Ser Gly Gly Gly
                115                 120                 125
Gly Ser Gly Gly Gly Ser Gly Gly Gly Ser Glu Leu Val Met
            130                 135                 140
Thr Gln Ser Pro Asp Ser Leu Ala Val Ser Leu Gly Glu Arg Ala Thr
145                 150                 155                 160
Ile Asn Cys Lys Ser Ser Gln Ser Val Leu Tyr Ser Ser Asn Asn Lys
                165                 170                 175
Ser Tyr Leu Ala Trp Tyr Gln Gln Lys Pro Gly Gln Pro Pro Lys Leu
            180                 185                 190
Leu Ile Tyr Trp Ala Ser Thr Arg Glu Ser Gly Val Pro Asp Arg Phe
            195                 200                 205
Ser Gly Ser Gly Ser Gly Thr Asp Phe Thr Leu Thr Ile Ser Ser Leu
210                 215                 220
Gln Ala Glu Asp Val Ala Val Tyr Tyr Cys Gln Gln Tyr Tyr Ser Ala
225                 230                 235                 240
Pro Leu Thr Phe Gly Gly Gly Thr Lys Val Glu Ile Lys Gly Gly Ser
                245                 250                 255
Ala Gly Ser Ala Gly Ser Ala Gly Ser Gly Gly Ser Asp Ile Gln Met
            260                 265                 270
Thr Gln Ser Pro Ser Ser Leu Ser Ala Ser Val Gly Asp Arg Val Thr
            275                 280                 285
Ile Thr Cys Arg Ala Ser Gln Asp Val Thr Thr Ala Val Ala Trp Tyr
            290                 295                 300
Gln Gln Lys Pro Gly Lys Ala Pro Lys Leu Leu Ile Tyr Trp Ala Ser
305                 310                 315                 320
Arg Leu His Asn Gly Val Pro Ser Arg Phe Ser Gly Ser Gly Ser Gly
                325                 330                 335
Thr Asp Phe Thr Leu Thr Ile Ser Ser Leu Gln Pro Glu Asp Phe Ala
            340                 345                 350
Thr Tyr Tyr Cys Gln Gln His Tyr Ser Thr Pro Leu Thr Phe Gly Gln
            355                 360                 365
Gly Thr Lys Val Glu Ile Lys Arg Thr Val Ala Ala Pro Ser Val Phe
            370                 375                 380
Ile Phe Pro Pro Ser Asp Glu Gln Leu Lys Ser Gly Thr Ala Ser Val
385                 390                 395                 400
Val Cys Leu Leu Asn Asn Phe Tyr Pro Arg Glu Ala Lys Val Gln Trp
                405                 410                 415
Lys Val Asp Asn Ala Leu Gln Ser Gly Asn Ser Gln Glu Ser Val Thr
            420                 425                 430
Glu Gln Asp Ser Lys Asp Ser Thr Tyr Ser Leu Ser Ser Thr Leu Thr
            435                 440                 445
Leu Ser Lys Ala Asp Tyr Glu Lys His Lys Val Tyr Ala Cys Glu Val
            450                 455                 460
```

```
Thr His Gln Gly Leu Ser Ser Pro Val Thr Lys Ser Phe Asn Arg Gly
465                 470                 475                 480

Glu Cys Gly Gly Ser Asp Tyr Lys Asp Asp Asp Lys
                485                 490
```

<210> SEQ ID NO 4
<211> LENGTH: 1125
<212> TYPE: DNA
<213> ORGANISM: Artificial Sequence
<220> FEATURE:
<223> OTHER INFORMATION: Description of Artificial Sequence:
      Synthetic polynucleotide
<220> FEATURE:
<223> OTHER INFORMATION: fusion sequence

<400> SEQUENCE: 4

```
gaagtgcagc tgctggaaag cggtggcggt ctggttaaac ctggcggtag tctgcgcctg      60
agttgcgccg ccagcggttt tacactgatc aactatcgca tgaactgggt gcgtcaggca     120
ccgggtaagg gtctggagtg ggttagcagc attagtagca gcagcagtta cattcactac     180
gccgatagcg tgaaaggccg cttcacaatt agccgcgata acgccgagaa cagcctgtat     240
ctgcagatga acagtttacg cgccgaagat accgccgtgt attattgcgt tcgcgaaggt     300
ccgcgtgcaa ccggctacag catggccgac gtttttcgata tttggggtca gggcaccatg     360
gtgacagtta gtagcggtgg tggtggtagt ggtggtggcg gcagcggtgg tggtggtagt     420
gaactggtga tgacccagag cccggatagc ctggcagtga gcctgggtga gcgtgccacc     480
atcaattgca aaagcagcca gagcgtgctg tacagcagca caacaagag ttacctggcc     540
tggtaccaac agaaaccggg ccagccgccg aaactgctga tttattgggc cagtacccgc     600
gaaagcggcg tgcctgatcg ttttagtggc agcggtagcg gcaccgactt taccctgacc     660
attagcagcc tgcaggccga ggatgtggca gtgtattact gccagcagta ttacagcgcc     720
ccgttaacct ttggcggcgg taccaaagtg gagatcaaag gtggcagtgc aggcagcgcc     780
ggtagtgcag gtagtggtgg tagcgacatc cagatgacac agagtccgag cagcctgagt     840
gccagcgttg gtgaccgtgt gaccattacc tgccgtgcca gccaggatgt taccacagcc     900
gttgcatggt atcagcagaa gccgggtaag gcccctaagt tactgatcta ctgggcaagc     960
cgcctgcata cggtgtgcc gagccgcttt agcggcagtg gtagcggtac cgatttcacc    1020
ctgaccatca gcagtctgca gccggaagat ttcgcaacct actactgtca gcagcattac    1080
agcaccccgc tgacctttgg ccagggcacc aaagtggaaa ttaaa               1125
```

<210> SEQ ID NO 5
<211> LENGTH: 723
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<223> OTHER INFORMATION: fusion sequence

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Tyr Tyr
            20                  25                  30

Asp Ile His Trp Val Arg Gln Ala Pro Gly Lys Gly Leu Glu Trp Val
        35                  40                  45
```

```
Ala Tyr Ile Asn Pro Gly Gly Gly Asn Thr Tyr Tyr Ala Asp Ser Val
     50                  55                  60

Lys Gly Arg Phe Thr Ile Ser Ala Asp Thr Ser Lys Asn Thr Ala Tyr
 65              70                  75                  80

Leu Gln Met Asn Ser Leu Arg Ala Glu Asp Thr Ala Val Tyr Tyr Cys
             85                  90                  95

Ala Arg Gln Leu Tyr Gly Asn Ser Phe Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Asp Lys Thr His Thr Cys Pro Pro Cys Pro Ala Pro
225                 230                 235                 240

Glu Leu Leu Gly Arg Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly Gly Ser Ala Gly Ser Ala Gly Ser
450                 455                 460

Ala Gly Ser Gly Gly Ser Glu Val Gln Leu Leu Glu Ser Gly Gly Gly
```

```
                      465                 470                 475                 480
Leu Val Lys Pro Gly Gly Ser Leu Arg Leu Ser Cys Ala Ala Ser Gly
                485                 490                 495

Phe Thr Leu Ile Asn Tyr Arg Met Asn Trp Val Arg Gln Ala Pro Gly
                500                 505                 510

Lys Gly Leu Glu Trp Val Ser Ile Ser Ser Ser Ser Ser Tyr Ile
                515                 520                 525

His Tyr Ala Asp Ser Val Lys Gly Arg Phe Thr Ile Ser Arg Asp Asn
530                 535                 540

Ala Glu Asn Ser Leu Tyr Leu Gln Met Asn Ser Leu Arg Ala Glu Asp
545                 550                 555                 560

Thr Ala Val Tyr Tyr Cys Val Arg Glu Gly Pro Arg Ala Thr Gly Tyr
                565                 570                 575

Ser Met Ala Asp Val Phe Asp Ile Trp Gly Gln Gly Thr Met Val Thr
                580                 585                 590

Val Ser Ser Gly Gly Gly Gly Ser Gly Gly Gly Gly Ser Gly Gly Gly
                595                 600                 605

Gly Ser Glu Leu Val Met Thr Gln Ser Pro Asp Ser Leu Ala Val Ser
610                 615                 620

Leu Gly Glu Arg Ala Thr Ile Asn Cys Lys Ser Ser Gln Ser Val Leu
625                 630                 635                 640

Tyr Ser Ser Asn Asn Lys Ser Tyr Leu Ala Trp Tyr Gln Gln Lys Pro
                645                 650                 655

Gly Gln Pro Pro Lys Leu Leu Ile Tyr Trp Ala Ser Thr Arg Glu Ser
                660                 665                 670

Gly Val Pro Asp Arg Phe Ser Gly Ser Gly Ser Gly Thr Asp Phe Thr
                675                 680                 685

Leu Thr Ile Ser Ser Leu Gln Ala Glu Asp Val Ala Val Tyr Tyr Cys
                690                 695                 700

Gln Gln Tyr Tyr Ser Ala Pro Leu Thr Phe Gly Gly Gly Thr Lys Val
705                 710                 715                 720

Glu Ile Lys
```

<210> SEQ ID NO 6
<211> LENGTH: 1614
<212> TYPE: DNA
<213> ORGANISM: Artificial Sequence
<220> FEATURE:
<223> OTHER INFORMATION: Description of Artificial Sequence:
       Synthetic polynucleotide
<220> FEATURE:
<223> OTHER INFORMATION: fusion sequence

<400> SEQUENCE: 6

```
gaggttcagc tggtggagtc tggcggtggc ctggtgcagc caggggggctc actccgtttg      60 tcctgtgcag cttctggctt cgcgtttaac tattatgata ttcattgggt gcgtcaggcc     120
ccgggtaagg gcctggaatg ggttgcatat attaacccgg gcggtggcaa cacctattat     180
gctgatagcg tcaagggccg tttcactata agcgcagaca catccaaaaa cacagcctac     240
ctacaaatga acagcttaag agctgaggac actgccgtct attattgtgc tcgccagctg     300
tatggcaaca gctttatgga ctactggggt caaggaaccc tggtcaccgt ctcctcggct     360
agcaccaagg gtccgagcgt gtttcctctg gcacctagca gtaaaagcac cagtggtggt     420
acagcagccc tgggttgcct ggtgaaggat tacttccgg agccggtgac cgttagttgg     480
aatagcggcg ccctgaccag tggcgttcat acatttccgg ccgtgctgca gagtagtggc     540
```

```
ctgtacagcc tgagtagcgt tgttaccgtt ccgagcagca gcctgggcac ccagacctat      600
atttgcaatg ttaaccataa accgagcaac acaaaagttg ataaaaaagt tgaaccgaag      660
agctgtgaca aaaccatac atgtgacaaa acacacacct gcccgccttg tccggcacct       720
gagctgctgg gtcgcccgag cgttttttctg tttcctccga aaccgaaaga caccacccag     780
aagagtctga gcctgagtcc tggcaaaggt ggatccgccg gtagcgcagg tagtgcaggt     840
agtggcggca gcgaagttca gctgttagaa agtggcggtg gtctggttaa gccgggcggt     900
agtctgcgcc tgagctgtgc agcaagtggt ttcaccctga tcaattatcg tatgaactgg     960
gtgcgccaag ccccgggtaa aggtctggag tgggttagta gtatcagcag cagcagcagt    1020
tacatccact atgccgatag cgttaagggc cgctttacaa tcagccgcga taatgccgag    1080
aatagcttat acctgcaaat gaacagtcta agggcggaag ataccgccgt ttactactgc    1140
gttcgtgaag ccctcgcgc aacaggctat agcatggcag acgtgttcga catttggggt     1200
cagggcacca tggtgaccgt tagtagcggc ggtggtggta gtggtggtgg cggtagtggt    1260
ggcggtggca gcgaactggt gatgacccag agtccggata gcctggccgt gagcttaggc    1320
gagcgtgcaa ccattaattg taaaagcagt cagagtgttc tgtatagtag caataacaag    1380
agctatctgg cctggtatca gcagaagccg ggccagccgc cgaaactgct gatttactgg    1440
gcaagcaccc gcgaaagtgg cgtgcctgat cgctttagtg gtagcggcag cggcaccgat    1500
tttaccctga ccattagcag tctgcaggcc gaggacgttg ccgtttatta ctgccagcag    1560
tactatagcg caccgctgac atttggcggt ggcaccaagg tggaaattaa ataa          1614
```

<210> SEQ ID NO 7  
<211> LENGTH: 485  
<212> TYPE: PRT  
<213> ORGANISM: Artificial Sequence  
<220> FEATURE:  
<223> OTHER INFORMATION: Description of Artificial Sequence:  
      Synthetic polypeptide  
<220> FEATURE:  
<223> OTHER INFORMATION: fusion sequence

<400> SEQUENCE: 7

```
Asp Ile Gln Met Thr Gln Ser Pro Ser Ser Leu Ser Ala Ser Val Gly
1               5                  10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Arg Leu His Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Gly Gly Ser Ala Gly Ser Ala
    210                 215                 220

Gly Ser Ala Gly Ser Gly Gly Ser Glu Val Gln Leu Leu Glu Ser Gly
225                 230                 235                 240

Gly Gly Leu Val Lys Pro Gly Gly Ser Leu Arg Leu Ser Cys Ala Ala
                245                 250                 255

Ser Gly Phe Thr Leu Ile Asn Tyr Arg Met Asn Trp Val Arg Gln Ala
            260                 265                 270

Pro Gly Lys Gly Leu Glu Trp Val Ser Ser Ile Ser Ser Ser Ser Ser
        275                 280                 285

Tyr Ile His Tyr Ala Asp Ser Val Lys Gly Arg Phe Thr Ile Ser Arg
    290                 295                 300

Asp Asn Ala Glu Asn Ser Leu Tyr Leu Gln Met Asn Ser Leu Arg Ala
305                 310                 315                 320

Glu Asp Thr Ala Val Tyr Tyr Cys Val Arg Glu Gly Pro Arg Ala Thr
                325                 330                 335

Gly Tyr Ser Met Ala Asp Val Phe Asp Ile Trp Gly Gln Gly Thr Met
            340                 345                 350

Val Thr Val Ser Ser Gly Gly Gly Ser Gly Gly Gly Ser Gly
        355                 360                 365

Gly Gly Gly Ser Glu Leu Val Met Thr Gln Ser Pro Asp Ser Leu Ala
370                 375                 380

Val Ser Leu Gly Glu Arg Ala Thr Ile Asn Cys Lys Ser Ser Gln Ser
385                 390                 395                 400

Val Leu Tyr Ser Ser Asn Asn Lys Ser Tyr Leu Ala Trp Tyr Gln Gln
                405                 410                 415

Lys Pro Gly Gln Pro Pro Lys Leu Leu Ile Tyr Trp Ala Ser Thr Arg
            420                 425                 430

Glu Ser Gly Val Pro Asp Arg Phe Ser Gly Ser Gly Ser Gly Thr Asp
        435                 440                 445

Phe Thr Leu Thr Ile Ser Ser Leu Gln Ala Glu Asp Val Ala Val Tyr
    450                 455                 460

Tyr Cys Gln Gln Tyr Tyr Ser Ala Pro Leu Thr Phe Gly Gly Gly Thr
465                 470                 475                 480

Lys Val Glu Ile Lys
            485

<210> SEQ ID NO 8
<211> LENGTH: 1455
<212> TYPE: DNA
<213> ORGANISM: Artificial Sequence
<220> FEATURE:
<223> OTHER INFORMATION: Description of Artificial Sequence:
      Synthetic polynucleotide
<220> FEATURE:
<223> OTHER INFORMATION: fusion sequence
<220> FEATURE:
<221> NAME/KEY: modified_base
<222> LOCATION: (1443)..(1443)
<223> OTHER INFORMATION: n is a, c, g, or t

<400> SEQUENCE: 8

```
gatatccaga tgacccagtc cccgagctcc ctgtccgcct ctgtgggcga tagggtcacc      60
atcacctgcc gggcgagcca ggatgtgacc accgctgtag cctggtatca acagaaacca     120
ggaaaagctc cgaagcttct gatttactgg gcgagccgtc ttcataatgg cgtgccgagc     180
cgctttagcg gcagcggctc cgggacggat ttcactctga ccatcagcag tctgcagccg     240
gaagacttcg caacttatta ctgtcagcaa cattatagca ccccgctgac gttcggacag     300
ggtaccaagg tggagatcaa acgtacggtg gcagcaccga gcgtgtttat ctttccgccg     360
agcgacgaac aactgaaaag tggcacagcc agcgtggtgt gtttactgaa caacttctat     420
cctcgcgagg ccaaggtgca gtggaaagtg gacaatgcac tgcagagtgg caatagccag     480
gagagcgtga ccgaacagga tagcaaagat agcacctata gcctgagtag caccctgacc     540
ctgagcaagg ccgattatga aagcacaag gtgtatgcat gcgaggttac ccatcagggc      600
ctgagcagcc cggtgaccaa aagctttaac cgtggcgaat gcggtggtag tggtggatcc     660
gccggtagcg caggtagtgc aggtagtggc ggcagcgaag ttcagctgtt agaaagtggc     720
ggtggtctgg ttaagccggg cggtagtctg cgcctgagct gtgcagcaag tggtttcacc     780
ctgatcaatt atcgtatgaa ctgggtgcgc caagccccgg gtaaaggtct ggagtgggtt     840
agtagtatca gcagcagcag cagttacatc cactatgccg atagcgttaa gggccgcttt     900
acaatcagcc gcgataatgc cgagaatagc ttatacctgc aaatgaacag tctaagggcg     960
gaagataccg ccgtttacta ctgcgttcgt gaaggccctc gcgcaacagg ctatagcatg    1020
gcagacgtgt tcgacatttg gggtcagggc accatggtga ccgttagtag cggcggtggt    1080
ggtagtggtg gtggcggtag tggtggcggt ggcagcgaac tggtgatgac ccagagtccg    1140
gatagcctgg ccgtgagctt aggcgagcgt gcaaccatta attgtaaaag cagtcagagt    1200
gttctgtata gtagcaataa caagagctat ctggcctggt atcagcagaa gccgggccag    1260
ccgccgaaac tgctgattta ctgggcaagc acccgcgaaa gtggcgtgcc tgatcgcttt    1320
agtggtagcg gcagcggcac cgattttacc ctgaccatta gcagtctgca ggccgaggac    1380
gttgccgttt attactgcca gcagtactat agcgcaccgc tgacatttgg cggtggcacc    1440
aangtggaaa ttaaa                                                      1455
```

<210> SEQ ID NO 9
<211> LENGTH: 723
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: fusion sequence

<400> SEQUENCE: 9

```
Glu Val Gln Leu Leu Glu Ser Gly Gly Gly Leu Val Lys Pro Gly Gly
  1               5                  10                  15

Ser Leu Arg Leu Ser Cys Ala Ala Ser Gly Phe Thr Leu Ile Asn Tyr
             20                  25                  30

Arg Met Asn Trp Val Arg Gln Ala Pro Gly Lys Gly Leu Glu Trp Val
         35                  40                  45

Ser Ser Ile Ser Ser Ser Ser Ser Tyr Ile His Tyr Ala Asp Ser Val
     50                  55                  60

Lys Gly Arg Phe Thr Ile Ser Arg Asp Asn Ala Glu Asn Ser Leu Tyr
 65                  70                  75                  80
```

```
Leu Gln Met Asn Ser Leu Arg Ala Glu Asp Thr Ala Val Tyr Tyr Cys
                85                  90                  95
Val Arg Glu Gly Pro Arg Ala Thr Gly Tyr Ser Met Ala Asp Val Phe
            100                 105                 110
Asp Ile Trp Gly Gln Gly Thr Met Val Thr Val Ser Ser Gly Gly Gly
        115                 120                 125
Gly Ser Gly Gly Gly Gly Ser Gly Gly Gly Gly Ser Glu Leu Val Met
    130                 135                 140
Thr Gln Ser Pro Asp Ser Leu Ala Val Ser Leu Gly Glu Arg Ala Thr
145                 150                 155                 160
Ile Asn Cys Lys Ser Ser Gln Ser Val Leu Tyr Ser Ser Asn Asn Lys
                165                 170                 175
Ser Tyr Leu Ala Trp Tyr Gln Gln Lys Pro Gly Gln Pro Pro Lys Leu
            180                 185                 190
Leu Ile Tyr Trp Ala Ser Thr Arg Glu Ser Gly Val Pro Asp Arg Phe
        195                 200                 205
Ser Gly Ser Gly Ser Gly Thr Asp Phe Thr Leu Thr Ile Ser Ser Leu
    210                 215                 220
Gln Ala Glu Asp Val Ala Val Tyr Tyr Cys Gln Gln Tyr Tyr Ser Ala
225                 230                 235                 240
Pro Leu Thr Phe Gly Gly Gly Thr Lys Val Glu Ile Lys Gly Gly Ser
                245                 250                 255
Ala Gly Ser Ala Gly Ser Ala Gly Ser Gly Gly Ser Glu Val Gln Leu
            260                 265                 270
Val Glu Ser Gly Gly Gly Leu Val Gln Pro Gly Gly Ser Leu Arg Leu
        275                 280                 285
Ser Cys Ala Ala Ser Gly Phe Ala Phe Asn Tyr Tyr Asp Met Phe Trp
    290                 295                 300
Val Arg Gln Ala Pro Gly Lys Gly Leu Glu Trp Val Ala Tyr Ile Lys
305                 310                 315                 320
Pro Gly Gly Gly Asn Thr Tyr Tyr Ala Asp Ser Val Lys Gly Arg Phe
                325                 330                 335
Thr Ile Ser Ala Asp Thr Ser Lys Asn Thr Ala Tyr Leu Gln Met Asn
            340                 345                 350
Ser Leu Arg Ala Glu Asp Thr Ala Val Tyr Tyr Cys Ala Arg Gln Leu
        355                 360                 365
Tyr Gly Asn Ser Phe Phe Asp Tyr Trp Gly Gln Gly Thr Leu Val Thr
    370                 375                 380
Val Ser Ser Ala Ser Thr Lys Gly Pro Ser Val Phe Pro Leu Ala Pro
385                 390                 395                 400
Ser Ser Lys Ser Thr Ser Gly Gly Thr Ala Ala Leu Gly Cys Leu Val
                405                 410                 415
Lys Asp Tyr Phe Pro Glu Pro Val Thr Val Ser Trp Asn Ser Gly Ala
            420                 425                 430
Leu Thr Ser Gly Val His Thr Phe Pro Ala Val Leu Gln Ser Ser Gly
        435                 440                 445
Leu Tyr Ser Leu Ser Ser Val Val Thr Val Pro Ser Ser Ser Leu Gly
    450                 455                 460
Thr Gln Thr Tyr Ile Cys Asn Val Asn His Lys Pro Ser Asn Thr Lys
465                 470                 475                 480
Val Asp Lys Lys Val Glu Pro Lys Ser Cys Asp Lys Thr His Thr Cys
                485                 490                 495
```

```
Asp Lys Thr His Thr Cys Pro Pro Cys Pro Ala Pro Glu Leu Leu Gly
            500                 505                 510

Arg Pro Ser Val Phe Leu Phe Pro Pro Lys Pro Lys Asp Thr Leu Met
        515                 520                 525

Ile Ser Arg Thr Pro Glu Val Thr Cys Val Val Val Asp Val Ser His
    530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
                565                 570                 575

Arg Val Val Ser Val Leu Thr Val Leu His Gln Asp Trp Leu Asn Gly
            580                 585                 590

Lys Glu Tyr Lys Cys Lys Val Ser Asn Lys Ala Leu Pro Ala Pro Ile
        595                 600                 605

Glu Lys Thr Ile Ser Lys Ala Lys Gly Gln Pro Arg Glu Pro Gln Val
    610                 615                 620

Tyr Thr Leu Pro Pro Ser Arg Glu Glu Met Thr Lys Asn Gln Val Ser
625                 630                 635                 640

Leu Thr Cys Leu Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
        675                 680                 685

Asp Lys Ser Arg Trp Gln Gln Gly Asn Val Phe Ser Cys Ser Val Met
    690                 695                 700

His Glu Ala Leu His Asn His Tyr Thr Gln Lys Ser Leu Ser Leu Ser
705                 710                 715                 720

Pro Gly Lys

<210> SEQ ID NO 10
<211> LENGTH: 1161
<212> TYPE: DNA
<213> ORGANISM: Artificial Sequence
<220> FEATURE:
<223> OTHER INFORMATION: Description of Artificial Sequence:
      Synthetic polynucleotide
<220> FEATURE:
<223> OTHER INFORMATION: fusion sequence

<400> SEQUENCE: 10
gaagttcagt tactggaaag tggcggcggc ctggttaaac cgggtggtag cctgcgtctg     60
agttgcgcag caagcggctt caccctgatc aactatcgca tgaactgggt gcgccaagca    120
ccgggtaagg gtctggagtg ggtgagcagc atcagcagca gcagcagcta catccactac    180
gcagacagcg ttaaaggccg cttcaccatt agccgcgata cgccgaaaa cagcctgtac    240 ctgcagatga cagtctaag gcggaggat accgcagtgt actactgcgt tcgtgaaggc    300
ccgcgtgcaa ccggctatag catggccgac gttttgata tttggggcca gggcaccatg    360
gtgaccgtga gtagtggtgg tggtggcagc ggtggtggcg gtagtggtgg tggtggcagt    420
gaactggtta tgacccagag tccggacagt ctggcagtga gctgggcga gcgtgcaacc    480 atcaactgta agagcagtca gagcgtgctg tatagtagca acaataaaag ctatctggcc    540
tggtatcagc agaagccggg tcagccgcct aagctgctga tttattgggc cagcacccgc    600
gaaagcggtg ttccggatcg ctttagcggt agcggcagcg gtaccgattt cacccctgacc    660
```

```
atcagcagcc tgcaggccga agatgtggcc gtgtattatt gccagcagta ctacagcgcc   720
ccgctgacct tggtggcgg taccaaggtg gaaattaaag gcggcagtgc cggtagtgcc   780
ggtagtgcag gtagcggcgg tagcgaggtt cagctggtgg aaagcggcgg tggtctggtt   840
cagcctggtg gtagcctgcg cctgagctgt gccgcaagcg gtttcgcatt taactactat   900
gacatgttct gggttcgcca ggcaccgggc aaaggtctgg aatgggtggc ctatatcaaa   960
ccgggcggcg gcaacaccta ctacgccgat agcgttaagg gtcgtttcac catcagcgcc  1020
gataccagca aaacaccgc ctatctgcag atgaatagcc taagggcgga agacaccgca  1080
gtgtattact gcgcacgcca gctgtacggc aacagctttt tcgattactg gggccagggt  1140
accctggtta ccgtgagcag c                                           1161
```

<210> SEQ ID NO 11
<211> LENGTH: 493
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<223> OTHER INFORMATION: fusion sequence

<400> SEQUENCE: 11

```
Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
    210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255
```

```
Ala Gly Ser Ala Gly Ser Ala Gly Ser Gly Gly Ser Asp Ile Gln Met
            260                 265                 270

Thr Gln Ser Pro Ser Ser Leu Ser Ala Ser Val Gly Asp Arg Val Thr
            275                 280                 285

Ile Thr Cys Lys Ala Ser Gln Asp Val Thr Thr Ala Val Ala Trp Tyr
            290                 295                 300

Gln Gln Lys Pro Gly Lys Ala Pro Lys Leu Leu Ile Tyr Trp Ala Ser
305                 310                 315                 320

Thr Arg His Thr Gly Val Pro Ser Arg Phe Ser Gly Ser Gly Ser Gly
                325                 330                 335

Thr Asp Phe Thr Leu Thr Ile Ser Ser Leu Gln Pro Glu Asp Phe Ala
            340                 345                 350

Thr Tyr Tyr Cys Gln Gln His Tyr Ser Thr Pro Leu Thr Phe Gly Gln
            355                 360                 365

Gly Thr Lys Val Glu Ile Lys Arg Thr Val Ala Ala Pro Ser Val Phe
            370                 375                 380

Ile Phe Pro Pro Ser Asp Glu Gln Leu Lys Ser Gly Thr Ala Ser Val
385                 390                 395                 400

Val Cys Leu Leu Asn Asn Phe Tyr Pro Arg Glu Ala Lys Val Gln Trp
                405                 410                 415

Lys Val Asp Asn Ala Leu Gln Ser Gly Asn Ser Gln Glu Ser Val Thr
            420                 425                 430

Glu Gln Asp Ser Lys Asp Ser Thr Tyr Ser Leu Ser Ser Thr Leu Thr
            435                 440                 445

Leu Ser Lys Ala Asp Tyr Glu Lys His Lys Val Tyr Ala Cys Glu Val
450                 455                 460

Thr His Gln Gly Leu Ser Ser Pro Val Thr Lys Ser Phe Asn Arg Gly
465                 470                 475                 480

Glu Cys Gly Gly Ser Asp Tyr Lys Asp Asp Asp Lys
                485                 490

<210> SEQ ID NO 12
<211> LENGTH: 1125
<212> TYPE: DNA
<213> ORGANISM: Artificial Sequence
<220> FEATURE:
<223> OTHER INFORMATION: Description of Artificial Sequence:
      Synthetic polynucleotide
<220> FEATURE:
<223> OTHER INFORMATION: fusion sequence

<400> SEQUENCE: 12
gaagttcagt tactggaaag tggcggcggc ctggttaaac cgggtggtag cctgcgtctg     60
agttgcgcag caagcggctt caccctgatc aactatcgca tgaactgggt gcgccaagca    120
ccgggtaagg gtctggagtg ggtgagcagc atcagcagca gcagcagcta catccactac    180
gcagacagcg ttaaaggccg cttcaccatt agccgcgata cgccgaaaaa cagcctgtac    240
ctgcagatga acagtctaag gcggaggat accgcagtgt actactgcgt tcgtgaaggc    300
ccgcgtgcaa ccggctatag catggccgac gttttttgata tttggggcca gggcaccatg    360
gtgaccgtga gtagtggtgg tggtggcagc ggtggtggcg tagtggtgg tggtggcagt    420 gaactggtta tgacccagag tccggacagt ctggcagtga gcctgggcga gcgtgcaacc    480
atcaactgta agagcagtca gagcgtgctg tatagtagca acaataaaag ctatctggcc    540
tggtatcagc agaagccggg tcagccgcct aagctgctga tttattgggc cagcacccgc    600
gaaagcggtg ttccggatcg ctttagcggt agcggcagcg gtaccgattt caccctgacc    660
```

```
atcagcagcc tgcaggccga agatgtggcc gtgtattatt gccagcagta ctacagcgcc    720
ccgctgacct ttggtggcgg taccaaggtg gaaattaaag gcggcagtgc cggtagtgcc    780
ggtagtgcag gtagcggcgg tagcgatatc cagatgaccc agagtccgag tagtctgagc    840
gccagcgttg gtgaccgcgt taccatcacc tgcaaggcca gccaggatgt taccaccgcc    900
gtggcctggt atcaacagaa accgggcaag gccccgaagc tgctgattta ttgggccagt    960
acacgccata caggcgtgcc gagccgtttt agtggcagcg gtagcggtac cgacttcacc   1020
ctgaccatca gtagcctgca accggaggat ttcgccacct actactgcca gcagcactac   1080
agcaccccgc tgacctttgg ccaaggtacc aaggtggaga ttaag                   1125
```

<210> SEQ ID NO 13
<211> LENGTH: 723
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<223> OTHER INFORMATION: fusion sequence

<400> SEQUENCE: 13

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Tyr Tyr
            20                  25                  30

Asp Met Phe Trp Val Arg Gln Ala Pro Gly Lys Gly Leu Glu Trp Val
        35                  40                  45

Ala Tyr Ile Lys Pro Gly Gly Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Gly Asn Ser Phe Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Asp Lys Thr His Thr Cys Pro Cys Pro Ala Pro
225                 230                 235                 240

Glu Leu Leu Gly Arg Pro Ser Val Phe Leu Phe Pro Pro Lys Pro Lys
                245                 250                 255

Asp Thr Leu Met Ile Ser Arg Thr Pro Glu Val Thr Cys Val Val Val
```

```
                260             265              270
Asp Val Ser His Glu Asp Pro Glu Val Lys Phe Asn Trp Tyr Val Asp
            275             280             285
Gly Val Glu Val His Asn Ala Lys Thr Lys Pro Arg Glu Glu Gln Tyr
            290             295             300
Asn Ser Thr Tyr Arg Val Val Ser Val Leu Thr Val Leu His Gln Asp
305             310             315             320
Trp Leu Asn Gly Lys Glu Tyr Lys Cys Lys Val Ser Asn Lys Ala Leu
                325             330             335
Pro Ala Pro Ile Glu Lys Thr Ile Ser Lys Ala Lys Gly Gln Pro Arg
            340             345             350
Glu Pro Gln Val Tyr Thr Leu Pro Pro Ser Arg Glu Glu Met Thr Lys
            355             360             365
Asn Gln Val Ser Leu Thr Cys Leu Val Lys Gly Phe Tyr Pro Ser Asp
            370             375             380
Ile Ala Val Glu Trp Glu Ser Asn Gly Gln Pro Glu Asn Asn Tyr Lys
385             390             395             400
Thr Thr Pro Pro Val Leu Asp Ser Asp Gly Ser Phe Phe Leu Tyr Ser
                405             410             415
Lys Leu Thr Val Asp Lys Ser Arg Trp Gln Gln Gly Asn Val Phe Ser
            420             425             430
Cys Ser Val Met His Glu Ala Leu His Asn His Tyr Thr Gln Lys Ser
            435             440             445
Leu Ser Leu Ser Pro Gly Lys Gly Gly Ser Ala Gly Ser Ala Gly Ser
            450             455             460
Ala Gly Ser Gly Gly Ser Glu Val Gln Leu Leu Glu Ser Gly Gly Gly
465             470             475             480
Leu Val Lys Pro Gly Gly Ser Leu Arg Leu Ser Cys Ala Ala Ser Gly
                485             490             495
Phe Thr Leu Ile Asn Tyr Arg Met Asn Trp Val Arg Gln Ala Pro Gly
            500             505             510
Lys Gly Leu Glu Trp Val Ser Ser Ile Ser Ser Ser Ser Ser Tyr Ile
            515             520             525
His Tyr Ala Asp Ser Val Lys Gly Arg Phe Thr Ile Ser Arg Asp Asn
            530             535             540
Ala Glu Asn Ser Leu Tyr Leu Gln Met Asn Ser Leu Arg Ala Glu Asp
545             550             555             560
Thr Ala Val Tyr Tyr Cys Val Arg Glu Gly Pro Arg Ala Thr Gly Tyr
                565             570             575
Ser Met Ala Asp Val Phe Asp Ile Trp Gly Gln Gly Thr Met Val Thr
            580             585             590
Val Ser Ser Gly Gly Gly Gly Ser Gly Gly Gly Gly Ser Gly Gly Gly
            595             600             605
Gly Ser Glu Leu Val Met Thr Gln Ser Pro Asp Ser Leu Ala Val Ser
            610             615             620
Leu Gly Glu Arg Ala Thr Ile Asn Cys Lys Ser Ser Gln Ser Val Leu
625             630             635             640
Tyr Ser Ser Asn Asn Lys Ser Tyr Leu Ala Trp Tyr Gln Gln Lys Pro
                645             650             655
Gly Gln Pro Pro Lys Leu Leu Ile Tyr Trp Ala Ser Thr Arg Glu Ser
            660             665             670
Gly Val Pro Asp Arg Phe Ser Gly Ser Gly Ser Gly Thr Asp Phe Thr
            675             680             685
```

```
Leu Thr Ile Ser Ser Leu Gln Ala Glu Asp Val Ala Val Tyr Tyr Cys
        690                 695                 700

Gln Gln Tyr Tyr Ser Ala Pro Leu Thr Phe Gly Gly Gly Thr Lys Val
705                 710                 715                 720

Glu Ile Lys

<210> SEQ ID NO 14
<211> LENGTH: 2172
<212> TYPE: DNA
<213> ORGANISM: Artificial Sequence
<220> FEATURE:
<223> OTHER INFORMATION: Description of Artificial Sequence:
      Synthetic polynucleotide
<220> FEATURE:
<223> OTHER INFORMATION: fusion sequence

<400> SEQUENCE: 14
gaagttcaac tggttgagag tggcggtggc ttagttcaac cgggcggtag tttacgcctg      60
agttgtgcag ccagcggttt cgccttcaac tattatgaca tgttttgggt gcgccaggca     120
ccgggtaaag gcctggagtg ggtggcctat atcaaaccgg gcggtggcaa cacctattac     180
gccgatagcg tgaaaggtcg ctttaccatc agcgcagata ccagcaagaa taccgcctac     240
ctgcagatga taagcctgcg tgccgaagac accgccgttt attattgcgc cgccagctg      300 tacggcaata gcttttttcga ttactggggc cagggcaccc tggttaccgt tagcagcgct     360
agcaccaagg gtccgagcgt gtttcctctg gcacctagca gtaaaagcac cagtggtggt     420
acagcagccc tgggttgcct ggtgaaggat tactttccgg agccggtgac cgttagttgg     480
aatagcggcg ccctgaccag tggcgttcat acatttccgg ccgtgctgca gagtagtggc     540
ctgtacagcc tgagtagcgt tgttaccgtt ccgagcagca gcctgggcac ccagacctat     600
atttgcaatg ttaaccataa accgagcaac acaaagttg ataaaaaagt tgaaccgaag      660
agctgtgaca aaacccatac atgtgacaaa acacacacct gcccgccttg tccggcacct     720
gagctgctgg gtcgcccgag cgttttcttg tttcctccga aaccgaaaga caccctgatg     780
atcagccgca cacctgaggt gacctgtgtt gtggtggatg tgagccacga agatcctgaa     840
gttaagttta ctggtatgt ggatggcgtg gaggtgcata atgccaagac aaagccgcgt      900
gaagagcagt acaacagcac ctatcgtgtt gttagtgtgc tgaccgttct gcaccaagat     960
tggctgaacg gcaaggagta taaatgcaag gttagcaata agccctgcc ggccccgatc     1020 gagaagacca tcagcaaagc caaggtcag ccgcgtgagc ctcaggtgta tacactgccg     1080
cctagccgtg aggagatgac caagaatcag gttagcctga cctgtctggt gaaaggcttt     1140
tacccgagcg atatcgccgt tgagtgggaa agcaatggtc agcctgagaa caactacaag     1200
accaccccgc ctgtttagaa cagtgatggt agcttttttct tatacagcaa actgaccgtt     1260
gataagagcc gctggcagca gggcaatgtg tttagctgca gtgttatgca tgaggccctg     1320
cataaccact ataccagaa gagtctgagc ctgagtcctg gcaaaggtgg atccgccggt     1380
agcgcaggta gtgcaggtag tggcggcagc gaagttcagc tgttagaaag tggcggtggt     1440
ctggttaagc cgggcggtag tctgcgcctg agctgtgcag caagtggttt caccctgatc     1500
aattatcgta tgaactgggt gcgccaagcc ccgggtaaag gtctggagtg ggttagtagt     1560
atcagcagca gcagcagtta catccactat gccgatagcg ttaagggccg ctttacaatc     1620
agccgcgata atgccgagaa tagcttatac ctgcaaatga acagtctaag gcggaagat      1680 accgccgttt actactgcgt tcgtgaaggc cctcgcgcaa caggctatag catggcagac     1740
```

-continued

```
gtgttcgaca tttggggtca gggcaccatg gtgaccgtta gtagcggcgg tggtggtagt      1800
ggtggtggcg gtagtggtgg cggtggcagc gaactggtga tgacccagag tccggatagc      1860
ctggccgtga gcttaggcga gcgtgcaacc attaattgta aaagcagtca gagtgttctg      1920
tatagtagca ataacaagag ctatctggcc tggtatcagc agaagccggg ccagccgccg      1980
aaactgctga tttactgggc aagcacccgc gaaagtggcg tgcctgatcg ctttagtggt      2040
agcggcagcg gcaccgattt taccctgacc attagcagtc tgcaggccga ggacgttgcc      2100
gtttattact gccagcagta ctatagcgca ccgctgacat ttggcggtgg caccaaggtg      2160
gaaattaaat aa                                                         2172
```

<210> SEQ ID NO 15
<211> LENGTH: 485
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: fusion sequence

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Gly Gly Ser Ala Gly Ser Ala
    210                 215                 220

Gly Ser Ala Gly Ser Gly Gly Ser Glu Val Gln Leu Leu Glu Ser Gly
225                 230                 235                 240

Gly Gly Leu Val Lys Pro Gly Gly Ser Leu Arg Leu Ser Cys Ala Ala
                245                 250                 255

Ser Gly Phe Thr Leu Ile Asn Tyr Arg Met Asn Trp Val Arg Gln Ala
```

```
            260                 265                 270
Pro Gly Lys Gly Leu Glu Trp Val Ser Ser Ile Ser Ser Ser Ser Ser
                275                 280                 285

Tyr Ile His Tyr Ala Asp Ser Val Lys Gly Arg Phe Thr Ile Ser Arg
            290                 295                 300

Asp Asn Ala Glu Asn Ser Leu Tyr Leu Gln Met Asn Ser Leu Arg Ala
305                 310                 315                 320

Glu Asp Thr Ala Val Tyr Tyr Cys Val Arg Glu Gly Pro Arg Ala Thr
                325                 330                 335

Gly Tyr Ser Met Ala Asp Val Phe Asp Ile Trp Gly Gln Gly Thr Met
                340                 345                 350

Val Thr Val Ser Ser Gly Gly Gly Ser Gly Gly Gly Gly Ser Gly
                355                 360                 365

Gly Gly Gly Ser Glu Leu Val Met Thr Gln Ser Pro Asp Ser Leu Ala
            370                 375                 380

Val Ser Leu Gly Glu Arg Ala Thr Ile Asn Cys Lys Ser Ser Gln Ser
385                 390                 395                 400

Val Leu Tyr Ser Ser Asn Asn Lys Ser Tyr Leu Ala Trp Tyr Gln Gln
                405                 410                 415

Lys Pro Gly Gln Pro Pro Lys Leu Leu Ile Tyr Trp Ala Ser Thr Arg
                420                 425                 430

Glu Ser Gly Val Pro Asp Arg Phe Ser Gly Ser Gly Ser Gly Thr Asp
                435                 440                 445

Phe Thr Leu Thr Ile Ser Ser Leu Gln Ala Glu Asp Val Ala Val Tyr
450                 455                 460

Tyr Cys Gln Gln Tyr Tyr Ser Ala Pro Leu Thr Phe Gly Gly Gly Thr
465                 470                 475                 480

Lys Val Glu Ile Lys
            485

<210> SEQ ID NO 16
<211> LENGTH: 1458
<212> TYPE: DNA
<213> ORGANISM: Artificial Sequence
<220> FEATURE:
<223> OTHER INFORMATION: Description of Artificial Sequence:
      Synthetic polynucleotide
<220> FEATURE:
<223> OTHER INFORMATION: fusion sequence

<400> SEQUENCE: 16
gacattcaga tgacccaaag tccgagcagc ctgagtgcca gtgttggtga tcgcgtgaca      60
atcacatgca aggccagtca ggacgtgacc accgcagtgg cctggtatca gcagaaaccg     120
ggtaaggccc cgaagctgct gatctattgg gccagtaccc gccacaccgg tgttcctagt     180
cgcttcagtg gcagtggcag cggcacagat ttcaccctga ccatcagcag cctgcaaccg     240
gaagattttg ccacctacta ctgccagcag cactatagca ccccgctgac ctttggccag     300
ggcaccaagg ttgagattaa acgtacggtg gcagcaccga gcgtgtttat ctttccgccg     360
agcgacgaac aactgaaaag tggcacagcc agcgtggtgt gtttactgaa caacttctat     420
cctcgcgagg ccaaggtgca gtggaaagtg gacaatgcac tgcagagtgg caatagccag     480
gagagcgtga ccgaacagga tagcaaagat agcacctata gcctgagtag caccctgacc     540
ctgagcaagg ccgattatga aaagcacaag gtgtatgcat gcgaggttac ccatcagggc     600
ctgagcagcc cggtgaccaa aagctttaac cgtggcgaat gcgtggtag tggtggatcc     660
```

```
gccggtagcg caggtagtgc aggtagtggc ggcagcgaag ttcagctgtt agaaagtggc    720
ggtggtctgg ttaagccggg cggtagtctg cgcctgagct gtgcagcaag tggtttcacc    780
ctgatcaatt atcgtatgaa ctgggtgcgc caagccccgg gtaaaggtct ggagtgggtt    840
agtagtatca gcagcagcag cagttacatc cactatgccg atagcgttaa gggccgcttt    900
acaatcagcc gcgataatgc cgagaatagc ttatacctgc aaatgaacag tctaagggcg    960
gaagataccg ccgttttacta ctgcgttcgt gaaggccctc gcgcaacagg ctatagcatg   1020
gcagacgtgt tcgacatttg ggtcagggca ccatggtga ccgttagtag cggcggtggt   1080
ggtagtggtg gtggcggtag tggtggcggt ggcagcgaac tggtgatgac ccagagtccg   1140
gatagcctgg ccgtgagctt aggcgagcgt gcaaccatta attgtaaaag cagtcagagt   1200
gttctgtata gtagcaataa caagagctat ctggcctggt atcagcagaa gccgggccag   1260
ccgccgaaac tgctgattta ctgggcaagc acccgcgaaa gtggcgtgcc tgatcgcttt   1320
agtggtagcg gcagcggcac cgattttacc ctgaccatta gcagtctgca ggccgaggac   1380
gttgccgttt attactgcca gcagtactat agcgcaccgc tgacatttgg cggtggcacc   1440
aaggtggaaa ttaaataa                                                 1458
```

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<223> OTHER INFORMATION: linker sequence

<400> SEQUENCE: 17

Gly Gly Ser Ala Gly Ser Ala Gly Ser Ala Gly Ser Gly Gly Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<223> OTHER INFORMATION: linker sequence

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 365
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 19

Glu Val Gln Leu Gln Glu Ser Gly Gly Gly Leu Met Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
 50                  55                  60

Ser Val Lys Gly Arg Phe Thr Ile Ser Arg Asp Asp Ser Lys Arg Ser
 65                  70                  75                  80

Val Tyr Leu Gln Met Asn Thr Leu Arg Ala Glu Asp Thr Gly Ile Tyr
             85                  90                  95

Tyr Cys Thr Arg Gly Asn Gly Asn Tyr Arg Ala Met Asp Tyr Trp Gly
            100                 105                 110

Gln Gly Thr Ser Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ala Ser Leu Ser Val Ser Val Gly Glu Thr Val Ser Ile Thr Cys Arg
145                 150                 155                 160

Ala Ser Glu Asn Ile Tyr Ser Ser Leu Ala Trp Tyr Gln Gln Lys Gln
                165                 170                 175

Gly Lys Ser Pro Gln Leu Leu Val Tyr Ser Ala Thr Ile Leu Ala Asp
            180                 185                 190

Gly Val Pro Ser Arg Phe Ser Gly Ser Gly Ser Gly Thr Gln Tyr Ser
        195                 200                 205

Leu Lys Ile Asn Ser Leu Gln Ser Glu Asp Phe Gly Thr Tyr Tyr Cys
    210                 215                 220

Gln His Phe Trp Gly Thr Pro Tyr Thr Phe Gly Gly Thr Lys Leu
225                 230                 235                 240

Glu Ile Lys Gly Gly Ser Ala Gly Ser Ala Gly Ser Ala Gly Ser Gly
                245                 250                 255

Gly Ser Asp Ile Gln Met Thr Gln Ser Pro Ser Ser Leu Ser Ala Ser
            260                 265                 270

Val Gly Asp Arg Val Thr Ile Thr Cys Arg Ala Ser Gln Asp Val Thr
        275                 280                 285

Thr Ala Val Ala Trp Tyr Gln Gln Lys Pro Gly Lys Ala Pro Lys Leu
    290                 295                 300

Leu Ile Tyr Trp Ala Ser Arg Leu His Asn Gly Val Pro Ser Arg Phe
305                 310                 315                 320

Ser Gly Ser Gly Ser Gly Thr Asp Phe Thr Leu Thr Ile Ser Ser Leu
                325                 330                 335

Gln Pro Glu Asp Phe Ala Thr Tyr Tyr Cys Gln Gln His Tyr Ser Thr
            340                 345                 350

Pro Leu Thr Phe Gly Gln Gly Thr Lys Val Glu Ile Lys
        355                 360                 365

<210> SEQ ID NO 20
<211> LENGTH: 1095
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 20
gaagttcagc tgcaggaaag cggcggtggt ctgatgcagc tggtggcag catgaaactg      60 agctgtgtgg ccagcggttt caccttcagc aactattgga tgaactgggt gcgtcagagt     120
ccggaaaaag gcctggaatg ggttgccgag atccgcctga agagtaacaa ctatgccacc     180
cattacgccg agagcgtgaa aggtcgcttt accatcagcc gtgatgacag caaacgcagc     240

```
gtgtatctgc agatgaacac attacgtgct gaagacaccg gtatctacta ttgcacccgc    300
ggcaacggca actatcgcgc catggattat tggggccagg gtaccagcgt gaccgttagt    360
agcggcggcg gtggtagtgg tggtggtggt agtggcggtg gcggtagcga cattcaaatg    420
acccagagtc ctgcaagcct gagcgtgagc gtgggtgaga ccgtgagcat acatgccgc     480 gccagcgaga acatttatag cagcctggcc tggtaccagc aaaaacaggg taaaagcccg    540
cagctgctgg tgtatagcgc caccattctg gcagatggtg tgccgagccg ttttagtggc    600
agtggcagtg gtacccagta cagcctgaaa atcaacagcc tgcagagcga agacttcggc    660
acctactact gtcagcactt tggggcaccc cgtataccnt ttggcggcgg taccaagctg    720
gaaatcaaag gtggatccgc cggtagcgca ggtagtgccg gtagcggtgg cagcgatatc    780
caaatgaccc agagcccgag tagcctgagt gcaagtgtgg gcgatcgcgt taccatcacc    840
tgtcgcgcaa gccaggacgt gacaaccgcc gtggcctggt atcagcagaa acctggtaaa    900
gccccgaagc tgctgattta ctgggccagc cgcctgcaca atggtgttcc gagtcgcttt    960
agcggcagtg gcagcggcac agactttaca ctgaccatta gcagcctgca gccggaggat   1020
tttgccacct attattgcca gcagcattac agtacaccgc tgaccttcgg ccagggtacc   1080
aaagtggaaa tcaaa                                                    1095

<210> SEQ ID NO 21
<211> LENGTH: 363
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 21
```

Glu Val Gln Leu Gln Glu Ser Gly Pro Glu Leu Glu Met Pro Gly Ala
1               5                   10                  15

Ser Val Lys Ile Ser Cys Lys Ala Ser Gly Ser Ser Phe Thr Gly Phe
            20                  25                  30

Ser Met Asn Trp Val Lys Gln Ser Asn Gly Lys Ser Leu Glu Trp Ile
        35                  40                  45

Gly Asn Ile Asp Thr Tyr Tyr Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Ser Ala Tyr Tyr Gly Ser Thr Phe Ala Tyr Trp Gly Gln Gly
            100                 105                 110

Thr Leu Val Thr Val Ser Ala Gly Gly Gly Ser Gly Gly Gly Gly
        115                 120                 125

Ser Gly Gly Gly Gly Ser Asp Ile Gln Met Thr Gln Ser Pro Ala Ser
    130                 135                 140

Leu Ser Ala Ser Val Gly Glu Thr Val Thr Ile Thr Cys Arg Ala Ser
145                 150                 155                 160

Glu Asn Ile Tyr Ser Tyr Leu Ala Trp Tyr Gln Gln Lys Gln Gly Lys
                165                 170                 175

Ser Pro Gln Leu Leu Val Tyr Asn Ala Lys Thr Leu Ile Glu Gly Val
            180                 185                 190

Pro Ser Arg Phe Ser Gly Ser Gly Ser Gly Thr Gln Phe Ser Leu Lys

```
              195                 200                 205
Ile Asn Ser Leu Gln Pro Glu Asp Phe Gly Ser Tyr Phe Cys Gln His
            210                 215                 220
His Phe Gly Thr Pro Phe Thr Phe Gly Ser Gly Thr Glu Leu Glu Ile
225                 230                 235                 240
Lys Gly Gly Ser Ala Gly Ser Ala Gly Ser Ala Gly Ser Gly Gly Ser
                245                 250                 255
Asp Ile Gln Met Thr Gln Ser Pro Ser Ser Leu Ser Ala Ser Val Gly
            260                 265                 270
Asp Arg Val Thr Ile Thr Cys Arg Ala Ser Gln Asp Val Thr Thr Ala
        275                 280                 285
Val Ala Trp Tyr Gln Gln Lys Pro Gly Lys Ala Pro Lys Leu Leu Ile
    290                 295                 300
Tyr Trp Ala Ser Arg Leu His Asn Gly Val Pro Ser Arg Phe Ser Gly
305                 310                 315                 320
Ser Gly Ser Gly Thr Asp Phe Thr Leu Thr Ile Ser Ser Leu Gln Pro
                325                 330                 335
Glu Asp Phe Ala Thr Tyr Tyr Cys Gln Gln His Tyr Ser Thr Pro Leu
            340                 345                 350
Thr Phe Gly Gln Gly Thr Lys Val Glu Ile Lys
            355                 360
```

<210> SEQ ID NO 22
<211> LENGTH: 1089
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
gaggtgcagc tgcaagaaag tggtccggaa ctggaaatgc cgggtgccag cgtgaaaatc     60
agctgcaaag ccagcggcag tagctttacc ggctttagca tgaactgggt gaaacagagc    120
aacggcaaga gcctggagtg gatcggcaat attgacacct actacggcgg caccacctat    180
aaccagaagt tcaaaggcaa agccacactg accgtggaca gagtagcag tacagcctac    240
atgcagctga aaagcctgac cagcgaggat agcgcagtgt attactgcgc acgcagcgcc    300
tattacggca gcacatttgc ctactggggt cagggtaccc tggtgacagt tagcgcaggc    360
ggtggtggca gtggtggtgg tggtagcggt ggtggtggca gcgacattca aatgacacag    420
agcccggcca gtctgagtgc aagcgttggc gaaaccgtga ccattacctg ccgtgccagc    480
gagaacatct atagctacct ggcctggtac cagcagaagc agggtaaaag ccctcagctg    540
ctggtgtaca atgccaaaac cctgatcgaa ggcgttccga gtcgctttag tggcagcggc    600
agtggcaccc agttcagcct gaaaatcaac agcctgcaac cggaagactt tggcagctac    660
ttctgccagc accatttggg cacaccgttc accttcggta gtggcaccga actggagatt    720
aaaggtggat ccgcaggtag cgcaggcagt gcaggcagcg gtggtagcga tatccagatg    780
acccaaagcc cgagcagctt aagtgccagc gtgggcgatc gcgtgaccat cacctgcaaa    840
gccagtcagg acgttaccac agccgtggcc tggtatcagc agaaaccggg taagccccct    900
aagctgctga tctattgggc cagcaccccgc cacacaggtg ttccgagtcg tttcagcggc    960
agcggtagcg gtaccgattt taccctgacc atcagcagcc tgcagccgga agacttcgca   1020
acatactact gccagcagca ctattctacc ccgctgacat cggccaggg cacaaaagtg   1080
``` gagattaaa                                                                                      1089

<210> SEQ ID NO 23
<211> LENGTH: 363
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 23

Glu Val Gln Leu Gln Glu Ser Gly Pro Glu Leu Met Pro Gly Ala
1               5                   10                  15

Ser Val Lys Ile Ser Cys Lys Ala Ser Gly Ser Phe Thr Gly Phe
                20                  25                  30

Ser Met Asn Trp Val Lys Gln Ser Asn Gly Lys Ser Leu Glu Trp Ile
        35                  40                  45

Gly Asn Ile Asp Thr Tyr Tyr Gly Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Ser Ala Tyr Tyr Gly Ser Thr Phe Ala Tyr Trp Gly Gln Gly
                100                 105                 110

Thr Leu Val Thr Val Ser Ala Gly Gly Gly Ser Gly Gly Gly Gly
            115                 120                 125

Ser Gly Gly Gly Gly Ser Asp Ile Gln Met Thr Gln Ser Pro Ala Ser
130                 135                 140

Leu Ser Ala Ser Val Gly Glu Thr Val Thr Ile Thr Cys Arg Ala Ser
145                 150                 155                 160

Glu Asn Ile Tyr Ser Tyr Leu Ala Trp Tyr Gln Gln Lys Gln Gly Lys
                165                 170                 175

Ser Pro Gln Leu Leu Val Tyr Asn Ala Lys Thr Leu Ile Glu Gly Val
            180                 185                 190

Pro Ser Arg Phe Ser Gly Ser Gly Ser Gly Thr Gln Phe Ser Leu Lys
        195                 200                 205

Ile Asn Ser Leu Gln Pro Glu Asp Phe Gly Ser Tyr Phe Cys Gln His
    210                 215                 220

His Phe Gly Thr Pro Phe Thr Phe Gly Ser Gly Thr Glu Leu Glu Ile
225                 230                 235                 240

Lys Gly Gly Ser Ala Gly Ser Ala Gly Ser Ala Gly Ser Gly Gly Ser
                245                 250                 255

Asp Ile Gln Met Thr Gln Ser Pro Ser Ser Leu Ser Ala Ser Val Gly
            260                 265                 270

Asp Arg Val Thr Ile Thr Cys Arg Ala Ser Gln Asp Val Thr Thr Ala
        275                 280                 285

Val Ala Trp Tyr Gln Gln Lys Pro Gly Lys Ala Pro Lys Leu Leu Ile
    290                 295                 300

Tyr Trp Ala Ser Arg Leu His Asn Gly Val Pro Ser Arg Phe Ser Gly
305                 310                 315                 320

Ser Gly Ser Gly Thr Asp Phe Thr Leu Thr Ile Ser Ser Leu Gln Pro
                325                 330                 335

Glu Asp Phe Ala Thr Tyr Tyr Cys Gln Gln His Tyr Ser Thr Pro Leu
            340                 345                 350

Thr Phe Gly Gln Gly Thr Lys Val Glu Ile Lys
        355                 360

<210> SEQ ID NO 24
<211> LENGTH: 1089
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 24

```
gaggtgcagc tgcaagaaag tggtccggaa ctggaaatgc cgggtgccag cgtgaaaatc      60
agctgcaaag ccagcggcag tagctttacc ggctttagca tgaactgggt gaaacagagc     120
aacggcaaga gcctggagtg gatcggcaat attgacacct actacggcgg caccacctat     180
aaccagaagt tcaaaggcaa agccacactg accgtggaca gagtagcaga tacagcctac     240
atgcagctga aaagcctgac cagcgaggat agcgcagtgt attactgcgc acgcagcgcc     300
tattacggca gcacatttgc ctactggggt cagggtaccc tggtgacagt tagcgcaggc     360
ggtggtggca gtggtggtgg tggtagcggt ggtggtggca gcgacattca aatgacacag     420
agcccggcca gtctgagtgc aagcgttggc gaaaccgtga ccattacctg ccgtgccagc     480
gagaacatct atagctacct ggcctggtac cagcagaagc agggtaaaag ccctcagctg     540
ctggtgtaca atgccaaaac cctgatcgaa ggcgttccga tcgctttag tggcagcggc     600
agtggcaccc agttcagcct gaaaatcaac agcctgcaac ggaagactt tggcagctac     660
ttctgccagc accattttgg cacaccgttc accttcggta gtggcaccga actggagatt     720
aaaggtggat ccgccggtag cgcaggtagt gccggtagcg gtggcagcga tatccaaatg     780
acccagagcc cgagtagcct gagtgcaagt gtgggcgatc gcgttaccat cacctgtcgc     840
gcaagccagg acgtgacaac cgccgtggcc tggtatcagc agaaacctgg taaagccccg     900
aagctgctga tttactgggc cagccgcctg cacaatggtg ttccgagtcg ctttagcggc     960
agtggcagcg gcacagactt tacactgacc attagcagcc tgcagccgga ggattttgcc    1020
acctattatt gccagcagca ttacagtaca ccgctgacct tcggccaggg taccaaagtg    1080
gaaatcaaa                                                            1089
```

<210> SEQ ID NO 25
<211> LENGTH: 713
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Tyr Tyr
            20                  25                  30

Asp Met Phe Trp Val Arg Gln Ala Pro Gly Lys Gly Leu Glu Trp Val
        35                  40                  45

Ala Tyr Ile Lys Pro Gly Gly Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys

```
            85                  90                  95
Ala Arg Gln Leu Tyr Gly Asn Ser Phe Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Asp Lys Thr His Thr Cys Pro Pro Cys Pro Ala Pro
225                 230                 235                 240

Glu Leu Leu Gly Arg Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly Gly Ser Ala Gly Ser Ala Gly Ser
    450                 455                 460

Ala Gly Ser Gly Gly Ser Glu Val Gln Leu Gln Glu Ser Gly Gly Gly
465                 470                 475                 480

Leu Met Gln Pro Gly Gly Ser Met Lys Leu Ser Cys Val Ala Ser Gly
                485                 490                 495

Phe Thr Phe Ser Asn Tyr Trp Met Asn Trp Val Arg Gln Ser Pro Glu
            500                 505                 510
```

```
Lys Gly Leu Glu Trp Val Ala Glu Ile Arg Leu Lys Ser Asn Asn Tyr
        515                 520                 525
Ala Thr His Tyr Ala Glu Ser Val Lys Gly Arg Phe Thr Ile Ser Arg
        530                 535                 540
Asp Asp Ser Lys Arg Ser Val Tyr Leu Gln Met Asn Thr Leu Arg Ala
545                 550                 555                 560
Glu Asp Thr Gly Ile Tyr Tyr Cys Thr Arg Gly Asn Gly Asn Tyr Arg
                565                 570                 575
Ala Met Asp Tyr Trp Gly Gln Gly Thr Ser Val Thr Val Ser Ser Gly
            580                 585                 590
Gly Gly Gly Ser Gly Gly Gly Ser Gly Gly Gly Ser Asp Ile
        595                 600                 605
Gln Met Thr Gln Ser Pro Ala Ser Leu Ser Val Ser Val Gly Glu Thr
    610                 615                 620
Val Ser Ile Thr Cys Arg Ala Ser Glu Asn Ile Tyr Ser Ser Leu Ala
625                 630                 635                 640
Trp Tyr Gln Gln Lys Gln Gly Lys Ser Pro Gln Leu Leu Val Tyr Ser
                645                 650                 655
Ala Thr Ile Leu Ala Asp Gly Val Pro Ser Arg Phe Ser Gly Ser Gly
            660                 665                 670
Ser Gly Thr Gln Tyr Ser Leu Lys Ile Asn Ser Leu Gln Ser Glu Asp
        675                 680                 685
Phe Gly Thr Tyr Tyr Cys Gln His Phe Trp Gly Thr Pro Tyr Thr Phe
    690                 695                 700
Gly Gly Gly Thr Lys Leu Glu Ile Lys
705                 710

<210> SEQ ID NO 26
<211> LENGTH: 2142
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 26
gaagttcaac tggttgagag tggcggtggc ttagttcaac cgggcggtag tttacgcctg      60
agttgtgcag ccagcggttt cgccttcaac tattatgaca tgttttgggt cgcgcaggca     120
ccgggtaaag gcctggagtg ggtggcctat atcaaaccgg gcggtggcaa cacctattac     180
gccgatagcg tgaaaggtcg ctttaccatc agcgcagata ccagcaagaa taccgcctac     240
ctgcagatga atagcctgcg tgccgaagac accgccgttt attattgcgc cgccagctg     300
tacggcaata gcttttttcga ttactggggc caggcacccc tggttaccgt tagcagcgct     360
agcaccaagg gtccgagcgt gtttcctctg gcacctagca gtaaaagcac cagtggtggt     420
acagcagccc tgggttgcct ggtgaaggat tactttccgg agccggtgac cgttagttgg     480
aatagcggcg ccctgaccag tggcgttcat acatttccgg ccgtgctgca gagtagtggc     540
ctgtacagcc tgagtagcgt tgttaccgtt ccgagcagca gcctgggcac ccagacctat     600
atttgcaatg ttaaccataa accgagcaac acaaaagttg ataaaaaagt tgaaccgaag     660
agctgtgaca aacccatac atgtgacaaa acacacacct gcccgccttg tccggcacct     720
gagctgctgg gtcgcccgag cgttttttctg tttcctccga aaccgaaaga cacccctgatg     780
atcagccgca cacctgaggt gacctgtgtt gtggtggatg tgagccacga agatcctgaa     840
```

```
gttaagttta actggtatgt ggatggcgtg gaggtgcata atgccaagac aaagccgcgt    900
gaagagcagt acaacagcac ctatcgtgtt gttagtgtgc tgaccgttct gcaccaagat    960
tggctgaacg gcaaggagta taaatgcaag gttagcaata aagccctgcc ggccccgatc   1020
gagaagacca tcagcaaagc caaggtcag ccgcgtgagc ctcaggtgta tacactgccg    1080
cctagccgtg aggagatgac caagaatcag gttagcctga cctgtctggt gaaaggcttt   1140
tacccgagcg atatcgccgt tgagtgggaa agcaatggtc agcctgagaa caactacaag   1200 accacccccgc ctgttttaga cagtgatggt agcttttttct tatacagcaa actgaccgtt   1260
gataagagcc gctggcagca gggcaatgtg tttagctgca gtgttatgca tgaggccctg   1320
cataaccact atcccagaa gagtctgagc ctgagtcctg gcaaaggtgg atccgcaggc   1380
agtgcaggta gtgccggcag cggtggtagt gaggttcagc tgcaggaaag cggcggcggc   1440
ttaatgcagc ctggcggtag catgaagctg agctgcgtgg ccagcggctt caccttagc    1500 aattactgga tgaactgggt cgcagagc ccggaaaaag gcctggaatg ggtggcagag     1560
atccgtctga agagcaacaa ctacgccacc cactatgccg aaagcgtgaa gggtcgcttt   1620
accatcagcc gcgatgacag caaacgcagc gtgtatctgc agatgaacac cctgcgtgca   1680
gaggacaccg gcatctatta ttgcaccccgc ggcaacggta attatcgcgc catggactac   1740 tgggggtcagg gtaccagcgt gaccgttagc agtggcggtg gtggtagcgg tggtggtggt   1800
agcggtggtg gtggcagcga tattcaaatg acccagagcc ctgccagcct gagcgtgagt   1860
gttggcgaaa ccgtgagcat cacctgccgc gccagcgaga acatctatag tagcctggcc   1920
tggtaccagc agaaacaggg caaaagcccg cagctgctgg tgtatagcgc aaccattctg   1980
gcagatggcg ttccgagccg tttttagcggt agcggcagcg gcacacagta cagcctgaag   2040
atcaacagcc tgcagagcga ggactttggc acctattact gccagcactt ttggggtacc   2100
ccgtatacct tcggcggcgg caccaaactg gaaattaaat aa                       2142
```

<210> SEQ ID NO 27
<211> LENGTH: 475
<212> TYPE: PRT
<213> ORGANISM: Artificial Sequence
<220> FEATURE:
<223> OTHER INFORMATION: Description of Artificial Sequence:
    Synthetic polypeptide

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Gly Ser Gly Gly Ser Ala Gly Ser Ala
210                 215                 220
Gly Ser Ala Gly Ser Gly Gly Ser Glu Val Gln Leu Gln Glu Ser Gly
225                 230                 235                 240
Gly Gly Leu Met Gln Pro Gly Gly Ser Met Lys Leu Ser Cys Val Ala
                245                 250                 255
Ser Gly Phe Thr Phe Ser Asn Tyr Trp Met Asn Trp Val Arg Gln Ser
            260                 265                 270
Pro Glu Lys Gly Leu Glu Trp Val Ala Glu Ile Arg Leu Lys Ser Asn
        275                 280                 285
Asn Tyr Ala Thr His Tyr Ala Glu Ser Val Lys Gly Arg Phe Thr Ile
290                 295                 300
Ser Arg Asp Asp Ser Lys Arg Ser Val Tyr Leu Gln Met Asn Thr Leu
305                 310                 315                 320
Arg Ala Glu Asp Thr Gly Ile Tyr Tyr Cys Thr Arg Gly Asn Gly Asn
                325                 330                 335
Tyr Arg Ala Met Asp Tyr Trp Gly Gln Gly Thr Ser Val Thr Val Ser
            340                 345                 350
Ser Gly Gly Gly Gly Ser Gly Gly Gly Ser Gly Gly Gly Gly Ser
        355                 360                 365
Asp Ile Gln Met Thr Gln Ser Pro Ala Ser Leu Ser Val Ser Val Gly
        370                 375                 380
Glu Thr Val Ser Ile Thr Cys Arg Ala Ser Glu Asn Ile Tyr Ser Ser
385                 390                 395                 400
Leu Ala Trp Tyr Gln Gln Lys Gln Gly Lys Ser Pro Gln Leu Leu Val
                405                 410                 415
Tyr Ser Ala Thr Ile Leu Ala Asp Gly Val Pro Ser Arg Phe Ser Gly
            420                 425                 430
Ser Gly Ser Gly Thr Gln Tyr Ser Leu Lys Ile Asn Ser Leu Gln Ser
        435                 440                 445
Glu Asp Phe Gly Thr Tyr Tyr Cys Gln His Phe Trp Gly Thr Pro Tyr
450                 455                 460
Thr Phe Gly Gly Gly Thr Lys Leu Glu Ile Lys
465                 470                 475
```

<210> SEQ ID NO 28
<211> LENGTH: 1428
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 28
gacattcaga tgacccaaag tccgagcagc ctgagtgcca gtgttggtga tcgcgtgaca      60

```
atcacatgca aggccagtca ggacgtgacc accgcagtgg cctggtatca gcagaaaccg    120
ggtaaggccc cgaagctgct gatctattgg gccagtaccc gccacaccgg tgttcctagt    180
cgcttcagtg gcagtggcag cggcacagat ttcaccctga ccatcagcag cctgcaaccg    240
gaagattttg ccacctacta ctgccagcag cactatagca ccccgctgac ctttggccag    300
ggcaccaagg ttgagattaa acgtacggtg gcagcaccga gcgtgtttat ctttccgccg    360
agcgacgaac aactgaaaag tggcacagcc agcgtggtgt gtttactgaa caacttctat    420
cctcgcgagg ccaaggtgca gtggaaagtg gacaatgcac tgcagagtgg caatagccag    480
gagagcgtga ccgaacagga tagcaaagat agcacctata gcctgagtag caccctgacc    540
ctgagcaagg ccgattatga aagcacaag gtgtatgcat gcgaggttac ccatcagggc    600
ctgagcagcc cggtgaccaa aagctttaac cgtggcgaat gcggtggtag tggtggatcc    660
gcaggcagtg caggtagtgc cggcagcggt ggtagtgagg ttcagctgca ggaaagcggc    720
ggcggcttaa tgcagcctgg cggtagcatg aagctgagct gcgtggccag cggcttcacc    780
tttagcaatt actggatgaa ctgggtgcgc cagagcccgg aaaaaggcct ggaatgggtg    840
gcagagatcc gtctgaagag caacaactac gccacccact atgccgaaag cgtgaagggt    900
cgctttacca tcagccgcga tgacagcaaa cgcagcgtgt atctgcagat gaacaccctg    960
cgtgcagagg acaccggcat ctattattgc acccgcggca acggtaatta tcgcgccatg   1020
gactactggg gtcagggtac cagcgtgacc gttagcagtg gcggtggtgg tagcggtggt   1080
ggtggtagcg gtggtggtgg cagcgatatt caaatgaccc agagccctgc cagcctgagc   1140
gtgagtgttg gcgaaaccgt gagcatcacc tgccgcgcca gcgagaacat ctatagtagc   1200
ctggcctggt accagcagaa acagggcaaa agcccgcagc tgctggtgta tagcgcaacc   1260
attctggcag atggcgttcc gagccgtttt agcggtagcg gcagcggcac acagtacagc   1320
ctgaagatca acagcctgca gagcgaggac tttggcacct attactgcca gcacttttgg   1380
ggtaccccgt ataccttcgg cggcggcacc aaactggaaa ttaaataa                1428
```

<210> SEQ ID NO 29
<211> LENGTH: 475
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Arg Leu His Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
            115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Gly Ser Ala Gly Ser Ala
    210                 215                 220

Gly Ser Ala Gly Ser Gly Gly Ser Glu Val Gln Leu Gln Glu Ser Gly
225                 230                 235                 240

Gly Gly Leu Met Gln Pro Gly Gly Ser Met Lys Leu Ser Cys Val Ala
                245                 250                 255

Ser Gly Phe Thr Phe Ser Asn Tyr Trp Met Asn Trp Val Arg Gln Ser
            260                 265                 270

Pro Glu Lys Gly Leu Glu Trp Val Ala Glu Ile Arg Leu Lys Ser Asn
        275                 280                 285

Asn Tyr Ala Thr His Tyr Ala Glu Ser Val Lys Gly Arg Phe Thr Ile
    290                 295                 300

Ser Arg Asp Asp Ser Lys Arg Ser Val Tyr Leu Gln Met Asn Thr Leu
305                 310                 315                 320

Arg Ala Glu Asp Thr Gly Ile Tyr Tyr Cys Thr Arg Gly Asn Gly Asn
                325                 330                 335

Tyr Arg Ala Met Asp Tyr Trp Gly Gln Gly Thr Ser Val Thr Val Ser
            340                 345                 350

Ser Gly Gly Gly Gly Ser Gly Gly Gly Ser Gly Gly Gly Gly Ser
        355                 360                 365

Asp Ile Gln Met Thr Gln Ser Pro Ala Ser Leu Ser Val Ser Val Gly
    370                 375                 380

Glu Thr Val Ser Ile Thr Cys Arg Ala Ser Glu Asn Ile Tyr Ser Ser
385                 390                 395                 400

Leu Ala Trp Tyr Gln Gln Lys Gln Gly Lys Ser Pro Gln Leu Leu Val
                405                 410                 415

Tyr Ser Ala Thr Ile Leu Ala Asp Gly Val Pro Ser Arg Phe Ser Gly
            420                 425                 430

Ser Gly Ser Gly Thr Gln Tyr Ser Leu Lys Ile Asn Ser Leu Gln Ser
        435                 440                 445

Glu Asp Phe Gly Thr Tyr Tyr Cys Gln His Phe Trp Gly Thr Pro Tyr
    450                 455                 460

Thr Phe Gly Gly Gly Thr Lys Leu Glu Ile Lys
465                 470                 475

<210> SEQ ID NO 30
<211> LENGTH: 1428
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 30
```

```
gatatccaga tgacccagtc cccgagctcc ctgtccgcct ctgtgggcga tagggtcacc        60
atcacctgcc gggcgagcca ggatgtgacc accgctgtag cctggtatca acagaaacca       120
ggaaaagctc cgaagcttct gatttactgg gcgagccgtc ttcataatgg cgtgccgagc       180
cgctttagcg gcagcggctc cgggacggat tcactctga ccatcagcag tctgcagccg        240
gaagacttcg caacttatta ctgtcagcaa cattatagca ccccgctgac gttcggacag       300
ggtaccaagg tggagatcaa acgtacggtg gcagcaccga gcgtgtttat ctttccgccg       360
agcgacgaac aactgaaaag tggcacagcc agcgtggtgt gtttactgaa caacttctat       420
cctcgcgagg ccaaggtgca gtggaaagtg acaatgcac tgcagagtgg caatagccag        480
gagagcgtga ccgaacagga tagcaaagat agcacctata gcctgagtag caccctgacc       540
ctgagcaagg ccgattatga gaagcacaag gtgtatgcat gcgaggttac ccatcagggc       600
ctgagcagcc cggtgaccaa aagctttaac cgtggcgaat gcggtggtag tggtggatcc       660
gcaggcagtg caggtagtgc cggcagcggt ggtagtgagg ttcagctgca ggaaagcggc       720
ggcggcttaa tgcagcctgg cggtagcatg aagctgagct gcgtggccag cggcttcacc       780
tttagcaatt actggatgaa ctgggtgcgc cagagcccgg aaaaaggcct ggaatgggtg       840
gcagagatcc gtctgaagag caacaactac gccacccact atgccgaaag cgtgaagggt       900
cgctttacca tcagccgcga tgacagcaaa cgcagcgtgt atctgcagat gaacaccctg       960
cgtgcagagg acaccggcat ctattattgc acccgcggca acggtaatta tcgcgccatg      1020
gactactggg gtcagggtac cagcgtgacc gttagcagtg gcggtggtgg tagcggtggt      1080
ggtggtagcg gtggtggtgg cagcgatatt caaatgaccc agagccctgc agcctgagc       1140 gtgagtgttg gcgaaaccgt gagcatcacc tgccgcgcca gcgagaacat ctatagtagc      1200
ctggcctggt accagcagaa acagggcaaa agcccgcagc tgctggtgta tagcgcaacc      1260
attctggcag atggcgttcc gagccgtttt agcggtagcg gcagcggcac acagtacagc      1320
ctgaagatca cagcctgca gagcgaggac tttggcaccc tattactgcca gcacttttgg      1380 ggtaccccgt ataccttcgg cggcggcacc aaactggaaa ttaaataa                   1428
```

<210> SEQ ID NO 31
<211> LENGTH: 710
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Tyr Tyr
            20                  25                  30

Asp Met Phe Trp Val Arg Gln Ala Pro Gly Lys Gly Leu Glu Trp Val
        35                  40                  45

Ala Tyr Ile Lys Pro Gly Gly Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Gly Asn Ser Phe Phe Asp Tyr Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Asp Lys Thr His Thr Cys Pro Pro Cys Pro Ala Pro
225                 230                 235                 240

Glu Leu Leu Gly Arg Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys Gly Gly Ser Ala Gly Ser Ala Gly Ser
    450                 455                 460

Ala Gly Ser Gly Gly Ser Glu Val Gln Leu Gln Glu Ser Gly Pro Glu
465                 470                 475                 480

Leu Glu Met Pro Gly Ala Ser Val Lys Ile Ser Cys Lys Ala Ser Gly
                485                 490                 495

Ser Ser Phe Thr Gly Phe Ser Met Asn Trp Val Lys Gln Ser Asn Gly
            500                 505                 510

Lys Ser Leu Glu Trp Ile Gly Asn Ile Asp Thr Tyr Tyr Gly Gly Thr
        515                 520                 525
```

```
Thr Tyr Asn Gln Lys Phe Lys Gly Lys Ala Thr Leu Thr Val Asp Lys
            530                 535                 540
Ser Ser Ser Thr Ala Tyr Met Gln Leu Lys Ser Leu Thr Ser Glu Asp
545                 550                 555                 560
Ser Ala Val Tyr Tyr Cys Ala Arg Ser Ala Tyr Tyr Gly Ser Thr Phe
                565                 570                 575
Ala Tyr Trp Gln Gly Thr Leu Val Thr Val Ser Ala Gly Gly Gly Gly
            580                 585                 590
Ser Gly Gly Gly Gly Ser Gly Gly Gly Ser Asp Ile Gln Met Thr
        595                 600                 605
Gln Ser Pro Ala Ser Leu Ser Ala Ser Val Gly Glu Thr Val Thr Ile
    610                 615                 620
Thr Cys Arg Ala Ser Glu Asn Ile Tyr Ser Tyr Leu Ala Trp Tyr Gln
625                 630                 635                 640
Gln Lys Gln Gly Lys Ser Pro Gln Leu Leu Val Tyr Asn Ala Lys Thr
                645                 650                 655
Leu Ile Glu Gly Val Pro Ser Arg Phe Ser Gly Ser Gly Ser Gly Thr
            660                 665                 670
Gln Phe Ser Leu Lys Ile Asn Ser Leu Gln Pro Glu Asp Phe Gly Ser
        675                 680                 685
Tyr Phe Cys Gln His His Phe Gly Thr Pro Phe Thr Phe Gly Ser Gly
690                 695                 700
Thr Glu Leu Glu Ile Lys
705                 710

<210> SEQ ID NO 32
<211> LENGTH: 2133
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 32
gaagttcaac tggttgagag tggcggtggc ttagttcaac cgggcggtag tttacgcctg     60
agttgtgcag ccagcggttt cgccttcaac tattatgaca tgttttgggt gcgccaggca    120
ccgggtaaag gcctggagtg ggtggcctat atcaaaccgg gcggtggcaa cacctattac    180
gccgatagcg tgaaaggtcg ctttaccatc agcgcagata ccagcaagaa taccgcctac    240
ctgcagatga atagcctgcg tgccgaagac accgccgttt attattgcgc cgccagctg     300 tacggcaata gcttttttcga ttactggggc cagggcaccc tggttaccgt tagcagcgct    360
agcaccaagg gtccgagcgt gtttcctctg gcacctagca gtaaaagcac cagtggtggt    420
acagcagccc tgggttgcct ggtgaaggat tactttccgg agccggtgac cgttagttgg    480
aatagcggcg ccctgaccag tggcgttcat acatttccgg ccgtgctgca gagtagtggc    540
ctgtacagcc tgagtagcgt tgttaccgtt ccgagcagca gcctgggcac ccagacctat    600
atttgcaatg ttaaccataa accgagcaac acaaaagttg ataaaaaagt tgaaccgaag    660
agctgtgaca aaacccatac atgtgacaaa acacacacct gcccgccttg tccggcacct    720
gagctgctgg gtcgcccgag cgttttttctg tttcctccga accgaaaga cccctgatg    780 atcagccgca cacctgaggt gacctgtgtt gtggtggatg tgagccacga agatcctgaa    840
gttaagttta ctggtatgt ggatggcgtg gaggtgcata atgccaagac aaagccgcgt    900
gaagagcagt acaacagcac ctatcgtgtt gttagtgtgc tgaccgttct gcaccaagat    960
```

-continued

```
tggctgaacg gcaaggagta taaatgcaag gttagcaata aagccctgcc ggccccgatc    1020
gagaagacca tcagcaaagc caaaggtcag ccgcgtgagc ctcaggtgta tacactgccg    1080
cctagccgtg aggagatgac caagaatcag gttagcctga cctgtctggt gaaaggcttt    1140
tacccgagcg atatcgccgt tgagtgggaa agcaatggtc agcctgagaa caactacaag    1200
accaccccgc ctgttttaga cagtgatggt agcttttttct tatacagcaa actgaccgtt    1260
gataagagcc gctggcagca gggcaatgtg tttagctgca gtgttatgca tgaggccctg    1320
cataaccact atacccagaa gagtctgagc ctgagtcctg gcaaaggtgg atccgccggt    1380
agcgcaggca gcgcaggtag tggtggtagc gaagttcagc tgcaggaaag tggcccggaa    1440
ctggaaatgc cgggcgccag cgtgaaaatc agttgcaaag ccagcggtag cagcttcaca    1500
ggcttcagca tgaactgggt gaagcagagc aacggtaaga gcctggagtg gatcggcaac    1560
attgacacct actatggcgg caccacctac aaccagaagt tcaaaggcaa ggccaccctg    1620
accgtggata aaagcagcag cacagcctac atgcagctga aaagcctgac cagcgaagat    1680
agcgccgtgt attactgcgc ccgtagcgcc tattacggca gcacctttgc atactggcag    1740
ggtaccctgg tgaccgtgag cgcaggtggt ggtggtagtg gtggtggtgg tagcggtggt    1800
ggcggtagtg acattcaaat gacccagagc cctgcaagcc tgagcgccag tgttggcgaa    1860
accgtgacca ttacatgccg cgccagcgaa aacatctata gttacctggc ctggtaccag    1920
cagaaacagg gcaaaagccc gcaactgctg gtgtataacg ccaaaacccct gattgagggc    1980 gtgccgagtc gcttcagcgg tagcggtagc ggtacacagt tcagtctgaa aatcaacagc    2040
ctgcagccgg aagacttcgg cagctacttt tgccagcacc actttggcac cccgtttaca    2100
tttggcagcg gcaccgagct ggaaattaaa taa                                 2133
```

<210> SEQ ID NO 33
<211> LENGTH: 472
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

Glu Ser Val Thr Glu Gln Asp Ser Lys Asp Ser Thr Tyr Ser Leu Ser
145                 150                 155                 160

Ser Thr Leu Thr Leu Ser Lys Ala Asp Tyr Glu Lys His Lys Val Tyr
            165                 170                 175

Ala Cys Glu Val Thr His Gln Gly Leu Ser Ser Pro Val Thr Lys Ser
        180                 185                 190

Phe Asn Arg Gly Glu Cys Gly Gly Ser Gly Gly Ser Ala Gly Ser Ala
    195                 200                 205

Gly Ser Ala Gly Ser Gly Gly Ser Glu Val Gln Leu Gln Glu Ser Gly
210                 215                 220

Pro Glu Leu Glu Met Pro Gly Ala Ser Val Lys Ile Ser Cys Lys Ala
225                 230                 235                 240

Ser Gly Ser Ser Phe Thr Gly Phe Ser Met Asn Trp Val Lys Gln Ser
            245                 250                 255

Asn Gly Lys Ser Leu Glu Trp Ile Gly Asn Ile Asp Thr Tyr Tyr Gly
        260                 265                 270

Gly Thr Thr Tyr Asn Gln Lys Phe Lys Gly Lys Ala Thr Leu Thr Val
    275                 280                 285

Asp Lys Ser Ser Ser Thr Ala Tyr Met Gln Leu Lys Ser Leu Thr Ser
290                 295                 300

Glu Asp Ser Ala Val Tyr Tyr Cys Ala Arg Ser Ala Tyr Tyr Gly Ser
305                 310                 315                 320

Thr Phe Ala Tyr Trp Gln Gly Thr Leu Val Thr Val Ser Ala Gly Gly
            325                 330                 335

Gly Gly Ser Gly Gly Gly Ser Gly Gly Gly Ser Asp Ile Gln
        340                 345                 350

Met Thr Gln Ser Pro Ala Ser Leu Ser Ala Ser Val Gly Glu Thr Val
    355                 360                 365

Thr Ile Thr Cys Arg Ala Ser Glu Asn Ile Tyr Ser Tyr Leu Ala Trp
370                 375                 380

Tyr Gln Gln Lys Gln Gly Lys Ser Pro Gln Leu Leu Val Tyr Asn Ala
385                 390                 395                 400

Lys Thr Leu Ile Glu Gly Val Pro Ser Arg Phe Ser Gly Ser Gly Ser
            405                 410                 415

Gly Thr Gln Phe Ser Leu Lys Ile Asn Ser Leu Gln Pro Glu Asp Phe
        420                 425                 430

Gly Ser Tyr Phe Cys Gln His His Phe Gly Thr Pro Phe Thr Phe Gly
    435                 440                 445

Ser Gly Thr Glu Leu Glu Ile Lys
450                 455

<210> SEQ ID NO 34
<211> LENGTH: 1419
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34
gacattcaga tgacccaaag tccgagcagc ctgagtgcca gtgttggtga tcgcgtgaca     60
atcacatgca aggccagtca ggacgtgacc accgcagtgg cctggtatca gcagaaaccg    120
ggtaaggccc cgaagctgct gatctattgg gccagtaccc gccacaccgg tgttcctagt    180

```
cgcttcagtg gcagtggcag cggcacagat tcaccctga ccatcagcag cctgcaaccg    240
gaagattttg ccacctacta ctgccagcag cactatagca ccccgctgac ctttggccag    300
ggcaccaagg ttgagattaa acgtacggtg gcagcaccga gcgtgtttat ctttccgccg    360
agcgacgaac aactgaaaag tggcacagcc agcgtggtgt gtttactgaa caacttctat    420
cctcgcgagg ccaaggtgca gtggaaagtg gacaatgcac tgcagagtgg caatagccag    480
gagagcgtga ccgaacagga tagcaaagat agcaccctata gcctgagtag caccctgacc    540
ctgagcaagg ccgattatga aagcacaag gtgtatgcat gcgaggttac ccatcagggc    600
ctgagcagcc cggtgaccaa aagctttaac cgtggcgaat cggtggtag tggtggatcc    660 gccggtagcg caggcagcgc aggtagtggt ggtagcgaag ttcagctgca ggaaagtggc    720
ccggaactgg aaatgccggg cgccagcgtg aaaatcagtt gcaaagccag cggtagcagc    780
ttcacaggct tcagcatgaa ctgggtgaag cagagcaacg taagagcct ggagtggatc    840 ggcaacattg acacctacta tggcggcacc acctacaacc agaagttcaa aggcaaggcc    900
accctgaccg tggataaaag cagcagcaca gcctacatgc agctgaaaag cctgaccagc    960
gaagatagcg ccgtgtatta ctgcgcccgt agcgcctatt acggcagcac ctttgcatac    1020
tggcagggta ccctggtgac cgtgagcgca ggtggtggtg gtagtggtgg tggtggtagc    1080
ggtggtggcg gtagtgacat tcaaatgacc cagagccctg caagcctgag cgccagtgtt    1140
ggcgaaaccg tgaccattac atgccgcgcc agcgaaaaca tctatagtta cctggcctgg    1200
taccagcaga acagggcaa aagcccgcaa ctgctggtgt ataacgccaa aacctgatt    1260 gagggcgtgc cgagtcgctt cagcggtagc ggtagcggta cacagttcag tctgaaaatc    1320
aacagcctgc agccggaaga cttcggcagc tactttgcc agcaccactt tggcaccccg    1380
tttacatttg gcagcggcac cgagctggaa attaaataa                          1419
```

<210> SEQ ID NO 35
<211> LENGTH: 472
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Gly Gly Ser Ala Gly Ser Ala
    210                 215                 220

Gly Ser Ala Gly Ser Gly Gly Ser Glu Val Gln Leu Gln Glu Ser Gly
225                 230                 235                 240

Pro Glu Leu Glu Met Pro Gly Ala Ser Val Lys Ile Ser Cys Lys Ala
                245                 250                 255

Ser Gly Ser Ser Phe Thr Gly Phe Ser Met Asn Trp Val Lys Gln Ser
            260                 265                 270

Asn Gly Lys Ser Leu Glu Trp Ile Gly Asn Ile Asp Thr Tyr Tyr Gly
        275                 280                 285

Gly Thr Thr Tyr Asn Gln Lys Phe Lys Gly Lys Ala Thr Leu Thr Val
    290                 295                 300

Asp Lys Ser Ser Ser Thr Ala Tyr Met Gln Leu Lys Ser Leu Thr Ser
305                 310                 315                 320

Glu Asp Ser Ala Val Tyr Tyr Cys Ala Arg Ser Ala Tyr Tyr Gly Ser
                325                 330                 335

Thr Phe Ala Tyr Trp Gln Gly Thr Leu Val Thr Val Ser Ala Gly Gly
            340                 345                 350

Gly Gly Ser Gly Gly Gly Gly Ser Gly Gly Gly Gly Ser Asp Ile Gln
        355                 360                 365

Met Thr Gln Ser Pro Ala Ser Leu Ser Ala Ser Val Gly Glu Thr Val
    370                 375                 380

Thr Ile Thr Cys Arg Ala Ser Glu Asn Ile Tyr Ser Tyr Leu Ala Trp
385                 390                 395                 400

Tyr Gln Gln Lys Gln Gly Lys Ser Pro Gln Leu Leu Val Tyr Asn Ala
                405                 410                 415

Lys Thr Leu Ile Glu Gly Val Pro Ser Arg Phe Ser Gly Ser Gly Ser
            420                 425                 430

Gly Thr Gln Phe Ser Leu Lys Ile Asn Ser Leu Gln Pro Glu Asp Phe
        435                 440                 445

Gly Ser Tyr Phe Cys Gln His His Phe Gly Thr Pro Phe Thr Phe Gly
    450                 455                 460

Ser Gly Thr Glu Leu Glu Ile Lys
465                 470

<210> SEQ ID NO 36
<211> LENGTH: 1419
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 36
gacattcaga tgacccaaag tccgagcagc ctgagtgcca gtgttggtga tcgcgtgaca      60
atcacatgca aggccagtca ggacgtgacc accgcagtgg cctggtatca gcagaaaccg     120

```
ggtaaggccc cgaagctgct gatctattgg gccagtaccc gccacaccgg tgttcctagt    180
cgcttcagtg gcagtggcag cggcacagat ttcaccctga ccatcagcag cctgcaaccg    240
gaagattttg ccacctacta ctgccagcag cactatagca ccccgctgac ctttggccag    300
ggcaccaagg ttgagattaa acgtacggtg gcagcaccga gcgtgtttat ctttccgccg    360
agcgacgaac aactgaaaag tggcacagcc agcgtggtgt gtttactgaa caacttctat    420
cctcgcgagg ccaaggtgca gtggaaagtg gacaatgcac tgcagagtgg caatagccag    480
gagagcgtga ccgaacagga tagcaaagat agcacctata gcctgagtag caccctgacc    540
ctgagcaagg ccgattatga aagcacaag gtgtatgcat gcgaggttac ccatcagggc    600
ctgagcagcc cggtgaccaa aagctttaac cgtggcgaat gcggtggtag tggtggatcc    660
gccggtagcg caggcagcgc aggtagtggt ggtagcgaag ttcagctgca ggaaagtggc    720
ccggaactgg aaatgccggg cgccagcgtg aaaatcagtt gcaaagccag cggtagcagc    780
ttcacaggct tcagcatgaa ctgggtgaag cagagcaacg gtaagagcct ggagtggatc    840
ggcaacattg acacctacta tggcggcacc acctacaacc agaagttcaa aggcaaggcc    900
accctgaccg tggataaaag cagcagcaca gcctacatgc agctgaaaag cctgaccagc    960
gaagatagcc ccgtgtatta ctgcgcccgt agcgccatt acggcagcac ctttgcatac   1020
tggcagggta ccctggtgac cgtgagcgca ggtggtggtg gtagtggtgg tggtggtagc   1080
ggtggtggcg gtagtgacat tcaaatgacc cagagccctg caagcctgag cgccagtgtt   1140
ggcgaaaccg tgaccattac atgccgcgcc agcgaaaaca tctatagtta cctggcctgg   1200
taccagcaga aacagggcaa aagcccgcaa ctgctggtgt ataacgccaa aaccctgatt   1260
gagggcgtgc cgagtcgctt cagcggtagc ggtagcggta cacagttcag tctgaaaatc   1320
aacagcctgc agccggaaga cttcggcagc tactttgcc agcaccactt tggcaccccg   1380
tttacatttg gcagcggcac cgagctggaa attaaataa                         1419
```

<210> SEQ ID NO 37
<211> LENGTH: 472
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Arg Leu His Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys Gly Gly Ser Gly Gly Ser Ala Gly Ser Ala
210                 215                 220

Gly Ser Ala Gly Ser Gly Gly Ser Glu Val Gln Leu Gln Glu Ser Gly
225                 230                 235                 240

Pro Glu Leu Glu Met Pro Gly Ala Ser Val Lys Ile Ser Cys Lys Ala
            245                 250                 255

Ser Gly Ser Ser Phe Thr Gly Phe Ser Met Asn Trp Val Lys Gln Ser
        260                 265                 270

Asn Gly Lys Ser Leu Glu Trp Ile Gly Asn Ile Asp Thr Tyr Tyr Gly
    275                 280                 285

Gly Thr Thr Tyr Asn Gln Lys Phe Lys Gly Lys Ala Thr Leu Thr Val
290                 295                 300

Asp Lys Ser Ser Ser Thr Ala Tyr Met Gln Leu Lys Ser Leu Thr Ser
305                 310                 315                 320

Glu Asp Ser Ala Val Tyr Tyr Cys Ala Arg Ser Ala Tyr Tyr Gly Ser
            325                 330                 335

Thr Phe Ala Tyr Trp Gln Gly Thr Leu Val Thr Val Ser Ala Gly Gly
        340                 345                 350

Gly Gly Ser Gly Gly Gly Gly Ser Gly Gly Gly Gly Ser Asp Ile Gln
    355                 360                 365

Met Thr Gln Ser Pro Ala Ser Leu Ser Ala Ser Val Gly Glu Thr Val
370                 375                 380

Thr Ile Thr Cys Arg Ala Ser Glu Asn Ile Tyr Ser Tyr Leu Ala Trp
385                 390                 395                 400

Tyr Gln Gln Lys Gln Gly Lys Ser Pro Gln Leu Leu Val Tyr Asn Ala
            405                 410                 415

Lys Thr Leu Ile Glu Gly Val Pro Ser Arg Phe Ser Gly Ser Gly Ser
        420                 425                 430

Gly Thr Gln Phe Ser Leu Lys Ile Asn Ser Leu Gln Pro Glu Asp Phe
    435                 440                 445

Gly Ser Tyr Phe Cys Gln His His Phe Gly Thr Pro Phe Thr Phe Gly
450                 455                 460

Ser Gly Thr Glu Leu Glu Ile Lys
465                 470

<210> SEQ ID NO 38
<211> LENGTH: 1419
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 38
gatatccaga tgacccagtc cccgagctcc ctgtccgcct ctgtgggcga tagggtcacc    60

```
atcacctgcc gggcgagcca ggatgtgacc accgctgtag cctggtatca acagaaacca    120
ggaaaagctc cgaagcttct gatttactgg gcgagccgtc ttcataatgg cgtgccgagc    180
cgctttagcg gcagcggctc cgggacggat ttcactctga ccatcagcag tctgcagccg    240
gaagacttcg caacttatta ctgtcagcaa cattatagca ccccgctgac gttcggacag    300
ggtaccaagg tggagatcaa acgtacggtg gcagcaccga gcgtgtttat ctttccgccg    360
agcgacgaac aactgaaaag tggcacagcc agcgtggtgt gtttactgaa caacttctat    420
cctcgcgagg ccaaggtgca gtggaaagtg gacaatgcac tgcagagtgg caatagccag    480
gagagcgtga ccgaacagga tagcaaagat agcacctata gcctgagtag cacccctgacc    540 ctgagcaagg ccgattatga aagcacaag gtgtatgcat gcgaggttac ccatcagggc    600
ctgagcagcc cggtgaccaa aagctttaac cgtggcgaat gcggtggtag tggtggatcc    660
gccggtagcg caggcagcgc aggtagtggt ggtagcgaag ttcagctgca ggaaagtggc    720
ccggaactgg aaatgccggg cgccagcgtg aaaatcagtt gcaaagccag cggtagcagc    780
ttcacaggct tcagcatgaa ctgggtgaag cagagcaacg taagagcct ggagtggatc    840 ggcaacattg acacctacta tggcggcacc acctacaacc agaagttcaa aggcaaggcc    900
accctgaccg tggataaaag cagcagcaca gcctacatgc agctgaaaag cctgaccagc    960
gaagatagcg ccgtgtatta ctgcgcccgt agcgcctatt acggcagcac ctttgcatac   1020
tggcagggta ccctggtgac cgtgagcgca ggtggtggtg gtagtggtgg tggtggtagc   1080
ggtggtggcg gtagtgacat tcaaatgacc cagagccctg caagcctgag cgccagtgtt   1140
ggcgaaaccg tgaccattac atgccgcgcc agcgaaaaca tctatagtta cctggcctgg   1200
taccagcaga aacagggcaa aagcccgcaa ctgctggtgt ataacgccaa aaccctgatt   1260
gagggcgtgc cgagtcgctt cagcggtagc ggtagcggta cacagttcag tctgaaaatc   1320
aacagcctgc agccggaaga cttcggcagc tactttttgcc agcaccactt tggcaccccg   1380
tttacatttg gcagcggcac cgagctggaa attaaataa                          1419
```

<210> SEQ ID NO 39

<400> SEQUENCE: 39

000

<210> SEQ ID NO 40

<400> SEQUENCE: 40

000

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 41

Ala Ser Thr Lys Gly Pro
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence:
       Synthetic polypeptide

<400> SEQUENCE: 42

Thr Val Ala Ala Pro
1               5

<210> SEQ ID NO 43
<211> LENGTH: 250
<212> TYPE: PRT
<213> ORGANISM: Artificial Sequence
<220> FEATURE:
<223> OTHER INFORMATION: Description of Artificial Sequence:
       Synthetic polypeptide

<400> SEQUENCE: 43

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Ala Ser Thr
        115                 120                 125

Lys Gly Pro Glu Val Gln Leu Val Glu Ser Gly Gly Gly Leu Val Gln
    130                 135                 140

Pro Gly Gly Ser Leu Arg Leu Ser Cys Ala Ala Ser Gly Phe Ala Phe
145                 150                 155                 160

Asn Tyr Tyr Asp Ile His Trp Val Arg Gln Ala Pro Gly Lys Gly Leu
                165                 170                 175

Glu Trp Val Ala Tyr Ile Asn Pro Gly Gly Asn Thr Tyr Tyr Ala
            180                 185                 190

Asp Ser Val Lys Gly Arg Phe Thr Ile Ser Ala Asp Thr Ser Lys Asn
        195                 200                 205

Thr Ala Tyr Leu Gln Met Asn Ser Leu Arg Ala Glu Asp Thr Ala Val
    210                 215                 220

Tyr Tyr Cys Ala Arg Gln Leu Tyr Gly Asn Ser Phe Met Asp Tyr Trp
225                 230                 235                 240

Gly Gln Gly Thr Leu Val Thr Val Ser Ser
                245                 250

<210> SEQ ID NO 44
<211> LENGTH: 750
<212> TYPE: DNA
<213> ORGANISM: Artificial Sequence
<220> FEATURE:
<223> OTHER INFORMATION: Description of Artificial Sequence:
       Synthetic polynucleotide

<400> SEQUENCE: 44

```
gaagtgcagc tgctggaaag cggcggtggc ctggtgaaac cgggtggtag tctgcgcctg    60
agttgcgccg ccagcggttt taccctgatc aactaccgca tgaactgggt gcgtcaggcc   120
ccgggcaaag gtctggagtg ggttagtagc atcagcagta gcagcagcta catccattac   180
gccgacagcg tgaaaggccg tttcaccatc agtcgcgata cgccgagaaa tagcctgtac   240
ctgcagatga acagcctgcg tgcagaagat accgccgtgt attactgcgt gcgcgaaggt   300
ccgcgtgcaa ccggttatag catggccgat gtgttcgata tttggggcca gggtaccatg   360
gtgaccgtga gcagtgccag caccaaaggt ccggaagttc agctggtgga aagcggtggt   420
ggtctggttc agccgggtgg tagcttacgt ctgagctgcg cagccagcgg ctttgccttc   480
aattattatg atattcattg ggttcgccaa gccccgggca agggcctgga atgggtggca   540
tatatcaatc cggtggcgg caacacctat tatgccgata gcgtgaaggg tcgctttacc   600
atcagcgccg ataccagcaa gaacaccgcc tatctgcaga tgaatagctt acgtgctgaa   660
gatacagccg tttactactg tgcccgccag ctgtatggca acagcttcat ggattattgg   720
ggccaaggca ccctggtgac cgttagcagc                                   750
```

<210> SEQ ID NO 45
<211> LENGTH: 225
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 45

Glu Leu Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Ser Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ala Pro Leu Thr Phe Gly Gly Gly Thr Lys Val Glu Ile
            100                 105                 110

Lys Thr Val Ala Ala Pro Asp Ile Gln Met Thr Gln Ser Pro Ser Ser
        115                 120                 125

Leu Ser Ala Ser Val Gly Asp Arg Val Thr Ile Thr Cys Arg Ala Ser
    130                 135                 140

Gln Asp Val Thr Thr Ala Val Ala Trp Tyr Gln Gln Lys Pro Gly Lys
145                 150                 155                 160

Ala Pro Lys Leu Leu Ile Tyr Trp Ala Ser Arg Leu His Asn Gly Val
                165                 170                 175

Pro Ser Arg Phe Ser Gly Ser Gly Ser Gly Thr Asp Phe Thr Leu Thr
            180                 185                 190

Ile Ser Ser Leu Gln Pro Glu Asp Phe Ala Thr Tyr Tyr Cys Gln Gln
        195                 200                 205

His Tyr Ser Thr Pro Leu Thr Phe Gly Gln Gly Thr Lys Val Glu Ile
    210                 215                 220

Lys
225

<210> SEQ ID NO 46
<211> LENGTH: 675
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 46

```
gaactggtga tgacccagag cccggatagc ctggcagtta gtctgggcga acgcgccacc      60
attaactgca aaagcagcca gagcgtgctg tatagcagca ataataaaag ctatctggca     120
tggtaccagc agaaaccggg tcagccgccg aagctgctga tctactgggc aagcacccgt     180
gaaagtggtg ttccggatcg ctttagcggc agcggcagcg gtacagattt caccctgacc     240
attagcagcc tgcaggccga agatgtggca gtgtattact gccagcagta ctatagcgca     300
ccgctgacct ttggtggcgg caccaaagtg gaaattaaga ccgtggccgc accggatatt     360
cagatgaccc aaagcccgag cagcctgagt gcaagcgtgg gtgatcgtgt gacaattacc     420
tgccgcgcaa gccaggatgt gaccaccgcc gtggcatggt atcaacagaa accgggcaaa     480
gccccgaaac tgctgattta ttgggccagc cgcctgcata atggcgttcc gagccgcttc     540
agcggtagcg gtagcggtac cgactttacc ctgaccatta gcagtctgca gccggaggat     600
tttgccacct actactgtca gcagcactat agcacccctc tgacctttgg ccagggcacc     660
aaggtggaaa tcaaa                                                      675
```

<210> SEQ ID NO 47
<211> LENGTH: 250
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 47

```
Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
            85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Ala Ser Thr
        115                 120                 125

Lys Gly Pro Glu Val Gln Leu Val Glu Ser Gly Gly Leu Val Gln
    130                 135                 140

Pro Gly Gly Ser Leu Arg Leu Ser Cys Ala Ala Ser Gly Phe Ala Phe
145                 150                 155                 160
```

```
Asn Tyr Tyr Asp Met Phe Trp Val Arg Gln Ala Pro Gly Lys Gly Leu
                165                 170                 175
Glu Trp Val Ala Tyr Ile Lys Pro Gly Gly Asn Thr Tyr Tyr Ala
            180                 185                 190
Asp Ser Val Lys Gly Arg Phe Thr Ile Ser Ala Asp Thr Ser Lys Asn
        195                 200                 205
Thr Ala Tyr Leu Gln Met Asn Ser Leu Arg Ala Glu Asp Thr Ala Val
    210                 215                 220
Tyr Tyr Cys Ala Arg Gln Leu Tyr Gly Asn Ser Phe Phe Asp Tyr Trp
225                 230                 235                 240
Gly Gln Gly Thr Leu Val Thr Val Ser Ser
                245                 250
```

```
<210> SEQ ID NO 48
<211> LENGTH: 750
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 48
gaggtgcagc tgctggagag cggtggtggt ctggtgaaac cgggcggtag cttacgcctg      60
agttgcgccg caagcggttt taccctgatc aactaccgca tgaactgggt tcgtcaggcc     120
ccgggcaagg gtctggaatg ggtgagcagc attagcagca gcagctacat ccactactac     180
gccgatagcg tgaaaggtcg cttcaccatc agccgcgaca tgccgaaaaa cagcctgtat     240
ctgcagatga acagcttacg cgccgaagat accgccgtgt actattgcgt tcgtgagggt     300
ccgcgtgcaa ccggctatag catggccgac gtgttcgata tctggggtca gggcaccatg     360
gtgaccgtta gcagcgccag caccaaaggt ccggaagtgc aactggtgga agtggcggt      420 ggtctggtgc agccgggtgg tagtctcgcg ctgagctgtg ccgcaagcgg ctttgccttt     480
aattattatg atatgttttg ggtgcgccag gcaccgggca aaggtctgga gtgggtggcc     540
tacattaagc cgggcggtgg caataccttt tatgccgaca gcgtgaaggg ccgctttacc     600
atcagcgccg acaccagcaa aaacaccgcc tacctgcaaa tgaatagctt acgtgctgaa     660
gacaccgcag tttattattg cgcccgccag ctgtatggca atagcttctt cgactattgg     720
ggccaaggca ccctggtgac agttagcagc                                      750
```

```
<210> SEQ ID NO 49
<211> LENGTH: 225
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 49

Glu Leu Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Ser Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
```

```
              65                  70                  75                  80
Ile Ser Ser Leu Gln Ala Glu Asp Val Ala Val Tyr Tyr Cys Gln Gln
                    85                  90                  95

Tyr Tyr Ser Ala Pro Leu Thr Phe Gly Gly Gly Thr Lys Val Glu Ile
                100                 105                 110

Lys Thr Val Ala Ala Pro Asp Ile Gln Met Thr Gln Ser Pro Ser Ser
                115                 120                 125

Leu Ser Ala Ser Val Gly Asp Arg Val Thr Ile Thr Cys Lys Ala Ser
            130                 135                 140

Gln Asp Val Thr Thr Ala Val Ala Trp Tyr Gln Gln Lys Pro Gly Lys
145                 150                 155                 160

Ala Pro Lys Leu Leu Ile Tyr Trp Ala Ser Thr Arg His Thr Gly Val
                165                 170                 175

Pro Ser Arg Phe Ser Gly Ser Gly Ser Gly Thr Asp Phe Thr Leu Thr
                180                 185                 190

Ile Ser Ser Leu Gln Pro Glu Asp Phe Ala Thr Tyr Tyr Cys Gln Gln
                195                 200                 205

His Tyr Ser Thr Pro Leu Thr Phe Gly Gln Gly Thr Lys Val Glu Ile
            210                 215                 220

Lys
225
```

```
<210> SEQ ID NO 50
<211> LENGTH: 675
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 50
gaactggtga tgacccagag cccggatagt ctggcagtta gcctgggcga acgcgccacc      60
attaactgca aaagcagcca gagcgtgctg tacagcagca caacaagag ctacctggcc     120 tggtatcagc agaaaccggg tcagcctccg aaactgctga tttactgggc aagcacccgt    180
gaaagtggcg tgccggatcg ctttagcggc agcggtagcg gtaccgattt caccctgaca    240
atcagcagcc tgcaggccga agatgttgcc gtgtactact gccagcagta ctacagcgcc    300
ccgttaacct tcggcggtgg caccaaagtg gagattaaaa ccgtggccgc cccggatatt    360
cagatgaccc aaagcccgag tagcctgagc gcaagcgtgg gtgatcgcgt gaccattacc    420
tgcaaagcca gccaggacgt gaccaccgca gttgcctggt accagcagaa gccgggcaaa    480
gcaccgaagc tgctgattta ttgggcaagc acccgccata ccggtgtgcc tagccgtttc    540
agcggtagtg gcagtggcac cgactttacc ctgaccatca gcagtctgca gccggaagac    600
ttcgccacct actattgcca acagcactac agcacccccgc tgacctttgg ccagggcacc    660
aaggtggaaa ttaag                                                     675
```

```
<210> SEQ ID NO 51
<211> LENGTH: 266
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 51

Met Gly Arg Leu Thr Ser Ser Phe Leu Leu Leu Ile Val Pro Ala Tyr
```

```
              1               5               10              15
              Val Leu Ser Gln Leu Thr Leu Lys Glu Ser Gly Pro Gly Ile Leu Lys
                              20                  25                  30
              Pro Ser Gln Thr Leu Ser Leu Thr Cys Ser Leu Ser Gly Phe Ser Leu
                              35                  40                  45
              Ser Thr Ser Gly Val Gly Val Gly Trp Phe Arg Gln Pro Ser Gly Lys
                              50                  55                  60
              Gly Leu Glu Trp Leu Ala Leu Ile Trp Trp Asp Asp Lys Tyr Tyr
              65                  70                  75                  80
              Asn Pro Ser Leu Lys Ser Gln Leu Ser Ile Ser Lys Asp Phe Ser Arg
                              85                  90                  95
              Asn Gln Val Phe Leu Lys Ile Ser Asn Val Asp Ile Ala Asp Thr Ala
                              100                 105                 110
              Thr Tyr Tyr Cys Ala Arg Arg Asp Pro Phe Gly Tyr Asp Asn Ala Met
                              115                 120                 125
              Gly Tyr Trp Gly Gln Gly Thr Ser Val Thr Val Ser Ser Ala Ser Thr
                              130                 135                 140
              Lys Gly Pro Glu Val Gln Leu Val Glu Ser Gly Gly Gly Leu Val Gln
              145                 150                 155                 160
              Pro Gly Gly Ser Leu Arg Leu Ser Cys Ala Ala Ser Gly Phe Ala Phe
                              165                 170                 175
              Asn Tyr Tyr Asp Ile His Trp Val Arg Gln Ala Pro Gly Lys Gly Leu
                              180                 185                 190
              Glu Trp Val Ala Tyr Ile Asn Pro Gly Gly Gly Asn Thr Tyr Tyr Ala
                              195                 200                 205
              Asp Ser Val Lys Gly Arg Phe Thr Ile Ser Ala Asp Thr Ser Lys Asn
                              210                 215                 220
              Thr Ala Tyr Leu Gln Met Asn Ser Leu Arg Ala Glu Asp Thr Ala Val
              225                 230                 235                 240
              Tyr Tyr Cys Ala Arg Gln Leu Tyr Gly Asn Ser Phe Met Asp Tyr Trp
                              245                 250                 255
              Gly Gln Gly Thr Leu Val Thr Val Ser Ser
                              260                 265

<210> SEQ ID NO 52
<211> LENGTH: 798
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 52
atgggtcgcc tgaccagtag ctttctgctg ctgattgtgc ctgcctatgt gttaagccag      60
ctgaccctga aggagagcgg cccgggtatt ctgaaaccta gccagaccct gagcctgacc     120
tgcagcctga gcggttttag cctgagtacc agcggtgtgg gcgttggttg gttccgccag     180
ccgagcggta aaggtctgga atggctggcc ctgatttggt gggatgatga taaatactac     240
aacccgagcc tgaaaagcca gctgagcatt agcaaagatt ttagccgcaa tcaggttttc     300
ctgaaaatca gcaacgtgga cattgccgac accgccacct actattgcgc cgccgcgac     360
ccgtttggct atgataacgc catgggctac tggggccagg gtaccagcgt taccgttagc     420
agcgccagca ccaaaggccc ggaagtgcag ctggttgaaa gcggtggtgg tctggttcag     480
ccgggtggta gtctgcgtct gagttgcgcc gccagcggct ttgccttcaa ttattatgat     540
```

```
atccattggg ttcgccaggc accgggtaag ggcctggaat gggtggcata cattaatccg    600
ggtggcggta acacctacta tgccgacagc gtgaaaggtc gcttcaccat cagcgccgat    660
accagcaaga acaccgccta tctgcagatg aacagcctgc gtgccgaaga taccgccgtg    720
tattattgtg cccgccagct gtatggcaac agcttcatgg attattgggg ccaaggcacc    780
ctggttaccg ttagcagc                                                  798
```

<210> SEQ ID NO 53
<211> LENGTH: 244
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 53

```
Met Gly Ile Lys Met Lys Ser Gln Thr Gln Ala Phe Val Phe Ala Phe
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Leu Thr Cys Lys
        35                  40                  45

Ala Ser Gln Asn Val Gly Thr Ala Val Ala Trp Tyr Gln Gln Lys Pro
    50                  55                  60

Gly Gln Ser Pro Lys Leu Leu Ile Tyr Ser Ala Ser Asn Arg Tyr Thr
65                  70                  75                  80

Gly Val Pro Asp Arg Phe Thr Gly Ser Gly Ser Gly Thr Asp Phe Thr
                85                  90                  95

Leu Thr Ile Ser Asn Met Gln Ser Glu Asp Leu Ala Asp Tyr Phe Cys
            100                 105                 110

Gln Gln Tyr Ser Ser Tyr Pro Leu Thr Phe Gly Ala Gly Thr Lys Leu
        115                 120                 125

Glu Leu Arg Arg Thr Val Ala Ala Pro Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Asp Val Thr Thr Ala Val Ala Trp Tyr Gln Gln Lys
                165                 170                 175

Pro Gly Lys Ala Pro Lys Leu Leu Ile Tyr Trp Ala Ser Arg Leu His
            180                 185                 190

Asn Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln His Tyr Ser Thr Pro Leu Thr Phe Gly Gln Gly Thr Lys
225                 230                 235                 240

Val Glu Ile Lys
```

<210> SEQ ID NO 54
<211> LENGTH: 732
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 54

```
atgggcatca aaatgaagag ccagacccag gcctttgtgt ttgcctttct gtggctgagt    60
ggcgtggatg gcgatatcgt gatgacccag agccaaaagt tcatgagcac cagcgtgggc   120
gatcgcgtga gcctgacctg caaagccagc cagaacgtgg gcaccgcagt ggcatggtac   180
cagcagaaac cgggccagag cccgaaactg ctgatctaca cgcaagcaa tcgctatacc   240
ggtgttccgg atcgctttac aggcagcggc agcggcaccg actttaccct gaccattagc   300
aacatgcaga gcgaagacct ggccgactat ttttgccagc agtacagcag ctatccgctg   360
acctttggcg ccggcaccaa attagaactg cgccgtaccg ttgccgcccc ggatattcag   420
atgacccaaa gcccgagtag cctgagcgca agcgtgggcg accgtgtgac cattacctgt   480
cgcgccagcc aggacgttac caccgcagtt gcctggtatc agcaaaaacc gggcaaagcc   540
ccgaagctgc tgatctattg gcaagtcgt ctgcataacg gcgttccgag ccgctttagc   600
ggcagtggta gcggcaccga tttcaccctg accatcagca gcctgcagcc ggaggatttt   660
gccacctact actgtcagca gcactacagc acaccgctga ccttcggcca gggcaccaag   720
gtggaaatta aa                                                       732
```

<210> SEQ ID NO 55
<211> LENGTH: 266
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Met Gly Arg Leu Thr Ser Ser Phe Leu Leu Ile Val Pro Ala Tyr
1               5                   10                  15
Val Leu Ser Gln Leu Thr Leu Lys Glu Ser Gly Pro Gly Ile Leu Lys
            20                  25                  30
Pro Ser Gln Thr Leu Ser Leu Thr Cys Ser Leu Ser Gly Phe Ser Leu
        35                  40                  45
Ser Thr Ser Gly Val Gly Val Gly Trp Phe Arg Gln Pro Ser Gly Lys
    50                  55                  60
Gly Leu Glu Trp Leu Ala Leu Ile Trp Trp Asp Asp Asp Lys Tyr Tyr
65                  70                  75                  80
Asn Pro Ser Leu Lys Ser Gln Leu Ser Ile Ser Lys Asp Phe Ser Arg
                85                  90                  95
Asn Gln Val Phe Leu Lys Ile Ser Asn Val Asp Ile Ala Asp Thr Ala
            100                 105                 110
Thr Tyr Tyr Cys Ala Arg Arg Asp Pro Phe Gly Tyr Asp Asn Ala Met
        115                 120                 125
Gly Tyr Trp Gly Gln Gly Thr Ser Val Thr Val Ser Ser Ala Ser Thr
    130                 135                 140
Lys Gly Pro Glu Val Gln Leu Val Glu Ser Gly Gly Leu Val Gln
145                 150                 155                 160
Pro Gly Gly Ser Leu Arg Leu Ser Cys Ala Ala Ser Gly Phe Ala Phe
                165                 170                 175
Asn Tyr Tyr Asp Met Phe Trp Val Arg Gln Ala Pro Gly Lys Gly Leu
            180                 185                 190
Glu Trp Val Ala Tyr Ile Lys Pro Gly Gly Gly Asn Thr Tyr Tyr Ala
        195                 200                 205
Asp Ser Val Lys Gly Arg Phe Thr Ile Ser Ala Asp Thr Ser Lys Asn
    210                 215                 220
```

```
Thr Ala Tyr Leu Gln Met Asn Ser Leu Arg Ala Glu Asp Thr Ala Val
225                 230                 235                 240

Tyr Tyr Cys Ala Arg Gln Leu Tyr Gly Asn Ser Phe Phe Asp Tyr Trp
                245                 250                 255

Gly Gln Gly Thr Leu Val Thr Val Ser Ser
            260                 265

<210> SEQ ID NO 56
<211> LENGTH: 798
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 56
atgggtcgcc tgaccagtag ctttctgctg ctgattgtgc ctgcctatgt gttaagccag      60
ctgaccctga aggagagcgg cccgggtatt ctgaaaccta gccagaccct gagcctgacc     120
tgcagcctga gcggttttag cctgagtacc agcggtgtgg cgttggttg gttccgccag      180 ccgagcggta aggtctggga atggctggcc ctgatttggt gggatgatga taaatactac     240
aacccgagcc tgaaaagcca gctgagcatt agcaaagatt ttagccgcaa tcaggttttc     300
ctgaaaatca gcaacgtgga cattgccgac accgccacct actattgcgc cgccgcgac      360 ccgtttggct atgataacgc catgggctac tggggccagg gtaccagcgt taccgttagc     420
agcgccagca ccaaaggccc ggaagtgcag ctggttgaaa gcggtggtgg tctggttcag     480
ccgggtggta gtctgcgtct gagttgcgcc gccagcggct ttgccttcaa ttattatgat     540
atgttttggg ttcgccaggc accgggtaag ggcctggaat gggtggcata cattaaaccg     600
ggtggcggta acacctacta tgccgacagc gtgaaaggtc gcttcaccat cagcgccgat     660
accagcaaga acaccgccta tctgcagatg aacagcctgc gtgccgaaga taccgccgtg     720
tattattgtg cccgccagct gtatggcaac agcttctttg attattgggg ccaaggcacc     780
ctggttaccg ttagcagc                                                  798

<210> SEQ ID NO 57
<211> LENGTH: 244
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 57

Met Gly Ile Lys Met Lys Ser Gln Thr Gln Ala Phe Val Phe Ala Phe
1               5                   10                  15

Leu Trp Leu Ser Gly Val Asp Gly Asp Ile Val Met Thr Gln Ser Gln
                20                  25                  30

Lys Phe Met Ser Thr Ser Val Gly Asp Arg Val Ser Leu Thr Cys Lys
            35                  40                  45

Ala Ser Gln Asn Val Gly Thr Ala Val Ala Trp Tyr Gln Gln Lys Pro
        50                  55                  60

Gly Gln Ser Pro Lys Leu Leu Ile Tyr Ser Ala Ser Asn Arg Tyr Thr
65                  70                  75                  80

Gly Val Pro Asp Arg Phe Thr Gly Ser Gly Ser Gly Thr Asp Phe Thr
                85                  90                  95

Leu Thr Ile Ser Asn Met Gln Ser Glu Asp Leu Ala Asp Tyr Phe Cys
            100                 105                 110
```

Gln Gln Tyr Ser Ser Tyr Pro Leu Thr Phe Gly Ala Gly Thr Lys Leu
            115                 120                 125

Glu Leu Arg Arg Thr Val Ala Ala Pro Asp Ile Gln Met Thr Gln Ser
        130                 135                 140

Pro Ser Ser Leu Ser Ala Ser Val Gly Asp Arg Val Thr Ile Thr Cys
145                 150                 155                 160

Lys Ala Ser Gln Asp Val Thr Thr Ala Val Ala Trp Tyr Gln Lys
                165                 170                 175

Pro Gly Lys Ala Pro Lys Leu Leu Ile Tyr Trp Ala Ser Thr Arg His
                180                 185                 190

Thr Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
        210                 215                 220

Cys Gln Gln His Tyr Ser Thr Pro Leu Thr Phe Gly Gln Gly Thr Lys
225                 230                 235                 240

Val Glu Ile Lys

<210> SEQ ID NO 58
<211> LENGTH: 732
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 58
atgggcatca aaatgaagag ccagacccag gcctttgtgt ttgcctttct gtggctgagt    60
ggcgtggatg cgatatcgt gatgacccag agccaaaagt tcatgagcac cagcgtgggc   120
gatcgcgtga gcctgacctg caaagccagc cagaacgtgg gcaccgcagt ggcatggtac   180
cagcagaaac cgggccagag cccgaaactg ctgatctaca gcgcaagcaa tcgctatacc   240
ggtgttccgg atcgctttac aggcagcggc agcggcaccg actttaccct gaccattagc   300
aacatgcaga gcgaagacct ggccgactat ttttgccagc agtacagcag ctatccgctg   360
acctttggcg ccggcaccaa attagaactg cgccgtaccg ttgccgcccc ggatattcag   420
atgacccaaa gcccgagtag cctgagcgca agcgtgggcg accgtgtgac cattacctgt   480
aaagccagcc aggacgttac caccgcagtt gcctggtatc agcaaaaacc gggcaaagcc   540
ccgaagctgc tgatctattg gcaagtacc cgtcataccg gcgttccgag ccgctttagc   600
ggcagtggta gcggcaccga tttcaccctg accatcagca gcctgcagcc ggaggatttt   660
gccacctact actgtcagca gcactacagc acaccgctga ccttcggcca gggcaccaag   720
gtggaaatta aa                                                       732

<210> SEQ ID NO 59
<211> LENGTH: 387
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 59

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr

```
                    20                  25                  30
Arg Met Asn Trp Val Arg Gln Ala Pro Gly Lys Gly Leu Glu Trp Val
                35                  40                  45
Ser Ser Ile Ser Ser Ser Ser Tyr Ile His Tyr Ala Asp Ser Val
 50                  55                  60
Lys Gly Arg Phe Thr Ile Ser Arg Asp Asn Ala Glu Asn Ser Leu Tyr
 65                  70                  75                  80
Leu Gln Met Asn Ser Leu Arg Ala Glu Asp Thr Ala Val Tyr Tyr Cys
                85                  90                  95
Val Arg Glu Gly Pro Arg Ala Thr Gly Tyr Ser Met Ala Asp Val Phe
                100                 105                 110
Asp Ile Trp Gly Gln Gly Thr Met Val Thr Val Ser Ser Gly Gly Gly
                115                 120                 125
Gly Ser Gly Gly Gly Gly Ser Gly Gly Gly Gly Ser Glu Leu Val Met
                130                 135                 140
Thr Gln Ser Pro Asp Ser Leu Ala Val Ser Leu Gly Glu Arg Ala Thr
145                 150                 155                 160
Ile Asn Cys Lys Ser Ser Gln Ser Val Leu Tyr Ser Ser Asn Asn Lys
                165                 170                 175
Ser Tyr Leu Ala Trp Tyr Gln Gln Lys Pro Gly Gln Pro Pro Lys Leu
                180                 185                 190
Leu Ile Tyr Trp Ala Ser Thr Arg Glu Ser Gly Val Pro Asp Arg Phe
                195                 200                 205
Ser Gly Ser Gly Ser Gly Thr Asp Phe Thr Leu Thr Ile Ser Ser Leu
                210                 215                 220
Gln Ala Glu Asp Val Ala Val Tyr Tyr Cys Gln Gln Tyr Tyr Ser Ala
225                 230                 235                 240
Pro Leu Thr Phe Gly Gly Gly Thr Lys Val Glu Ile Lys Gly Gly Ser
                245                 250                 255
Ala Gly Ser Ala Gly Ser Ala Gly Ser Gly Gly Ser Glu Val Gln Leu
                260                 265                 270
Val Glu Ser Gly Gly Gly Leu Val Gln Pro Gly Gly Ser Leu Arg Leu
                275                 280                 285
Ser Cys Ala Ala Ser Gly Phe Ala Phe Asn Tyr Tyr Asp Ile His Trp
                290                 295                 300
Val Arg Gln Ala Pro Gly Lys Gly Leu Glu Trp Val Ala Tyr Ile Asn
305                 310                 315                 320
Pro Gly Gly Gly Asn Thr Tyr Tyr Ala Asp Ser Val Lys Gly Arg Phe
                325                 330                 335
Thr Ile Ser Ala Asp Thr Ser Lys Asn Thr Ala Tyr Leu Gln Met Asn
                340                 345                 350
Ser Leu Arg Ala Glu Asp Thr Ala Val Tyr Tyr Cys Ala Arg Gln Leu
                355                 360                 365
Tyr Gly Asn Ser Phe Met Asp Tyr Trp Gly Gln Gly Thr Leu Val Thr
                370                 375                 380
Val Ser Ser
385

<210> SEQ ID NO 60
<211> LENGTH: 375
<212> TYPE: PRT
<213> ORGANISM: Artificial Sequence
<220> FEATURE:
<223> OTHER INFORMATION: Description of Artificial Sequence:
      Synthetic polypeptide
```

<400> SEQUENCE: 60

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Ser Glu Leu Val Met
130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Gly Ser Asp Ile Gln Met
            260                 265                 270

Thr Gln Ser Pro Ser Ser Leu Ser Ala Ser Val Gly Asp Arg Val Thr
        275                 280                 285

Ile Thr Cys Arg Ala Ser Gln Asp Val Thr Thr Ala Val Ala Trp Tyr
290                 295                 300

Gln Gln Lys Pro Gly Lys Ala Pro Lys Leu Leu Ile Tyr Trp Ala Ser
305                 310                 315                 320

Arg Leu His Asn Gly Val Pro Ser Arg Phe Ser Gly Ser Gly Ser Gly
                325                 330                 335

Thr Asp Phe Thr Leu Thr Ile Ser Ser Leu Gln Pro Glu Asp Phe Ala
            340                 345                 350

Thr Tyr Tyr Cys Gln Gln His Tyr Ser Thr Pro Leu Thr Phe Gly Gln
        355                 360                 365

Gly Thr Lys Val Glu Ile Lys
370                 375

<210> SEQ ID NO 61
<211> LENGTH: 258
<212> TYPE: PRT

<213> ORGANISM: Artificial Sequence
<220> FEATURE:
<223> OTHER INFORMATION: Description of Artificial Sequence:
    Synthetic polypeptide

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asn Tyr Tyr
            20                  25                  30

Asp Ile His Trp Val Arg Gln Ala Pro Gly Lys Gly Leu Glu Trp Val
        35                  40                  45

Ala Tyr Ile Asn Pro Gly Gly Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Gly Asn Ser Phe Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Asp Lys Thr His Thr Cys Pro Pro Cys Pro Ala Pro
225                 230                 235                 240

Glu Leu Leu Gly Arg Pro Ser Val Phe Leu Phe Pro Pro Lys Pro Lys
                245                 250                 255

Asp Thr

<210> SEQ ID NO 62
<211> LENGTH: 279
<212> TYPE: PRT
<213> ORGANISM: Artificial Sequence
<220> FEATURE:
<223> OTHER INFORMATION: Description of Artificial Sequence:
    Synthetic polypeptide

<400> SEQUENCE: 62

Thr Gln Lys Ser Leu Ser Leu Ser Pro Gly Lys Gly Gly Ser Ala Gly
1               5                   10                  15

Ser Ala Gly Ser Ala Gly Ser Gly Gly Ser Glu Val Gln Leu Leu Glu
            20                  25                  30

Ser Gly Gly Gly Leu Val Lys Pro Gly Gly Ser Leu Arg Leu Ser Cys
        35                  40                  45

Ala Ala Ser Gly Phe Thr Leu Ile Asn Tyr Arg Met Asn Trp Val Arg
    50                  55                  60

Gln Ala Pro Gly Lys Gly Leu Glu Trp Val Ser Ser Ile Ser Ser Ser
65                  70                  75                  80

Ser Ser Tyr Ile His Tyr Ala Asp Ser Val Lys Gly Arg Phe Thr Ile
            85                  90                  95

Ser Arg Asp Asn Ala Glu Asn Ser Leu Tyr Leu Gln Met Asn Ser Leu
            100                 105                 110

Arg Ala Glu Asp Thr Ala Val Tyr Tyr Cys Val Arg Glu Gly Pro Arg
            115                 120                 125

Ala Thr Gly Tyr Ser Met Ala Asp Val Phe Asp Ile Trp Gly Gln Gly
    130                 135                 140

Thr Met Val Thr Val Ser Ser Gly Gly Gly Ser Gly Gly Gly Gly Gly
145                 150                 155                 160

Ser Gly Gly Gly Gly Ser Glu Leu Val Met Thr Gln Ser Pro Asp Ser
                165                 170                 175

Leu Ala Val Ser Leu Gly Glu Arg Ala Thr Ile Asn Cys Lys Ser Ser
            180                 185                 190

Gln Ser Val Leu Tyr Ser Ser Asn Asn Lys Ser Tyr Leu Ala Trp Tyr
            195                 200                 205

Gln Gln Lys Pro Gly Gln Pro Pro Lys Leu Leu Ile Tyr Trp Ala Ser
210                 215                 220

Thr Arg Glu Ser Gly Val Pro Asp Arg Phe Ser Gly Ser Gly Ser Gly
225                 230                 235                 240

Thr Asp Phe Thr Leu Thr Ile Ser Ser Leu Gln Ala Glu Asp Val Ala
            245                 250                 255

Val Tyr Tyr Cys Gln Gln Tyr Tyr Ser Ala Pro Leu Thr Phe Gly Gly
            260                 265                 270

Gly Thr Lys Val Glu Ile Lys
            275

<210> SEQ ID NO 63
<211> LENGTH: 774
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 63
gaggttcagc tggtggagtc tggcggtggc ctggtgcagc caggggggctc actccgtttg      60 tcctgtgcag cttctggctt cgcgtttaac tattatgata ttcattgggt gcgtcaggcc     120
ccgggtaagg gcctggaatg ggttgcatat attaacccgg gcggtggcaa cacctattat     180
gctgatagcg tcaagggccg tttcactata agcgcagaca catccaaaaa cacagcctac     240
ctacaaatga acagcttaag agctgaggac actgccgtct attattgtgc tcgccagctg     300
tatggcaaca gctttatgga ctactggggt caaggaaccc tggtcaccgt ctcctcggct     360
agcaccaagg gtccgagcgt gtttcctctg gcacctagcg taaaagcac cagtggtggt     420 acagcagccc tgggttgcct ggtgaaggat tactttccgg agccggtgac cgttagttgg     480
aatagcggcg ccctgaccag tggcgttcat acatttccgg ccgtgctgca gagtagtggc     540
ctgtacagcc tgagtagcgt tgttaccgtt ccgagcagca gcctgggcac ccagacctat     600
atttgcaatg ttaaccataa accgagcaac acaaaagttg ataaaaaagt tgaaccgaag     660
agctgtgaca aaacccatac atgtgacaaa acacacacct gcccgccttg tccggcacct     720
gagctgctgg gtcgcccgag cgttttttctg tttcctccga aaccgaaaga cacc          774

<210> SEQ ID NO 64
<211> LENGTH: 840
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 64

```
acccagaaga gtctgagcct gagtcctggc aaaggtggat ccgccggtag cgcaggtagt      60
gcaggtagtg gcggcagcga agttcagctg ttagaaagtg gcggtggtct ggttaagccg     120
ggcggtagtc tgcgcctgag ctgtgcagca agtggtttca ccctgatcaa ttatcgtatg     180
aactgggtgc gccaagcccc gggtaaaggt ctggagtggg ttagtagtat cagcagcagc     240
agcagttaca tccactatgc cgatagcgtt aagggccgct ttacaatcag ccgcgataat     300
gccgagaata gcttatacct gcaaatgaac agtctaaggg cggaagatac cgccgtttac     360
tactgcgttc gtgaaggccc tcgcgcaaca ggctatagca tggcagacgt gttcgacatt     420
tggggtcagg gcaccatggt gaccgttagt agcggcggtg gtggtagtgg tggtggcggt     480
agtggtggcg gtggcagcga actggtgatg acccagagtc cggatagcct ggccgtgagc     540
ttaggcgagc gtgcaaccat taattgtaaa agcagtcaga gtgttctgta tagtagcaat     600
aacaagagct atctggcctg gtatcagcag aagccgggcc agccgccgaa actgctgatt     660
tactgggcaa gcacccgcga aagtggcgtg cctgatcgct ttagtggtag cggcagcggc     720
accgatttta ccctgaccat tagcagtctg caggccgagg acgttgccgt ttattactgc     780
cagcagtact atagcgcacc gctgacattt ggcggtggca ccaaggtgga aattaaataa     840
```

<210> SEQ ID NO 65
<211> LENGTH: 485
<212> TYPE: PRT
<213> ORGANISM: Artificial Sequence
<220> FEATURE:
<223> OTHER INFORMATION: Description of Artificial Sequence:
      Synthetic polypeptide
<220> FEATURE:
<221> NAME/KEY: VARIANT
<222> LOCATION: (481)..(481)
<223> OTHER INFORMATION: Any amino acid

<400> SEQUENCE: 65

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Arg Leu His Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys Gly Gly Ser Gly Gly Ser Ala Gly Ser Ala
210                 215                 220

Gly Ser Ala Gly Ser Gly Gly Ser Glu Val Gln Leu Leu Glu Ser Gly
225                 230                 235                 240

Gly Gly Leu Val Lys Pro Gly Gly Ser Leu Arg Leu Ser Cys Ala Ala
                245                 250                 255

Ser Gly Phe Thr Leu Ile Asn Tyr Arg Met Asn Trp Val Arg Gln Ala
            260                 265                 270

Pro Gly Lys Gly Leu Glu Trp Val Ser Ser Ile Ser Ser Ser Ser Ser
            275                 280                 285

Tyr Ile His Tyr Ala Asp Ser Val Lys Gly Arg Phe Thr Ile Ser Arg
290                 295                 300

Asp Asn Ala Glu Asn Ser Leu Tyr Leu Gln Met Asn Ser Leu Arg Ala
305                 310                 315                 320

Glu Asp Thr Ala Val Tyr Tyr Cys Val Arg Glu Gly Pro Arg Ala Thr
                325                 330                 335

Gly Tyr Ser Met Ala Asp Val Phe Asp Ile Trp Gly Gln Gly Thr Met
            340                 345                 350

Val Thr Val Ser Ser Gly Gly Gly Ser Gly Gly Gly Gly Ser Gly Gly
            355                 360                 365

Gly Gly Gly Ser Glu Leu Val Met Thr Gln Ser Pro Asp Ser Leu Ala
            370                 375                 380

Val Ser Leu Gly Glu Arg Ala Thr Ile Asn Cys Lys Ser Ser Gln Ser
385                 390                 395                 400

Val Leu Tyr Ser Ser Asn Asn Lys Ser Tyr Leu Ala Trp Tyr Gln Gln
                405                 410                 415

Lys Pro Gly Gln Pro Pro Lys Leu Leu Ile Tyr Trp Ala Ser Thr Arg
            420                 425                 430

Glu Ser Gly Val Pro Asp Arg Phe Ser Gly Ser Gly Ser Gly Thr Asp
            435                 440                 445

Phe Thr Leu Thr Ile Ser Ser Leu Gln Ala Glu Asp Val Ala Val Tyr
450                 455                 460

Tyr Cys Gln Gln Tyr Tyr Ser Ala Pro Leu Thr Phe Gly Gly Gly Thr
465                 470                 475                 480

Xaa Val Glu Ile Lys
            485

<210> SEQ ID NO 66
<211> LENGTH: 387
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 66

```
Glu Val Gln Leu Leu Glu Ser Gly Gly Gly Leu Val Lys Pro Gly
1               5                   10                  15

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
        35                  40                  45

Ser Ser Ile Ser Ser Ser Ser Tyr Ile His Tyr Ala Asp Ser Val
50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
            85                  90                  95

Val Arg Glu Gly Pro Arg Ala Thr Gly Tyr Ser Met Ala Asp Val Phe
        100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Val Met
    130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
            165                 170                 175

Ser Tyr Leu Ala Trp Tyr Gln Gln Lys Pro Gly Gln Pro Pro Lys Leu
        180                 185                 190

Leu Ile Tyr Trp Ala Ser Thr Arg Glu Ser Gly Val Pro Asp Arg Phe
        195                 200                 205

Ser Gly Ser Gly Ser Gly Thr Asp Phe Thr Leu Thr Ile Ser Ser Leu
210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
            245                 250                 255

Ala Gly Ser Ala Gly Ser Ala Gly Ser Gly Ser Glu Val Gln Leu
        260                 265                 270

Val Glu Ser Gly Gly Gly Leu Val Gln Pro Gly Gly Ser Leu Arg Leu
275                 280                 285

Ser Cys Ala Ala Ser Gly Phe Ala Phe Asn Tyr Tyr Asp Met Phe Trp
    290                 295                 300

Val Arg Gln Ala Pro Gly Lys Gly Leu Glu Trp Val Ala Tyr Ile Lys
305                 310                 315                 320

Pro Gly Gly Gly Asn Thr Tyr Tyr Ala Asp Ser Val Lys Gly Arg Phe
            325                 330                 335

Thr Ile Ser Ala Asp Thr Ser Lys Asn Thr Ala Tyr Leu Gln Met Asn
        340                 345                 350

Ser Leu Arg Ala Glu Asp Thr Ala Val Tyr Tyr Cys Ala Arg Gln Leu
        355                 360                 365

Tyr Gly Asn Ser Phe Phe Asp Tyr Trp Gly Gln Gly Thr Leu Val Thr
370                 375                 380

Val Ser Ser
385

<210> SEQ ID NO 67
<211> LENGTH: 375
```

```
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 67
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Lys | Pro | Gly | Gly |
| 1 | | | | 5 | | | | | 10 | | | | | 15 |

Ser Leu Arg Leu Ser Cys Ala Ala Ser Gly Phe Thr Leu Ile Asn Tyr
            20                  25                  30

Arg Met Asn Trp Val Arg Gln Ala Pro Gly Lys Gly Leu Glu Trp Val
            35                  40                  45

Ser Ser Ile Ser Ser Ser Ser Tyr Ile His Tyr Ala Asp Ser Val
 50                  55                  60

Lys Gly Arg Phe Thr Ile Ser Arg Asp Asn Ala Glu Asn Ser Leu Tyr
 65                  70                  75                  80

Leu Gln Met Asn Ser Leu Arg Ala Glu Asp Thr Ala Val Tyr Tyr Cys
                85                  90                  95

Val Arg Glu Gly Pro Arg Ala Thr Gly Tyr Ser Met Ala Asp Val Phe
            100                 105                 110

Asp Ile Trp Gly Gln Gly Thr Met Val Thr Val Ser Ser Gly Gly Gly
            115                 120                 125

Gly Ser Gly Gly Gly Gly Ser Gly Gly Gly Gly Ser Glu Leu Val Met
 130                 135                 140

Thr Gln Ser Pro Asp Ser Leu Ala Val Ser Leu Gly Glu Arg Ala Thr
145                 150                 155                 160

Ile Asn Cys Lys Ser Ser Gln Ser Val Leu Tyr Ser Ser Asn Asn Lys
                165                 170                 175

Ser Tyr Leu Ala Trp Tyr Gln Gln Lys Pro Gly Gln Pro Pro Lys Leu
            180                 185                 190

Leu Ile Tyr Trp Ala Ser Thr Arg Glu Ser Gly Val Pro Asp Arg Phe
            195                 200                 205

Ser Gly Ser Gly Ser Gly Thr Asp Phe Thr Leu Thr Ile Ser Ser Leu
 210                 215                 220

Gln Ala Glu Asp Val Ala Val Tyr Tyr Cys Gln Gln Tyr Tyr Ser Ala
225                 230                 235                 240

Pro Leu Thr Phe Gly Gly Gly Thr Lys Val Glu Ile Lys Gly Gly Ser
                245                 250                 255

Ala Gly Ser Ala Gly Ser Ala Gly Ser Gly Gly Ser Asp Ile Gln Met
            260                 265                 270

Thr Gln Ser Pro Ser Ser Leu Ser Ala Ser Val Gly Asp Arg Val Thr
            275                 280                 285

Ile Thr Cys Lys Ala Ser Gln Asp Val Thr Thr Ala Val Ala Trp Tyr
            290                 295                 300

Gln Gln Lys Pro Gly Lys Ala Pro Lys Leu Leu Ile Tyr Trp Ala Ser
305                 310                 315                 320

Thr Arg His Thr Gly Val Pro Ser Arg Phe Ser Gly Ser Gly Ser Gly
                325                 330                 335

Thr Asp Phe Thr Leu Thr Ile Ser Ser Leu Gln Pro Glu Asp Phe Ala
            340                 345                 350

Thr Tyr Tyr Cys Gln Gln His Tyr Ser Thr Pro Leu Thr Phe Gly Gln
            355                 360                 365

Gly Thr Lys Val Glu Ile Lys
            370                 375

<210> SEQ ID NO 68
<211> LENGTH: 365
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Glu Val Gln Leu Gln Glu Ser Gly Gly Gly Leu Met Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Arg Ser
65                  70                  75                  80

Val Tyr Leu Gln Met Asn Thr Leu Arg Ala Glu Asp Thr Gly Ile Tyr
                85                  90                  95

Tyr Cys Thr Arg Gly Asn Gly Asn Tyr Arg Ala Met Asp Tyr Trp Gly
            100                 105                 110

Gln Gly Thr Ser Val Thr Val Ser Gly Gly Gly Ser Gly Gly
        115                 120                 125

Gly Gly Ser Gly Gly Gly Ser Asp Ile Gln Met Thr Gln Ser Pro
    130                 135                 140

Ala Ser Leu Ser Val Ser Val Gly Glu Thr Val Ser Ile Thr Cys Arg
145                 150                 155                 160

Ala Ser Glu Asn Ile Tyr Ser Ser Leu Ala Trp Tyr Gln Gln Lys Gln
                165                 170                 175

Gly Lys Ser Pro Gln Leu Leu Val Tyr Ser Ala Thr Ile Leu Ala Asp
            180                 185                 190

Gly Val Pro Ser Arg Phe Ser Gly Ser Gly Ser Gly Thr Gln Tyr Ser
        195                 200                 205

Leu Lys Ile Asn Ser Leu Gln Ser Glu Asp Phe Gly Thr Tyr Tyr Cys
    210                 215                 220

Gln His Phe Trp Gly Thr Pro Tyr Thr Phe Gly Gly Thr Lys Leu
225                 230                 235                 240

Glu Ile Lys Gly Gly Ser Ala Gly Ser Ala Gly Ser Ala Gly Ser Gly
                245                 250                 255

Gly Ser Asp Ile Gln Met Thr Gln Ser Pro Ser Ser Leu Ser Ala Ser
            260                 265                 270

Val Gly Asp Arg Val Thr Ile Thr Cys Lys Ala Ser Gln Asp Val Thr
        275                 280                 285

Thr Ala Val Ala Trp Tyr Gln Gln Lys Pro Gly Lys Ala Pro Lys Leu
    290                 295                 300

Leu Ile Tyr Trp Ala Ser Thr Arg His Thr Gly Val Pro Ser Arg Phe
305                 310                 315                 320

Ser Gly Ser Gly Ser Gly Thr Asp Phe Thr Leu Thr Ile Ser Ser Leu
                325                 330                 335

Gln Pro Glu Asp Phe Ala Thr Tyr Tyr Cys Gln Gln His Tyr Ser Thr
            340                 345                 350

Pro Leu Thr Phe Gly Gln Gly Thr Lys Val Glu Ile Lys

<210> SEQ ID NO 69
<211> LENGTH: 1095
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 69

```
gaagttcagc tgcaggaaag cggcggtggt ctgatgcagc tggtggcag catgaaactg       60
agctgtgtgg ccagcggttt caccttcagc aactattgga tgaactgggt gcgtcagagt     120
ccggaaaaag gcctggaatg ggttgccgag atccgcctga agagtaacaa ctatgccacc     180
cattacgccg agagcgtgaa aggtcgcttt accatcagcc gtgatgacag caaacgcagc     240
gtgtatctgc agatgaacac attacgtgct gaagacaccg gtatctacta ttgcacccgc     300
ggcaacggca actatcgcgc catggattat tggggccagg gtaccagcgt gaccgttagt     360
agcggcggcg gtggtagtgg tggtggtggt agtggcggtg gcggtagcga cattcaaatg     420
acccagagtc ctgcaagcct gagcgtgagc gtgggtgaga ccgtgagcat acatgccgc     480
gccagcgaga acatttatag cagcctggcc tggtaccagc aaaaacaggg taaaagcccg     540
cagctgctgg tgtatagcgc caccattctg gcagatggtg tgccgagccg ttttagtggc     600
agtggcagtg gtacccagta cagcctgaaa atcaacagcc tgcagagcga agacttcggc     660
acctactact gtcagcactt ttggggcacc ccgtatacct ttggcggcgg taccaagctg     720
gaaatcaaag gtggatccgc aggtagcgca ggcagtgcag gcagcggtgg tagcgatatc     780
cagatgaccc aaagcccgag cagcttaagt gccagcgtgg gcgatcgcgt gaccatcacc     840
tgcaaagcca gtcaggacgt taccacagcc gtggcctggt atcagcagaa accgggtaaa     900
gcccctaagc tgctgatcta ttgggccagc acccgccaca caggtgttcc gagtcgtttc     960
agcggcagcg gtagcggtac cgattttacc ctgaccatca gcagcctgca gccggaagac    1020
ttcgcaacat actactgcca gcagcactat tctaccccgc tgacattcgg ccagggcaca    1080
aaagtggaga ttaaa                                                    1095
```

<210> SEQ ID NO 70
<211> LENGTH: 363
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 70

```
Glu Val Gln Leu Gln Glu Ser Gly Pro Glu Leu Glu Met Pro Gly Ala
1               5                   10                  15

Ser Val Lys Ile Ser Cys Lys Ala Ser Gly Ser Ser Phe Thr Gly Phe
            20                  25                  30

Ser Met Asn Trp Val Lys Gln Ser Asn Gly Lys Ser Leu Glu Trp Ile
        35                  40                  45

Gly Asn Ile Asp Thr Tyr Tyr Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95
```

```
Ala Arg Ser Ala Tyr Tyr Gly Ser Thr Phe Ala Tyr Trp Gly Gln Gly
            100                 105                 110

Thr Leu Val Thr Val Ser Ala Gly Gly Gly Ser Gly Gly Gly Gly
        115                 120                 125

Ser Gly Gly Gly Gly Ser Asp Ile Gln Met Thr Gln Ser Pro Ala Ser
130                 135                 140

Leu Ser Ala Ser Val Gly Glu Thr Val Thr Ile Thr Cys Arg Ala Ser
145                 150                 155                 160

Glu Asn Ile Tyr Ser Tyr Leu Ala Trp Tyr Gln Gln Lys Gln Gly Lys
                165                 170                 175

Ser Pro Gln Leu Leu Val Tyr Asn Ala Lys Thr Leu Ile Glu Gly Val
            180                 185                 190

Pro Ser Arg Phe Ser Gly Ser Gly Ser Gly Thr Gln Phe Ser Leu Lys
        195                 200                 205

Ile Asn Ser Leu Gln Pro Glu Asp Phe Gly Ser Tyr Phe Cys Gln His
    210                 215                 220

His Phe Gly Thr Pro Phe Thr Phe Gly Ser Gly Thr Glu Leu Glu Ile
225                 230                 235                 240

Lys Gly Gly Ser Ala Gly Ser Ala Gly Ser Ala Gly Ser Gly Gly Ser
                245                 250                 255

Asp Ile Gln Met Thr Gln Ser Pro Ser Ser Leu Ser Ala Ser Val Gly
            260                 265                 270

Asp Arg Val Thr Ile Thr Cys Lys Ala Ser Gln Asp Val Thr Thr Ala
        275                 280                 285

Val Ala Trp Tyr Gln Gln Lys Pro Gly Lys Ala Pro Lys Leu Leu Ile
    290                 295                 300

Tyr Trp Ala Ser Thr Arg His Thr Gly Val Pro Ser Arg Phe Ser Gly
305                 310                 315                 320

Ser Gly Ser Gly Thr Asp Phe Thr Leu Thr Ile Ser Ser Leu Gln Pro
                325                 330                 335

Glu Asp Phe Ala Thr Tyr Tyr Cys Gln Gln His Tyr Ser Thr Pro Leu
            340                 345                 350

Thr Phe Gly Gln Gly Thr Lys Val Glu Ile Lys
        355                 360

<210> SEQ ID NO 71
<211> LENGTH: 475
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Arg Leu His Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
```

```
                    85                  90                  95
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Gly Gly Ser Ala Gly Ser Ala
                210                 215                 220

Gly Ser Ala Gly Ser Gly Gly Ser Glu Val Gln Leu Gln Glu Ser Gly
225                 230                 235                 240

Gly Gly Leu Met Gln Pro Gly Gly Ser Met Lys Leu Ser Cys Val Ala
                245                 250                 255

Ser Gly Phe Thr Phe Ser Asn Tyr Trp Met Asn Trp Val Arg Gln Ser
            260                 265                 270

Pro Glu Lys Gly Leu Glu Trp Val Ala Glu Ile Arg Leu Lys Ser Asn
        275                 280                 285

Asn Tyr Ala Thr His Tyr Ala Glu Ser Val Lys Gly Arg Phe Thr Ile
                290                 295                 300

Ser Arg Asp Asp Ser Lys Arg Ser Val Tyr Leu Gln Met Asn Thr Leu
305                 310                 315                 320

Arg Ala Glu Asp Thr Gly Ile Tyr Tyr Cys Thr Arg Gly Asn Gly Asn
                325                 330                 335

Tyr Arg Ala Met Asp Tyr Trp Gly Gln Gly Thr Ser Val Thr Val Ser
            340                 345                 350

Ser Gly Gly Gly Gly Ser Gly Gly Gly Gly Ser Gly Gly Gly Gly Ser
        355                 360                 365

Asp Ile Gln Met Thr Gln Ser Pro Ala Ser Leu Ser Val Ser Val Gly
    370                 375                 380

Glu Thr Val Ser Ile Thr Cys Arg Ala Ser Glu Asn Ile Tyr Ser Ser
385                 390                 395                 400

Leu Ala Trp Tyr Gln Gln Lys Gln Gly Lys Ser Pro Gln Leu Leu Val
                405                 410                 415

Tyr Ser Ala Thr Ile Leu Ala Asp Gly Val Pro Ser Arg Phe Ser Gly
            420                 425                 430

Ser Gly Ser Gly Thr Gln Tyr Ser Leu Lys Ile Asn Ser Leu Gln Ser
        435                 440                 445

Glu Asp Phe Gly Thr Tyr Tyr Cys Gln His Phe Trp Gly Thr Pro Tyr
                450                 455                 460

Thr Phe Gly Gly Gly Thr Lys Leu Glu Ile Lys
465                 470                 475

<210> SEQ ID NO 72
<211> LENGTH: 472
<212> TYPE: PRT
<213> ORGANISM: Artificial Sequence
```

<220> FEATURE:
<223> OTHER INFORMATION: Description of Artificial Sequence:
      Synthetic polypeptide

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Trp Ala Ser Arg Leu His Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Ser Gly Ser Ala Gly Ser Ala
    210                 215                 220

Gly Ser Ala Gly Ser Gly Gly Ser Glu Val Gln Leu Gln Glu Ser Gly
225                 230                 235                 240

Pro Gly Leu Glu Met Pro Gly Ala Ser Val Lys Ile Ser Cys Lys Ala
                245                 250                 255

Ser Gly Ser Ser Phe Thr Gly Phe Ser Met Asn Trp Val Lys Gln Ser
            260                 265                 270

Asn Gly Lys Ser Leu Glu Trp Ile Gly Asn Ile Asp Thr Tyr Tyr Gly
        275                 280                 285

Gly Thr Thr Tyr Asn Gln Lys Phe Lys Gly Lys Ala Thr Leu Thr Val
    290                 295                 300

Asp Lys Ser Ser Ser Thr Ala Tyr Met Gln Leu Lys Ser Leu Thr Ser
305                 310                 315                 320

Glu Asp Ser Ala Val Tyr Tyr Cys Ala Arg Ser Ala Tyr Tyr Gly Ser
                325                 330                 335

Thr Phe Ala Tyr Trp Gln Gly Thr Leu Val Thr Val Ser Ala Gly Gly
            340                 345                 350

Gly Gly Ser Gly Gly Gly Gly Ser Gly Gly Gly Gly Ser Asp Ile Gln
        355                 360                 365

Met Thr Gln Ser Pro Ala Ser Leu Ser Ala Ser Val Gly Glu Thr Val
    370                 375                 380

Thr Ile Thr Cys Arg Ala Ser Glu Asn Ile Tyr Ser Tyr Leu Ala Trp

-continued

```
385                 390                 395                 400
Tyr Gln Gln Lys Gln Gly Lys Ser Pro Gln Leu Leu Val Tyr Asn Ala
                405                 410                 415

Lys Thr Leu Ile Glu Gly Val Pro Ser Arg Phe Ser Gly Ser Gly Ser
            420                 425                 430

Gly Thr Gln Phe Ser Leu Lys Ile Asn Ser Leu Gln Pro Glu Asp Phe
        435                 440                 445

Gly Ser Tyr Phe Cys Gln His His Phe Gly Thr Pro Phe Thr Phe Gly
    450                 455                 460

Ser Gly Thr Glu Leu Glu Ile Lys
465                 470
```

MULTI-SPECIFIC ANTIBODIES FOR CROSS-NEUTRALIZATION OF MULTIPLE FILOVIRUS GLYCOPROTEINS

CROSS-REFERENCE TO RELATED APPLICATIONS

This application is a divisional of U.S. application Ser. No. 16/548,309, filed Aug. 22, 2019, now U.S. Pat. No. 11,135,292, which is divisional of U.S. application Ser. No. 15/404,662, filed Jan. 12, 2017, now U.S. Pat. No. 10,391, 171, which is a continuation-in-part of PCT International Application No. PCT/US2015/57499, filed Oct. 27, 2015, which claims benefit of U.S. Provisional Application Nos. 62/131,472, filed Mar. 11, 2015 and 62/069,516, filed Oct. 28, 2014. The entire contents of these applications are incorporated herein by reference in their entirety.

STATEMENT OF GOVERNMENT SUPPORT

This invention was made with government support under grant numbers AI009762 and AI090249 and GM007482 awarded by the National Institutes of Health. The government has certain rights in the invention.

SEQUENCE LISTING

The instant application contains a Sequence Listing in computer readable form. The computer readable form is hereby incorporated by reference in its entirety. Said ASCII copy, created on May 1, 2024, is named AET-00403_SL.txt and is 194,066 bytes in size.

BACKGROUND OF THE INVENTION

Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

Ebola virus is an NIAID Category A biodefense pathogen that causes severe and rapidly progressing hemorrhagic fever with human case fatalities of 50-90%. There are currently no FDA-approved vaccines or therapies for Ebola virus infection. Among the five species of Ebola virus, the *Zaire* and *Sudan* variants (EBOV and SUDV, respectively) are the most pathogenic and both have resulted in recurring outbreaks. Together, EBOV and SUDV account for over 95% of EBOV-related deaths reported to date.

Herein are disclosed multi-specific antibodies for cross-neutralization of multiple filovirus glycoproteins.

SUMMARY OF THE INVENTION

This invention provides a composition comprising (1) a first single chain variable fragment (scFv) comprising at least one CDR directed to a membrane glycoprotein pre-fusion core of a first species of filovirus, which first scFv is covalently joined to (2) a first polypeptide of an immunoglobulin G (IgG) comprising at least one CDR directed to a membrane glycoprotein pre-fusion core of a second species of filovirus, wherein the first species of filovirus and second species of filovirus are different species.

A composition is also provided comprising (i) a first single chain variable fragment (scFv) comprising at least one CDR directed to a membrane glycoprotein pre-fusion core of a first species of filovirus, which first scFv is covalently joined to (ii) a first polypeptide of an immunoglobulin G (IgG) comprising at least one CDR directed to a membrane glycoprotein pre-fusion core of a second species of filovirus, the IgG having covalently joined thereto, at a different location from the attachment of (i) thereto, (iii) a second single chain variable fragment (scFv) comprising at least one CDR directed to a membrane glycoprotein pre-fusion core of a third species of filovirus, wherein the first species of filovirus and second species of filovirus and third species of filovirus are all different species. In an embodiment, one species-specific scFv is fused to the light chain of an IgG, and different species-specific scFv is fused to the heavy chain of the IgG.

Also provided is an isolated nucleic acid encoding any of the compositions described herein.

Also provided is a method of treating a filovirus infection in a subject comprising administering an amount of a bispecific composition described herein to the subject effective to treat a filovirus infection in a subject.

Also provided is a method of preventing a filovirus infection in a subject comprising administering an amount of a bispecific composition described herein to the subject effective to inhibit a filovirus infection in a subject.

Also provided is a method of preventing a filovirus infection of a mammalian cell comprising contacting the filovirus with an amount of a bispecific composition described herein effective to inhibit a filovirus infection of a mammalian cell.

Also provided is a method of treating a filovirus infection in a subject comprising administering an amount of a trispecific composition described herein to the subject effective to treat a filovirus infection in a subject.

Also provided is a method of preventing a filovirus infection in a subject comprising administering an amount of a trispecific composition described herein to the subject effective to inhibit a filovirus infection in a subject.

Also provided is a method of preventing a filovirus infection of a mammalian cell comprising contacting the filovirus with an amount of a trispecific composition described herein effective to inhibit a filovirus infection of a mammalian cell.

Herein are disclosed cross-neutralizing, bispecific monoclonal antibody constructs against Ebola variants such as EBOV and SUDV. Recent structural studies indicate that the base of the envelope glycoprotein (GP) is susceptible to neutralization by antibodies in these two species. However, current EBOV and SUDV antibodies targeting this region are narrowly strain specific and therefore have limited therapeutic utility. Herein a fusion approach is disclosed whereby, for example, the IgG of one species-specific antibody (e.g., SUDV) is genetically fused to the scFv of another species-specific antibody (e.g., EBOV) to create a cross-species neutralizing antibody (or vice versa). This strategy can also be extended to generate trispecific antibody constructs. Antibody therapies against Ebolaviruses and other filoviruses have demonstrated post-exposure efficacy in nonhuman primates, but no cross-neutralizing antibodies exist. Therefore, the cross-neutralizing, bispecific antibodies disclosed herein fill a much needed gap in Ebola therapeutics.

BRIEF DESCRIPTION OF THE DRAWINGS

FIG. 1A-1B: Structure of the prefusion GP1-GP2 spike and GP conformational changes that lead to viral membrane fusion. (A) Structure of the GP1-GP2 spike ectodomain (PDB ID: 3CSY, (13)). The GP1 subunits are shown in surface-shaded view and GP2 as rods and loops. One GP1 subunit is colored to show the subdomains: b, base; h, head; gc, glycan cap. fp, fusion peptide; TM, transmembrane domain. C, GP C-terminus. (B) Membrane fusion-associated conformational rearrangements in GP2 inferred from its pre-fusion and putative post-fusion structures (PDB ID: 1EBO, ref. 17)

FIG. 2. Survival of NHPs administered EBOV-specific serum IgGs upon viral challenge. Animals 7, 8, and 9 survived but the control animal (5) died 8-days post-exposure. (These data are from ref. 21, Dye et al.).

FIG. 10A-10D. Animal challenge experiments. Percent survival and median percent weight change for mouse-adapted EBOV (A) and SUDV (B) challenges with antibody treatment. Mice were treated with a single post-exposure dose (200 μg at 24 hours) for EBOV or two post-exposure doses (500 μg at days +1 and +4) for SUDV. Statistical p-values are listed against PBS and F4 controls for EBOV and against Z.6D8 control for SUDV (**, $p<0.0001$; , $p<0.01$; *, $p<0.05$; p-values greater that 0.05 are listed numerically; na, not applicable). (C and D) Rechallenge of surviving mice from initial challenge cohorts, with no further antibody treatment.

DETAILED DESCRIPTION OF THE INVENTION

Figure 3:
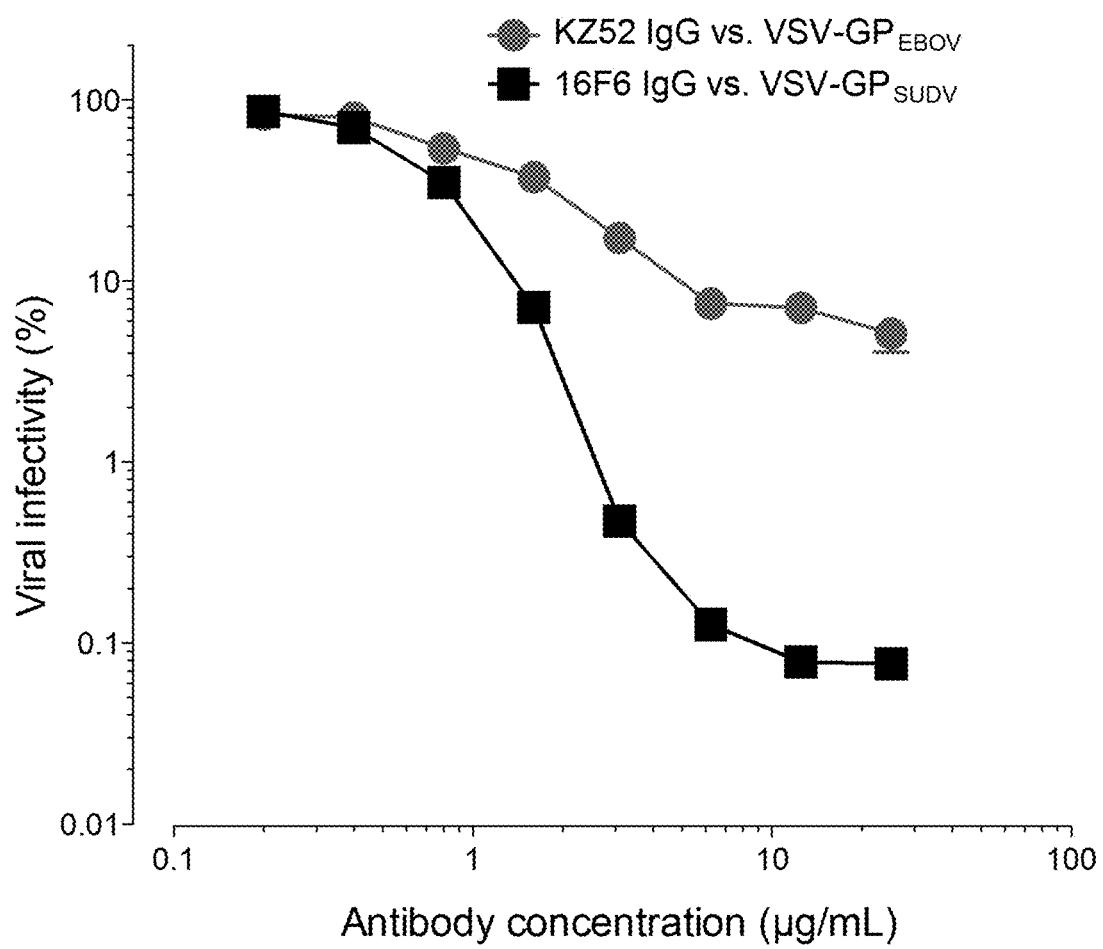
FIG. 3. Head-to-head comparison of KZ52 IgG vs. VSV-GPEBOV and 16F6 IgG vs. VSV-GPSUDV.

Herein is described A composition is provided comprising (1) a first single chain variable fragment (scFv) comprising at least one CDR directed to a membrane glycoprotein pre-fusion core of a first species of filovirus, which first scFv is covalently joined to (2) a first polypeptide of an immunoglobulin G (IgG) comprising at least one CDR directed to a membrane glycoprotein pre-fusion core of a second species of filovirus, wherein the first species of filovirus and second species of filovirus are different species.

In an embodiment of the composition, the first scFv comprises three different heavy chain CDRs and three different light chain CDRs, each CDR directed to the membrane glycoprotein pre-fusion core of the first species of filovirus.

In an embodiment of the composition, the IgG comprises at least three different heavy chain CDRs and at least three different light chain CDRs, each CDR directed to the membrane glycoprotein pre-fusion core of the second species of filovirus.

In an embodiment of the compositions, the first scFv is covalently joined at its N terminal to a C terminal of a first polypeptide of the IgG. In an embodiment of the compositions, the first polypeptide of the IgG is a heavy chain. In an embodiment of the compositions, the first polypeptide of the IgG is a light chain.

In an embodiment of the compositions, the first scFv is covalently joined at its C terminal to an N terminal of a first polypeptide of the IgG. In an embodiment of the compositions, the first polypeptide of the IgG is a heavy chain. In an embodiment of the compositions, the first polypeptide of the IgG is a light chain.

In an embodiment of the compositions, the scFv is covalently joined to the first polypeptide via a polypeptide linker.

In an embodiment of the compositions, the polypeptide linker comprises the sequence GGSAGSAGSAGSGGS (SEQ ID NO:17).

In an embodiment of the compositions, a $V_H$ sequence of the first scFv has a sequence identical to $V_H$ sequence of a human or a humanized antibody directed to the membrane glycoprotein pre-fusion core of the first species of filovirus.

In an embodiment of the compositions, a $V_L$ sequence of the first scFv has a sequence identical to $V_L$ sequence of a human or a humanized antibody directed to the membrane glycoprotein pre-fusion core of the first species of filovirus.

In an embodiment of the compositions, the $V_H$ sequence of the scFv is joined to the $V_L$ sequence of the first scFv by a polypeptide linker. In an embodiment of the compositions, the polypeptide linker is majority glycine residues. In an embodiment of the compositions, the polypeptide linker is GGGGSGGGGSGGGGS (SEQ ID NO:18).

In an embodiment of the compositions, the composition comprises a second scFv, wherein the second scFv is covalently joined to a second polypeptide of the IgG. In an embodiment of such compositions, a $V_L$ sequence of the first scFv has a sequence identical to $V_L$ sequence of a human or a humanized antibody directed to the membrane glycoprotein pre-fusion core of the first species of filovirus. In an embodiment of the compositions, a $V_H$ sequence of the IgG has a sequence identical to $V_H$ sequence of a human or a humanized IgG antibody directed to the membrane glycoprotein pre-fusion core of the second species of filovirus. In an embodiment of the compositions, a $V_L$ sequence of the IgG has a sequence identical to $V_L$ sequence of a human or a humanized IgG antibody directed to the membrane glycoprotein pre-fusion core of the second species of filovirus.

In an embodiment of the compositions, the IgG is a neutralizing antibody for the second species of filovirus.

In an embodiment of the compositions, the first species of filovirus and the second species of filovirus are both Ebolavirus species. In an embodiment of the compositions, the Ebola virus species are *Zaire ebolavirus* and *Sudan ebolavirus*.

A composition is also provided comprising (i) a first single chain variable fragment (scFv) comprising at least one CDR directed to a membrane glycoprotein pre-fusion core of a first species of filovirus, which first scFv is covalently joined to (ii) a first polypeptide of an immunoglobulin G (IgG) comprising at least one CDR directed to a membrane glycoprotein pre-fusion core of a second species of filovirus, the IgG having covalently joined thereto, at a different location from the attachment of (i) thereto, (iii) a second single chain variable fragment (scFv) comprising at least one CDR directed to a membrane glycoprotein pre-fusion core of a third species of filovirus, wherein the first species of filovirus and second species of filovirus and third species of filovirus are all different species.

In an embodiment of the composition, the first scFv comprises three different heavy chain CDRs and three different light chain CDRs, each CDR directed to the membrane glycoprotein pre-fusion core of the first species of filovirus, and the second scFv comprises three different heavy chain CDRs and three different light chain CDRs, each CDR directed to the membrane glycoprotein pre-fusion core of the third species of filovirus. In an embodiment of the composition, the IgG comprises at least three different heavy chain CDRs and at least three different light chain CDRs, each CDR directed to the membrane glycoprotein pre-fusion core of the second species of filovirus.

In an embodiment of the compositions, the first scFv is covalently joined at its N terminal to a C terminal of a first polypeptide of the IgG, and the second scFv is covalently joined to a different location on the IgG. In an embodiment of the compositions, the first polypeptide of the IgG is a heavy chain. In an embodiment of the compositions, the first polypeptide of the IgG is a light chain.

In an embodiment of the compositions, the first scFv is covalently joined at its C terminal to an N terminal of a first polypeptide of the IgG, and the second scFv is covalently joined to a different location on the IgG. In an embodiment of the compositions, the first polypeptide of the IgG is a heavy chain. In an embodiment of the compositions, the first polypeptide of the IgG is a light chain.

In an embodiment of the compositions, the first and second scFvs are each covalently joined to the first polypeptide, each via a separate polypeptide linker. In an embodiment of the compositions, the first and second scFvs are each covalently joined to different polypeptides of the IgG, each via a separate polypeptide linker. In an embodiment of the compositions, the polypeptide linkers each comprise the sequence GGSAGSAGSAGSGGS (SEQ ID NO:17).

In an embodiment of the compositions, a $V_H$ sequence of the first scFv has a sequence identical to $V_H$ sequence of a human or a humanized antibody directed to the membrane glycoprotein pre-fusion core of the first species of filovirus. In an embodiment of the compositions, a $V_H$ sequence of the second scFv has a sequence identical to $V_H$ sequence of a human or a humanized antibody directed to the membrane glycoprotein pre-fusion core of the third species of filovirus.

In an embodiment of the compositions, a $V_L$ sequence of the first scFv has a sequence identical to $V_L$ sequence of a human or a humanized antibody directed to the membrane glycoprotein pre-fusion core of the first species of filovirus. In an embodiment of the compositions, a $V_L$ sequence of the second scFv has a sequence identical to $V_L$ sequence of a human or a humanized antibody directed to the membrane glycoprotein pre-fusion core of the third species of filovirus.

In an embodiment of the compositions, the VH sequence of the first scFv is joined to the VL sequence of the scFv by a polypeptide linker. In an embodiment of the compositions, the VH sequence of the second scFv is joined to the VL sequence of the scFv by a polypeptide linker. In an embodiment of the compositions, the polypeptide linker is majority glycine residues. In an embodiment of the compositions, the polypeptide linker is GGGGSGGGGSGGGGS (SEQ ID NO:18).

In an embodiment of the compositions, the IgG is a neutralizing antibody for the second species of filovirus.

In an embodiment of the compositions, the first species of filovirus and the second species of filovirus and third species of filovirus are all Ebolavirus species. In an embodiment of the compositions, the Ebola virus species include *Zaire ebolavirus* and *Sudan ebolavirus*. In an embodiment of the compositions, the at least one species of filovirus and is an Ebolavirus species and at least one species of filovirus is a Marburg virus.

Also provided is an isolated nucleic acid encoding any of the compositions described herein.

Also provided is a method of treating a filovirus infection in a subject comprising administering an amount of a bispecific composition described herein to the subject effective to treat a filovirus infection in a subject.

Also provided is a method of preventing a filovirus infection in a subject comprising administering an amount of a bispecific composition described herein to the subject effective to inhibit a filovirus infection in a subject.

Also provided is a method of preventing a filovirus infection of a mammalian cell comprising contacting the filovirus with an amount of a bispecific composition described herein effective to inhibit a filovirus infection of a mammalian cell. In an embodiment of the method, the cell is an antigen presenting cell. In an embodiment of the method, the cell is a dendritic cell or a macrophage. In an embodiment of the method, the cell is human.

Also provided is a method of treating a filovirus infection in a subject comprising administering an amount of a trispecific composition described herein to the subject effective to treat a filovirus infection in a subject.

Also provided is a method of preventing a filovirus infection in a subject comprising administering an amount of a trispecific composition described herein to the subject effective to inhibit a filovirus infection in a subject.

Also provided is a method of preventing a filovirus infection of a mammalian cell comprising contacting the filovirus with an amount of a trispecific composition described herein effective to inhibit a filovirus infection of a mammalian cell. In an embodiment of the method, the cell is an antigen presenting cell. In an embodiment of the method, the cell is a dendritic cell or a macrophage. In an embodiment of the method, the cell is human.

Also provided is a method of treating a filovirus infection in a subject comprising administering an amount of a bispecific composition described herein to the subject effective to treat a filovirus infection in a subject. Also provided is a method of preventing a filovirus infection in a subject comprising administering an amount of a bispecific composition described herein to the subject effective to inhibit a filovirus infection in a subject. Also provided is a method of preventing a filovirus infection of a mammalian cell comprising contacting the filovirus with an amount of a bispecific composition described herein effective to inhibit a filovirus infection of a mammalian cell. In an embodiment of the method, the cell is an antigen presenting cell. In an embodiment of the method, the cell is a dendritic cell or a macrophage. In an embodiment of the method, the cell is human. Also provided is a method of treating a filovirus infection in a subject comprising administering an amount of a trispecific composition described herein to the subject effective to treat a filovirus infection in a subject. Also provided is a method of preventing a filovirus infection in a subject comprising administering an amount of a trispecific composition described herein to the subject effective to inhibit a filovirus infection in a subject. Also provided is a method of preventing a filovirus infection of a mammalian cell comprising contacting the filovirus with an amount of a trispecific composition described herein effective to inhibit a filovirus infection of a mammalian cell. In an embodiment of the method, the cell is an antigen presenting cell. In an embodiment of the method, the cell is a dendritic cell or a macrophage. In an embodiment of the method, the cell is human. In an embodiment of all of the methods described herein, the subject is human.

Also provided is a portion of an recombinant dual-variable-domain antibody, the portion comprising:
(1) a heavy chain amino acid sequence comprising in N terminal to C terminal order (i) a first $V_H$ amino acid sequence comprising at least one CDR directed to a membrane glycoprotein pre-fusion core of a first species of filovirus, (ii) a 4, 5, 6, 7, or 8 amino acid first linker sequence, (iii) a second $V_H$ amino acid sequence comprising at least one CDR directed to a membrane glycoprotein pre-fusion core of a second species of filovirus, (iv) an immunoglobulin G $C_H1$ amino acid sequence, (v) an immunoglobulin G hinge amino acid sequence, (vi) an immunoglobulin G $C_H2$ amino acid sequence, (vii) an immunoglobulin G $C_H3$ amino acid sequence, which is bound via one or more inter-chain disulfide bond(s) to
(2) a light chain amino acid sequence comprising in N terminal to C terminal order (i) a first $V_L$ amino acid sequence comprising at least one CDR directed to a membrane glycoprotein pre-fusion core of a first species of filovirus, (ii) a 4, 5, 6, 7, or 8 amino acid second linker sequence, (iii) a second $V_L$ amino acid sequence comprising at least one CDR directed to a membrane glycoprotein pre-fusion core of a second species of filovirus, (iv) an immunoglobulin G $C_L$ amino acid sequence, wherein the first species of filovirus and second species of filovirus are different species.

In an embodiment, (1) and (2) are bound via an inter-chain disulfide bond between the $C_H1$ amino acid sequence and the $C_L$ amino acid sequence. Also provided is a construct comprising two of the recombinant dual-variable-domain antibodies (or portions) as described together by one or more disulfide bonds between the heavy chain amino acid sequence of each. In an embodiment, the two recombinant dual-variable-domain antibodies are joined together by two disulfide bonds between the immunoglobulin G hinge amino acid sequences of each. In an embodiment, the 4, 5, 6, 7, or 8 amino acid first linker sequence is a 6 amino acid first linker sequence. In an embodiment, the 6 amino acid first linker sequence is ASTKGP (SEQ ID NO:41). In an embodiment, the 4, 5, 6, 7, or 8 amino acid second linker sequence is 5 amino acid second linker sequence. In an embodiment, the 5 amino acid second linker sequence is TVAAP (SEQ ID NO:42).

In an embodiment, the first $V_H$ amino acid sequence comprises three different heavy chain CDRs each of the three CDRs directed to the membrane glycoprotein pre-fusion core of the first species of filovirus. In an embodiment, the first $V_L$ amino acid sequence comprises three different light chain CDRs each of the three CDRs directed to the membrane glycoprotein pre-fusion core of the first species of filovirus. In an embodiment, the second $V_H$ amino acid sequence comprises three different heavy chain CDRs each of the three CDRs directed to the membrane glycoprotein pre-fusion core of the second species of filovirus. In an embodiment, the second $V_L$ amino acid sequence comprises three different light chain CDRs each of the three CDRs directed to the membrane glycoprotein pre-fusion core of the second species of filovirus.

In an embodiment, the first species of filovirus and the second species of filovirus are both Ebolavirus species. In an embodiment, the Ebola virus species are *Zaire ebolavirus* and *Sudan ebolavirus*.

Also provided is an isolated nucleic acid encoding a recombinant dual-variable-domain antibody or a construct as described herein. In an embodiment, the isolated nucleic acid is, or comprises, a cDNA.

Also provided is a method of treating a filovirus infection in a subject comprising administering an amount of the recombinant dual-variable-domain antibody or construct described herein to the subject effective to treat a filovirus infection in a subject. Also provided is a method of preventing a filovirus infection in a subject comprising administering an amount of the recombinant dual-variable-domain antibody or construct described herein to the subject effective to inhibit a filovirus infection in a subject. Also provided is a method of preventing a filovirus infection of a mammalian cell comprising contacting the filovirus with an amount of the recombinant dual-variable-domain antibody or construct described herein effective to inhibit a filovirus infection of a mammalian cell. In an embodiment, the cell is an antigen presenting cell. In an embodiment, the cell is a dendritic cell or a macrophage. In an embodiment, the cell is human.

In an embodiment of all of the methods described herein, the subject is human.

As used herein, "treating" a specified condition means ameliorating one or more symptoms of an extant condition, for example, a filovirus infection.

As used herein, "preventing" a specified condition means reducing the development of, or reducing the extent of, one or more symptoms of the condition, for example a filovirus infection, as compared to the development or extent the condition takes in the absence of preventative treatment. In an embodiment, "preventing" as used herein does not mean an absolute prevention, but a lessened extent of the condition brought about prophylactically.

Exemplary E10/F4-KZ52 scFv Bispecifics Sequences: the following exemplary amino acid sequences are provided, for the compositions of the invention as relating to the embodiments of antibodies E10 and F4, with non-limiting exemplary nucleotide sequences (in view of the degeneracy of the genetic code).

E10-KZ52 HC N' Fusion Sequence:

```
Amino Acid (SEQ ID NO: 1):
EVQLLESGGLVKPGGSLRLSACCSGFTLINYRMNWVRQAPGKGLEWVSSI

SSSSSYIHYADSVKGRFTISRDNAENSLYLQMNSLRAEDTAVYYCVREGP

RATGYSMADVFDIWGQGTMVTVSSGGGGSGGGGSGGGGSELVMTQSPDSL

AVSLGERATINCKSSQSVLYSSNNKSYLAWYQQKPGQPPKLLIYWASTRE

SGVPDRFSGSGSGTDFTLTISSLQAEDVAVYYCQQYYSAPLTFGGGTKVE

IKGGSAGSAGSAGSGGSEVQLVESGGGLVQPGGSLRLSCAASGFAFNYYD

IHWVRQAPGKGLEWVAYINPGGGNTYYADSVKGRFTISADTSKNTAYLQM

NALRAEDTAVYYCARQLYGNSFMDYWGQGTLVTVSSASTKGPSVFPLAPS

SKSTSGGTAALGCLVKDYFPEPVTVSWNSGALTSGVHTFPAVLQSSGLYS

LSSVVTVPSSSLGTQTYICNVNHKPSNTKVDKKVEPKSCDKTHTCDKTHT

CPPCPAPELLGRPSVFLFPPKPKDTLMISRTPEVTCVVVDVSHEDPEVKF

NWYVDGVEVHNAKTKPREEQYNSTYRVVSVLTVLHQDWLNGKEYKCKVSN

KALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSC

SVMHEALHNHYTQKSLSLSPGK
```

Underlined region is glycine-rich linker polypeptide. Bold region is fusion linker polypeptide. Italicized region is CH1-CH3 for the HC and the CL region.

Nucleotide (SEQ ID NO: 2):
GAAGTGCAGTTACTGGAAAGCGGCGGCGGCCTGGTTAAACCTGGCGGTAG

TCTGCGTCTGAGTTGCGCCGCCAGCGGTTTCACCCTGATCAACTACCGCA

TGAACTGGGTGCGTCAGGCACCGGGTAAAGGCCTGGAGTGGGTGAGCAGC

ATTAGCAGCAGCAGCAGCTATATTCACTACGCCGACAGCGTGAAAGGCCG

CTTTACCATCAGCCGCGACAATGCCGAGAACAGTCTGTATCTGCAGATGA

ACAGCCTAAGGGCGGAAGATACAGCCGTGTACTACTGTGTGCGCGAAGGC

CCTCGCGCAACCGGCTATAGCATGGCAGACGTGTTTGATATCTGGGGTCA

GGGCACCATGGTTACAGTTAGCAGTGGTGGTGGTGGTAGTGGTGGCGGTG

GTAGCGGTGGTGGTGGCAGTGAACTGGTGATGACCCAGAGCCCGGATAGC

TTAGCCGTGAGTCTGGGCGAAAGGGCGACCATTAACTGCAAAAGCAGCCA

GAGCGTGCTGTACAGCAGCAACAACAAGAGCTACCTGGCATGGTATCAGC

AAAAACCGGGTCAGCCTCCGAAACTGCTGATCTATTGGGCAAGCACCCGC

GAAAGTGGTGTTCCGGATCGCTTCAGCGGTAGTGGCAGCGGTACCGATTT

CACCCTGACCATCAGCAGTCTGCAGGCCGAGGACGTTGCAGTGTATTACT

GTCAGCAGTACTACAGCGCCCCGCTGACCTTTGGCGGCGGCACCAAAGTT

GAAATTAAGGGCGGCAGTGCAGGCAGCGCCGGTAGTGCCGGTAGTGGTGG

TAGCGAAGTTCAGCTGGTTGAAAGTGGCGGCGGTCTGGTGCAGCCTGGTG

GTAGTCTGCGTCTGAGTTGTGCCGCCAGCGGCTTTGCCTTCAATTACTAT

GACATTCATTGGGTTCGCCAGGCCCCGGGTAAAGGTCTGGAATGGGTTGC

ATATATCAACCCGGGTGGCGGTAACACCTACTATGCCGACAGCGTTAAGG

GTCGCTTCACCATCAGCGCAGATACCAGCAAAAACACCGCCTACCTGCAG

ATGAATAGCCTGCGTGCAGAAGATACCGCCGTTTACTACTGTGCCCGCCA

GCTGTACGGCAATAGCTTCATGGACTATTGGGGCCAGGGCACCTTAGTTA

CCGTGAGCAGC

Combined (SEQ ID NO: 1 and 2):
gaagtgcagttactggaaagcggcggcggcctggttaaacctggcggtag
 E  V  Q  L  L  E  S  G  G  G  L  V  K  P  G  G  S tctgcgtctgagttgcgccgccagcggtttcaccctgatcaactaccgca
 L  R  L  S  C  A  A  S  G  F  T  L  I  N  Y  R tgaactgggtgcgtcaggcaccgggtaaaggcctggagtgggtgagcagc
 M  N  W  V  R  Q  A  P  G  K  G  L  E  W  V  S  S attagcagcagcagcagctatattcactacgccgacagcgtgaaaggccg
 I  S  S  S  S  Y  I  H  Y  A  D  S  V  K  G  R ctttaccatcagccgcgacaatgccgagaacagtctgtatctgcagatga
 F  T  I  S  R  D  N  A  E  N  S  L  Y  L  Q  M acagcctaagggcggaagatacagccgtgtactactgtgtgcgcgaaggc
 N  S  L  R  A  E  D  T  A  V  Y  Y  C  V  R  E  G cctcgcgcaaccggctatagcatggcagacgtgtttgatatctggggtca
 P  R  A  T  G  Y  S  M  A  D  V  F  D  I  W  G  Q gggcaccatggttacagttagcagtggtggtggtggtagtggtggcggtg
 G  T  M  V  T  V  S  S  G  G  G  G  S  G  G  G gtagcggtggtggtggcagtgaactggtgatgacccagagcccggatagc
 G  S  G  G  G  G  S  E  L  V  M  T  Q  S  P  D  S ttagccgtgagtctgggcgaaagggcgaccattaactgcaaaagcagcca
 L  A  V  S  L  G  E  R  A  T  I  N  C  K  S  S  Q gagcgtgctgtacagcagcaacaacaagagctacctggcatggtatcagc
 S  V  L  Y  S  S  N  N  K  S  Y  L  A  W  Y  Q aaaaaccgggtcagcctccgaaactgctgatctattgggcaagcacccgc
 Q  K  P  G  Q  P  P  K  L  L  I  Y  W  A  S  T  R gaaagtggtgttccggatcgcttcagcggtagtggcagcggtaccgattt
 E  S  G  V  P  D  R  F  S  G  S  G  S  G  T  D  F caccctgaccatcagcagtctgcaggccgaggacgttgcagtgtattact
 T  L  T  I  S  S  L  Q  A  E  D  V  A  V  Y  Y gtcagcagtactacagcgccccgctgacctttggcggcggcaccaaagtt
 C  Q  Q  Y  Y  S  A  P  L  T  F  G  G  G  T  K  V gaaattaagggcggcagtgcaggcagcgccggtagtgccggtagtggtgg
 E  I  K  G  G  S  A  G  S  A  G  S  A  G  S  G  G tagcgaagttcagctggttgaaagtggcggcggtctggtgcagcctggtg
 S  E  V  Q  L  V  E  S  G  G  G  L  V  Q  P  G gtagtctgcgtctgagttgtgccgccagcggctttgccttcaattactat
 G  S  L  R  L  S  C  A  A  S  G  F  A  F  N  Y  Y gacattcattgggttcgccaggccccgggtaaaggtctggaatgggttgc
 D  I  H  W  V  R  Q  A  P  G  K  G  L  E  W  V  A atatatcaacccgggtggcggtaacacctactatgccgacagcgttaagg
 Y  I  N  P  G  G  G  N  T  Y  Y  A  D  S  V  K gtcgcttcaccatcagcgcagataccagcaaaaacaccgcctacctgcag
 G  R  F  T  I  S  A  D  T  S  K  N  T  A  Y  L  Q atgaatagcctgcgtgcagaagataccgccgtttactactgtgcccgcca
 M  N  S  L  R  A  E  D  T  A  V  Y  Y  C  A  R  Q gctgtacggcaatagcttcatggactattggggccagggcaccttagtta
 L  Y  G  N  S  F  M  D  Y  W  G  Q  G  T  L  V ccgtgagcagc
 T  V  S  S E10-KZ52 LC N' Fusion Sequence:
Amino Acid (SEQ ID NO: 3):
EVQLLESGGGLVKPGGSLRLSCAASGFTLINYRMNWVRQAPGKGLEWVSS

ISSSSSYIHYADSVKGRFTISRDNAENSLYLQMNSLRAEDTAVYYCVREG

PRATGYSMADVFDIWGQGTMVTVSSGGGGSGGGGSGGGGSELVMTQSPDS

LAVSLGERATINCKSSQSVLYSSNNKSYLAWYQQKPGQPPKLLIYWASTR

ESGVPDRFSGSGSGTDFTLTISSLQAEDVAVYYCQQYYSAPLTFGGGTKV

EIKGGSAGSAGSAGSGGSDIQMTQSPSSLSASVGDRVTITCRASQDVTTA

VAWYQQKPGKAPKLLIYWASRLHNGVPSRFSGSGSGTDFTLTISSLQPED

FATYYCQQHYSTPLTFGQGTKVEIK*RTVAAPSVFIFPPSDEQLKSGTASV*

*VCLLNNFYPREAKVQWKVDNALQSGNSQESVTEQDSKDSTYSLSSTLTLSK*

*ADYEKHKVYACEVTHQGLSSPVTKSFNRGECGGSDYKDDDDK*

Underlined region is glycine-rich linker polypeptide. Bold region is fusion linker polypeptide. Italicized region is CH1-CH3 for the HC and the CL region.

Nucleotide (SEQ ID NO: 4):
GAAGTGCAGCTGCTGGAAAGCGGTGGCCGTCTGGTTAAACCTGGCGGTAGTCT

GCGCCTGAGTTGCGCCGCCAGCGGTTTTACACTGATCAACTATCGCATGAACTG

-continued

```
GGTGCGTCAGGCACCGGGTAAGGGTCTGGAGTGGGTTAGCAGCATTAGTAGCA
GCAGCAGTTACATTCACTACGCCGATAGCGTGAAAGGCCGCTTCACAATTAGCC
GCGATAACGCCGAGAACAGCCTGTATCTGCAGATGAACAGTTTACGCGCCGAA
GATACCGCCGTGTATTATTGCGTTCGCGAAGGTCCGCGTGCAACCGGCTACAGC
ATGGCCGACGTTTTCGATATTTGGGGTCAGGGCACCATGGTGACAGTTAGTAGC
GGTGGTGGTGGTAGTGGTGGTGGCGGCAGCGGTGGTGGTGGTAGTGAACTGGT
GATGACCCAGAGCCCGGATAGCCTGGCAGTGAGCCTGGGTGAGCGTGCCACCA
TCAATTGCAAAAGCAGCCAGAGCGTGCTGTACAGCAGCAACAACAAGAGTTAC
CTGGCCTGGTACCAACAGAAACCGGGCCAGCCGCCGAAACTGCTGATTTATTGG
GCCAGTACCCGCGAAAGCGGCGTGCCTGATCGTTTTAGTGGCAGCGGTAGCGG
CACCGACTTTACCCTGACCATTAGCAGCCTGCAGGCCGAGGATGTGGCAGTGTA
TTACTGCCAGCAGTATTACAGCGCCCCGTTAACCTTTGGCGGCGGTACCAAAGT
GGAGATCAAAGGTGGCAGTGCAGGCAGCGCCGGTAGTGCAGGTAGTGGTGGTA
GCGACATCCAGATGACACAGAGTCCGAGCAGCCTGAGTGCCAGCGTTGGTGAC
CGTGTGACCATTACCTGCCGTGCCAGCCAGGATGTTACCACAGCCGTTGCATGG
TATCAGCAGAAGCCGGGTAAGGCCCCTAAGTTACTGATCTACTGGGCAAGCCG
CCTGCATAACGGTGTGCCGAGCCGCTTTAGCGGCAGTGGTAGCGGTACCGATTT
GACCCTGACCATCAGCAGTCTGCAGCCGGAAGATTTCGCAACCTACTACTGTCA
GCCAGCATTACAGCACCCCGCTGACCTTTGGCCAGGGCACCAAAGTGGAAATTA
AA
```

Combined (SEQ ID NO: 3 and 4):

```
gaagtgcagctgctggaaagcggtggcgtctggttaaacctggcggtagtctgcgcctg
 E  V  Q  L  V  E  S  G  G  G  L  V  Q  P  G  G  S  L  R  L agttgcgccgccagcggttttacactgatcaactatcgcatgaactgggtgcgtcaggca
 S  C  A  A  S  G  F  T  L  I  N  Y  R  M  N  W  V  R  Q  A ccgggtaagggtctggagtgggttagcagcattagtagcagcagcagttacattcactac
 P  G  K  G  L  E  W  V  S  S  I  S  S  S  S  S  Y  I  H  Y gccgatagcgtgaaaggccgcttcacaattagccgcgataacgccgagaacagcctgtat
 A  D  S  V  K  G  R  F  T  I  S  R  D  N  A  E  N  S  L  Y ctgcagatgaacagtttacgcgccgaagataccgccgtgtattattgcgttcgcgaaggt
 L  Q  M  N  S  L  R  A  E  D  T  A  V  Y  Y  C  V  R  E  G ccgcgtgcaaccggctacagcatggccgacgttttcgatatttggggtcagggcaccatg
 P  R  A  T  G  Y  S  M  A  D  V  F  D  I  W  G  Q  G  T  M gtgacagttagtagcggtggtggtggtagtggtggtggcggcagcggtggtggtggtagt
 V  T  V  S  S  G  G  G  G  S  G  G  G  G  S  G  G  G  G  S gaactggtgatgacccagagcccggatagcctggcagtgagcctgggtgagcgtgccacc
 E  L  V  M  T  Q  S  P  D  S  L  A  V  S  L  G  E  R  A  T atcaattgcaaaagcagccagagcgtgctgtacagcagcaacaacaagagttacctggcc
 I  N  C  K  S  S  Q  S  V  L  Y  S  S  N  N  K  S  Y  L  A tggtaccaacagaaaccgggccagccgccgaaactgctgatttattgggccagtacccgc
 W  Y  Q  Q  K  P  G  Q  P  P  K  L  L  I  Y  W  A  S  T  R gaaagcggcgtgcctgatcgttttagtggcagcggtagcggcaccgactttacccctgacc
 E  S  G  V  P  D  R  F  S  G  S  G  S  G  T  D  F  T  L  T attagcagcctgcaggccgaggatgtggcagtgtattactgccagcagtattacagcgcc
 I  S  S  L  Q  A  E  D  V  A  V  Y  Y  C  Q  Q  Y  Y  S  A ccgttaacctttggcggcggtaccaaagtggagatcaaaggtggcagtgcaggcagcgcc
 P  L  T  F  G  G  G  T  K  V  E  I  K  G  G  S  A  G  S  A
```

```
ggtagtgcaggtagtggtggtagcgacatccagatgacacagagtccgagcagcctgagt
 G  S  A  G  S  G  G  S  D  I  Q  M  T  Q  S  P  S  S  L  S gccagcgttggtgaccgtgtgaccattacctgccgtgccagccaggatgttaccacagcc
 A  S  V  G  D  R  V  T  I  T  C  R  A  S  Q  D  V  T  T  A gttgcatggtatcagcagaagccgggtaaggcccctaagttactgatctactgggcaagc
 V  A  W  Y  Q  Q  K  P  G  K  A  P  K  L  L  I  Y  W  A  S cgcctgcataacggtgtgccgagccgctttagcggcagtggtagcggtaccgatttcacc
 R  L  H  N  G  V  P  S  R  F  S  G  S  G  S  G  T  D  F  T ctgaccatcagcagtctgcagccggaagatttcgcaacctactactgtcagcagcattac
 L  T  I  S  S  L  Q  P  E  D  F  A  T  Y  Y  C  Q  Q  H  Y agcacccCgctgacctttggccagggcaccaaagtggaaattaaa
 S  T  P  L  T  F  G  Q  G  T  K  V  E  I  K
```

E10-KZ52 HC C' Fusion Sequence:
Amino Acid (SEQ ID NO: 5):
EVQLVESGGGLVQPGGSLRLSCAASGFAFNYYDIHWVRQAPGKGLEVWV

AYINPGGGNTYYADSVKGRFTISADTSKNTAYLQMNSLRAEDTAVYYCARQLYGN

SFFDYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDK

KVEPKSCDKTHTCDKTHTCPPCPAPELLGRPSVFLFPPKPKDTLMISRTPEVTCVVV

DVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSCSVMHE

ALHNHYTQKSLSLSPGKGGSAGSAGSAGSGGSEVQLLESGGGLVKPGGSLRLSCA

ASGFTLINYRMNWVRQAPGKGLEWVSSISSSSSYIHYADSVKGRFTISRDNAENSLY

LQMNSLRAEDTAVYYCVREGPRATGYSMADVFDIWGQGTMVTVSS<u>GGGGSGGG</u>

<u>GSGGGGS</u>ELVMTQSPDSLAVSLGERATINCKSSQSVLYSSNNKSYLAWYQQKPGQP

PKLLIYWASTRESGVPDRFSGSGSGTDFTLTISSLQAEDVAYYYCQQYYSAPLTFGG

GTKVEIK

40

Underlined region is linker polypeptide. Bold region is fusion linker polypeptide.

```
GAGGTTCAGCTGGTGGAGTCTGGCGGTGGCCTGGTGCAGCCAGGGGGCTCACT

CCGTTTGTCCTGTGCAGCTTCTGGCTTCGCGTTTAACTATTATGATATTCATTGG

GTGCGTCAGGCCCCGGGTAAGGGCCTGGAATGGGTTGCATATATTAACCCGGG

CGGTGGCAACACCTATTATGCTGATAGGGTCAAGGGCCGTTTCACTATAAGCGC

AGACACATCCAAAAACACAGCCTACCTACAAATGAACAGCTTAAGAGCTGAGG

ACACTGCCGTCTATTATTGTGCTCGCCAGCTGTATGGCAACAGCTTTATGGACT

ACTGGGGTCAAGGAACCCTGGTCACCGTCTCCTCGGCTAGGACCAAGGGTCCGA

GCGTGTTTCCTCTGGCACCTAGCAGTAAAAGCACCAGTGGTGGTACAGCAGCCC

TGGGTTGCCTGGTGAAGGATTACTTTCCGGAGCCGGTGACCGTTAGTTGGAATA

GCGGCGCCCTGACCAGTGGCGTTCATACATTTCCGGCCGTGCTGCAGAGTAGTG

GCCTGTACAGCCTGAGTAGCGTTGTTACCGTTCCGAGCAGCAGCCTGGGCACCC

AGACCTATATTTGCAATGTTAACCATAAACCGAGCAACACAAAAGTTGATAAA

AAAGTTGAACCGAAGAGCTGTGACAAAACCCATACATGTGACAAAACACACAC

CTGCCCCGCCTTGTCCGGCACCTGAGCTGCTGGGTCGCCCGAGCGTTTTTCTGTTT
```

```
CCTCCGAAACCGAAAGACACC[ . . . ]ACCCAGAAGAGTCTGAGCCTGAGTCCTGGC

AAAGGTGGATCCGCCGGTAGCGGCAGGTAGTGCAGGTAGTGGCGGCAGCGAAGT

TCAGCTGTTAGAAAGTGGCGGTGGTCTGGTTAAGCCGGGCGGTAGTCTGCGCCT

GAGCTGTGCAGCAAGTGGTTTCACCCTGATCAATTATCGTATGAACTGGGTGCG

CCAAGCCCCGGGTAAAGGTCTGGAGTGGGTTAGTAGTATCAGCAGCAGCAGCA

GTTACATCCACTATGCCGATAGCGTTAAGGGCCGCTTTACAATCAGCCGCGATA

ATGCCGAGAATAGCTTATACCTGCAAATGAACAGTCTAAGGGCGGAAGATACC

GCCGTTTACTACTGCGTTCGTGAAGGCCCTCGCGCAACAGGCTATAGCATGGCA

GACGTGTTCGACATTTGGGGTCAGGGCACCATGGTGACCGTTAGTAGCGGCGGT

GGTGGTAGTGGTGGTGGCGGTAGTGGTGGCGGTGGCAGCGAACTGGTGATGAC

CCAGAGTCCGGATAGCCTGGCCGTGAGCTTAGGCGAGCGTGCAACCATTAATTG

TAAAAGCAGTCAGAGTGTTCTGTATAGTAGCAATAACAAGAGCTATCTGGCCTG

GTATCAGCAGAAGCCGGGCCAGCCGCCGAAACTGCTGATTTACTGGGCAAGCA

CCCGCGAAAGTGGCGTGCCTGATCGCTTTAGTGGTAGCGGCAGCGGCACCGATT

TTACCCTGACCATTAGCAGTCTGCAGGCCGAGGACGTTGCCGTTTATTACTGCC

AGCAGTACTATAGCGCACCGCTGACATTTGGCGGTGGCACCAAGGTGGAAATT

AAATAA

Combined (SEQ ID NO: 5 and 6):
gaggttcagctggtggagtctggcggtggcctggtgcagccaggggggctcactccgtttg
 E  V  Q  L  V  E  S  G  G  G  L  V  Q  P  G  G  S  L  R  L tcctgtgcagcttctggcttcgcgtttaactattatgatattcattgggtgcgtcaggcc
 S  C  A  A  S  G  F  A  F  N  Y  Y  D  I  H  W  V  R  Q  A ccgggtaagggcctggaatgggttgcatatattaacccgggcggtggcaacacctattat
 P  G  K  G  L  E  W  V  A  Y  I  N  P  G  G  G  N  T  Y  Y gctgatagcgtcaagggccgtttcactataagcgcagacacatccaaaaacacagcctac
 A  D  S  V  K  G  R  F  T  I  S  A  D  T  S  K  N  T  A  Y ctacaaatgaacagcttaagagctgaggacactgccgtctattattgtgctcgccagctg
 L  Q  M  N  S  L  R  A  E  D  T  A  V  Y  Y  C  A  R  Q  L tatggcaacagctttatggactactggggtcaaggaaccctggtcaccgtctcctcggct
 Y  G  N  S  F  M  D  Y  W  G  Q  G  T  L  V  T  V  S  S  A agcaccaagggtccgagcgtgtttcctctggcacctagcagtaaaagcaccagtggtggt
 S  T  K  G  P  S  V  F  P  L  A  P  S  S  K  S  T  S  G  G acagcagccctgggttgcctggtgaaggattactttccggagccggtgaccgttagttgg
 T  A  A  L  G  C  L  V  K  D  Y  F  P  E  P  V  T  V  S  W aatagcggcgccctgaccagtggcgttcatacatttccggccgtgctgcagagtagtggc
 N  S  G  A  L  T  S  G  V  H  T  F  P  A  V  L  Q  S  S  G ctgtacagcctgagtagcgttgttaccgttccgagcagcagcctgggcacccagacctat
 L  Y  S  L  S  S  V  V  T  V  P  S  S  S  L  G  T  Q  T  Y atttgcaatgttaaccataaaccgagcaacacaaaagttgataaaaaagttgaaccgaag
 I  C  N  V  N  H  K  P  S  N  T  K  V  D  K  K  V  E  P  K agctgtgacaaaacccatacatgtgacaaaacacacacctgcccgccttgtccggcacct
 S  C  D  K  T  H  T  C  D  K  T  H  T  C  P  P  C  P  A  P gagctgctgggtcgcccgagcgttttttctgtttcctccgaaaccgaaagacacc [ . . . ]
 E  L  L  G  R  P  S  V  F  L  F  P  P  K  P  K  D  T  [ . . . ]

acccagaagagtctgagcctgagtcctggcaaaggtggatccgccggtagcgcaggtagt
 T  Q  K  S  L  S  L  S  P  G  K  G  G  S  A  G  S  A  G  S gcaggtagtggcggcagcgaagttcagctgttagaaagtggcggtggtctggttaagccg
 A  G  S  G  G  S  E  V  Q  L  L  E  S  G  G  G  L  V  K  P
```

-continued

```
ggcggtagtctgcgcctgagctgtgcagcaagtggtttcaccctgatcaattatcgtatg
 G  G  S  L  R  L  S  C  A  A  S  G  F  T  L  I  N  Y  R  M aactgggtgcgccaagccccgggtaaaggtctggagtgggttagtagtatcagcagcagc
 N  W  V  R  Q  A  P  G  K  G  L  E  W  V  S  S  I  S  S  S agcagttacatccactatgccgatagcgttaagggccgctttacaatcagccgcgataat
 S  S  Y  I  H  Y  A  D  S  V  K  G  R  F  T  I  S  R  D  N gccgagaatagcttatacctgcaaatgaacagtctaagggcggaagataccgccgtttac
 A  E  N  S  L  Y  L  Q  M  N  S  L  R  A  E  D  T  A  V  Y tactgcgttcgtgaaggccctcgcgcaacaggctatagcatggcagacgtgttcgacatt
 Y  C  V  R  E  G  P  R  A  T  G  Y  S  M  A  D  V  F  D  I tggggtcagggcaccatggtgaccgttagtagcggcggtggtggtagtggtggtggcggt
 W  G  Q  G  T  M  V  T  V  S  S  G  G  G  G  S  G  G  G  G agtggtggcggtggcaccgaactggtgatgacccagagtccggatagcctggccgtgagc
 S  G  G  G  G  S  E  L  V  M  T  Q  S  P  D  S  L  A  V  S ttaggcgagcgtgcaaccattaattgtaaaagcagtcagagtgttctgtatagtagcaat
 L  G  E  R  A  T  I  N  C  K  S  S  Q  S  V  L  Y  S  S  N aacaagagctatctggcctggtatcagcagaagccgggccagccgccgaaactgctgatt
 N  K  S  Y  L  A  W  Y  Q  Q  K  P  G  Q  P  P  K  L  L  I tactgggcaagcacccgcgaaagtggcgtgcctgatcgctttagtggtagcggcagcggc
 Y  W  A  S  T  R  E  S  G  V  P  D  R  F  S  G  S  G  S  G accgattttaccctgaccattagcagtctgacggccgaggacgttgccgtttattactgc
 T  D  F  T  L  T  I  S  S  L  Q  A  E  D  V  A  V  Y  Y  C cagcagtactatagcgcaccgctgacatttggcggtggcaccaaggtggaaattaaataa
 Q  Q  Y  Y  S  A  P  L  T  F  G  G  G  T  K  V  E  I  K  -
```

E10-KZ52 LC C' Fusion Sequence:
Amino Acid (SEQ ID NO: 7):
DIQMTQSPSSLSASVGDRVTITCKASQDVTTAVAWYQQKPGKAPKLLIY

WASRLHNGVPSRFSGSGSGTDFTLTISSLQPEDFATYYCQQHYSTPLTFGQGTKVEI

KRTVAAPSVFIFPPSDEQLKSGTASVVCLLNNFYPREAKVGWKVDNALQSGNSQES

VTEQDSKDSTYSLSSTLTLSKADYEKHKVYACEVTHQGLSSPVTKSFNRGECGGSG

GSAGSAGSAGSGGSEVQLLESGGGLVKPGGSLRLSCAASGFTLINYRMNWVRQAP

GKGLEWVSSISSSSSYIHYADSVKGRFTISRDNAENSLYLQMNSLRAEDTAVYYCY

REGFRATGYSMADVFDIWGQGTMVTVSS<u>GGGGSGGGGSGGGGS</u>ELVMTQSPDSL

AVSLGERATINCKSSQSVLYSSNNKSYLAWYQQKPGQPPKLLIYWASTRESGVPDR

FSGSGSGTDFTLTISSLQAEDVAVYYCQQYYSAPLTFGGGTKVEIK

Underlined region is linker polypeptide. Bold region is fusion linker polypeptide.

Nucleotide (SEQ ID NO: 8):
GATATCCAGATGACCCAGTCCCCGAGCTCCCTGTCCGCCTCTGTGGGCGATAGG

GTCACCATCACCTGCCGGGCGAGCCAGGATGTGACCACCGCTGTAGCCTGGTAT

CAACAGAAACCAGGAAAAGCTCCGAAGCTTCTGATTTACTGGGCGAGCCGTCTT

CATAATGGCGTGCCGAGCCGCTTTAGCGGCAGCGGCTCCGGGACGGATTTCACT

CTGACCATCAGCAGTCTGCAGCCGGAAGACTTCGCAACTTATTACTGTCAGCAA

CATTATAGCACCCCGCTGACGTTCGGACAGGGTACCAAGGTGGAGATCAAACG

TACGGTGGCAGCACCGAGCGTGTTTATCTTTCCGCCGAGCGACGAACAACTGAA

AAGTGGCACAGCCAGCGTGGTGTGTTTACTGAACAACTTCTATCCTCGCGAGGC

CAAGGTGCAGTGGAAAGTGGACAATGCACTGCAGAGTGGCAATAGCCAGGAGA

-continued

```
GCGTGACCGAACAGGATAGCAAAGATAGCACCTATAGCCTGAGTAGCACCCTG

ACCCTGAGCAAGGCCGATTATGAGAAGCACAAGGTGTATGCATGCGAGGTTAC

CCATCAGGGCCTGAGCAGCCCGGTGACCAAAAGCTTTAACCGTGGCGAATGCG

GTGGTAGTGGTGGATCCGCCGGTAGCGCAGGTAGTGCAGGTAGTGGCGGCAGC

GAAGTTCAGCTGTTAGAAAGTGGCGGTGGTCTGGTTAAGCCGGGCGGTAGTCTG

CGCCTGAGCTGTGCAGCAAGTGGTTTCACCCTGATCAATTATCGTATGAACTGG

GTGCGCCAAGCCCCGGGTAAAGGTCTGGAGTGGGTTAGTAGTATCAGCAGCAG

CAGCAGTTACATCCACTATGCCGATAGCGTTAAGGGCCGCTTTACAATCAGCCG

CGATAATGCCGAGAATAGCTTATACCTGCAAATGAACAGTCTAAGGGCGGAAG

ATACCGCCGTTTACTACTGCGTTCGTGAAGGCCCTCGCGCAACAGGCTATAGCA

TGGCAGACGTGTTCGACATTTGGGGTCAGGGCACCATGGTGACCGTTAGTAGCG

GCGGTCGGTGGTAGTGGTGGTGGCGGTAGTGGTGGCGGTGGCAGCGAACTGGTG

ATGACCCAGAGTCCGGATAGCCTGGCCGTGAGCTTAGGCGAGCGTGCAACCAT

TAATTGTAAAAGCAGTCAGAGTGTTCTGTATAGTAGCAATAACAAGAGCTATCT

GGCCTGGTATCAGCAGAAGCCGGGCCAGCCGCCGAAACTGCTGATTTACTGGG

CAAGCACCCGCGAAAGTGGCGTGCCTGATCGCTTTAGTGGTAGCGGCAGCGGC

ACCGATTTTACCCTGACCATTAGCAGTCTGCAGGCCGAGGACGTTGCCGTTTAT

TACTGCCAGCAGTACTATAGCGCACCGCTGACATTTGGCGGTGGCACCAANGTG

GAAATTAAA
```

Combined (SEQ ID NO: 7 and 8):

```
gatatccagatgacccagtccccgagctccctgtccgcctctgtgggcgatagggtcacc
 D  I  Q  M  T  Q  S  P  S  S  L  S  A  S  V  G  D  R  V  T atcacctgccgggcgagccaggatgtgaccaccgctgtagcctggtatcaacagaaacca
 I  T  C  R  A  S  Q  D  V  T  T  A  V  A  W  Y  Q  Q  K  P ggaaaagctccgaagcttctgatttactgggcgagccgtcttcataatggcgtgccgagc
 G  K  A  P  K  L  L  I  Y  W  A  S  R  L  H  N  G  V  P  S cgctttagcggcagcggctccgggacggatttcactctgaccatcagcagtctgcagccg
 R  F  S  G  S  G  S  G  T  D  F  T  L  T  I  S  S  L  Q  P gaagacttcgcaacttattactgtcagcaacattatagccaccccgctgacgttcggacag
 E  D  F  A  T  Y  Y  C  Q  Q  H  Y  S  T  P  L  T  F  G  Q ggtaccaaggtggagatcaaacgtacggtggcagcaccgagcgtgtttatctttccgccg
 G  T  K  V  E  I  K  R  T  V  A  A  P  S  V  F  I  F  P  P agcgacgaacaactgaaaagtggcacagccagcgtggtgtgtttactgaacaacttctat
 S  D  E  Q  L  K  S  G  T  A  S  V  V  C  L  L  N  N  F  Y cctcgcgaggccaaggtgcagtggaaagtggacaatgcactgcagagtggcaatagccag
 P  R  E  A  K  V  Q  W  K  V  D  N  A  L  Q  S  G  N  S  Q gagagcgtgaccgaacaggatagcaaagatagcacctatagcctgagtagcaccctgacc
 E  S  V  T  E  Q  D  S  K  D  S  T  Y  S  L  S  S  T  L  T ctgagcaaggccgattatgagaagcacaaggtgtatgcatgcgaggttacccatcagggc
 L  S  K  A  D  Y  E  K  H  K  V  Y  A  C  E  V  T  H  Q  G ctgagcagcccggtgaccaaaagctttaaccgtggcgaatgcggtggtagtggtggatcc
 L  S  S  P  V  T  K  S  F  N  R  G  E  C  G  G  S  G  G  S gccggtagcgcaggtagtgcaggtagtggcggcagcgaagttcagctgttagaaagtggc
 A  G  S  A  G  S  A  G  S  G  G  S  E  V  Q  L  L  E  S  G ggtggtctggttaagccgggcggtagtctgcgcctgagctgtgcagcaagtggtttcacc
 G  G  L  V  K  P  G  G  S  L  R  L  S  C  A  A  S  G  F  T ctgatcaattatcgtatgaactgggtgcgccaagccccgggtaaaggtctggagtgggtt
 L  I  N  Y  R  M  N  W  V  R  Q  A  P  G  K  G  L  E  W  V
```

```
agtagtatcagcagcagcagcagttacatccactatgccgatagcgttaagggccgcttt
 S   S   I   S   S   S   S   S   Y   I   H   Y   A   D   S   V   K   G   R   F acaatcagccgcgataatgccgagaatagcttatacctgcaaatgaacagtctaagggcg
 T   I   S   R   D   N   A   E   N   S   L   Y   L   Q   M   N   S   L   R   A gaagataccgccgtttactactgcgttcgtgaaggccctcgcgcaacaggctatagcatg
 E   D   T   A   V   Y   Y   C   V   R   E   G   P   R   A   T   G   Y   S   M gcagacgtgttcgacatttggggtcagggcaccatggtgaccgttagtagcggcggtggt
 A   D   V   F   D   I   W   G   Q   G   T   M   V   T   V   S   S   G   G   G ggtagtggtggtggcggtagtggtggcggtggcagcgaactggtgatgacccagagtccg
 G   S   G   G   G   S   G   G   G   S   E   L   V   M   T   Q   S   P gatagcctggccgtgagcttaggcgagcgtgcaaccattaattgtaaaagcagtcagagt
 D   S   L   A   V   S   L   G   E   R   A   T   I   N   C   K   S   S   Q   S gttctgtatagtagcaataacaagagctatctggcctggtatcagcagaagccgggccag
 V   L   Y   S   S   N   N   K   S   Y   L   A   W   Y   Q   Q   K   P   G   Q ccgccgaaactgctgatttactgggcaagcacccgcgaaagtggcgtgcctgatcgcttt
 P   P   K   L   L   I   Y   W   A   S   T   R   E   S   G   V   P   D   R   F agtggtagcggcagcggcaccgattttaccctgaccattagcagtctgcaggccgaggac
 S   G   S   G   S   G   T   D   F   T   L   T   I   S   S   L   Q   A   E   D gttgccgtttattactgccagcagtactatagcgcaccgctgacatttggcggtggcacc
 V   A   V   Y   Y   C   Q   Q   Y   Y   S   A   P   L   T   F   G   G   T aangtggaaattaaa
 X   V   E   I   K F4-KZ52 HC N'Fusion Sequence:
Amino Acid (SEQ ID NO: 9):
EVQLLESGGGLVKPGGSLRLSCAASGFTLINYRMNWVRQAPGKGLEWVSSISSSSS

YIHYADSVKGRFTISRDNAENSLYLQMNSLRAEDTAVYYCVREGPRATGYSMADV

FDIWGQTMVTVSSGGGGSGGGGSGGGGSELVMTQSPDSLAVSLGERATINCKSS

QSVLYSSNNKSYLAWYQQKPGQPPKLLIYWASTRESGVFDRFSGSGSGTDFTLTISS

LQAEDVAVYYCQQYYSAPLTFGGGTKVEIKGGSAGSAGSAGSGGSEVQLVESGG

GLVQPGGSLRLSCAASGFAFNYYDMFWVRQAPGKGLEWVAYIKPGGGNTYYADS

VKGRFTISADTSKNTAYLQMNSLRAEDTAVYYCARQLYGNSFFDYWGQGTLVTVS

*SASTKGPSVFPLAPSSKSTSGGTAALGCLVKDYFPEPVTVSWNSGALTSGVHTFPAVLQSS*

*GLYSLSSVVTVPSSSLGTQTYICNVNHKPSNTKVDKKVEPKSCDKTHTCDKTHTCPPCPA*

*PELLGRPSVFLFPPKPKDTLMISRTPEVTCVVVDVSHEDPEVKFNWYVDGVEVHNAKTK*

*PREEQYNSTYRVVSVLTVLHQDWLNGKEYKCKVSNKALPAPIEKTISKAKGQPREPQVYT*

*LPPSREEMTKNQVSLTCLVKGFYPSDLAVEWESNGQPENNYKTTPPVLDSDGSFFLYSKL*

*TVDKSRWQQGNVFSCSVMHEALHNHYTQKSLSLSPGK*
```

Underlined region is glycine-rich linker polypeptide. Bold region is fusion linker polypeptide. Italicized region is CH1-CH3 for the HC and the CL region.

```
Nucleotide (SEQ ID NO: 10):
GAAGTTCAGTTACTGGAAAGTGGCGGCGGCCTGGTTAAACCGGGTGGTAGCCT

GCGTCTGAGTTGCGCAGCAAGCGGCTTCACCCTGATCAACTATCGCATGAACTG

GGTGCGCCAAGCACCGGGTAAGGGTCTGGAGTGGGTGAGCAGCATCAGCAGCA

GCAGCAGCTACATCCACTACGCAGACAGCGTTAAAGGCCGCTTCACCATTAGCC

GCGATAACGCCGAAAACAGCCTGTACCTGCAGATGAACAGTCTAAGGGCGGAG

GATACCGCAGTGTACTACTGCGTTCGTGAAGGCCCGCGTGCAACCGGCTATAGC
```

-continued
ATGGCCGACGTTTTTGATATTTGGGGCCAGGGCACCATGGTGACCGTGAGTAGT

GGTGGTGGTGGCAGCGGTGGTGGCGGTAGTGGTGGTGGTGGCAGTGAACTGGT

TATGACCCAGAGTCCGGACAGTCTGGCAGTGAGCCTGGGCGAGCGTGCAACCA

TCAACTGTAAGAGCAGTCAGAGCGTGCTGTATAGTAGCAACAATAAAAGCTAT

CTGGCGTGGTATCAGCAGAAGCCGGGTCAGCCGCCTAAGCTGCTGATTTATTGG

GCCAGCACCCGCGAAAGCGGTGTTCCGGATCGCTTTAGCGGTAGCGGCAGCGG

TACCGATTTCACCCTGACCATCAGCAGCCTGCAGGCCGAAGATGTGGCCGTGTA

TTATTGCCAGCAGTACTACAGCGCCCCGCTGACCTTTGGTGGCGGTACCAAGGT

GGAAATTAAAGGCGGCAGTGCCGGTAGTGCCGGTAGTGCAGGTAGCGGCGGTA

GCGAGGTTCAGCTGGTGGAAAGCGGCGGTGGTCTGGTTCAGCCTGGTGGTAGC

CTGCGCCTGAGCTGTGCCGCAAGCGGTTTCGCATTTAACTACTATGACATGTTCT

GGGTTCGCCAGGCACCGGGCAAAGGTCTGGAATGGGTGGCCTATATCAAACCG

GGCGGCGGCAACACCTACTACGCCGATAGCGTTAAGGGTCGTTTCACCATCAGC

GCCGATACCAGCAAAAACACCGCCTATCTGCAGATGAATAGCCTAAGGGCGGA

AGACACCGCAGTGTATTACTGCGCACGCCAGCTGTACGGCAACAGCTTTTTCGA

TTACTGGGGCCAGGGTACCCTGGTTACCGTGAGCAGC

Combined (SEQ ID NO: 9 and 10):
gaagttcagttactggaaagtggcggcggcctggttaaaccgggtggtagcctgcgtctg
 E   V   Q   L   L   E   S   G   G   G   L   V   K   P   G   G   S   L   R   L agttgcgcagcaagcggcttcaccctgatcaactatcgcatgaactgggtgcgccaagca
 S   C   A   A   S   G   F   T   L   I   N   Y   R   M   N   W   V   R   Q   A ccgggtaagggtctggagtgggtgagcagcatcagcagcagcagcagctacatccactac
 P   G   K   G   L   E   W   V   S   S   I   S   S   S   S   S   Y   I   H   Y gcagacagcgttaaaggccgcttcaccattagcgcgataacgccgaaaacagcctgtac
 A   D   S   V   K   G   R   F   T   I   S   R   D   N   A   E   N   S   L   Y ctgcagatgaacagtctaagggcggaggataccgcagtgtactactgcgttcgtgaaggc
 L   Q   M   N   S   L   R   A   E   D   T   A   V   Y   Y   C   V   R   E   G ccgcgtgcaaccggctatagcatggccgacgttttttgatatttggggccagggcaccatg
 P   R   A   T   G   Y   S   M   A   D   V   F   D   I   W   G   Q   G   T   M gtgaccgtgagtagtggtggtggtggcagcggtggtggcggtagtggtggtggtggcagt
 V   T   V   S   S   G   G   G   G   S   G   G   G   G   S   G   G   G   G   S gaactggttatgacccagagtccggacagtctggcagtgagcctgggcgagcgtgcaacc
 E   L   V   M   T   Q   S   P   D   S   L   A   V   S   L   G   E   R   A   T atcaactgtaagagcagtcagagcgtgctgtatagtagcaacaataaaagctatctggcc
 I   N   C   K   S   S   Q   S   V   L   Y   S   S   N   N   K   S   Y   L   A tggtatcagcagaagccgggtcagccgcctaagctgctgatttattgggccagcacccgc
 W   Y   Q   Q   K   P   G   Q   P   P   K   L   L   I   Y   W   A   S   T   R gaaagcggtgttccggatcgctttagcggtagcggcagcggtaccgatttcaccctgacc
 E   S   G   V   P   D   R   F   S   G   S   G   S   G   T   D   F   T   L   T atcagcagcctgcaggccgaagatgtggccgtgtattattgccagcagtactacagcgcc
 I   S   S   L   Q   A   E   D   V   A   V   Y   Y   C   Q   Q   Y   Y   S   A ccgctgacctttggtggcggtaccaaggtggaaattaaaggcggcagtgccggtagtgcc
 P   L   T   F   G   G   G   T   K   V   E   I   K   G   G   S   A   G   S   A ggtagtgcaggtagcggcggtagcgaggttcagctggtggaaagcggcggtggtctggtt
 G   S   A   G   S   G   G   S   E   V   Q   L   V   E   S   G   G   G   L   V cagcctggtggtagcctgcgcctgagctgtgccgcaagcggtttcgcatttaactactat
 Q   P   G   G   S   L   R   L   S   C   A   A   S   G   F   A   F   N   Y   Y gacatgttctgggttcgccaggcaccgggcaaaggtctggaatgggtggcctatatcaaa
 D   M   F   W   V   R   Q   A   P   G   K   G   L   E   W   V   A   Y   I   K

```
ccgggcggcggcaacacctactacgccgatagcgttaagggtcgtttcaccatcagcgcc
 P  G  G  G  N  T  Y  Y  A  D  S  V  K  G  R  F  T  I  S  A gataccagcaaaaacaccgcctatctgcagatgaatagcctaagggcggaagacaccgca
 D  T  S  K  N  T  A  Y  L  Q  M  N  S  L  R  A  E  D  T  A gtgtattactgcgcacgccagctgtacggcaacagcttttcgattactggggccagggt
 V  Y  Y  C  A  R  Q  L  Y  G  N  S  F  F  D  T  W  G  Q  G accctggttaccgtgagcagc
 T  L  V  T  V  S  S F4-KZ52 LC N' Fusion Sequence
Amino Acid (SEQ ID NO: 11):
EVQLLESGGGLVKPGGSLRLSCAASGFTLINYRMNWVRQAPGKGLEWVSSISSSSS

YIHYADSVKGRFTISRDNAENSLYLQMNSLRAEDTAVYYCVREGPRATGYSMADV

FDIWGQGTMVTVSSGGGGSGGGGSGGGGSELVMTQSPDSLAVSLGERATINCKSS

QSVLYSSNNKSYLAWYQQKPGQPPKLLIYWASTRESGVPDRFSGSGSGTDFTLTISS

LQAEDVAVYYCQQYYSAPLTFGGGTKVEIKGGSAGSAGSAGSGGSDIQMTQSPSS

LSASVGDRVTITCKASQDVTTAVAWYQQKPGKAPKLLIYWASTRHTGVPSRFSGS

GSGTDFTLTISSLQPEDFATYYCQQHYSTPLTFGQGTKVEIK*RTVAAPSVFIFPPSDEQ*

*LKSGTASVVCLLNNFYPREAKVQWKVDNALQSGNSQESVTEQDSKDSTYSLSSTLTLSKA*

*DYEKHKVYACEVTHQGLSSPVTKSFNRGECGGSDYKDDDDK*
```

Underlined region is glycine-rich linker polypeptide. Bold region is fusion linker polypeptide. Italicized region is CH1-CH3 for the HC and the CL region.

```
Nucleotide (SEQ ID NO: 12):
GAAGTTCAGTTACTGGAAAGTGGCGGCGGCCTGGTTAAACCGGGTGGTAGCCT

GCGTCTGAGTTGCGCAGCAAGCGGCTTCACCCTGATCAACTATCGCATGAACTG

GGTGCGCCAAGCACCGGGTAAGGGTCTGGAGTGGGTGAGCAGCATCAGCAGCA

GCAGCAGCTACATCCACTACGCAGACAGCGTTAAAGGCCGCTTCACCATTAGCC

GCGATAACGCCGAAAACAGCCTGTACCTGCAGATGAACAGTCTAAGGGCGGAG

GATACCGCAGTGTACTACTGCGTTCGTGAAGGCCCGCGTGCAACCGGCTATAGC

ATGGCCGACGTTTTTGATATTTGGGGCCAGGGCACCATGGTGACCGTGAGTAGT

GGTGGTGGTGGCAGCGGTGGTGGCGGTAGTGGTGGTGCTGGCAGTGAACTGGT

TATGACCCAGAGTCCGGACAGTCTGGCAGTGAGCCTGGGCGAGCGTGCAACCA

TCAACTGTAAGAGCAGTCAGAGCGTGCTGTATAGTAGCAACAATAAAAGCTAT

CTGGCCTGGTATCAGCAGAAGCCGGGTCAGCCGCCTAAGCTGCTGATTTATTGG

GCCAGACCCGCGAAAGCGGTGTTCCGGATCGCTTTAGCGGTAGCGGCAGCGG

TACCGATTTCACCCTGACCATCAGCAGCCTGCAGGCCGAAGATGTGGCCGTGTA

TTATTGCCAGCAGTACTACAGCGCCCCGCTGACCTTTGGTGGCGGTACCAAGGT

GGAAATTAAAGGCGGCAGTGCCGTAGTGCCGGTAGTGCAGGTAGCGGCGGTA

GCGATATCCAGATGACCCAGAGTCCGAGTAGTCTGAGCGCCAGCGTTGGTGAC

CGCGTTACCATCACCTGCAAGGCCAGCCAGGATGTTACCACCGCCGTGGCCTGG

TATCAACAGAAACCGGGCAAGGCCCCGAAGCTGCTGATTTATTGGGCCSGTAC

ACGCCATACAGGCGTGCCGAGCCGTTTTAGTGGCAGCGGTAGCGGTACCGACTT
```

```
CACCCTGACCATCAGTAGCCTGCAACCGGAGGATTTCGCGACCTACTACTGCCA

GCAGCACTACAGCACCCCGCTGACCTTTGGCCAAGGTACCAAGGTGGAGATTA

AG
```

Combined (SEQ ID NO: 11 and 12):
```
gaagttcagttactggaaagtggcggcggcctggttaaaccgggtggtagcctgcgtctg
 E   V   Q   L   L   E   S   G   G   G   L   V   K   P   G   G   S   L   R   L agttgcgcagcaagcggcttcaccctgatcaactatcgcatgaactgggtgcgccaagca
 S   C   A   A   S   G   F   T   L   I   N   Y   R   M   N   W   V   R   Q   A ccgggtaagggtctggagtgggtgagcagcatcagcagcagcagctacatccactac
 P   G   K   G   L   E   W   V   S   S   I   S   S   S   S   Y   I   H   Y gcagacagcgttaaaggccgcttcaccattagccgcgataacgccgaaaacagcctgtac
 A   D   S   V   K   G   R   F   T   I   S   R   D   N   A   E   N   S   L   Y ctgcagatgaacagtctaagggcggaggataccgcagtgtactactgcgttcgtgaaggc
 L   Q   M   N   S   L   R   A   E   D   T   A   V   Y   Y   C   V   R   E   G ccgcgtgcaaccggctatagcatggccgacgtttttgatatttggggccagggcaccatg
 P   R   A   T   G   Y   S   M   A   D   V   F   D   I   W   G   Q   G   T   M gtgaccgtgagtagtggtggtggtggcagcggtggtggcggtagtggtggtggtggcagt
 V   T   V   S   S   G   G   G   G   S   G   G   G   G   S   G   G   G   G   S gaactggttatgacccagagtccggacagtctggcagtgagcctgggcgagcgtgcaacc
 E   L   V   M   T   Q   S   P   D   S   L   A   V   S   L   G   E   R   A   T atcaactgtaagagcagtcagagcgtgctgtatagtagcaacaataaaagctatctggcc
 I   N   C   K   S   S   Q   S   V   L   Y   S   S   N   N   K   S   Y   L   A tggtatcagcagaagccgggtcagccgcctaagctgctgatttattgggccagcacccgc
 W   Y   Q   Q   K   P   G   Q   P   P   K   L   L   I   Y   W   A   S   T   R gaaagcggtgttccggatcgctttagcggtagcggcagcggtaccgatttcacccTgacc
 E   S   G   V   P   D   R   F   S   G   S   G   S   G   T   D   F   T   L   T atcagcagcctgcaggccgaagatgtggccgtgtattattgccagcagtactacagcgcc
 I   S   S   L   Q   A   E   D   V   A   V   Y   Y   C   Q   Q   Y   Y   S   A ccgctgacctttggtggcggtaccaaggtggaaattaaaggcggcagtgccggtagtgcc
 P   L   T   F   G   G   G   T   K   V   E   I   K   G   G   S   A   G   S   A ggtagtgcaggtagcggcggtagcgatatccagatgacccagagtccgagtagtctgagc
 G   S   A   G   S   G   G   S   D   I   Q   M   T   Q   S   P   S   S   L   S gccagcgttggtgaccgcgttaccatcacctgcaaggccagccaggatgttaccaccgcc
 A   S   V   G   D   R   V   T   I   T   C   K   A   S   Q   D   V   T   T   A gtggcctggtatcaacagaaaccgggcaaggccccgaagctgctgatttattgggccagt
 V   A   W   Y   Q   Q   K   P   G   K   A   P   K   L   L   I   Y   W   A   S acacgccatacaggcgtgccgagccgttttagtggcagcggtagcggtaccgacttcacc
 T   R   H   T   G   V   P   S   R   F   S   G   S   G   S   G   T   D   F   T ctgaccatcagtagcctgcaaccggaggatttcgccacctactactgccagcagcactac
 L   T   I   S   S   L   Q   P   E   D   F   A   T   Y   Y   C   Q   Q   H   Y agcacccCgctgacctttggccaaggtaccaaggtggagattaag
 S   T   P   L   T   F   G   Q   G   T   K   V   E   I   K
```

F4-KZ52 HC C' Fusion Sequence:
Amino Acid (SEQ ID NO: 13):
EVQLVESGGGLVQPGGSLRLSCAASGFAFNYYDMFWVRQAPGKGLEW

VAYIKPGGGNTYYADSVKGFTISADTSKNTAYLQMNSLRAEDTAVYYCARQLYG

NSFFDYWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDK

KVEPKSCDKFHTCDKTHFCPPCPAPELLGRPSVFLFPPKPKDTLMISRTPEVTCVVV

DVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPS

-continued

```
DIAVEWESNGQPENNYKTTPPVLDSDGSFFLYSKLTVDKSRWQQGNVFSCSVMHE
ALHNHYTQKSLSLSPGKGGSAGSAGSAGSGGSEVQLLESGGGLVKPGGSLRLSCA
ASGFTLINYRMNWVRQAPGKGLEWVSSISSSSSYIHYADSVKGRFTISRDNAENSLY
LQMNSLRAEDTAVYYCVREGPRATGYSMADVFDIWGQGTMVTVSSGGGGSGGG
GSGGGGSELVMTQSPDSLAVSLGERATINCKSSQSVLYSSNNKSYLAWYQQKPGQP
PKLLIYWASTRESGVPDRFSGSGSGTDFTLTISSLQAEDVAVYYCQQYYSAPLTFGG
GTKVEIK
```

Underlined region is glycine-rich linker polypeptide. Bold region is fusion linker polypeptide.

```
Nucleotide (SEQ ID NO: 14):
GAAGTTCAACTGGTTGAGAGTGGCGGTGGCTTAGTTCAACCGGGCGGTAGTTTA
CGCCTGAGTTGTGCAGCCAGCGGTTTCGCCTTCAACTATTATGACATGTTTTGGG
TGCGCCAGGCACCGGGTAAAGGCCTGGAGTGGGTGGCCTATATCAAACCXGGGC
GGTGGCAACACCTATTACGCCGATAGCGTGAAAGGTCGCTTTACCATCAGCGCA
GATACCAGCAAGAATACCGCCTACCTGCAGATGAATAGCCTGCGTGCCGAAGA
CACCGCCGTTTATATTGCGCCCGCCAGCTGTACGGCAATAGCTTTTTCGATTAC
TGGGGCCAGGGCACCCTGGTTACCGTTAGCAGCGCTAGCACCAAGGGTCCGAG
CGTGTTTCCTCTGGCACCTAGCAGTAAAAGCACCAGTGGTGGTACAGCAGCCCT
GGGTTGCCTGGTGAAGGATTACTTTCCGGAGCCGGTGACCGTTAGTTGGAATAG
CGGCGCCCTGACCAGTGGCGTTCATACATTTCCGGCCGTGCTGCAGAGTAGTGG
CCTGTACAGCCTGAGTAGCGTTGT1ACCGTTCCGAGCAGCAGCCTGGGCACCCA
GACCTATATTTGCAATGTTAACCATAAACCGAGCAACACAAAAGTTGATAAAA
AAGTTGAACCGAAGAGCTGTGACAAAACCCATACATGTGACAAAACACACACC
TGCCCGCCTTGTCCGGCACCTGAGCTCGTGGGTCGCCCGAGCGTTTTTCTGTTTC
CTCCGAAACCGAAAGACACCCTGATGATCAGCCGCACACCTGAGGTGACCTGT
GTTGTGGTGGATGTGAGCCACGAAGATCCTGAAGTTAAGTTTAACTGGTATGTG
GATGGCGTGGAGGTGCATAATGCCAAGACAAAGCCGCGTGAAGAGCAGTACAA
CAGCACCTATCGTGTTGTTAGTGTGCTGACCGTTCTGCACCAAGATTGGCTGAA
CGGCAAGGAGTATAAATGCAAGGTTAGCAATAAAGCCCTGCCGGCCGCGATCG
AGAAGACCATCAGCAAAGCCAAAGGTCAGCCGCGTGAGCCTCAGGTGTATACA
CTGCCGCCTAGCCGTGAGGAGATGACCAAGAATCAGGTTAGCCIGACCTGTCTG
GTGAAAGGCTTTTACCCGAGCGATATCGCCGTTGAGTGGGAAAGCAATGGTCA
GCCTGAGAACAACTACAAGACCACCCCGCCTGTTTTAGACAGTGATGGTAGCTT
TTTCTTATACAGCAAACTGACCGTTGATAAGAGCCGCTGGCAGCAGGGCAATGT
GTTTAGCTGCAGTGTTATGCATGAGGCCCTGCATAACCACTATACCCAGAAGAG
TCTGAGCCTGAGTCCTGGCAAAGGTGGATCCGCCGGTAGCGCAGGTAGTGCAG
GTAGTGGCGGCAGCGAAGTTCAGCTGTTAGAAAGTGGCGGTGGTCTGGTTAAG
CCGGGCGGTAGTCTGCGCCTGAGCTGTGCAGCAAGTGGTTTCACCCTGATCAAT
TATCGTATGAACTGGGTGCGCCAAGCCCCGGGTAAAGGTCTGGAGTGGGTTAGT
AGTATCAGCAGCAGCAGCAGTTACATCCACTATGCCGATAGCGTTAAGGGCCG
```

-continued

```
CTTTACAATCAGCCGCGATAATGCCGAGAATAGCTTATACCTGCAAATGAACAG

TCTAAGGGCGGAAGATACCGCCGTTTACTACTGCGTTCGTGAAGGCCCTCGCGC

AACAGGCTATAGCATGGCAGACGTGTTCGACATTTGGGGTCAGGGGACCATGG

TGACCGTTAGTAGCGGCGGTGGTGGTAGTGGTGGTGGCGGTAGTGGTGGCGGT

GGCAGCGAACTGGTGATGACCCAGAGTCCGGATAGCCTGGCCGTGAGCTTAGG

CGAGCGTGCAACCATTAATTGTAAAAGCAGTCAGAGTGTTCTGTATAGTAGCAA

TAACAAGAGCTATCTGGCCTGGTATCAGCAGAAGCCGGGCCAGCCGCCGAAAC

TGCTGATTTACTGGGCAAGCACCCGCGAAAGTGGCGTGCCTGATCGCTTTAGTG

GTAGCGGCAGCGGCACCGATTTTACCCTGACCATTAGCAGTCTGCAGGCCGAGG

ACGTTGCCGTTTATTACTGCCAGCAGTACTATAGCGCACCGCTGACATTTGGCG

GTGGCACCAAGGTGGAAATTAAATAA
```

Combined (SEQ ID NO: 13 and 14):

```
gaagttcaactggttgagagtggcggtggcttagttcaaccgggcggtagtttacgcctg
 E   V   Q   L   V   E   S   G   G   G   L   V   Q   P   G   G   S   L   R   L agttgtgcagccagcggtttcgccttcaactattatgacatgttttgggtgcgccaggca
 S   C   A   A   S   G   F   A   F   N   Y   Y   D   M   F   W   V   R   Q   A ccgggtaaaggcctggagtgggtggcctatatcaaaccgggcggtggcaacacctattac
 P   G   K   G   L   E   W   V   A   Y   I   K   P   G   G   G   N   T   Y   Y gccgatagcgtgaaaggtcgctttaccatcagcgcagataccagcaagaataccgcctac
 A   D   S   V   K   G   R   F   T   I   S   A   D   T   S   K   N   T   A   Y ctgcagatgaatagcctgcgtgccgaagacaccgccgtttattattgcgcccgccagctg
 L   Q   M   N   S   L   R   A   E   D   T   A   V   Y   Y   C   A   R   Q   L tacggcaatagcttttttcgattactggggccagggcaccctggttaccgttagcagcgct
 Y   G   N   S   F   F   D   Y   W   G   Q   G   T   L   V   T   V   S   S   A agcaccaagggtccgagcgtgtttcctctggcacctagcagtaaaagcaccagtggtggt
 S   T   K   G   P   S   V   F   P   L   A   P   S   S   K   S   T   S   G   G acagcagccctgggttgcctggtgaaggattactttccggagccggtgaccgttagttgg
 T   A   A   L   G   C   L   V   K   D   Y   F   P   E   P   V   T   V   S   W aatagcggcgccctgaccagtggcgttcatacatttccggccgtgctgcagagtagtggc
 N   S   G   A   L   T   S   G   V   H   T   F   P   A   V   L   Q   S   S   G ctgtacagcctgagtagcgttgttaccgttccgagcagcagcctgggcacccagacctat
 L   Y   S   L   S   S   V   V   T   V   P   S   S   S   L   G   T   Q   T   Y atttgcaatgttaaccataaaccgagcaacacaaaagttgataaaaaagttgaaccgaag
 I   C   N   V   N   H   K   P   S   N   Y   K   V   D   K   K   V   E   P   K agctgtgacaaaacccatacatgtgacaaaacacacacctgcccgccttgtccggcacct
 S   C   D   K   T   H   T   C   D   K   T   H   T   C   P   P   C   P   A   P gagctgctgggtcgcccgagcgttttttctgtttcctccgaaaccgaaagacacccctgatg
 E   L   L   G   R   P   S   V   F   L   F   P   P   K   P   K   D   T   L   M atcagccgcacacctgaggtgacctgtgttgtggtggatgtgagccacgaagatcctgaa
 I   S   R   T   P   E   V   T   C   V   V   V   D   V   S   H   E   D   P   E gttaagtttaactggtatgtggatggcgtggaggtgcataatgccaagacaaagccgcgt
 V   K   F   N   W   Y   V   D   G   V   E   V   H   N   A   K   T   K   P   R gaagagcagtacaacagcacctatcgtgttgttagtgtgctgaccgttctgcaccaagat
 E   E   Q   Y   N   S   T   Y   R   V   V   S   V   L   T   V   L   H   Q   D tggctgaacggcaaggagtatatgcaaggttagcaataaagccctgccggcccccgatc
 W   L   N   G   K   E   Y   K   C   K   V   S   N   K   A   L   P   A   P   I gagaagaccatcagcaaagccaaaggtcagccgcgtgagcctcaggtgtatacactgccg
 E   K   T   I   S   K   A   K   G   Q   P   R   E   P   Q   V   Y   T   L   P
```

```
cctagccgtgaggagatgaccaagaatcaggttagcctgacctgtctggtgaaaggcttt
 P   S   R   E   E   M   T   K   N   Q   V   S   L   T   C   L   V   K   G   F tacccgagcgatatcgccgttgagtgggaaagcaatggtcagcctgagaacaactacaag
 Y   P   S   D   I   A   V   E   W   E   S   N   G   Q   P   E   N   N   Y   K accaccccgcctgttttagacagtgatggtagcttttcttatacagcaaactgaccgtt
 T   T   P   P   V   L   D   S   D   G   S   F   F   L   Y   S   K   L   T   V gataagagccgctggcagcagggcaatgtgtttagctgcagtgttatgcatgaggccctg
 D   K   S   R   W   Q   Q   G   N   V   F   S   C   S   V   M   H   E   A   L cataaccactatacccagaagagtctgagcctgagtcctggcaaaggtggatccgccggt
 H   N   H   Y   T   Q   K   S   L   S   L   S   P   G   K   G   G   S   A   G agcgcaggtagtgcaggtagtggcggcagcgaagttcagctgttagaaagtggcggtggt
 S   A   G   S   A   G   S   G   G   S   E   V   Q   L   L   E   S   G   G   G ctggttaagccgggcggtagtctgcgcctgagctgtgcagcaagtggtttcaccctgatc
 L   V   K   P   G   G   S   L   R   L   S   C   A   A   S   G   F   T   L   I aattatcgtatgaactgggtgcgccaagccccgggtaaaggtctggagtgggttagtagt
 N   Y   R   M   N   W   V   R   Q   A   P   G   K   G   L   E   W   V   S   S atcagcagcagcagcagttacatccactatgccgatagcgttaagggccgctttacaatc
 I   S   S   S   S   S   Y   I   H   T   A   D   S   V   K   G   R   F   T   I agccgcgataatgccgagaatagcttatacctgcaaatgaacagtctaagggcggaagat
 S   R   D   N   A   E   N   S   L   Y   L   Q   M   N   S   L   R   A   E   D accgccgtttactactgcgttcgtgaaggccctcgcgcaacaggctatagcatggcagac
 T   A   V   Y   Y   C   V   R   E   G   P   R   A   T   G   Y   S   M   A   D gtgttcgacatttggggtcagggcaccatggtgaccgttagtagcggcggtggtggtagt
 V   F   D   I   W   G   Q   G   T   M   V   T   V   S   S   G   G   G   G   S ggtggtggcggtagtggtggcggtggcagcgaactggtgatgacccagagtccggatagc
 G   G   G   G   S   G   G   G   G   S   E   L   V   M   T   Q   S   P   D   S ctggccgtgagcttaggcgagcgtgcaaccattaattgtaaaagcagtcagagtgttctg
 L   A   V   S   L   G   E   R   A   T   I   N   C   K   S   S   Q   S   V   L tatagtagcaataacaagagctatctggcctggtatcagcagaagccgggccagccgccg
 Y   S   S   N   N   K   S   Y   L   A   W   Y   Q   Q   K   P   G   Q   P   P aaactgctgatttactgggcaagcacccgcgaaagtggcgtgcctgatcgctttagtggt
 K   L   L   I   Y   W   A   S   T   R   E   S   G   V   P   D   R   F   S   G agcggcagcggcaccgattttacccctgaccattagcagtctgcaggccgaggacgttgcc
 S   G   S   G   T   D   F   T   L   T   I   S   S   L   Q   A   E   D   V   A gtttattactgccagcagtactatagcgcaccgctgacatttggcggtggcaccaaggtg
 V   Y   Y   C   Q   Q   Y   Y   S   A   P   L   T   F   G   G   G   T   K   V gaaattaaataa
 E   I   K   -

F4-KZ52 LC C' Fusion Sequence:
Amino Acid (SEQ ID NO: 15):
DIQMTQSPSSLSASVGDRVTITCKASQDVTTAVAWYQQKPGKAPKLLIY

WASTRHTGVPSRFSGSGSGTDFTLTISSLQPEDFATYYCQQHYSTPLTFGQGTKVEI

KRTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGECGGSG

GSAGSAGSAGSGGSEVQLLESGGGLVKPGGSLRLSCAASGFTLINYRMNWVRQAP

GKGLEWVSSISSSSSYIHYADSVKGRFTISRDNAENSLYLQMNSLRAEDTAVYYCV

REGPRATGYSMADVFDIWGQGTMVTVSSGGGGSGGGGSGGGGSELVMTQSPPSL

AVSLGERATINCKSSQSVLYSSNNKSYLAWYQQKPGQPPKLLIYWASTRESGVPDR

FSGSGSGTDFTLTISSLQAEDVAVYYCQQYYSAPLTFGGGTKVEIK
```

Underlined region is glycine-rich linker polypeptide. Bold region is fusion linker polypeptide.

```
Nucleotide (SEQ ID NO: 16):
GACATTCAGATGACCCAAAGTCCGAGCAGCCTGAGTGCCAGTGTTGGTGATCGC

GTGACAATCACATGCAAGGCCAGTCAGGACGTGACCACCGCAGTGGCCTGGTA

TCAGCAGAAACCGGGTAAGGCCCCGAAGCTGCTGATCTATTGGGCCAGTACCC

GCCACACCGGTGTTCCTAGTCGCTTCAGTGGCAGTGGCAGCGGCACAGATTTCA

CCCTGACCATCAGCAGCCTGCAACCGGAAGATTTTGCCACCTACTACTGCCAGC

AGCACTATAGCACCCCGCTGACCTTTGGCCAGGGCACCAAGGTTGAGATTAAAC

GTACGGTGGCAGCACCGAGCGTGTTTATCTTTCCGCCGAGCGACGAACAACTGA

AAAGTGGCACAGCCAGCGTGGTGTGTTTACTGAACAACTTCTATCCTCGCGAGG

CCAAGGTGCAGTGGAAAGTGGACAATGCACTGCAGAGTGGCAATAGCCAGGAG

AGCGTGACCGAACAGGATAGCAAAGATAGCACCTATAGCCTGAGTAGCACCCT

GACCCTGAGCAAGGCCGATTATGAGAAGCACAAGGTGTATGCATGCGAGGTTA

CCCATCAGGGCCTGAGCAGCCCGGTGACCAAAAGCTTTAACCGTGGCGAATGC

GGTGGTAGTGGTGGATCCGCCGGTAGCGCAGGTAGTGCAGGTAGTGGCGGCAG

CGAAGTTCAGCTGTTAGAAAGTGGCGGTGGTCTGGTTAAGCCGGGCGGTAGTCT

GCGCCTGAGCTGTGCAGCAAGTGGTTTCACCCTGATCAATTATCGTATGAACTG

GGTGCGCCAAGCCCCGGGTAAAGGTCTGGAGTGGGTTAGTAGTATCAGCAGCA

GCAGCAGTTACATCCACTATGCCGATAGCGTTAAGGGCCGCTTTACAATCAGCC

GCGATAATGCCGAGAATAGCTTATACCTGCAAATGAACAGTCTAAGGGCGGAA

GATACCGCCGTTTACTACTGCGTTCGTGAAGGCCCTCGCGCAACAGGCTATAGC

ATGGCAGACGTGTTCGACATTTGGGGTCAGGGCACCATGGTGACCGTTAGTAGC

GGCGGTGGTGGTAGTGGTGGTGGCGGTAGTGGTGGCGGTGGCAGCGAACTGGT

GATGACCCAGAGTCCGGATAGCCTGGCCGTGAGCTTAGGCGAGCGTGCAACCA

TTAATTGTAAAAGCAGTCAGAGTGTTCTGTATAGTAGCAATAACAAGAGCTATC

TGGCCTGGTATCAGCAGAAGCCGGGCCAGCCGCCGAAACTGCTGATTTACTGG

GCAAGCACCCGCGAAAGTGGCGTGCCTGATCGCTTTAGTGGTAGCGGCAGCGG

CACCGATTTTACCCTGACCATTAGCAGTCTGCAGGCCGAGGACGTTGCCGTTTA

TTACTGCCAGCAGTACTATAGCGCACCGCTGACATTTGGCGGTGGCACCAAGGT

GGAAATTAAATAA

Combined (SEQ ID NO: 15 and 16):
gacattcagatgacccaaagtccgagcagcctgagtgccagtgttggtgatcgcgtgaca
 D   I   Q   M   T   Q   S   P   S   S   L   S   A   S   V   G   D   R   V   T atcacatgcaaggccagtcaggacgtgaccaccgcagtggcctggtatcagcagaaaccg
 I   T   C   K   A   S   Q   D   V   T   T   A   V   A   W   Y   Q   Q   K   P ggtaaggccccgaagctgctgatctattgggccagtacccgccacaccggtgttcctagt
 G   K   A   P   K   L   L   I   Y   W   A   S   T   R   H   T   G   V   P   S cgcttcagtggcagtggcagcggcacagatttcaccctgaccatcagcagcctgcaaccg
 R   F   S   G   S   G   S   G   T   D   F   T   L   T   I   S   S   L   Q   P gaagattttgccacctactactgccagcagcactatagcaccccgctgacctttggccag
 E   D   F   A   T   Y   Y   C   Q   Q   H   Y   S   T   P   L   T   F   G   Q ggcaccaaggttgagattaaacgtacggtggcagcaccgagcgtgtttatctttccgccg
 G   T   K   V   E   I   K   R   T   V   A   A   P   S   V   F   I   F   P   P agcgacgaacaactgaaaagtggcacagccagcgtggtgtgtttactgaacaacttctat
 S   D   E   Q   L   K   S   G   T   A   S   V   V   C   L   L   N   N   F   Y
```

```
cctcgcgaggccaaggtgcagtggaaagtggacaatgcactgcagagtggcaatagccag
 P   R   E   A   K   V   Q   W   K   V   D   N   A   L   Q   S   G   N   S   Q gagagcgtgaccgaacaggatagcaaagatagcacctatagcctgagtagcaccctgacc
 E   S   V   T   E   Q   D   S   K   D   S   T   Y   S   L   S   S   T   L   T ctgagcaaggccgattatgagaagcacaaggtgtatgcatgcgaggttacccatcagggc
 L   S   K   A   D   Y   E   K   H   K   V   Y   A   C   E   V   T   H   Q   G ctgagcagcccggtgaccaaaagctttaaccgtggcgaatgcggtggtagtggtggatcc
 L   S   S   P   V   T   K   S   F   N   R   G   E   C   G   G   S   G   G   S gccggtagcgcaggtagtgcaggtagtggcggcagcgaagttcagctgttagaaagtggc
 A   G   S   A   G   S   A   G   S   G   G   S   E   V   Q   L   L   E   S   G ggtggtctggttaagccgggcggtagtctgcgcctgagctgtgcagcaagtggtttcacc
 G   G   L   V   K   P   G   G   S   L   R   L   S   C   A   A   S   G   F   T ctgatcaattatcgtatgaactgggtgcgccaagccccgggtaaaggtctggagtgggtt
 L   I   N   Y   R   M   N   W   V   R   Q   A   P   G   K   G   L   E   W   V agtagtatcagcagcagcagcagttacatccactatgccgatagcgttaagggccgcttt
 S   S   I   S   S   S   S   S   Y   I   H   Y   A   D   S   V   K   G   R   F acaatcagccgcgataatgccgagaatagcttatacctgcaaatgaacagtctaagggcg
 T   I   S   R   D   N   A   E   N   S   L   Y   L   Q   M   N   S   L   R   A gaagataccgccgtttactactgcgttcgtgaaggccctcgcgcaacaggctatagcatg
 E   D   T   A   V   Y   Y   C   V   R   E   G   P   R   A   T   G   Y   S   M gcagacgtgttcgacatttggggtcagggcaccatggtgaccgttagtagcggcggtggt
 A   D   V   F   D   I   W   G   Q   G   T   M   V   T   V   S   S   G   G   G ggtagtggtggtggcggtagtggtggcggtggcagcgaactggtgatgacccagagtccg
 G   S   G   G   G   G   S   G   G   G   G   S   E   L   V   M   T   Q   S   P gatagcctggccgtgagcttaggcgagcgtgcaaccattaattgtaaaagcagtcagagt
 D   S   L   A   V   S   L   G   E   R   A   T   I   N   C   K   S   S   Q   S gttctgtatagtagcaataacaagagctatctggcctggtatcagcagaagccgggccag
 V   L   Y   S   S   N   N   K   S   Y   L   A   W   Y   Q   Q   K   P   G   Q ccgccgaaactgctgatttactgggcaagcacccgcgaaagtggcgtgcctgatcgcttt
 P   P   K   L   L   I   Y   W   A   S   T   R   E   S   G   V   P   D   R   F agtggtagcggcagcggcaccgatttttaccctgaccattagcagtctgcaggccgaggac
 S   G   S   G   S   G   T   D   F   T   L   T   I   S   S   L   Q   A   E   D gttgccgtttattactgccagcagtactatagcgcaccgctgacatttggcggtggcacc
 V   A   V   Y   Y   C   Q   Q   Y   Y   S   A   P   L   T   F   G   G   T aaggtggaaattaaataa
 K   V   E   I   K   -

F4-2G4 LC N' Fusion Sequence:
Amino acid (SEQ ID NO: 17):
EVQLQESGGGLMQPGGSMKLSCVASGFTFSNYWMNWVRQSPEKGLEWVAEIRLK

SNNYATHYAESVKGRFTISRDDSKRSVYLQMNTLRAEDTGIYYCTRGNGNYRAMDYWGQGT

SVTVSSGGGGSGGGGSGGGGSDIQMTQSPASLSVSVGETVSITCRASENIYSSLAWYQQKQ

GKSPQLLVYSATILADGVPSRFSGSGSGTQYSLKINSLQSEDFGTYYCQHFWGTPYTFGGG

TKLEIKGGSAGSAGSAGSGGSDIQMTQSPSSLSASVGDRVTITCKASQDVTTAVAWYQQKP

GKAPKLLIYWASTRHTGVPSRFSGSGSGTDFTLTISSLQPEDFATYYCQQHYSTPLTFGQG

TKVEIK

Underlined region is glycine-rich linker polypeptide. Bold region
is fusion linker polypeptide.
Nucleotide (SEQ ID NO: 18):
GAAGTTCAGCTGCAGGAAAGCGGCGGTGGTCTGATGCAGCCTGGTGGCAGCATG

AAACTGAGCTGTGTGGCCAGCGGTTTCACCTTCAGCAACTATTGGATGAACTGGGTGCGTC

AGAGTCCGGAAAAAGGCCTGGAATGGGTTGCCGAGATCCGCCTGAAGAGTAACAACTATGC

CACCCATTACGCCGAGAGCGTGAAAGGTCGCTTTACCATCAGCCGTGATGACAGCAAACGC
```

-continued

```
AGCGTGTATCTGCAGATGAACACATTACGTGCTGAAGACACCGGTATCTACTATTGCACCC

GCGGCAACGGCAACTATCGCGCCATGGATTATTGGGGCCAGGGTACCAGCGTGACCGTTAG

TAGCGGCGGCGGTGGTAGTGGTGGTGGTGGTAGTGGCGGTGGCGGTAGCGACATTCAAATG

ACCCAGAGTCCTGCAAGCCTGAGCGTGAGCGTGGGTGAGACCGTGAGCATCACATGCGGCG

CCAGCGAGAACATTTATAGCAGCCTGGCCTGGTACCAGCAAAAACAGGGTAAAAGCCCGCA

GCTGCTGGTGTATAGCGCCACCATTCTGGCAGATGGTGTGCCGAGCCGTTTTAGTGGCAGT

GGCAGTGGTACCCAGTACAGCCTGAAAATCAACAGCCTGCAGAGCGAAGACTTCGGCACCT

ACTACTGTCAGCACTTTTGGGGCACCCCGTATACCTTTGGCGGCGGTACCAAGCTGGAAAT

CAAAGGTGGATCCGCAGGTAGCGCAGGCAGTGCAGGCAGCGGTGGTAGCGATATCCAGATG

ACCCAAAGCCCGAGCAGCTTAAGTGCCAGCGTGGGCGATCGCGTGACCATCACCTGCAAAG

CCAGTCAGGACGTTACCACAGCCGTGGCCTGGTATCAGCAGAAACCGGGTAAAGCCCCTAA

GCTGCTGATCTATTGGGCCAGCACCCGCCACACAGGTGTTCCGAGTCGTTTCAGCGGCAGC

GGTAGCGGTACCGATTTTACCCTGACCATCAGCAGCCTGCAGCCGGAAGACTTCGCAACAT

ACTACTGCCAGCAGCACTATTCTACCCCGCTGACATTCGGCCAGGGCACAAAAGTGGAGAT

TAAA
```

Combined (SEQ ID NO: 17 and 18):

```
gaagttcagctgcaggaaagcggcggtggtctgatgcagcctggtggcagcatgaaactg
 E   V   Q   L   Q   E   S   G   G   G   L   M   Q   P   G   G   S   M   K   L agctgtgtggccagcggtttcaccttcagcaactattggatgaactgggtgcgtcagagt
 S   C   V   A   S   G   F   T   F   S   N   Y   W   M   N   W   V   R   Q   S ccggaaaaaggcctggaatgggttgccgagatccgcctgaagagtaacaactatgccacc
 P   E   K   G   L   E   W   V   A   E   I   R   L   K   S   N   N   Y   A   T cattacgccgagagcgtgaaaggtcgctttaccatcagccgtgatgacagvaaacgcagc
 H   Y   A   E   S   V   K   G   R   F   T   I   S   R   D   D   S   K   R   S gtgtatctgcagatgaacacattacgtgctgaagacaccggtatctactattgcacccgc
 V   Y   L   Q   M   N   T   L   R   A   E   D   T   G   I   Y   Y   C   T   R ggcaacggcaactatcgcgccatggattattggggccagggtaccagcgtgaccgttagt
 G   N   G   N   Y   R   A   M   D   Y   W   G   Q   G   T   S   V   T   V   S agcggcggcggtggtagtggtggtggtggtagtggcggtggcggtagcgacattcaaatg
 S   G   G   G   G   S   G   G   G   G   S   G   G   G   G   S   D   I   Q   M acccagagtcctgcaagcctgagcgtgagcgtgggtgagaccgtgagcatcacatgccgc
 T   Q   S   P   A   S   L   S   V   S   V   G   E   T   V   S   I   T   C   R gccagcgagaacatttatagcagcctggcctggtaccagcaaaaacagggtaaaagcccg
 A   S   E   N   I   Y   S   S   L   A   W   Y   Q   Q   K   Q   G   K   S   P cagctgctggtgtatagcgccaccattctggcagatggtgtgccgagccgttttagtggc
 Q   L   L   V   Y   S   A   T   I   L   A   D   G   V   P   S   R   F   S   G agtggcagtggtacccagtacagcctgaaaatcaacagcctgcagagcgaagacttcggc
 S   G   S   G   T   Q   Y   S   L   K   I   N   S   L   Q   S   E   D   F   G acctactactgtcagcacttttggggcaccccgtatacctttggcggcggtaccaagctg
 T   Y   Y   C   Q   H   F   W   G   T   P   Y   T   F   G   G   G   T   K   L gaaatcaaaggtggatccgcaggtagcgcaggcagtgcaggcagcggtggtagcgatatc
 E   I   K   G   G   S   A   G   S   A   G   S   A   G   S   G   G   S   D   I cagatgacccaaagcccgagcagcttaagtgccagcgtgggcgatcgcgtgaccatcacc
 Q   M   T   Q   S   P   S   S   L   S   A   S   V   G   D   R   V   T   I   T tgcaaagccagtcaggacgttaccacagccgtggcctggtatcagcagaaaccgggtaaa
 C   K   A   S   Q   D   V   T   T   A   V   A   W   Y   Q   Q   K   P   G   K gcccctaagctgctgatctattgggccagcacccgccacacaggtgttccgagtcgtttc
 A   P   K   L   L   I   Y   W   A   S   T   R   H   T   G   V   P   S   R   F
```

```
agcggcagcggtagcggtaccgattttaccctgaccatcagcagcctgcagccggaagac
 S  G  S  G  S  G  T  D  F  T  L  T  I  S  S  L  Q  P  E  D ttcgcaacatactactgccagcagcactattctaccccgctgacattcggccagggcaca
 F  A  T  Y  Y  C  Q  Q  H  Y  S  T  P  L  T  F  G  Q  G  T aaagtggagattaaa
 K  V  E  I  K
```

E10-2G4 LC N' Fusion Sequence - Amino Acid (SEQ ID NO: 19):
EVQLQESGGGLMQPGGSMKLSCVASGFTFSNYWMNWVRQSPEKGLEWVAEIRLK

SNNYATHYAESVKGRFTISRDDSKRSVYLQMNTLRAEDTGIYYCTRGNGNYRAMDYWGQGT

SVTVSS<u>GGGGSGGGGSGGGGS</u>DIQMTQSPASLSVSVGETVSITCRASENIYSSLRWYQQKQ

GKSPQLLVYSATILADGVPSRFSGSGSGTQYSLKINSLQSEDFGTYYCQHFWGTPYTFGGG

TKLEIKGGSAGSAGSAGSGGSDIQMTQSPSSLSASVGDRVTITCRASQDVTTAVAWYQQKP

GKAPKLLIYWASRLHNGVPSRFSGSGSGTDFTLTISSLQPEDFATYYCQQHYSTPLTFGQG

TKVEIK

Underlined region is glycine-rich linker polypeptide. Bold region is fusion linker polypeptide.
Nucleotide (SEQ ID NO: 20):
GAAGTTCAGCTGCAGGAAAGCGGCGGTGGTCTGATGCAGCCTGGTGGCAGCATG

AAACTGAGCTGTGTGGCCAGCGGTTTTCACCTTCAGCAACTATTGGATGAACTGGGTGCGTC

AGAGTCCGGAAAAAGGCCTGGAATGGGTTGCCGAGATCCGCCTGAAGAGTAACAACTATGC

CACCCATTACGCCGAGAGCGTGAAAGGTCGCTTTACCATCAGCCGTGATGACAGCAAACGC

AGCGTGTATCTGCAGATGAACACATTACGTGCTGAAGACACCGGTATCTACTATTGCACCC

GCGGCAACGGCAACTATCGCGCCATGGATTATTGGGGCCAGGGTACCAGCGTGACCGTTAG

TAGCGGCGGCGGTGGTAGTGGTGGTGGTGGTAGTGGCGGTGGCGGTAGCGACATTCAAATG

ACCCAGAGTCCTGCAAGCCTGAGCGTGAGCGTGGGTGAGACCGTGAGCATCACATGCGGCG

CCAGCGAGAACATTTATAGCAGCCTGGCCTGGTACCAGCAAAAACAGGGTAAAAGCCCCGCA

GGTGCTGGTGTATAGCGCCACCATTCTGGCAGATGGTGTGCCGAGCCGTTTTAGTGGCAGT

GGCAGTGGTACCCAGTACAGCCTGAAAATCAACAGCCTGCAGAGCGAAGACTTCGGCACCT

ACTACTGTCAGCACTTTTGGGGCACCCCGTATACCTTTGGCGGCGGTACCAAGCTGGAAAT

CAAAGGTGGATCCGCCGGTAGCGCAGGTAGTGCCGGTAGCGGTGGCAGCGATATCCAAATG

ACCCAGAGCCCGAGTAGCCTGAGTGCAAGTGTGGGCGATCGCGTTACCATCACCTGTCGCG

CAAGCCAGGACGTGACAACCGCCGTGGCCTGGTATCAGCAGAAACCTGGTAAAGCCCCGAA

GCTGCTGATTTACTGGGCCAGCCGCCTGCACAATGGTGTTCCGAGTCGCTTTAGCGGCAGT

GGCAGCGGCACAGACTTTACACTGACCATTAGCAGCCTGCAGCCGGAGGATTTTGCCACCT

ATTATTGCCAGCAGCATTACAGTACACCGCTGACCTTCGGCCAGGGTACCAAAGTGGAAAT

CAAA

Combined (SEQ ID NO: 19 and 20):
```
gaagttcagctgcaggaaagcggcggtggtctgatgcagcctggtggcagcatgaaactg
 E  V  Q  L  Q  E  S  G  G  G  L  M  Q  P  G  G  S  M  K  L agctgtgtggccagcggtttcaccttcagcaactattggatgaactgggtgcgtcagagt
 S  C  V  A  S  G  F  T  F  S  N  Y  W  M  N  W  V  R  Q  S ccggaaaaaggcctggaatgggttgccgagatccgcctgaagagtaacaactatgccacc
 P  E  K  G  L  E  W  V  A  E  I  R  L  K  S  N  N  Y  A  T cattacgccgagagcgtgaaaggtcgctttaccatcagccgtgatgacagcaaacgcagc
 H  Y  A  E  S  V  K  G  R  F  T  I  S  R  D  D  S  K  R  S gtgtatctgcagatgaacacattacgtgctgaagacaccggtatctactattgcacccgc
 V  Y  L  Q  M  N  T  L  R  A  E  D  T  G  I  Y  Y  C  T  R
```

```
ggcaacggcaactatcgcgccatggattattgggccagggtaccagcgtgaccgttagt
 G  N  G  N  Y  R  A  M  D  Y  W  G  Q  G  T  S  V  T  V  S agcggcggcggtggtagtggtggtggtggtagtggcggtggcggtagcgacattcaaatg
 S  G  G  G  G  S  G  G  G  G  S  G  G  G  G  S  D  I  Q  M acccagagtcctgcaagcctgagcgtgagcgtgggtgagaccgtgagcatcacatgccgc
 T  Q  S  P  A  S  L  S  V  S  V  G  E  T  V  S  I  T  C  R gccagcgagaacatttatagcagcctggcctggtaccagcaaaaacagggtaaaagcccg
 A  S  E  N  I  Y  S  S  L  A  W  Y  Q  Q  K  Q  G  K  S  P cagctgctggtgtatagcgccaccattctggcagatggtgtgccgagccgttttagtggc
 Q  L  L  V  Y  S  A  T  I  L  A  D  G  V  P  S  R  F  S  G agtggcagtggtacccagtacagcctgaaaatcaacagcctgcagagcgaagacttcggc
 S  G  S  G  T  Q  Y  S  L  K  I  N  S  L  Q  S  E  D  F  G acctactactgtcagcacttttggggcaccccgtatacctttggcggcggtaccaagctg
 T  Y  Y  C  Q  H  F  W  G  T  P  Y  T  F  G  G  G  T  K  L gaaatcaaaggtggatccgccggtagcgcaggtagtgccggtagcggtggcagcgatatc
 E  I  K  G  G  S  A  G  S  A  G  S  A  G  S  G  G  S  D  I caaatgacccagagcccgagtagcctgagtgcaagtgtgggcgatcgcgttaccatcacc
 Q  M  T  Q  S  P  S  S  L  S  A  S  V  G  D  R  V  T  I  T tgtcgcgcaagccaggacgtgacaaccgccgtggcctggtatcagcagaaacctggtaaa
 C  R  A  S  Q  D  V  T  T  A  V  A  W  Y  Q  Q  K  P  G  K gccccgaagctgctgatttactgggccagccgcctgcacaatggtgttccgagtcgcttt
 A  P  K  L  L  I  Y  W  A  S  R  L  H  N  G  V  P  S  R  F agcggcagtggcagcggcacagactttacactgaccattagcagcctgcagccggaggat
 S  G  S  G  S  G  T  D  F  T  L  T  I  S  S  L  Q  P  E  D tttgccacctattattgccagcagcattacagtacaccgctgaccttcggccagggtacc
 F  A  T  Y  Y  C  Q  Q  H  Y  S  T  P  L  T  F  G  Q  G  T aaagtggaaatcaaa
 K  V  E  I  K F4-4G7 LC N' Fusion Sequence - Amino Acid (SEQ ID NO: 21):

EVQLQESGPELEMPGASVKISCKASGSSFTGFSMNWVKQSNGKSLEWIGNIDTY

YGGTTYNQKFKGKATLTVDKSSSTAYMQLKSLTSEDSAVYYCARSAYYGSTFAYWGQGTLV

TVSAGGGGSGGGGSGGGGSDIQMTQSPASLSASVGETVTITCRASENIYSYLAWYQQKQGK

SPQLLVYNAKTLIEGVPSRFSGSGSGTQFSLKINSLQPEDFGSYFCQHHFGTPFTFGSGTE

LEIKGGSAGSAGSAGSGGSDIQMTQSPSSLSASVGDRVTITCRASQDVTTAVAWYQQKPGK

APKLLIYWASRLHNGVPSRFSGSGSGTDFTLTISSLQPEDFATYYCQQHYSTPLTFGQGTK

VEIK
```

Underlined region is glycine-rich linker polypeptide. Bold region is fusion linker polypeptide.

```
Nucleotide (SEQ ID NO: 22):
GAGGTGCAGCTGCAAGAAAGTGGTCCGGAACTGGAAATGCCGGGTGCCAG

CGTGAAAATCAGCTGCAAAGCCAGCGGCAGTAGCTTTACCGGCTTTAGCA

TGAACTGGGTGAAACAGAGCAACGGCAAGAGCCTGGAGTGGATCGGCAAT

ATTGACACCTACTACGGCGGCACCACCTATAACCAGAAGTTCAAAGGCAA

AGCCACACTGACCGTGGACAAGAGTAGCAGTACAGCCTACATGCAGCTGA

AAAGCCTGACCAGCGAGGATAGCGCAGTGTATTACTGCGCACGCAGCGCC

TATTACGGCAGCACATTTGCCTACTGGGGTCAGGGTACCCTGGTGACAGT

TAGCGCAGGCGGTGGTGGCAGTGTGGTGGTGGTAGCGGTGGTGGTGGCAG

CGACATTCAAATGACACAGAGCCCGGCCAGTCTGAGTGCAAGCGTTGGCG

AAACCGTGACCATTACCTGCCGTGCCAGCGAGAACATCTATAGCTACCTG

GCCTGGTACCAGCAGAAGCAGGGTAAAAGCCCTCAGCTGCTGGTGTACAA

TGCCAAAACCCTGATCGAAGGCGTTCCGAGTCGCTTTAGTGGCAGCGGCA

GTGGCACCCAGTTCAGCCTGAAAATCAACAGCCTGCAACCGGAAGACTTT

GGCAGCTACTTCTGCCAGCACCATTTTGGCACACCGTTCACCTTCGGTAG

TGGCACCGAACTGGAGATTAAAGGTGGATCCGCAGGTAGCGCAGGCAGTG

CAGGCAGCGGTGGTAGCGATATCCAGATGACCCAAAGCCCGAGCAGCTTA

AGTGCCAGCGTGGGCGATCGCGTGACCATCACCTGCAAAGCCAGTCAGGA
```

-continued
```
CGTTACCACAGCCGTGGCCTGGTATCAGCAGAAACCGGGTAAAGCCCCTA

AGCTGCTGATCTATTGGGCCAGCACCCGCCACACAGGTGTTCCGAGTCGT

TTCAGCGGCAGCGGTAGCGGTACCGATTTTACCCTGACCATCAGCAGCCT

GCAGCCGGAAGACTTCGCAACATACTACTGCCAGCAGCACTATTCTACCC

CGCTGACATTCGGCCAGGGCACAAAAGTGGAGATTAAA
```

Combined (SEQ ID NO: 21 and 22):
```
gaggtgcagctgcaagaaagtggtccggaactggaaatgccgggtgccag
 E  V  Q  L  Q  E  S  G  P  E  L  E  M  P  G  A  S cgtgaaaatcagctgcaaagccagcggcagtagctttaccggctttagca
 V  K  I  S  C  K  A  S  G  S  S  F  T  G  F  S  M tgaactgggtgaaacagagcaacggcaagagcctggagtggatcggcaat
 N  W  V  K  Q  S  N  G  K  S  L  E  W  I  G  N attgacacctactacggcggcaccacctataaccagaagttcaaaggcaa
 I  D  T  Y  Y  G  G  T  T  Y  N  Q  K  F  K  G  K agccacactgaccgtggacaagagtagcagtacagcctacatgcagctga
 A  T  L  T  V  D  K  S  S  S  T  A  Y  M  Q  L  K aaagcctgaccagcgaggatagcgcagtgtattactgcgcacgcagcgcc
 S  L  T  S  E  D  S  A  V  Y  Y  C  A  R  S  A tattacggcagcacatttgcctactggggtcagggtaccctggtgacagt
 Y  Y  G  S  T  F  A  Y  W  G  Q  G  T  L  V  T  V tagcgcaggcggtggtggcagtggtggtggtggtagcggtggtggtggca
 S  A  G  G  G  G  S  G  G  G  G  S  G  G  G  G  S gcgacattcaaatgacacagagcccggccagtctgagtgcaagcgttggc
 D  I  Q  M  T  Q  S  P  A  S  L  S  A  S  V  G gaaaccgtgaccattacctgccgtgccagcgagaacatctatagctacct
 E  T  V  T  I  T  C  R  A  S  E  N  I  Y  S  Y  L ggcctggtaccagcagaagcagggtaaaagccctcagctgctggtgtaca
 A  W  Y  Q  Q  K  Q  G  K  S  P  Q  L  L  V  Y  N atgccaaaaccctgatcgaaggcgttccgagtcgctttagtggcagcggc
 A  K  T  L  I  E  G  V  P  S  R  F  S  G  S  G agtggcacccagttcagcctgaaaatcaacagcctgcaaccggaagactt
 S  G  T  Q  F  S  L  K  I  N  S  L  Q  P  E  D  F tggcagctacttctgccagcaccattttggcacaccgttcaccttcggta
 G  S  Y  F  C  Q  H  H  F  G  T  P  F  T  F  G  S gtggcaccgaactggagattaaaggtggatccgcaggtagcgcaggcagt
 G  T  E  L  E  I  K  G  G  S  A  G  S  A  G  S gcaggcagcggtggtagcgatatccagatgacccaaagcccgagcagctt
 A  G  S  G  G  S  D  I  Q  M  T  Q  S  P  S  S  L aagtgccagcgtgggcgatcgcgtgaccatcacctgcaaagccagtcagg
 S  A  S  V  G  D  R  V  T  I  T  C  K  A  S  Q  D acgttaccacagccgtggcctggtatcagcagaaacccgggtaaagcccct
 V  T  T  A  V  A  W  Y  Q  Q  K  P  G  K  A  P aagctgctgatctattgggccagcacccgccacacaggtgttccgagtcg
 K  L  L  I  Y  W  A  S  T  R  H  T  G  V  P  S  F tttcagcggcagcggtagcggtaccgattttaccctgaccatcagcagcc
 F  S  G  S  G  S  G  T  D  F  T  L  T  I  S  S  L tgcagccggaagacttcgcaacatactactgccagcagcactattctacc
 Q  P  E  D  F  A  T  Y  Y  C  Q  Q  H  Y  S  T ccgctgacattcggccagggcacaaaagtggagattaaa
 P  L  T  F  G  Q  G  T  K  V  E  I  K
```

E10-4G7 LC N' Fusion Sequence-Amino Acid
(SEQ ID NO: 23):
```
EVQLQESGPELEMPGASVKISCKASGSSFTGFSMNWVKQSNGKSLEWIGN

IDTYYGGTTYNQKFKGKATLTVDKSSSTAYMQLKSLTSEDSAVYYCARSA

YYGSTFAYWGQGTLTVSAGGGGSGGGGSGGGGSDIQMTQSPASLSASVGE

TVTITCRASENIYSYLAWYQQKQGKSPQLLVYNAKTLIEGVPSRFSGSGS

GTQFSLKINSLQPEDFGSYFCQHHFGTPFTFGSGTELEIKGGSAGSAGSA

GSGGSDIQMTQSPSSLSASVGDRVTITCRASQDVTTAVAWYQQKPGKAPK

LLIYWASRLHNGVPSRFSGSGSGTDFTLTISSLQPEDFATYYCQQHYSTP

LTFGQGTKVEIK
```

Underlined region is glycine-rich linker polypeptide. Bold region is fusion linker polypeptide.

Nucleotide (SEQ ID NO: 24):
```
GAGGTGCAGCTGCAAGAAAGTGGTCCGGAACTGGAAATGCCGGGTGCCAG

CGTGAAAATCAGCTGCAAAGCCAGCGGCAGTAGCTTTACCGGCTTTAGCA

TGAACTGGGTGAAACAGAGCAACGGCAAGAGCCTGGAGTGGATCGGCAAT

ATTGACACCTACTACGGCGGCACCACCTATAACCAGAAGTTCAAAGGCAA

AGCCACACTGACCGTGGACAAGAGTAGCAGTACAGCCTACATGCAGCTGA

AAAGCCTGACCAGCGAGGATAGCGCAGTGTATTACTGCGCACGCAGCGCC

TATTACGGCAGCACATTTTGCCTACTGGGGTCAGGGTACCCTGGTGACAG

TTAGCGCAGGCGGTGGTGGCAGTGGTGGTGGTGGTAGCGGTGGTGGTGGCA

AGCGACATTCAAATGACACAGAGCCCGGCCAGTCTGAGTGCAAGCGTTGG

CGAAACCGTGACCATTACCTGCCGTGCCAGCGAGAACATCTATAGCTACC

TGGCCTGGTACCAGCAGAAGCAGGGTAAAAGCCCTCAGCTGCTGGTGTAC

AATGCCAAAACCCTGATCGAAGGCGTTCCGAGTCGCTTTAGTGGCAGCGG

CAGTGGCACCCAGTTCAGCCTGAAAATCAACAGCCTGCAACCGGAAGACT

TTGGCAGCTACTTCTGCCAGCACCATTTTGGCACACCGTTCACCTTCGGT

AGTGGCACCGAACTGGAGATTAAAGGTGGATCCGCCGGTAGCGCAGGTAG

TGCCGGTAGCGGTGGCAGCGATATCCAAATGACCCAGAGCCCGAGTAGCC

TGAGTGCAAGTGTGGGCGATCGCGTTACCATCACCTGTCGCGCAAGCCAG

GACGTGACAACCGCCGTGGCCTGGTATCAGCAGAAACCTGGTAAAGCCCC

GAAGCTGCTGATTTACTGGGCCAGCCGCCTGCACAATGGTGTTCCGAGTC

GCTTTAGCGGCAGTGGCAGCGGCACAGACTTTACACTGACCATTAGCAGC

CTGCAGCCGGAGGATTTTGCCACCTATTATTGCCAGCAGCATTACAGTAC

ACCGCTGACCTTCGGCCAGGGTACCAAAGTGGAAATCAAA
```

Combined (SEQ ID NO: 23 and 24):
```
gaggtgcagctgcaagaaagtggtccggaactggaaatgccgggtgccag
 E  V  Q  L  Q  E  S  G  P  E  L  E  M  P  G  A  S cgtgaaaatcagctgcaaagccagcggcagtagctttaccggctttagca
 V  K  I  S  C  K  A  S  G  S  S  F  T  G  F  S  M tgaactgggtgaaacagagcaacggcaagagcctggagtggatcggcaat
 N  W  V  K  Q  S  N  G  K  S  L  E  W  I  G  N attgacacctactacggcggcaccacctataaccagaagttcaaaggcaa
 I  D  T  Y  Y  G  G  T  T  Y  N  Q  K  F  K  G  K
```

```
agccacactgaccgtggacaagagtagcagtacagcctacatgcagctga
 A  T  L  T  V  D  K  S  S  S  T  A  Y  M  Q  L  K aaagcctgaccagcgaggatagcgcagtgtattactgcgcacgcagcgcc
  S  L  T  S  E  D  S  A  V  Y  Y  C  A  R  S  A tattacggcagcacatttgcctactggggtcagggtaccctggtgacagt
 Y  Y  G  S  T  F  A  Y  W  G  Q  G  T  L  V  T  V tagcgcaggcggtggtggcagtggtggtggtggtagcggtggtggtggca
 S  A  G  G  G  G  S  G  G  G  G  S  G  G  G  G  S gcgacattcaaatgacacagagcccggccagtctgagtgcaagcgttggc
  D  I  Q  M  T  Q  S  P  A  S  L  S  A  S  V  G gaaaccgtgaccattacctgccgtgccagcgagaacatctatagctacct
 E  T  V  T  I  T  C  R  A  S  E  N  I  Y  S  Y  L ggcctggtaccagcagaagcagggtaaaagccctcagctgctggtgtaca
  A  W  Y  Q  Q  K  Q  G  K  S  P  Q  L  L  V  Y  N atgccaaaaccctgatcgaaggcgttccgagtcgctttagtggcagcggc
 A  K  T  L  I  E  G  V  P  S  R  F  S  G  S  G agtggcacccagttcagcctgaaaatcaacagcctgcaaccggaagactt
 S  G  T  Q  F  S  L  K  I  N  S  L  Q  P  E  D  F tggcagctacttctgccagcaccattttggcacaccgttcaccttcggta
  G  S  Y  F  C  Q  H  H  F  G  T  P  F  T  F  G  S gtggcaccgaactggagattaaaggtggatccgccggtagcgcaggtagt
  F  T  E  L  E  I  K  G  G  S  A  G  S  A  G  S gccggtagcggtggcagcgatatccaaatgacccagagcccgagtagcct
 A  G  S  G  G  S  D  I  Q  M  T  Q  S  P  S  S  L gagtgcaagtgtgggcgatcgcgttaccatcacctgtcgcgcaagccagg
  S  A  S  V  G  D  R  V  T  I  T  C  R  A  S  Q  D acgtgacaaccgccgtggcctggtatcagcagaaacctggtaaagccccg
 V  T  T  A  V  A  W  Y  Q  Q  K  P  G  K  A  P aagctgctgatttactgggccagccgcctgcacaatggtgttccgagtcg
 K  L  L  I  Y  W  A  S  R  L  H  N  G  V  P  S  R ctttagcggcagtggcagcggcacagactttacactgaccattagcagcc
  F  S  G  S  G  S  G  T  D  F  T  L  T  I  S  S  L tgcagccggaggattttgccacctattattgccagcagcattacagtaca
 Q  P  E  D  F  A  T  Y  Y  C  Q  Q  H  Y  S  T ccgctgaccttcggccagggtaccaaagtggaaatcaaa
 P  L  T  F  G  Q  G  T  K  V  E  I  K
```

F4-2G4 HC C' Fusion Sequence-Amino Acid
(SEQ ID NO: 25):
EVQLVESGGGLVQPGGSLRLSCAASGFAFNYYDMFWVRQAPGKGLEWVAY
IKPGGGNTYYADSVKGRFTISADTSKNTAYLQMNSLRAEDTAVYYCARQL
YGNSFFDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCDKTHTCPPCPAPELLGRPSVFL
FPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYK
TTPPVLDSDGSFFLYSKLTVDKSRWQQGNVFSCSVMHEALHNHYTQKSLS
LSPGKGGSAGSAGSAGSGGSEVQLQESGGGLMQPGGSMKLSCVASGFTFS
NYWMNWVRQSPEKGLEWVAEIRLKSNNYATHYAESVKGRFTISRDDSKRS
VYLQMNTLRAEDTGIYYCTRGNGNYRAMDYWGQGTSVTVSS<u>GGGGSGGGG</u>
<u>SGGGGS</u>DIQMTQSPASLSVSVGETVSITRVRASENIYSSLAWYQQKQGKS
PQLLVYSATILADGVPSRFSGSGSTQYSLKINSLQSEDFGTYYCQHFWGT
PYTFGGGTKLEIK Underlined region is glycine-rich linker polypeptide. Bold region is fusion linker polypeptide.

Nucleotide (SEQ ID NO: 26):
GAAGTTCAACTGGTTGAGAGTGGCGGTGGCTTAGTTCAACCGGGCGGTAG
TTTACGCCTGAGTTGTGCAGCCAGCGGTTTCGCCTTCAACTATTATGACA
TGTTTTGGGTGCGCCAGGCACCGGGTAAAGGCCTGGAGTGGGTGGCCTAT
ATCAAACCGGGCGGTGGCAACACCTATTACGCCGATAGCGTGAAAGGTCG
CTTTACCATCAGCGCAGATACCAGCAAGAATACCGCCTACCTGCAGATGA
ATAGCCTGCGTGCCGAAGACACCGCCGTTTATTATTGCGCCCGCCAGCTG
TACGGCAATAGCTTTTTCGATTACTGGGGCCAGGGCACCCTGGTTACCGT
TAGCAGCGCTAGCACCAAGGGTCCGAGCGTGTTTCCTCTGGCACCTAGCA
GTAAAAGCACCAGTGGTGGTACAGCAGCCCTGGGTTGCCTGGTGAAGGAT
TACTTTCCGGAGCCGGTGACCGTTAGTTGGAATAGCGGCGCCCTGACCAG
TGGCGTTCATACATTTCCGGCCGTGCTGCAGAGTAGTGGCCTGTACAGCC
TGAGTAGCGTTGTTACCGTTCCGAGCAGCAGCCTGGGCACCCAGACCTAT
ATTTGCAATGTTAACCATAAACCGAGCAACACAAAAGTTGATAAAAAAGT
TGAACCGAAGAGCTGTGACAAAACCCATACATGTGACAAAACACACACCT
GCCCGCCTTGTCCGGCACCTGAGCTGCTGGGTCGCCCGAGCGTTTTTCTG
TTTCCTCCGAAACCGAAAGACACCCTGATGATCAGCCGCACACCTGAGGT
GACCTGTGTTGTGGTGGATGTGAGCCACGAAGATCCTGAAGTTAAGTTTA
ACTGGTATGTGGATGGCGTGGAGGTGCATAATGCCAAGACAAAGCCGCGT
GAAGAGCAGTACAACAGCACCTATCGTGTTGTTAGTGTGCTGACCGTTCT
GCACCAAGATTGGCTGAACGGCAAGGAGTATAAATGCAAGGTTAGCAATA
AAGCCCTGCCGGCCCCGATCGAGAAGACCATCAGCAAAGCCAAAGGTCAG
CCGCGTGAGCCTCAGGTGTATACACTGCCGCCTAGCCGTGAGGAGATGAC
CAAGAATCAGGTTAGCCTGACCTGTCTGGTGAAAGGCTTTTACCCGAGCG
ATATCGCCGTTGAGTGGGAAAGCAATGGTCAGCCTGAGAACAACTACAAG
ACCACCCCGCCTGTTTTAGACAGTGATGGTAGCTTTTTCTTATACAGCAA
ACTGACCGTTGATAAGAGCCGCTGGCAGCAGGGCAATGTGTTTAGCTGCA
GTGTTATGCATGAGGCCCTGCATAACCACTATACCCAGAAGAGTCTGAGC
CTGAGTCCTGGCAAAGGTGGATCCGCAGGCAGTGCAGGTAGTGCCGGCAG
CGGTGGTAGTGAGGTTCAGCTGCAGGAAAGCGGCGGCGGCTTAATGCAGC
CTGGCGGTAGCATGAAGCTGAGCTGCGTGGCCAGCGGCTTCACCTTTAGC
AATTACTGGATGAACTGGGTGCGCCAGAGCCCGGAAAAAGGCCTGGAATG
GGTGGCAGAGATCCGTCTGAAGAGCAACAACTACGCCACCCACTATGCCG
AAAGCGTGAAGGGTCGCTTTACCATCAGCCGCGATGACAGCAAACGCAGC
GTGTATCTGCAGATGAACACCCTGCGTGCAGAGGACACCGGCATCTATTA
TTGCACCCGCGGCAACGGTAATTATCGCGCCATGGACTACTGGGGTCAGG

```
GTACCAGCGTGACCGTTAGCAGTGGCGGTGGTGGTAGCGGTGGTGGTGGT

AGCGGTGGTGGTGGCAGCGATATTCAAATGACCCAGAGCCCTGCCAGCCT

GAGCGTGAGTGTTGGCGAAACCGTGAGCATCACCTGCCGCGCCAGCGAGA

ACATCTATAGTAGCCTGGCCTGGTACCAGCAGAAACAGGGCAAAAGCCCG

CAGCTGCTGGTGTATAGCGCAACCATTCTGGCAGATGGCGTTCCGAGCCG

TTTTAGCGGTAGCGGCAGCGGCACACAGTACAGCCTGAAGATCAACAGCC

TGCAGAGCGAGGACTTTGGCACCTATTACTGCCAGCACTTTTGGGGTACC

CCGTATACCTTCGGCGGCGGCACCAAACTGGAAATTAAATAA
```

Combined (SEQ ID NO: 25 and 26):
```
gaagttcaactggttgagagtggcggtggcttagttcaacccgggcggtag
 E  V  Q  L  V  E  S  G  G  G  L  V  Q  P  G  G  S tttacgcctgagttgtgcagccagcggtttcgccttcaactattatgaca
 L  R  L  S  C  A  A  S  G  F  A  F  N  Y  Y  D  M tgttttgggtgcgccaggcaccgggtaaaggcctggagtgggtggcctat
 F  W  V  R  Q  A  P  G  K  G  L  E  W  V  A  Y atcaaaccgggcggtggcaacacctattacgccgatagcgtgaaaggtcg
 I  K  P  G  G  G  N  T  Y  Y  A  D  S  V  K  G  R ctttaccatcagccagataccagcaagaataccgcctacctgcagatga
 F  T  I  S  A  S  T  K  S  N  T  A  Y  L  Q  M  N atagcctgcgtgccgaagacaccgccgtttattattgcgcccgccagctg
 S  L  R  A  E  D  T  A  V  Y  Y  C  A  R  Q  L tacggcaatagcttttttcgattactggggccagggcacccttggttaccgt
 Y  G  N  S  F  F  D  Y  W  G  Q  G  T  L  V  T  V tagcagcgctagcaccaagggtccgagcgtgtttcctctggcacctagca
 S  S  A  S  T  K  G  P  S  V  F  P  L  A  P  S  S gtaaaagcaccagtggtgtacagcagccctgggttgcctggtgaaggat
 K  S  T  S  G  G  T  A  A  L  G  C  L  V  K  D tactttccggagccggtgaccgttagttggaatagcggcgccctgaccag
 Y  F  P  E  P  V  T  V  S  W  N  S  G  A  L  T  S tggcgttcatacatttccggccgtgctgcagagtagtggcctgtacagcc
 G  V  H  T  F  P  A  V  L  Q  S  S  G  L  Y  S  L tgagtagcgttgttaccgttccgagcagcagcctgggcacccagacctat
 S  S  V  V  T  V  P  S  S  S  L  G  T  Q  T  Y atttgcaatgttaaccataaaccgagcaacacaaaagttgataaaaaagt
 I  C  N  V  N  H  K  P  S  N  T  K  V  D  K  K  V tgaaccgaagagctgtgacaaaaaccatacatgtgacaaaacacacacctt
 E  P  K  S  C  D  K  T  H  T  C  D  K  T  H  T  C gcccgccttgtccggcacctgagctgctgggtcgcccgagcgttttttctg
 P  P  C  P  A  P  E  L  L  G  R  P  S  V  F  L tttcctccgaaaccgaaagacacccctgatgatcagccgcacacctgaggt
 F  P  P  K  P  K  D  T  L  M  I  S  R  T  P  E  V gacctgtgttgtggtggatgtgagccacgaagatcctgaagttaagttta
 T  C  V  V  V  D  V  S  H  E  D  P  E  V  K  F  N actggtatgtggatggcgtggaggtgcataatgccaagacaaagccgcgt
 W  Y  V  D  G  V  E  V  H  N  A  K  T  K  P  R gaagagcagtacaacagcacctatcgtgttgttagtgtgctgaccgttct
 E  E  Q  Y  N  S  T  Y  R  V  V  S  V  L  T  V  L gcaccaagattggctgaacggcaaggagtataaatgcaaggttagcaata
 H  Q  D  W  L  N  G  K  E  Y  K  C  K  V  S  N  K aagccctgccgcccccgatcgagaagaccatcagcaaagccaaaggtcag
 A  L  P  A  P  I  E  K  T  I  S  K  A  K  G  Q
```

```
ccgcgtgagcctcaggtgtatacactgccgcctagccgtgaggagatgac
 P  R  E  P  Q  V  Y  T  L  P  P  S  R  E  E  M  T caagaatcaggttagcctgacctgtctggtgaaaggcttttacccgagcg
 K  N  Q  V  S  L  T  C  L  V  K  G  F  Y  P  S  D atatcgccgttgagtgggaaagcaatggtcagcctgagaacaactacaag
 I  A  V  E  W  E  S  N  G  Q  P  E  N  N  Y  K accaccccgcctgtttttagacagtgatggtagcttttttcttatacagcaa
 T  T  P  P  V  L  D  S  D  G  S  F  F  L  Y  S  K actgaccgttgataagagccgctggcagcagggcaatgtgtttagctgca
 L  T  V  D  K  S  R  W  Q  Q  G  N  V  F  S  C  S gtgttatgcatgaggcccctgcataaccactatacccagaagagtctgagc
 V  M  H  E  A  L  H  N  H  Y  T  Q  K  S  L  S ctgagtcctggcaaaggtggatccgcaggcagtgcaggtagtgccggcag
 L  S  P  G  K  G  G  S  A  G  S  A  G  S  A  G  S cggtggtagtgaggttcagctgcaggaaagcggcggcggcttaatgcagc
 G  G  S  E  V  Q  L  Q  E  S  G  G  G  L  M  Q  P ctggcggtagcatgaagctgagctgcgtggccagcggcttcacctttagc
 G  G  S  M  K  L  S  C  V  A  S  G  F  T  F  S aattactggatgaactgggtgcgccagagcccggaaaaaggcctggaatg
 N  Y  W  M  N  W  V  R  Q  S  P  E  K  G  L  E  W ggtggcagagatccgtctgaagagcaacaactacgccacccactatgccg
 V  A  E  I  R  L  K  S  N  N  Y  A  T  H  Y  A  E aaagcgtgaagggtcgcttttaccatcagccgcgatgacagcaaacgcagc
 S  V  K  G  R  F  T  I  S  R  D  D  S  K  R  S gtgtatctgcagatgaacaccctgcgtgcagaggacaccggcatctatta
 V  Y  L  Q  M  N  T  L  R  A  E  D  T  G  I  Y  Y ttgcacccgcggcaacggtaattatcgcgccatggactactggggtcagg
 C  T  R  G  N  G  N  Y  R  A  M  D  Y  W  G  Q  G gtaccagcgtgaccgttagcagtggcggtggtggtagcggtggtggtggt
 T  S  V  T  V  S  S  G  G  G  G  S  G  G  G  G agcggtggtggtggcagcgatattcaaatgacccagagccctgccagcct
 S  G  G  G  G  S  D  I  Q  M  T  Q  S  P  A  S  L gagcgtgagtgttggcgaaaccgtgagcatcacctgccgcgccagcgaga
 S  V  S  V  G  E  T  V  S  I  T  C  R  A  S  E  N acatctatagtagcctggcctggtaccagcagaaacagggcaaaagcccg
 I  Y  S  S  L  A  W  Y  Q  Q  K  Q  G  K  S  P cagctgctggtgtatagcgcaaccattctggcagatggcgttccgagccg
 Q  L  L  V  Y  S  A  T  I  L  A  D  G  V  P  S  R ttttagcggtagcggcagcggcacacagtacagcctgaagatcaacagcc
 F  S  G  S  G  S  G  T  Q  Y  S  L  K  I  N  S  L tgcagagcgaggactttggcacctattactgccagcacttttggggtacc
 Q  S  E  D  F  G  T  Y  Y  C  Q  H  F  W  G  T ccgtataccttcggcggcggcaccaaactggaaattaaataa
 P  Y  T  F  G  G  G  T  K  L  E  I  K  -
```

F4-2G4 LC C' Fusion Sequence-Amino Acid
(SEQ ID NO: 27):

DIQMTQSPSSLSASVGDRVTITCKASQDVTTAVAWYQQKPGKAPKLLIYW

ASTRHTGVPSRFSGSGSGTDFTLTISSLQPEDFATYYCQQHYSTPLTFGQ

GTKVEIKRTVAAPSVFIFPPSDEQLKSGTASVVCLLNNFYPREAKVQWKV

DNALQSGNSQESVTEQDSKDSTYSLSSTLTSKADYEKHKVYACEVTHQGL

SSPVTKSFNRGECGGSGGSAGSAGSAGSGGSEVQLQESGGGLMQPGGSMK

LSCVASGFTFSNYWMNWVRQSPEKGLEWVAEIRLKSNNYATHYAESVKGR

RFTISRDDSKRSVYLQMNTLRAEDTGIYYCTRGNGNYRAMDYWGQGTSVT

-continued

VSS<u>GGGGSGGGGSGGGGS</u>DIQMTQSPASLSVSVGETVSITVRASENIYSS

LAWYQQKQGKSPQLLVYSATILADGVPSRFSGSGSGTQYSLKINSLQSED

FGTYYCQHFWGTPYTFGGGTKLEIK

Underlined region is glycine-rich linker polypeptide. Bold region is fusion linker polypeptide.

Nucleotide (SEQ ID NO: 28):
GACATTCAGATGACCCAAAGTCCGAGCAGCCTGAGTGCCAGTGTTGGTGA

TCGCGTGACAATCACATGCAAGGCCAGTCAGGACGTGACCACCGCAGTGG

CCTGGTATCAGCAGAAACCGGGTAAGGCCCCGAAGCTGCTGATCTATTGG

GCCAGTACCCGCCACACCGGTGTTCCTAGTCGCTTCAGTGGCAGTGGCAG

CGGCACAGATTTCACCCTGACCATCAGCAGCCTGCAACCGGAAGATTTTG

CCACCTACTACTGCCAGCAGCACTATAGCACCCCGCTGACCTTTGGCCAG

GGCACCAAGGTTGAGATTAAACGTACGGTGGCAGCACCGAGCGTGTTTAT

CTTTCCGCCGAGCGACGAACAACTGAAAAGTGGCACAGCCAGCGTGGTGT

GTTTACTGAACAACTTCTATCCTCGCGAGGCCAAGGTGCAGTGGAAAGTG

GACAATGCACTGCAGAGTGGCAATAGCCAGGAGAGCGTGACCGAACAGGA

TAGCAAAGATAGCACCTATAGCCTGAGTAGCACCCTGACCCTGAGCAAGG

CCGATTATGAGAAGCACAAGGTGTATGCATGCGAGGTTACCCATCAGGGC

CTGAGCAGCCCGGTGACCAAAAGCTTTAACCGTGGCGAATGCGGTGGTAG

TGGTGGATCCGCAGGCAGTGCAGGTAGTGCCGGCAGCGGTGGTAGTGAGG

TTCAGCTGCAGGAAAGCGGCGGCGGCTTAATGCAGCCTGGCGGTAGCATG

AAGCTGAGCTGCGTGGCCAGCGGCTTCACCTTTAGCAATTACTGGATGAA

CTGGGTGCGCCAGAGCCCGAAAAAGGCCTGGAATGGGTGGCAGAGATCC

GTCTGAAGAGCAACAACTACGCCACCCACTATGCCGAAAGCGTGAAGGGT

CGCTTTACCATCAGCCGCGATGACAGCAAACGCAGCGTGTATCTGCAGAT

GAACACCCTGCGTGCAGAGCATCAGCCGCGATGACAGCAAACGCAGCGTG

TATCTGCAGATGAACACCCTGCGTGCAGAGGTCAGGGTACCAGCGTGACC

GTTAGCAGTGGCGGTGGTGGTAGCGGTGGTGGTGGTAGCGGTGGTGGTGG

CAGCGATATTCAAATGACCCAGAGCCCTGCCAGCCTGAGCGTGAGTGTTG

GCGAAACCGTGAGCATCACCTGCCGCGCCAGCGAGAACATCTATAGTAGC

CTGGCCTGGTACCAGCAGAAACAGGGCAAAAGCCCGCAGCTGCTGGTGTA

TAGCGCAACCATTCTGGCAGATGGCGTTCCGAGCCGTTTTAGCGGTAGCG

GCAGCGGCACACAGTACAGCCTGAAGATCAACAGCCTGCAGAGCGAGGAC

TTTGGCACCTATTACTGCCAGCACTTTTGGGGTACCCCGTATACCTTCGG

CGGCGGCACCAAACTGGAAATTAAATA

Combined (SEQ ID NO: 27 and 28):
gacattcagatgacccaaagtccgagcagcctgagtgccagtgttggtga
 D  I  Q  M  T  Q  S  P  S  S  L  S  A  S  V  G  D tcgcgtgacaatcacatgcaaggccagtcaggacgtgaccaccgcagtgg
 R  V  T  I  T  C  K  A  S  Q  D  V  T  T  A  V  A cctggtatcagcagaaacccgggtaaggccccgaagctgctgatctattgg
 W  Y  Q  Q  K  P  G  K  A  P  K  L  L  I  Y  W gccagtacccgccacaccggtgttcctagtcgcttcagtggcagtggcag
 A  S  T  R  H  T  G  V  P  S  R  F  S  G  S  G  S cggcacagatttcaccctgaccatcagcagcctgcaaccggaagattttg
 G  T  D  F  T  L  T  I  S  S  L  Q  P  E  D  F  A ccacctactactgccagcagcactatagcaccccgctgacctttggccag
 T  Y  Y  C  Q  Q  H  Y  S  T  P  L  T  F  G  Q ggcaccaaggttgagattaaacgtacggtggcagcaccgagcgtgtttat
 G  T  K  V  E  I  K  R  T  V  A  A  P  S  V  F  I ctttccgccgagcgacgaacaactgaaaagtggcacagccagcgtggtgt
 F  P  P  S  D  E  Q  L  K  S  G  T  A  S  V  V  C gtttactgaacaacttctatcctcgcgaggccaaggtgcagtggaaagtg
 L  L  N  N  F  Y  P  R  E  A  K  V  Q  W  K  V gacaatgcactgcagagtggcaatagccaggagagcgtgaccgaacagga
 D  N  A  L  Q  S  G  N  S  Q  E  S  V  T  E  Q  D tagcaaagatagcacctatagcctgagtagcaccctgaccctgagcaagg
 S  K  D  S  T  Y  S  L  S  S  T  L  T  L  S  K  A ccgattatgagaagcacaaggtgtatgcatgcgaggttacccatcagggc
 D  Y  E  K  H  K  V  Y  A  C  E  V  T  H  Q  G ctgagcagcccggtgaccaaaagctttaaccgtggcgaatgcggtggtag
 L  S  S  P  V  T  K  S  F  N  R  G  E  C  G  G  S tggtggatccgcaggcagtgcaggtagtgccggcagcggtggtagtgagg
 G  G  S  A  G  S  A  G  S  A  G  S  G  G  S  E  V ttcagctgcaggaaagcggcggcggcttaatgcagcctggcggtagcatg
 Q  L  Q  E  S  G  G  G  L  M  Q  P  G  G  S  M aagctgagctgcgtggccagcggcttcacctttagcaattactggatgaa
 K  L  S  C  V  A  S  G  F  T  F  S  N  Y  W  M  N ctgggtgcgccagagcccgaaaaaggcctggaatgggtggcagagatcc
 W  V  R  Q  S  P  E  K  G  L  E  W  V  A  E  I  R gtctgaagagcaacaactacgccacccactatgccgaaagcgtgaagggt
 L  K  S  N  N  Y  A  T  H  Y  A  E  S  V  K  G cgctttaccatcagccgcgatgacagcaaacgcagcgtgtatctgcagat
 R  F  T  I  S  R  D  D  S  K  R  S  V  Y  L  Q  M gaacaccctgcgtgcagaggacaccggcatctattattgcacccgcggca
 N  T  L  R  A  E  D  T  G  I  Y  Y  C  T  R  G  N acggtaattatcgcgccatggactactggggtcagggtaccagcgtgacc
 G  N  Y  R  A  M  D  Y  W  G  Q  G  T  S  V  T gttagcagtggcggtggtggtagcggtggtggtggtagcggtggtggtgg
 V  S  S  G  G  G  G  S  G  G  G  G  S  G  G  G  G cagcgatattcaaatgacccagagccctgccagcctgagcgtgagtgttg
 S  D  I  Q  M  T  Q  S  P  A  S  L  S  V  S  V  G gcgaaaccgtgagcatcacctgccgcgccagcgagaacatctatagtagc
 E  T  V  S  I  T  C  R  A  S  E  N  I  Y  S  S ctggcctggtaccagcagaaacagggcaaaagcccgcagctgctggtgta
 L  A  W  Y  Q  Q  K  G  K  S  P  Q  L  L  V  Y tagcgcaaccattctggcagatggcgttccgagccgttttagcggtagcg
 S  A  T  I  L  A  D  G  V  P  S  R  F  S  G  S  G gcagcggcacacagtacagcctgaagatcaacagcctgcagagcgaggac
 S  G  T  Q  Y  S  L  K  I  N  S  L  Q  S  E  D tttggcacctattactgccagcacttttggggtaccccgtataccttcgg
 F  G  T  Y  Y  C  Q  H  F  W  G  T  P  Y  T  F  G cggcggcaccaaactggaaattaaataa
 G  G  T  K  L  E  I  K  -

E10-2G4 LC C' Fusion Sequence-Amino Acid
(SEQ ID NO: 29):
DIQMTQSPSSLSASVGDRVTITCKASQDVTTAVAWYQQKPGKAPKLLIYW

ASRLHNGVPSRFSGSGSGTDFTLTISSLQPEDFATYYCQQHYSTPLTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECGGSGGSAGSAGSAGSGGSEVQLQESGGGLMQPGGSM

KLSCVASGFTFSNYWMNWVRQSPEKGLEWVAEIRLKSNNYATHYAESVKG

RFTISRDDSKRSVYLQMNTLRAEDTGIYYCTRGNGNYRAMDYWGQGTSVT

VSSGGGGSGGGGSGGGGSDIQMTQSPASLSVSVGETVSITCRASENIYSS

LAWYQQKQGKSPQLLVYSATILADGVPSRFSGSGSGTQYSLKINSLQSED

FGTYYCQHFWGTPYTFGGGTKLEIK

Underlined region is glycine-rich linker polypeptide. Bold region is fusion linker polypeptide.

Nucleotide (SEQ ID NO: 30):
GATATCCAGATGACCCAGTCCCCGAGCTCCCTGTCCGCCTCTGTGGGCGA

TAGGGTCACCATCACCTGCCGGGCGAGCCAGGATGTGACCACCGCTGTAG

CCTGGTATCAACAGAAACCAGGAAAAGCTCCGAAGCTTCTGATTTACTGG

GCGAGCCGTCTTCATAATGGCGTGCCGAGCCGCTTTAGCGGCAGCGGCTC

CGGGACGGATTTCACTCTGACCATCAGCAGTCTGCAGCCGGAAGACTTCG

CAACTTATTACTGTCAGCAACATTATAGCACCCCGCTGACGTTCGGACAG

GGTACCAAGGTGGAGATCAAACGTACGGTGGCAGCACCGAGCGTGTTTAT

CTTTCCGCCGAGCGACGAACAACTGAAAAGTGGCACAGCCAGCGTGGTGT

GTTTACTGAACAACTTCTATCCTCGCGAGGCCAAGGTGCAGTGGAAAGTG

GACAATGCACTGCAGAGTGGCAATAGCCAGGAGAGCGTGACCGAACAGGA

TAGCAAAGATAGCACCTATAGCCTGAGTAGCACCCTGACCCTGAGCAAGG

CCGATTATGAGAAGCACAAGGTGTATGCATGCGAGGTTACCCATCAGGGC

CTGAGCAGCCCGGTGACCAAAAGCTTTAACCGTGGCGAATGCGGTGGTAG

TGGTGGATCCGCAGGCAGTGCAGGTAGTGCCGGCAGCGGTGGTAGTGAGG

TTCAGCTGCAGGAAAGCGGCGGCGGCTTAATGCAGCCTGGCGGTAGCATG

AAGCTGAGCTGCGTGGCCAGCGGCTTCACCTTTAGCAATTACTGGATGAA

CTGGGTGCGCCAGAGCCCGGAAAAAGGCCTGGAATGGGTGGCAGAGATCC

GTCTGAAGAGCAACAACTACGCCACCCACTATGCCGAAAGCGTGAAGGGT

CGCTTTACCATCAGCCGCGATGACAGCAAACGCAGCGTGTATCTGCAGAT

GAACACCCTGCGTGCAGAGGACACCGGCATCTATTATTGCACCCGCGGCA

ACGGTAATTATCGCGCCATGGACTACTGGGGTCAGGGTACCAGCGTGACC

GTTAGCAGTGGCGGTGGTGGTAGCGGTGGTGGTGGTAGCGGTGGTGGTGG

CAGCGATATTCAAATGACCCAGAGCCCTGCCAGCCTGAGCGTGAGTGTTG

GCGAAACCGTGAGCATCACCTGCCGCGCCAGCGAGAACATCTATAGTAGC

CTGGCCTGGTACCAGCAGAAACAGGGCAAAAGCCCGCAGCTGCTGGTGTA

TAGCGCAACCATTCTGGCAGATGGCGTTCCGAGCCGTTTTAGCGGTAGCG

GCAGCGGCACACAGTACAGCCTGAAGATCAACAGCCTGCAGAGCGAGGAC

TTTGGCACCTATTACTGCCAGCACTTTTGGGGTACCCCGTATACCTTCGG

CGGCGGCACCAAACTGGAAATTAAATAA

Combined (SEQ ID NO. 29 and 30):

```
gatatccagatgacccagtccccgagctccctgtccgcctctgtgggcga
 D  I  Q  M  T  Q  S  P  S  S  L  S  A  S  V  G  D
tagggtcaccatcacctgccgggcgagccaggatgtgaccaccgctgtag
 R  V  T  I  T  C  R  A  S  Q  D  V  T  T  A  V  A
cctggtatcaacagaaaccaggaaaagctccgaagcttctgatttactgg
 W  Y  Q  Q  K  P  G  K  A  P  K  L  L  I  Y  W
gcgagccgtcttcataatggcgtgccgagccgctttagcggcagcggctc
 A  S  R  L  H  N  G  V  P  S  R  F  S  G  S  G  S
cgggacggatttcactctgaccatcagcagtctgcagccggaagacttcg
 G  T  D  F  T  L  T  I  S  S  L  Q  P  E  D  F  A
caacttattactgtcagcaacattatagcaccccgctgacgttcggacag
 T  Y  Y  C  Q  Q  H  Y  S  T  P  L  T  F  G  Q
ggtaccaaggtggagatcaaacgtacggtggcagcaccgagcgtgtttat
 G  T  K  V  E  I  K  R  T  V  A  A  P  S  V  F  I
ctttccgccgagcgacgaacaactgaaaagtggcacagccagcgtggtgt
 F  P  P  S  D  E  Q  L  K  S  G  T  A  S  V  V  C
gtttactgaacaacttctatcctcgcgaggccaaggtgcagtggaaagtg
 L  L  N  N  F  Y  P  R  E  A  K  V  Q  W  K  V
gacaatgcactgcagagtggcaatagccaggagagcgtgaccgaacagga
 D  N  A  L  Q  S  G  N  S  Q  E  S  V  T  E  Q  D
tagcaaagatagcacctatagcctgagtagcaccctgaccctgagcaagg
 S  K  D  S  T  Y  S  L  S  S  T  L  T  L  S  K  A
ccgattatgagaagcacaaggtgtatgcatgcgaggttacccatcagggc
 D  Y  E  K  H  K  V  Y  A  C  E  V  T  H  Q  G
ctgagcagcccggtgaccaaaagctttaaccgtggcgaatgcggtggtag
 L  S  S  P  V  T  K  S  F  N  R  G  E  C  G  G  S
tggtggatccgcaggcagtgcaggtagtgccggcagcggtggtagtgagg
 G  G  S  A  G  S  A  G  S  A  G  S  G  G  S  E  V
ttcagctgcaggaaagcggcggcggcttaatgcagcctggcggtagcatg
 Q  L  Q  E  S  G  G  G  L  M  Q  P  G  G  S  M
aagctgagctgcgtggccagcggcttcacctttagcaattactggatgaa
 K  L  S  C  V  A  S  G  F  T  F  S  N  Y  W  M  N
ctgggtgcgccagagcccggaaaaaggcctggaatgggtggcagagatcc
 W  V  R  Q  S  P  E  K  G  L  E  W  V  A  E  I  R
gtctgaagagcaacaactacgccacccactatgccgaaagcgtgaagggt
 L  K  S  N  N  Y  A  T  H  Y  A  E  S  V  K  G
cgctttaccatcagccgcgatgacagcaaacgcagcgtgtatctgcagat
 R  F  T  I  S  R  D  D  S  K  R  S  V  Y  L  Q  M
gaacaccctgcgtgcagaggacaccggcatctattattgcacccgcggca
 N  T  L  R  A  E  D  T  G  I  Y  Y  C  T  R  G  N
acggtaattatcgcgccatggactactggggtcagggtaccagcgtgacc
 G  N  Y  R  A  M  D  Y  W  G  Q  G  T  S  V  T
gttagcagtggcggtggtggtagcggtggtggtggtagcggtggtggtgg
 V  S  S  G  G  G  G  S  G  G  G  G  S  G  G  G  G
cagcgatattcaaatgacccagagccctgccagcctgagcgtgagtgttg
 S  D  I  Q  M  T  Q  S  P  A  S  L  S  V  S  V  G
gcgaaaccgtgagcatcacctgccgcgccagcgagaacatctatagtagc
 E  T  V  S  I  T  C  R  A  S  E  N  I  Y  S  S
ctggcctggtaccagcagaaacagggcaaaagcccgcagctgctggtgta
 L  A  W  Y  Q  Q  K  Q  G  K  S  P  Q  L  L  V  Y
```

-continued

```
tagcgcaaccattctggcagatggcgttccgagccgttttagcggtagcg
 S  A  T  I  L  A  D  G  V  P  S  R  F  S  G  S  G gcagcggcacacagtacagcctgaagatcaacagcctgcagagcgaggac
 S  G  T  Q  Y  S  L  K  I  N  S  L  Q  S  E  D tttggcacctattactgccagcacttttggggtaccccgtataccttcgg
 F  G  T  Y  Y  C  Q  H  F  W  G  T  P  Y  T  F  G cggcggcaccaaactggaaattaaataa
 G  G  T  K  L  E  I  K  -
```

F4-4G7 HC C' Fusion Sequence-Amino Acid
(SEQ ID NO: 31):
EVQLVESGGGLVQPGGSLRLSCAASGFAFNYYDMFWVRQAPGKGLEWVAY
IKPGGGNTYYADSVKGRFTISADTSKNTAYLQMNSLRAEDTAVYYCARQL
YGNSFFDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCDKTHTCPPCPAPELLGRPSVFL
PPKPKDTLMISRTPEVTCVVVDVSHEDPEVKFNWYVDGVEVHNAKTKPRE
EQYNSTYRVVSVLTVLHQDWLNGKEYKCKVSNAKLPAPIEKTISKAKGQP
REPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSL
SPGKGGSAGSAGSAGSGGSEVQLQESGPELEMPGASVKISKCASGSSFTG
FTGFSMNWVKQSNGKSLEWIGNIDTYYGGTTYNQKFKGKATLTVDKSSST
AYMQLKSLTSEDSAVYYCARSAYYGSTFAYWGQGTLVTVSA<u>GGGGSGGGG</u>
<u>SGGGGS</u>DIQMTQSPASLSASVGETVTITCRASENIYSYLAWYQQKGKSP
QLLVYNAKTLIEGVPSRFSGSGSGTQFSLKINSLQPEDFGSYFCQHHFGT
PFTFGSGTELEIK Underlined region is glycine-rich linker polypeptide. Bold region is fusion linker polypeptide.

```
Nucleotide (SEQ ID NO: 32):
GAAGTTCAACTGGTTGAGAGTGGCGGTGGCTTAGTTCAACCGGGCGGTAG
TTTACGCCTGAGTTGTGCAGCCAGCGGTTTCGCCTTCAACTATTATGACA
TGTTTTGGGTGCGCCAGGCACCGGGTAAAGGCCTGGAGTGGGTGGCCTAT
ATCAAACCGGGCGGTGGCAACACCTATTACGCCGATAGCGTGAAAGGTCG
CTTTACCATCAGCGCAGATACCAGCAAGAATACCGCCTACCTGCAGATGA
ATAGCCTGCGTGCCGAAGACACCGCCGTTTATTATTGCGCCCGCCAGCTG
TACGGCAATAGCTTTTTCGATTACTGGGGCCAGGGCACCCTGGTTACCGT
TAGCAGCGCTAGCACCAAGGGTCCGAGCGTGTTTCCTCTGGCACCTAGCA
GTAAAAGCACCAGTGGTGGTACAGCAGCCCTGGGTTGCCTGGTGAAGGAT
TACTTTCCGGAGCCGGTGACCGTTAGTTGGAATAGCGGCGCCCTGACCAG
TGGCGTTCATACATTTCCGGCCGTGCTGCAGAGTAGTGGCCTGTACAGCC
TGAGTAGCGTTGTTACCGTTCCGAGCAGCAGCCTGGGCACCCAGACCTAT
ATTTGCAATGTTAACCATAAACCGAGCAACACAAAAGTTGATAAAAAAGT
TGAACCGAAGAGCTGTGACAAAACCCATACATGTGACAAAACACACACCT
GCCCGCCTTGTCCGGCACCTGAGCTGCTGGGTCGCCCGAGCGTTTTTCTG
```

-continued

```
TTTCCTCCGAAACCGAAAGACACCCTGATGATCAGCCGCACACCTGAGGT
GACCTGTGTTGTGGTGGATGTGAGCCACGAAGATCCTGAAGTTAAGTTTA
ACTGGTATGTGGATGGCGTGGAGGTGCATAATGCCAAGACAAAGCCGCGT
GAAGAGCAGTACAACAGCACCTATCGTGTTGTTAGTGTGCTGACCGTTCT
GCACCAAGATTGGCTGAACGGCAAGGAGTATAAATGCAAGGTTAGCAATA
AAGCCCTGCCGGCCCCGATCGAGAAGACCATCAGCAAAGCCAAAGGTCAG
CCGCGTGAGCCTCAGGTGTATACACTGCCGCCTAGCCGTGAGGAGATGAC
CAAGAATCAGGTTAGCCTGACCTGTCTGGTGAAAGGCTTTTACCCGAGCG
ATATCGCCGTTGAGTGGGAAAGCAATGGTCAGCCTGAGAACAACTACAAG
ACCACCCCGCCTGTTTTAGACAGTGATGGTAGCTTTTTCTTATACAGCAA
ACTGACCGTTGATAAGAGCCGCTGGCAGCAGGGCAATGTGTTTAGCTGCA
GTGTTATGCATGAGGCCCTGCATAACCACTATACCCAGAAGAGTCTGAGC
CTGAGTCCTGGCAAAGGTGGATCCGCCGGTAGCGCAGGCAGCGCAGGTAG
TGGTGGTAGCGAAGTTCAGCTGCAGGAAAGTGGCCCGGAACTGGAAATGC
CGGGCGCCAGCGTGAAAATCAGTTGCAAAGCCAGCGGTAGCAGCTTCACA
GGCTTCAGCATGAACTGGGTGAAGCAGAGCAACGGTAAGAGCCTGGAGTG
GATCGGCAACATTGACACCTACTATGGCGGCACCACCTACAACCAGAAGT
TCAAAGGCAAGGCCACCCTGACCGTGGATAAAAGCAGCAGCACAGCCTAC
ATGCAGCTGAAAAGCCTGACCAGCGAAGATAGCGCCGTGTATTACTGCGC
CCGTAGCGCCTATTACGGCAGCACCTTTGCATACTGGCAGGGTACCCTGG
TGACCGTGAGCGCAGGTGGTGGTGGTAGTGGTGGTGGTAGCGGTGGT
GGCGGTAGTGACATTCAAATGACCCAGAGCCCTGCAAGCCTGAGCGCCAG
TGTTGGCGAAACCGTGACCATTACATGCCGCGCCAGCGAAAACATCTATA
GTTACCTGGCCTGGTACCAGCAGAAACAGGGCAAAAGCCCGCAACTGCTG
GTGTATAACGCCAAAACCCTGATTGAGGGCGTGCCGAGTCGCTTCAGCGG
TAGCGGTAGCGGTACACAGTTCAGTCTGAAAATCAACAGCCTGCAGCCGG
AAGACTTCGGCAGCTACTTTTGCCAGCACCACTTTGGCACCCCGTTTACA
TTTGGCAGCGGCACCGAGCTGGAAATTAAATAA
```

```
Combined (SEQ ID NO: 31 and 32):
gaagttcaactggttgagagtggcggtggcttagttcaaccgggcggtag
 E  V  Q  L  V  E  S  G  G  G  L  V  Q  P  G  G  S tttacgcctgagttgtgcagccagcggtttcgccttcaactattatgaca
 L  R  L  S  C  A  A  S  G  F  A  F  N  Y  Y  D  M tgttttgggtgcgccaggcaccgggtaaaggcctggagtgggtggcctat
 F  W  V  R  Q  A  P  G  K  G  L  E  W  V  A  Y atcaaaccgggcggtggcaacacctattacgccgatagcgtgaaaggtcg
 I  K  P  G  G  G  N  T  Y  Y  A  D  S  V  K  G  R ctttaccatcagcgcagataccagcaagaataccgcctacctgcagatga
 F  T  I  S  A  D  T  S  K  N  T  A  Y  L  Q  M  N atagcctgcgtgccgaagacaccgccgtttattattgcgcccgccagctg
  S  L  R  A  E  D  T  A  V  Y  Y  C  A  R  Q  L tacggcaatagcttttttcgattactggggccagggcaccctggttaccgt
 Y  G  N  S  F  F  D  Y  W  G  Q  G  T  L  V  T  V tagcagcgctagcaccaagggtccgagcgtgtttcctctggcacctagca
 S  S  A  S  T  K  G  P  S  V  F  P  L  A  P  S  S
```

```
gtaaaagcaccagtggtggtacagcagccctgggttgcctggtgaaggat
 K  S  T  S  G  G  T  A  A  L  G  C  L  V  K  D tactttccggagccggtgaccgttagttggaatagcggcgccctgaccag
 Y  F  P  E  P  V  T  V  S  W  N  S  G  A  L  T  S tggcgttcatacatttccggccgtgctgcagagtagtggcctgtacagcc
 G  V  H  T  F  P  A  V  L  Q  S  S  G  L  Y  S  L tgagtagcgttgttaccgttccgagcagcagcctgggcacccagacctat
 S  S  V  V  T  V  P  S  S  S  L  G  T  Q  T  Y atttgcaatgttaaccataaaccgagcaacacaaaagttgataaaaagt
 I  C  N  V  N  H  K  P  S  N  T  K  V  D  K  K  V tgaaccgaagagctgtgacaaaacccatacatgtgacaaaacacacct
 E  P  K  S  C  D  K  T  H  T  C  D  K  T  H  T  C gcccgccttgtccggcacctgagctgctgggtcgcccgagcgttttctg
 P  P  C  P  A  P  E  L  L  G  R  P  S  V  F  L tttcctccgaaaccgaaagacacccctgatgatcagccgcacacctgaggt
 F  P  P  K  P  K  D  T  L  M  I  S  R  T  P  E  V gacctgtgttgtggtggatgtgagccacgaagatcctgaagttaagttta
 T  C  V  V  V  D  V  S  H  E  D  P  E  V  K  F  N actggtatgtggatggcgtggaggtgcataatgccaagcaaagccgcgt
 W  Y  V  D  G  V  E  V  H  N  A  K  T  K  P  R gaagagcagtacaacagcacctatcgtgttgttagtgtgctgaccgttct
 E  E  Q  Y  N  S  T  Y  R  V  V  S  V  L  T  V  L gcaccaagattggctgaacggcaaggagtataaatgcaaggttagcaata
 H  Q  D  W  L  N  G  K  E  Y  K  C  K  V  S  N  K aagccctgccgcccccgatcgagaagaccatcagcaaagccaaaggtcag
 A  L  P  A  P  I  E  K  T  I  S  K  A  K  G  Q ccgcgtgagcctcaggtgtatacactgccgcctagccgtgaggagatgac
 P  R  E  P  Q  V  Y  T  L  P  P  S  R  E  E  M  T caagaatcaggttagcctgacctgtctggtgaaaggcttttacccgagcg
 K  N  Q  V  S  L  T  C  L  V  K  G  F  Y  P  S  D atatcgccgttgagtgggaaagcaatggtcagcctgagaacaactacaag
 I  A  V  E  W  E  S  N  G  Q  P  E  N  N  Y  K accaccccgcctgttttagacagtgatggtagcttttcttatacagcaa
 T  T  P  P  V  L  D  S  D  G  S  F  F  L  Y  S  K actgaccgttgataagagccgctggcagcagggcaatgtgtttagctgca
 L  T  V  D  K  S  R  W  Q  Q  G  N  V  F  S  C  S gtgttatgcatgaggccctgcataaccactatacccagaagagtctgagc
 V  M  H  E  A  L  H  N  H  Y  T  Q  K  S  L  S ctgagtcctggcaaaggtggatccgccggtagcgcaggcagcgcaggtag
 L  S  P  G  K  G  G  S  A  G  S  A  G  S  A  G  S tggtggtagcgaagttcagctgcaggaaagtggcccggaactggaaatgc
 G  G  S  E  V  Q  L  Q  E  S  G  P  E  L  E  M  P cgggcgccagcgtgaaaatcagttgcaaagccagcggtagcagcttcaca
 G  A  S  V  K  I  S  C  K  A  S  G  S  S  F  T ggcttcagcatgaactgggtgaagcagagcaacggtaagagcctggagtg
 G  F  S  M  N  W  V  K  Q  S  N  G  K  S  L  E  W gatcggcaacattgacacctactatggcggcaccacctacaaccagaagt
 I  G  N  I  D  T  Y  Y  G  G  T  T  Y  N  Q  K  F tcaaaggcaaggccacccctgaccgtggataaaagcagcagcacagcctac
 K  G  K  A  T  L  T  V  D  K  S  S  S  T  A  Y atgcagctgaaaagcctgaccagcgaagatagcgccgtgtattactgcgc
 M  Q  L  K  S  L  T  S  E  D  S  A  V  Y  Y  C  A ccgtagcgcctattacggcagcacctttgcatactggcagggtaccctgg
 R  S  A  Y  Y  G  S  T  F  A  Y  W  Q  G  T  L  V tgaccgtgagcgcaggtggtggtggtagtggtggtggtggtagcggtggt
 T  V  S  A  G  G  G  G  S  G  G  G  G  S  G  G ggcggtagtgacattcaaatgacccagagccctgcaagcctgagcgccag
 G  G  S  D  I  Q  M  T  Q  S  P  A  S  L  S  A  S tgttggcgaaaccgtgaccattacatgccgcgccagcgaaaacatctata
 V  G  E  T  V  T  I  T  C  R  A  S  E  N  I  Y  S gttacctggcctggtaccagcagaaacagggcaaaagcccgcaactgctg
 Y  L  A  W  Y  Q  Q  K  Q  G  K  S  P  Q  L  L gtgtataacgccaaaaccctgattgagggcgtgccgagtcgcttcagcgg
 V  Y  N  A  K  T  L  I  E  G  V  P  S  R  F  S  G tagcggtagcggtacacagttcagtctgaaaatcaacagcctgcagccgg
 S  G  S  G  T  Q  F  S  L  K  I  N  S  L  Q  P  E aagacttcggcagctacttttgccagcaccactttggcaccccgtttaca
 D  F  G  S  Y  F  C  Q  H  H  F  G  T  P  F  T tttggcagcggcaccgagctggaaattaaata
 F  G  S  G  T  E  L  E  I  K  -
```

F4-4G7 LC C' Fusion Sequence-Amino Acid
(SEQ ID NO: 33):

DIQMTQSPSSLSASVGDRVTITCKASQDVTTAVAWYQQKPGKAPKLLIYW

ASTRHTGVPSRFSGSGSGTDFTLTISSLQPEDFATYYCQQHYSTPLTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECGGSGGSAGSAGSAGSGGSEVQLQESGPELEMPGASV

KISCKASGSSFTGFSMNWVKQSNGKSLEWIGNIDTYYGGTTYNQKFKGKA

TLTVDKSSSTAYMQLKSLTSEDSAVYYCARSAYYGSTFAYWGQGLVTVSA

<u>GGGGSGGGGSGGGGS</u>DIQMTQSPASLSASVGETVTITCRASENIYSYLAW

YQQKQGKSPQLLVYNAKTLIEGVPSRFSGSGSGTQFSLKINSLQPEDFGS

YFCQHHFGTPFTFGSGTELEIKI

Underlined region is glycine-rich linker polypeptide. Bold region is fusion linker polypeptide.

Nucleotide (SEQ ID NO: 34):
GACATTCAGATGACCCAAAGTCCGAGCAGCCTGAGTGCCAGTGTTGGTGA

TCGCGTGACAATCACATGCAAGGCCAGTCAGGACGTGACCACCGCAGTGG

CCTGGTATCAGCAGAAACCGGGTAAGGCCCCGAAGCTGCTGATCTATTGG

GCCAGTACCCGCCACACCGGTGTTCCTAGTCGCTTCAGTGGCAGTGGCAG

CGGCACAGATTTCACCCTGACCATCAGCAGCCTGCAACCGGAAGATTTTG

CCACCTACTACTGCCAGCAGCACTATAGCACCCCGCTGACCTTTGGCCAG

GGCACCAAGGTTGAGATTAAACGTACGGTGGCAGCACCGAGCGTGTTTAT

CTTTCCGCCGAGCGACGAACAACTGAAAAGTGGCACAGCCAGCGTGGTGT

GTTTACTGAACAACTTCTATCCTCGCGAGGCCAAGGTGCAGTGGAAAGTG

GACAATGCACTGCAGAGTGGCAATAGCCAGGAGAGCGTGACCGAACAGGA

TAGCAAAGATAGCACCTATAGCCTGAGTAGCACCCTGACCCTGAGCAAGG

CCGATTATGAGAAGCACAAGGTGTATGCATGCGAGGTTACCCATCAGGGC

CTGAGCAGCCCGGTGACCAAAAGCTTTAACCGTGGCGAATGCGGTGGTAG

TGGTGGATCCGCCGGTAGCGCAGGCAGCGCAGGTAGTGGTGGTAGCGAAG

TTCAGCTGCAGGAAAGTGGCCCGGAACTGGAAATGCCGGGCGCCAGCGTG

```
AAAATCAGTTGCAAAGCCAGCGGTAGCAGCTTCACAGGCTTCAGCATGAA

CTGGGTGAAGCAGAGCAACGGTAAGAGCCTGGAGTGGATCGGCAACATTG

ACACCTACTATGGCGGCACCACCTACAACCAGAAGTTCAAAGGCAAGGCC

ACCCTGACCGTGGATAAAAGCAGCAGCACAGCCTACATGCAGCTGAAAAG

CCTGACCAGCGAAGATAGCGCCGTGTATTACTGCGCCCGTAGCGCCTATT

ACGGCAGCACCTTTGCATACTGGCAGGGTACCCTGGTGACCGTGAGCGCA

GGTGGTGGTGGTAGTGGTGGTGGTGGTAGCGGTGGTGGCGGTAGTGACAT

TCAAATGACCCAGAGCCCTGCAAGCCTGAGCGCCAGTGTTGGCGAAACCG

TGACCATTACATGCCGCGCCAGCGAAAACATCTATAGTTACCTGGCCTGG

TACCAGCAGAAACAGGGCAAAAGCCCGCAACTGCTGGTGTATAACGCCAA

AACCCTGATTGAGGGCGTGCCGAGTCGCTTCAGCGGTAGCGGTAGCGGTA

CACAGTTCAGTCTGAAAATCAACAGCCTGCAGCCGGAAGACTTCGGCAGC

TACTTTTGCCAGCACCACTTTGGCACCCCGTTTACATTTGGCAGCGGCAC

CGAGCTGGAAATTAAATAA
```

Combined (SEQ ID NO: 33 and 34):
```
gacattcagatgacccaaagtccgagcagcctgagtgccagtgttggtga
 D  I  Q  M  T  Q  S  P  S  S  L  S  A  S  V  G  D tcgcgtgacaatcacatgcaaggccagtcaggacgtgaccaccgcagtgg
  R  V  T  I  T  C  K  A  S  Q  D  V  T  T  A  V  A cctggtatcagcagaaaccgggtaaggccccgaagctgctgatctattgg
   W  Y  Q  Q  K  P  G  K  A  P  K  L  L  I  Y  W gccagtacccgccacaccggtgttcctagtcgcttcagtggcagtggcag
  A  S  T  R  H  T  G  V  P  S  R  F  S  G  S  G  S cggcacagatttcacccctgaccatcagcagcctgcaaccggaagattttg
 G  T  D  F  T  L  T  I  S  S  L  Q  P  E  D  F  A ccacctactactgccagcagcactatagcaccccgctgacctttggccag
  T  Y  Y  C  Q  Q  H  Y  S  T  P  L  T  F  G  Q ggcaccaaggttgagattaaacgtacggtggcagcaccgagcgtgtttat
 G  T  K  V  E  I  K  R  T  V  A  A  P  S  V  F  I ctttccgccgagcgacgaacaactgaaaagtggcacagccagcgtggtgt
  F  P  P  S  D  E  Q  L  K  S  G  T  A  S  V  V  C gtttactgaacaacttctatcctcgcgaggccaaggtgcagtggaaagtg
   L  L  N  N  F  Y  P  R  E  A  K  V  Q  W  K  V gacaatgcactgcagagtggcaatagccaggagagcgtgaccgaacagga
  D  N  A  L  Q  S  G  N  S  Q  E  S  V  T  E  Q  D tagcaaagatagcacctatagcctgagtagcaccctgaccctgagcaagg
   S  K  D  S  T  Y  S  L  S  S  T  L  T  L  S  K  A ccgattatgagaagcacaaggtgtatgcatgcgaggttacccatcagggc
  D  Y  E  K  H  K  V  Y  A  C  E  V  T  H  Q  G ctgagcagcccggtgaccaaaagctttaaccgtggcgaatgcggtggtag
  L  S  S  P  V  T  K  S  F  N  R  G  E  C  G  G  S tggtggatccgccggtagcgcaggcagcgcaggtagtggtggtagcgaag
  G  G  S  A  G  S  A  G  S  A  G  S  G  G  S  E  V ttcagctgcaggaaagtggcccggaactggaaatgccgggcgccagcgtg
  Q  L  Q  E  S  G  P  E  L  E  M  P  G  A  S  V aaaatcagttgcaaagccagcggtagcagcttcacaggcttcagcatgaa
 K  I  S  C  K  A  S  G  S  S  F  T  G  F  S  M  N ctgggtgaagcagagcaacggtaagagcctggagtggatcggcaacattg
 W  V  K  Q  S  N  G  K  S  L  E  W  I  G  N  I  D acacctactatggcggcaccacctacaaccagaagttcaaaggcaaggcc
 T  Y  Y  G  G  T  T  Y  N  Q  K  F  K  G  K  A accctgaccgtggataaaagcagcagcacagcctacatgcagctgaaaag
 T  L  T  V  D  K  S  S  S  T  A  Y  M  Q  L  K  S cctgaccagcgaagatagcgccgtgtattactgcgcccgtagcgcctatt
 L  T  S  E  D  S  A  V  Y  Y  C  A  R  S  A  Y  Y acggcagcacctttgcatactggcagggtaccctggtgaccgtgagcgca
 G  S  T  F  A  Y  W  Q  G  T  L  V  T  V  S  A ggtggtggtggtagtggtggtggtggtagcggtggtggcggtagtgacat
 G  G  G  G  S  G  G  G  G  S  G  G  G  G  S  D  I tcaaatgacccagagccctgcaagcctgagcgccagtgttggcgaaaccg
 Q  M  T  Q  S  P  A  S  L  S  A  S  V  G  E  T  V tgaccattacatgccgcgccagcgaaaacatctatagttacctggcctgg
  T  I  T  C  R  A  S  E  N  I  Y  S  Y  L  A  W taccagcagaaacagggcaaaagcccgcaactgctggtgtataacgccaa
Y  Q  Q  K  Q  G  K  S  P  Q  L  L  V  Y  N  A  K aaccctgattgagggcgtgccgagtcgcttcagcggtagcggtagcggta
  T  L  I  E  G  V  P  S  R  F  S  G  S  G  S  G  T cacagttcagtctgaaaatcaacagcctgcagccggaagacttcggcagc
  Q  F  S  L  K  I  N  S  L  Q  P  E  D  F  G  S tacttttgccagcaccactttggcaccccgtttacatttggcagcggcac
 Y  F  C  Q  H  H  F  G  T  P  F  T  F  G  S  G  T cgagctggaaattaaataa
 E  L  E  I  K  -
```

F4-4G7 LC C' Fusion Sequence-Amino Acid
(SEQ ID NO: 35):
DIQMTQSPSSLSASVGDRVTITCKASQDVTTAVAWYQQKPGKAPKLLIYW

ASTRHTGVPSRFSGSGSGTDFTLTISSLQPEDFATYYCQQHYSTPLTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGECGGSGGSAGSAGSAGSGGSEVQLQESGPELEMPGASV

KISCKASGSSFTGFSMNWVKQSNGKSLEWIGNIDTYYGGTTYNQKFKGKA

TLTVDKSSSTAYMQLKSLTSEDSAVYYCARSAYYGSTFAYWQGTLVTVSA

<u>GGGGSGGGGSGGGGS</u>DIQMTQSPASLSASVGETVTITCRASENIYSYLAW

YQQKQGKSPQLLVYNAKTLIEGVPSRFSGSGSGTQFSLKINSLQPEDFGS

YFCQHHFGTPFTFGSGTELEIK

Underlined region is glycine-rich linker polypeptide. Bold region is fusion linker polypeptide.

Nucleotide (SEQ ID NO: 36):
```
GACATTCAGATGACCCAAAGTCCGAGCAGCCTGAGTGCCAGTGTTGGTGATCGC

GTGACAATCACATGCAAGGCCAGTCAGGACGTGACCACCGCAGTGGCCTGGTATCAGCAGA

TAGTCGCTTCAGTGGCAGTGGCAGCGGCACAGATTTCACCCTGACCATCAGCAGCCTGCAA
```

-continued

```
CCGGAAGATTTTGCCACCTACTACTGCCAGCAGCACTATAGCACCCCGCTGACCTTTGGCC

AGGGCACCAAGGTTGAGATTAAACGTACGGTGGCAGCACCGAGCGTGTTTATCTTTCCGCC

GAGCGACGAACAACTGAAAAGTGGCACAGCCAGCGTGGTGTGTTTACTGAACAACTTCTAT

CCTCGCGAGGCCAAGGTGCAGTGGAAAGTGGACAATGCACTGCAGAGTGGCAATAGCCAGG

AGAGCGTGACCGAACAGGATAGCAAAGATAGCACCTATAGCCTGAGTAGCACCCTGACCCT

GAGCAAGGCCGATTATGAGAAGCACAAGGTGTATGCATGCGAGGTTACCCATCAGGGCCTG

AGCAGCCCGGTGACCAAAAGCTTTAACCGTGGCGAATGCGGTGGTAGTGGTGGATCCGCCG

GTAGCGCAGGCAGCGCAGGTAGTGGTGGTAGCGAAGTTCAGCTGCAGGAAAGTGGCCCGGA

ACTGGAAATGCCGGGCGCCAGCGTGAAAATCAGTTGCAAAGCCAGCGGTAGCAGCTTCACA

GGCTTCAGCATGAACTGGGTGAAGCAGAGCAACGGTAAGAGCCTGGAGTGGATCGGCAACA

TTGACACCTACTATGGCGGCACCACCTACAACCAGAAGTTCAAAGGCAAGGCCACCCTGAC

CGTGGATAAAAGCAGCAGCACAGCCTACATSCAGCTGAAAAGCCTGACCAGCGAAGATAGC

GCCGTGTATTACTGCGCCCGTAGCGCCTATTACGGCAGCACCTTTGCATACTGGCAGGGTA

CCCTGGTGACCGTGAGCGCAGGTGGTGGTGGTAGTGGTGGTGGTGGTAGCGGTGGTGGCGG

TAGTGACATTCAAATGACCCAGAGCCCTGCAAGCCTGAGCGCCAGTGTTGGCGAAACCGTG

ACCATTACATGCCGCGCCAGCGAAAACATCTATAGTTACCTGGCCTGGTACCAGCAGAAAC

AGGGCAAAAGCCCGCAACTGCTGGTGTATAACGCCAAAACCCTGATTGAGGGCGTGCCGAG

TCGCTTCAGCGGTAGCGGTAGCGGTACACAGTTCAGTCTGAAAATCAACAGCCTGCAGCCG

GAAGACTTCGGCAGCTACTTTTGCCAGCACCACTTTGGCAGCCCGTTTACATTTGGCAGCG

GCACCGAGCTGGAAATTAAATAA

Combined (SEQ ID NO: 35 and 36):
gacattcagatgacccaaagtccgagcagcctgagtgccagtgttggtgatcgcgtgaca
 D  I  Q  M  T  Q  S  P  S  S  L  S  A  S  V  G  D  R  V  T atcacatgcaaggccagtcaggacgtgaccaccgcagtggcctggtatcagcagaaaccg
 I  T  C  K  A  S  Q  D  V  T  T  A  V  A  W  Y  Q  Q  K  P ggtaaggccccgaagctgctgatctattgggccagtacccgccacaccggtgttcctagt
 G  K  A  P  K  L  L  I  Y  W  A  S  T  R  H  T  G  V  P  S cgcttcagtggcagtggcagcggcacagatttcaccctgaccatcagcagcctgcaaccg
 R  F  S  G  S  G  S  G  T  D  F  T  L  T  I  S  S  L  Q  P gaagatttTgccacctactactgccagcagcactatagcacccCgctgacctttggccag
 E  D  F  A  T  Y  Y  C  Q  Q  H  Y  S  T  P  L  T  F  G  Q ggcaccaaggttgagattaaacgtacggtggcagcaccgagcgtgtttatctttccgccg
 G  T  K  V  E  I  K  R  T  V  A  A  P  S  V  F  I  F  P  P agcgacgaacaactgaaaagtggcacagccagcgtggtgtgtttactgaacaacttctat
 S  D  E  Q  L  K  S  G  T  A  S  V  V  C  L  L  N  N  F  Y cctcgcgaggccaaggtgcagtggaaagtggacaatgcactgcagagtggcaatagccag
 P  R  E  A  K  V  Q  W  K  V  D  N  A  L  Q  S  G  N  S  Q gagagcgtgaccgaacaggatagcaaagatagcacctatagcctgagtagcaccctgacc
 E  S  V  T  E  Q  D  S  K  D  S  T  Y  S  L  S  S  T  L  T ctgagcaaggccgattatgagaagcacaaggtgtatgcatgcgaggttacccatcagggc
 L  S  K  A  D  Y  E  K  H  K  V  Y  A  C  E  V  T  H  Q  G ctgagcagcccggtgaccaaaagctttaaccgtggcgaatgcggtggtagtggtggatcc
 L  S  S  P  V  T  K  S  F  N  R  G  E  C  G  G  S  G  G  S gccggtagcgcaggcagcgcaggtagtggtggtagcgaagttcagctgcaggaaagtggc
 A  G  S  A  G  S  A  G  S  G  G  S  E  V  Q  L  Q  E  S  G ccggaactggaaatgccgggcgccagcgtgaaaatcagttgcaaagccagcggtagcagc
 P  E  L  E  M  P  G  A  S  V  K  I  S  C  K  A  S  G  S  S
```

-continued

```
ttcacaggcttcagcatgaactgggtgaagcagagcaacggtaagagcctggagtggatc
 F  T  G  F  S  M  N  W  V  K  Q  S  N  G  K  S  L  E  W  I ggcaacattgacacctactatggcggcaccacctacaaccagaagttcaaaggcaaggcc
 G  N  I  D  T  Y  Y  G  G  T  T  Y  N  Q  K  F  K  G  K  A accctgaccgtggataaaagcagcagcacagcctacatgcagctgaaaagcctgaccagc
 T  L  T  V  D  K  S  S  S  T  A  Y  M  Q  L  K  S  L  T  S gaagatagcgccgtgtattactgcgcccgtagcgcctattacggcagcacctttgcatac
 E  D  S  A  V  Y  Y  C  A  R  S  A  Y  Y  G  S  T  F  A  Y tggcagggtaccctggtgaccgtgagcgcaggtggtggtggtagtggtggtggtggtagc
 W  Q  G  T  L  V  T  V  S  A  G  G  G  S  G  G  G  G  S ggtggtggcggtagtgacattcaaatgacccagagccctgcaagcctgagcgccagtgtt
 G  G  G  G  S  D  I  Q  M  T  Q  S  P  A  S  L  S  A  S  V ggcgaaaccgtgaccattacatgccgcgccagcgaaaacatctatagttacctggcctgg
 G  E  T  V  T  I  T  C  R  A  S  E  N  I  Y  S  Y  L  A  W taccagcagaaacagggcaaaagcccgcaactgctggtgtataacgccaaaaccctgatt
 Y  Q  Q  K  Q  G  K  S  P  Q  L  L  V  Y  N  A  K  T  L  I gagggcgtgccgagtcgcttcagcggtagcggtagcggtacacagttcagtctgaaaatc
 E  G  V  P  S  R  F  S  G  S  G  S  G  T  Q  F  S  L  K  I aacagcctgcagccggaagacttcggcagctactttttgccagcaccactttggcaccccg
 N  S  L  Q  P  E  D  F  G  S  Y  F  C  Q  H  H  F  G  T  P tttacatttggcagcggcaccgagctggaaattaaataa
 F  T  F  G  S  G  T  E  L  E  I  K  -
```

E10-4G7 LC C' Fusion Sequence-Amino Acid (SEQ ID NO: 37):
DIQMTQSPSSLSASVGDRVTITCKASQDVTTAVAWYQQKPGKAPKLLIYWASRL

HNGVPSRFSGSGSGTDFTLTISSLQPEDFATYYCQQHYSTPLTFGQGTKVEIKRTVAAPSV

FIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGECGGSGGSAGSAGSAGSGGSEVQLQ

ESGPELEMPGASVKISCKASGSSFTGFSMNWVKQSNGKSLEWIGNIDTYYGGTTYNQKFKG

KATLTVDKSSSTAYMQLKSLTSEDSAVYYCARSAYYGSTFAYWQGTLVTVSA<u>GGGGSGGGG</u>

<u>SGGGGS</u>DIQMTQSPASLSASVGETVTITCRASENIYSYLAWYQQKQGKSPQLLVYNAKTLI

EGVPSRFSGSGSGTQFSLKINSLQPEDFGSYFCQHHFGTPFTFGSGTELEIK

Underlined region is glycine-rich linker polypeptide. Bold region is fusion linker polypeptide.

```
Nucleotide (SEQ ID NO: 38):
GATATCCAGATGACCCAGTCCCCGAGCTCCCTGTCCGCCTCTGTGGGCGATAGG

GTCACCATCACCTGCCGGGCGAGCCAGGATGTGACCACCGCTGTAGCCTGGTATCAACAGA

AACCAGGAAAAGCTCCGAAGCTTCTGATTTACTGGGCGAGCCGTCTTCATAATGGCGTGCC

GAGCCGCTTTAGCGGCAGCGGCTCCGGGACGGATTTCACTCTGACCATCAGCAGTCTGCAG

CCGGAAGACTTCGCAACTTATTACTGTCAGCAACATTATAGCACCCCGCTGACGTTCGGAC

AGGGTACCAAGGTGGAGATCAAACGTACGGTGGCAGCACCGAGCGTGTTTATCTTTCCGCC

GAGCGACGAACAACTGAAAAGTGGCACAGCCAGCGTGGTGTGTTTACTGAACAACTTCTAY

CCTCGCGAGGCCAAGGTGCAGTGGAAAGTGGACAATGCACTGCAGAGTGGCAATAGCCAGG

AGAGCGTGACCGAACAGGATAGCAAAGATAGCACCTATAGCCTGAGTAGCACCCTGACCCT

GAGCAAGGCCGATTATGAGAAGCACAAGGTGTATGCATGCGAGGTTACCCATCAGGGCCTG

AGCAGCCCGGTGACCAAAAGCTTTAACCGTGGCGAATGCGGTGGTAGTGGTGGATCCGCCG

GTAGCGCAGGCAGCGCAGGTAGTGGTGGTAGCGAAGTTCAGCTGCAGGAAAGTGGCCCGGA
```

-continued

```
ACTGGAAATGCCGGGCGCCAGCGTGAAAATCAGTTGCAAAGCCAGCGGTAGCAGCTTCACA

GGCTTCAGCATGAACTGGGTGAAGCAGAGCAACGGTAAGAGCCTGGAGTGGATCGGCAACA

TTGACACCTACTATGGCGGCACCACCTACAACCAGAAGTTCAAAGGCAAGGCCACCCTGAC

CGTGGATAAAAGCAGCAGCACAGCCTACATGCAGCTGAAAAGCCTGACCAGCGAAGATAGC

GCCGTGTATTACTGCGCCCGTAGCGCCTATTACGGCAGCACCTTTGCATACTGCCAQGGTA

CCCTGGTGACCGTGAGCGCAGGTGGTGGTGGTAGTGGTGGTGGTGGTAGCGGTGGTGGCGG

TAGTGACATTCAAATGACCCAGAGCCCTGCAAGCCTGAGCGCCAGTGTTGGCGAAACCGTG

ACCATTACATGCCGCGCCAGCGAAAACATCTATAGTTACCTGGCCTGGTACCAGCAGAAAC

AGGGCAAAAGCCCGCAACTGCTGGTGTATAACGCCAAAACCCTGATTGAGGGCGTGCCGAG

TCGCTTCAGCGGTAGCGGTAGCGGTACACAGTTCAGTCTGAAAATCAACAGCCTGCAGCCG

GAAGACTTCGGCAGCTACTTTTGCCAGCACCACTTTGGCACCCCGTTTACATTTGGCAGCG

GCACCGAGCTGGAAATTAAATAA
```

Combined (SEQ ID NO: 37 and 38):

```
gatatccagatgacccagtccccgagctcctgtccgcctctgtgggcgatagggtcacc
D   I   Q   M   T   Q   S   P   S   S   L   S   A   S   V   G   D   R   V   T atcacctgccgggcgagccaggatgtgaccaccgctgtagcctggtatcaacagaaacca
I   T   C   R   A   S   Q   D   V   T   T   A   V   A   W   Y   Q   Q   K   P ggaaaagctccgaagcttctgatttactgggcgagccgtcttcataatggcgtgccgagc
G   K   A   P   K   L   L   I   Y   W   A   S   R   L   H   N   G   V   P   S cgctttagcggcagcggctccgggacggatttcactctgaccatcagcagtctgcagccg
R   F   S   G   S   G   S   G   T   D   F   T   L   T   I   S   S   L   Q   P gaagacttcgcaacttattactgtcagcaacattatagcaccccgctgacgttcggacag
E   D   F   A   T   Y   Y   C   Q   Q   H   Y   S   T   P   L   T   F   G   Q ggtaccaaggtggagatcaaacgtacggtggcagcaccgagcgtgtttatctttccgccg
G   T   K   V   E   I   K   R   T   V   A   A   P   S   V   F   I   F   P   P agcgacgaacaactgaaaagtggcacagccagcgtggtgtgtttactgaacaacttctat
S   D   E   Q   L   K   S   G   T   A   S   V   V   C   L   L   N   N   F   Y cctcgcgaggccaaggtgcagtggaaagtggacaatgcactgcagagtggcaatagccag
P   R   E   A   K   V   Q   W   K   V   D   N   A   L   Q   S   G   N   S   Q gagagcgtgaccgaacaggatagcaaagatagcacctatagcctgagtagcaccctgacc
E   S   V   T   E   Q   D   S   K   D   S   T   Y   S   L   S   S   T   L   T ctgagcaaggccgattatgagaagcacaaggtgtatgcatgcgaggttacccatcagggc
L   S   K   A   D   Y   E   K   H   K   V   Y   A   C   E   V   T   H   Q   G ctgagcagcccggtgaccaaaagctttaaccgtggcgaatgcggtggtagtggtggatcc
L   S   S   P   V   T   K   S   F   N   R   G   E   C   G   G   S   G   G   S gccggtagcgcaggcagcgcaggtagtggtggtagcgaagttcagctgcaggaaagtggc
A   G   S   A   G   S   A   G   S   G   G   S   E   V   Q   L   Q   E   S   G ccggaactggaaatgccgggcgccagcgtgaaaatcagttgcaaagccagcggtagcagc
P   E   L   E   M   P   G   A   S   V   K   I   S   C   K   A   S   G   S   S ttcacaggcttcagcatgaactgggtgaagcagagcaacggtaagagcctggagtggatc
F   T   G   F   S   M   N   W   V   K   Q   S   N   G   K   S   L   E   W   I ggcaacattgacacctactatggcggcaccacctacaaccagaagttcaaaggcaaggcc
G   N   I   D   T   Y   Y   G   G   T   T   Y   N   Q   K   F   K   G   K   A accctgaccgtggataaaagcagcagcacagcctacatgcagctgaaaagcctgaccagc
T   L   T   V   D   K   S   S   S   T   A   Y   M   Q   L   K   S   L   T   S gaagatagcgccgtgtattactgcgcccgtagcgcctattacggcagcacctttgcatac
E   D   S   A   V   Y   Y   C   A   R   S   A   Y   Y   G   S   T   F   A   Y tggcagggtaccctggtgaccgtgagcgcaggtggtggtggtagtggtggtggtggtagc
W   Q   G   T   L   V   T   V   S   A   G   G   G   G   S   G   G   G   G   S ggtggtggcggtagtgacattcaaatgacccagagccctgcaagcctgagcgccagtgtt
G   G   G   G   S   D   I   Q   M   T   Q   S   P   A   S   L   S   A   S   V
```

-continued

```
ggcgaaaccgtgaccattacatgccgcgccagcgaaaacatctatagttacctggcctgg
G  E  T  V  T  I  T  C  R  A  S  E  N  I  Y  S  Y  L  A  W taccagcagaaacagggcaaaagcccgcaactgctggtgtataacgccaaaaccctgatt
Y  Q  Q  K  Q  G  K  S  P  Q  L  L  V  Y  N  A  K  T  L  I gagggcgtgccgagtcgcttcagcggtagcggtagcggtacacagttcagtctgaaaatc
E  G  V  P  S  R  F  S  G  S  G  S  G  T  Q  G  S  L  K  I aacagcctgcagccggaagacttcggcagctacttttgccagcaccactttggcaccccg
N  S  L  Q  P  E  D  F  G  S  Y  F  C  Q  H  H  F  G  T  P tttacatttggcagcggcaccgagctggaaattaaataa
F  T  F  G  S  G  T  E  L  E  I  K  -
```

In an embodiment of any of the antibodies and/or scFv described herein (of the compositions described herein), the antibody and/or scFv is a neutralizing antibody/scFv with respect to the relevant Ebola virus.

In an embodiment, the antibody or scFv binds the relevant Ebola virus glycoprotein pre-fusion core, which is a hetero-hexamer of three copies of the GP1 and 3 copies of the GP2.

Exemplary Dual-Variable Domain (DVD) Bispecifics Sequences: the following exemplary DVD amino acid sequences (LC and HC) are provided, for the compositions of the invention as relating to the embodiments of antibodies E10, F4, KZ52, and 13C6 with non-limiting exemplary nucleotide sequences (in view of the degeneracy of the genetic code). The DVD constructs are dual-specific, tetravalent immunoglobulin G (IgG)-like molecules, termed dual-variable-domain immunoglobulin. In an embodiment, the sequences of the DVD except for the first and second linker amino acid sequences (such as the CDRs, the CH regions, the hinge regions, the CL region, sequences) are based on human IgG sequences).

E10-KZ52 HC DVD Fusion sequence-Amino Acid (SEQ ID NO 43):

EVQLLESGGGLVKPGGSLRLSCAASGFTLINYRMNWVRQAPGKGLEWVS

SISSSSSYIHYADSVKGRFTISRDNAENSLYLQMNSLRAEDTAVYYCVR

EGPRATGYSMADVFDIWGQGTMVTVSS<u>ASTKGP</u>EVQLVESGGGLVQPGG

SLRLSCAASGFAFNYYDIHWVRQAPGKGLEWVAYINPGGGNTYYADSVK

GRFTISADTSKNTAYLQMNSLRAEDTAVYYCARQLYGNSFMDYWGQGTL

VTVSS

Underlined bold region is amino acid linker sequence.

```
Nucleotide (SEQ ID NO: 44):
GAAGTGCAGCTGCTGGAAAGCGGCGGTGGCCTGGTGAAACCGGGTG

GTAGTCTGCGCCTGAGTTGCGCCGCCAGCGGTTTTACCCTGATCAACTACCGCA

TGAACTGGGTGCGTCAGGCCCCGGGCAAAGGTCTGGAGTGGGTTAGTAGCATC

AGCAGTAGCAGCAGCTACATCCATTACGCCGACAGCGTGAAAGGCCGTTTCAC

CATCAGTCGCGATAACGCCGAGAATAGCCTGTACCTGCAGATGAACAGCCTGC

GTGCAGAAGATACCGCCGTGTATTACTGCGTGCGCGAAGGTCCGCGTGCAACC

GGTTATAGCATGGCCGATGTGTTCGATATTTGGGGCCAGGGTACCATGGTGACC

GTGAGCAGTGCCAGCACCAAAGGTCCGGAAGTTCAGCTGGTGGAAAGCGGTGG

TGGTCTGGTTCAGCCGGGTGGTAGCTTACGTCTGAGCTGCGCAGCCAGCGGCTT

TGCCTTCAATTATTATGATATTCATTGGGTCGCCAAGCCCCGGGCAAGGGCCT

GGAATGGGTGGCATATATCAATCCGGGTGGCGGCAACACCTATTATGCCGATA

GCGTGAAGGGTCGCTTTACCATCAGCGCCGATACCAGCAAGAACACCGCCTATC

TGCAGATGAATAGCTTACGTGCTGAAGATACAGCCGTTTACTACTGTGCCCGCC

AGCTGTATGGCAACAGCTTCATGGATTATTGGGGCCAAGGCACCCTGGTGACCG

TTAGCAGC

Combined (SEQ ID NOS: 43 and 44):
gaagtgcagctgctggaaagcggcggtggcctggtgaaaccgggtggtagtctgcgcctg
E  V  Q  L  L  E  S  G  G  G  L  V  K  P  G  G  S  L  R  L agttgcgccgccagcggttttaccctgatcaactaccgcatgaactgggtgcgtcaggcc
S  C  A  A  S  G  F  T  L  I  N  Y  R  M  N  W  V  R  Q  A ccgggcaaaggtctggagtgggttagtagcatcagcagtagcagcagctacatccattac
P  G  K  G  L  E  W  V  S  S  I  S  S  S  S  S  Y  I  H  Y
```

-continued

```
gccgacagcgtgaaaggccgtttcaccatcagtcgcgataacgccgagaatagcctgtac
 A  D  S  V  K  G  R  F  T  I  S  R  D  N  A  E  N  S  L  Y ctgcagatgaacagcctgcgtgcagaagataccgccgtgtattactgcgtgcgcgaaggt
 L  Q  M  N  S  L  R  A  E  D  T  A  V  Y  Y  C  V  R  E  G ccgcgtgcaaccggttatagcatggccgatgtgttcgatatttggggccagggtaccatg
 P  R  A  T  G  Y  S  M  A  D  V  F  D  I  W  G  Q  G  T  M gtgaccgtgagcagtgccagcaccaaaggtccggaagttcagctggtggaaagcggtggt
 V  T  V  S  S  A  S  T  K  G  P  E  V  Q  L  V  E  S  G  G ggtctggttcagccgggtggtagcttacgtctgagctgcgcagccagcggctttgccttc
 G  L  V  Q  P  G  G  S  L  R  L  S  C  A  A  S  G  F  A  F aattattatgatattcattgggttcgccaagccccgggcaagggcctggaatgggtggca
 N  Y  Y  D  I  H  W  V  R  Q  A  P  G  K  G  L  E  W  V  A tatatcaatccgggtggcggcaacacctattatgccgatagcgtgaagggtcgctttacc
 Y  I  N  P  G  G  G  N  T  Y  Y  A  D  S  V  K  G  R  F  T atcagcgccgataccagcaagaacaccgcctatctgcagatgaatagcttacgtgctgaa
 I  S  A  D  T  S  K  N  T  A  Y  L  Q  M  N  S  L  R  A  E gatacagccgtttactactgtgcccgccagctgtatggcaacagcttcatggattattgg
 D  T  A  V  Y  Y  C  A  R  Q  L  Y  G  N  S  F  M  D  Y  W ggccaaggcaccctggtgaccgttagcagc
 G  Q  G  T  L  V  T  V  S  S
```

E10-KZ52 LC DVD Fusion sequence-Amino Acid (SEQ ID NO: 45):
ELVMTQSPDSLAVSLGERATINCKSSQSVLYSSNNKSYLAWYQQKPGQPPKLLIYW

ASTRESGVPDRFSGSGSGTDFTLTISSLQAEDVAVYYCQQYYSAPLTFGGGTKVEIK

TVAAPDIQMTQSPSSLSASVGDRVTITCRASQDVTTAVAWYQQKPGKAPKLLIYW

ASRLHNGVPSRFSGSGSGTDFTLTISSLQPEDFATYYCQQHYSTPLTFGQGTKVEIK

Underlined bold region is amino acid linker sequence.

```
Nucleotide (SEQ ID NO: 46):
GAACTGGTGATGACCCAGAGCCCGGATAGCCTGGCAGTTAGTCTGGG

CGAACGCGCCACCATTAACTGCAAAAGCAGCCAGAGCGTGCTGTATAGCAGCA

ATAATAAAAGCTATCTGGCATGGTACCAGCAGAAACCGGGTCAGCCGCCGAAG

CTGCTGATCTACTGGGCAAGCACCCGTGAAAGTGGTGTTCCGGATCGCTTTAGC

GGCAGCGGCAGCGGTACAGATTTCACCCTGACCATTAGCAGCCTGCAGGCCGA

AGATGTGGCAGTGTATTACTGCCAGCAGTACTATAGCGCACCGCTGACCTTTGG

TGGCGGCACCAAAGTGGAAATTAAGACCGTGGCCGCACCGGATATTCAGATGA

CCCAAAGCCCGAGCAGCCTGAGCTGCAAGCGTGGGTGATCGTGTGACAATTACC

TGCCGCGCAAGCCAGGATGTGACCACCGCCGTGGCATGGTATCAACAGAAACC

GGGCAAAGCCCCGAAACTGCTGATTTATTGGGCCAGCCGCCTGCATAATGGCGT

TCCGAGCCGCTTCAGCGGTAGCGGTAGCGGTACCGACTTTACCCTGACCATTAG

CAGTCTGCAGCCGGAGGATTTTGCCACCTACTACTGTCAGCAGCACTATAGCAC

CCCTCTGACCTTTGGCCAGGGCACCAAGGTGGAAATCAAA
```

```
Combined (SEQ ID NO: 45 and 46):
gaactggtgatgacccagagcccggatagcctggcagttagtctgggcgaacgcgccacc
 E  L  V  M  T  Q  S  P  D  S  L  A  V  S  L  G  E  R  A  T attaactgcaaaagcagccagagcgtgctgtatagcagcaataataaaagctatctggca
 I  N  C  K  S  S  Q  S  V  L  Y  S  S  N  N  K  S  Y  L  A tggtaccagcagaaaccgggtcagccgccgaagctgctgatctactgggcaagcacccgt
 W  Y  Q  Q  K  P  G  Q  P  P  K  L  L  I  Y  W  A  S  T  R
```

-continued

```
gaaagtggtgttccggatcgctttagcggcagcggcagcggtacagatttcaccctgacc
 E  S  G  V  P  D  R  F  S  G  S  G  S  G  T  D  F  T  L  T attagcagcctgcaggccgaagatgtggcagtgtattactgccagcagtactatagcgca
 I  S  S  L  Q  A  E  D  V  A  V  Y  Y  C  Q  Q  Y  Y  S  A ccgctgacctttggtggcggcaccaaagtggaaattaagaccgtggccgcaccggatatt
 P  L  T  F  G  G  G  T  K  V  E  I  K  T  V  A  A  P  D  I cagatgacccaaagcccgagcagcctgagtgcaagcgtgggtgatcgtgtgacaattacc
 Q  M  T  Q  S  P  S  S  L  S  A  S  V  G  D  R  V  T  I  T tgccgcgcaagccaggatgtgaccaccgccgtggcatggtatcaacagaaaccgggcaaa
 C  R  A  S  Q  D  V  T  T  A  V  A  W  Y  Q  Q  K  P  G  K gccccgaaactgctgatttattgggccagccgcctgcataatggcgttccgagccgcttc
 A  P  K  L  L  I  Y  W  A  S  R  L  H  N  G  V  P  S  R  F agcggtagcggtagcggtaccgactttaccctgaccattagcagtctgcagccggaggat
 S  G  S  G  S  G  T  D  F  T  L  T  I  S  S  L  Q  P  E  D tttgccacctactactgtcagcagcactatagcaccccctctgacctttggccagggcacc
 F  A  T  Y  Y  C  Q  Q  H  Y  S  T  P  L  T  F  G  Q  G  T aaggtggaaatcaaa
 R  V  E  I  K F4-KZ52 HC DVD Fusion sequence-Amino Acid (SEQ ID NO: 47):
EVQLLESGGGLVKPGGSLRLSCAASGFTLINYRMNWVRQAPGKGLEWV

SSISSSSSYIHYADSVKGRFTISRDNAENSLYLQMNSLRAEDTAVYYCVREGPRATG

YSMADVFDIWGQGTMVTVSSASTKGPEVQLVESGGGLVQPGGSLRLSCAASGFAF

NYYDMFWVRQAPGKGLEWVAYIKPGGGNTYYADSVKGRFTISADTSKNTAYLQM

NSLRAEDTAVYYCARQLYGNSFFDYWGQGTLVTVSS
```

Underlined bold region is amino acid linker sequence.

```
Nucleotide (SEQ ID NO: 48):
GAGGTGCAGCTGCTGGAGAGCGGTGGTGGTCTGGTGAAACCGGGCG

GTAGCTTACGCCTGAGTTGCGCCGCAAGCGGTTTTACCCTGATCAACTACCGCA

TGAACTGGGTTCGTCAGGCCCCGGGCAAGGGTCTGGAATGGGTGAGCAGCATT

AGCAGCAGCAGCAGCTACATCCACTACGCCGATAGCGTGAAAGGTCGCTTCAC

CATCAGCCGCGACAATGCCGAAAACAGCCTGTATCTGCAGATGAACAGCTTAC

GCGCCGAAGATACCGCCGTGTACTATTGCGTTCGTGAGGGTCCGCGTGCAACCG

GCTATAGCATGGCCGACGTGTTCGATATCTGGGGTCAGGGCACCATGGTGACCG

TTAGCAGCGCCAGCACCAAAGGTCCGGAAGTGCAACTGGTGGAAAGTGGCGGT

GGTCTGGTGCAGCCGGGTGGTAGTCTGCGCCTGAGCTGTGCCGCAAGCGGCTTT

GCCTTTAATTATTATGATATGTTTTGGGTGCGCCAGGCACCGGGCAAAGGTCTG

GAGTGGGTGGCCTACATTAAGCCGGGCGGTGGCAATACCTATTATGCCGACAG

CGTGAAGGGCCGCTTTACCATCAGCGCCGACACCAGCAAAAACACCGCCTACC

TGCAAATGAATAGCTTACGTGCTGAAGACACCGCAGTTTATTATTGCGCCCGCC

AGCTGTATGGCAATAGCTTCTTCGACTATTGGGGCCAAGGCACCCTGGTGACAG

TTAGCAGC

Combined (SEQ ID NO: 47 and 48):
gaggtgcagctgctggagagcggtggtggtctggtgaaaccgggcggtagcttacgcctg
 E  V  Q  L  L  E  S  G  G  G  L  V  K  P  G  G  S  L  R  L agttgcgccgcaagcggttttaccctgatcaactaccgcatgaactgggttcgtcaggcc
 S  C  A  A  S  G  F  T  L  I  N  Y  R  M  N  W  V  R  Q  A
```

```
ccgggcaagggtctggaatgggtgagcagcattagcagcagcagctacatccactac
 P  G  K  G  L  E  W  V  S  S  I  S  S  S  S  S  Y  I  H  Y gccgatagcgtgaaggtcgcttcaccatcagccgcgacaatgccgaaaacagcctgtat
 A  D  S  V  K  G  R  F  T  I  S  R  D  N  A  E  N  S  L  Y ctgcagatgaacagcttacgcgccgaagataccgccgtgtactattgcgttcgtgagggt
 L  Q  M  N  S  L  R  A  E  D  T  A  V  Y  Y  C  V  R  E  G ccgcgtgcaaccggctatagcatggccgacttgttcgatatctggggtcagggcaccatg
 P  R  A  T  G  Y  S  M  A  D  V  F  D  I  W  G  Q  G  T  M gtgaccgttagcagcgccagcaccaaaggtccggaagtgcaactggtggaaagtggcggt
 V  T  V  S  S  A  S  T  K  G  P  E  V  Q  L  V  E  S  G  G ggtctggtgcagccgggtggtagtctgcgcctgagctgtgccgcaagcggctttgccttt
 G  L  V  Q  P  G  G  S  L  R  L  S  C  A  A  S  G  F  A  F aattattatgatatgttttgggtgcgccaggcaccgggcaaaggtctggagtgggtggcc
 N  Y  Y  D  M  F  W  V  R  Q  A  P  G  K  G  L  E  W  V  A tacattaagccgggcggtggcaatacctattatgccgacagcgtgaagggccgctttacc
 Y  I  K  P  G  G  G  N  T  Y  Y  A  D  S  V  K  G  R  F  T atcagcgccgacaccagcaaaaacaccgcctacctgcaaatgaatagcttagctgctgaa
 I  S  A  D  T  S  K  N  T  A  Y  L  Q  M  N  S  L  R  A  E gacaccgcagtttattattgcgcccgccagctgtatggcaatagcttcttcgactattgg
 D  T  A  V  Y  Y  C  A  R  Q  L  Y  G  N  S  F  F  D  Y  W ggccaaggcaccctggtgacagttagcagc
 G  Q  G  T  L  V  T  V  S  S
```

F4-KZ52 LC DVD Fusion sequence-Amino Acid (SEQ ID NO: 49):
ELVMTQSPDSLAVSLGERATINCKSSQSVLYSSNNKSYLAWYQQKPGQP

PKLLIYWASTRESGVPDRFSGSGSGTDFTLTISSLQAEDVAVYYCQQYYSAPLTFGG

GTKVEIKTVAAPDIQMTQSPSSLSASVGDRVTITCKASQDVTTAVAWYQQKPGKAP

KLLIYWASTRHTGVPSRFSGSGSGTDFTLTISSLQPEDFATYYCQQHYSTPLTFGQGT

KVEIK

Underlined bold region is amino acid linker sequence.

```
Nucleotide (SEQ ID NO: 50):
GAACTGGTGATGACCCAGAGCCCGGATAGTCTGGCAGTTAGCCTGGG

CGAACGCGCCACCATTAACTGCAAAAGCAGCCAGAGCGTGCTGTACAGCAGCA

ACAACAAGAGCTACCTGGCCTGGTATCAGCAGAAACCGGGTCAGCCTCCGAAA

CTGCTGATTTACTGGGCAAGCACCCGTGAAAGTGGCGTGCCGGATCGCTTTAGC

GGCAGCGGTAGCGGTACCGATTTCACCCTGACAATCAGCAGCCTGCAGGCCGA

AGATGTTGCCGTGTACTACTGCCAGCAGTACTACAGCGCCCCGTTAACCTTCGG

CGGTGGCACCAAAGTGGAGATTAAAACCGTGGCCGCCCCGGATATTCAGATGA

CCCAAAGCCCGAGTAGCCTGAGCGCAAGCGTGGGTGATCGCGTGACCTATTACC

TGCAAAGCCAGCCAGGACGTGACCACCGCAGTTGCCTGGTACCAGCAGAAGCC

GGGCAAAGCACCCGAAGCTGCTGATTTATTGGGCAAGCACCCGCCATACCGGTG

TGCCTAGCCGTTTCAGCGGTAGTGGCAGTGGCACCGACTTTACCCTGACCATCA

GCAGTCTGCAGCCGGAAGACTTCGCCACCTACTATTGCCAACAGCACTACAGCA

CCCCGCTGACCTTTGGCCAGGGCACCAGGTGGAAATTAAG

Combined (SEQ ID NO: 49 and 50):
gaactggtgatgacccagagcccggatagtctggcagttagcctgggcgaacgcgccacc
 E  L  V  M  T  Q  S  P  D  S  L  A  V  S  L  G  E  R  A  T attaactgcaaaagcagccagagcgtgctgtacagcagcaacaacaagagctacctggcc
 I  N  C  K  S  S  Q  S  V  L  Y  S  S  N  N  K  S  Y  L  A
```

-continued

```
tggtatcagcagaaaccgggtcagcctccgaaactgctgatttactgggcaagcacccgt
 W   Y   Q   Q   K   P   G   Q   P   P   K   L   L   I   Y   W   A   S   T   R gaaagtggcgtgccggatcgctttagcggcagcggtagcggtaccgatttcaccctgaca
 E   S   G   V   P   D   R   F   S   G   S   G   S   G   T   D   F   T   L   T atcagcagcctgcaggccgaagatgttgccgtgtactactgccagcagtactacagcgcc
 I   S   S   L   Q   A   E   D   V   A   V   Y   Y   C   Q   Q   Y   Y   S   A ccgttaaccttcggcggtggcaccaaagtggagattaaaaccgtggccgccccggatatt
 P   L   T   F   G   G   G   T   K   V   E   I   K   T   V   A   A   P   D   I cagatgacccaaagcccgagtagcctgagcgcaagcgtgggtgatcgcgtgaccattacc
 Q   M   T   Q   S   P   S   S   L   S   A   S   V   G   D   R   V   T   I   T tgcaaagccagccaggacgtgaccaccgcagttgcctggtaccagcagaagccgggcaaa
 C   K   A   S   Q   D   V   T   T   A   V   A   W   Y   Q   Q   K   P   G   K gcaccgaagctgctgatttattgggcaagcacccgccataccggtgtgcctagccgtttc
 A   P   K   L   L   I   Y   W   A   S   T   R   H   T   G   V   P   S   R   F agcggtagtggcagtggcaccgactttaccctgaccatcagcagtctgcagccggaagac
 S   G   S   G   S   G   T   D   F   T   L   T   I   S   S   L   Q   P   E   D ttcgccacctactattgccaacagcactacagcacccccgctgacctttggccagggcacc
 F   A   T   Y   Y   C   Q   Q   H   Y   S   T   P   L   T   F   G   Q   G   T aaggtggaaattaag
 K   V   E   I   K E10-13C6 HC DVD Fusion sequence-Amino Acid (SEQ ID NO: 51):
MGRLTSSFLLIVPAYVLSQLTLKESGPGILKPSQTLSLTCSLSGFSLSTSG

VGVGWFRQPGKGLEWLALIWWDDDKYYNPSLKSQLSISKDFSRNQVFLKISNVDI

ADTATYYCARRDPFGYDNAMGYWGQGTSVTVSSASTKGPEVQLVESGGGLVQPG

GSLRLSCAASGFAFNYYDIHWVRQAPGKGLEWVAYINPGGGNTYYADSVKGRFTI

SADTSKNTAYLQMNSLRAEDTAVYYCARQLYGNSFMDYWGQGTLVYVSS
                                                                   35
```

Underlined bold region is amino acid linker sequence.

```
Nucleotide (SEQ ID NO: 52):
ATGGGTCGCCTGACCAGTAGCTTTCTGCTGCTGATTGTGCCTGCCTAT

GTGTTAAGCCAGCTGACCCTGAAGGAGAGCGGCCCGGGTATTCTGAAACCTAG

CCAGACCCTGAGCCTGACCTGCAGCCTGAGCGGTTTTAGCCTGAGTACCAGCGG

TGTGGGCGTTGGTTGGTTCCGCCAGCCGAGCGGTAAAGGTCTGGAATGGCTGGC

CCTGATTTGGTGGGATGATGATAAATACTACAACCCGAGCCTGAAAAGCCAGCT

GAGCATTAGCAAAGATTTTAGCCGCAATCAGGTTTTCCTGAAAATCAGCAACGT

GGACATTGCCGACACCGCCACCTACTATTGCGCCCGCCGCGACCCGTTTGGCTA

TGATAACGCCATGGGCTACTGGGGCCAGGGTACCAGCGTTACCGTTAGCAGCG

CCAGCACCAAAGGCCCGGAAGTGCAGCTGGTTGAAAGCGGTGGTGGTCTGGTT

CAGCCGGGTGGTAGTCTGCGTCTGAGTTGCGCCGCCAGCGGCTTTGCCTTCAAT

TATTATGATATCCATTGGGTTCGCCAGGCACCGGGTAAGGGCCTGGAATGGGTG

GCATACATTAATCCGGGTGGCGGTAACACCTACTATGCCGACAGCGTGAAAGG

TCGCTTCACCATCAGCGCCGATACCAGCAAGAACACCGCCTATCTGCAGATGAA

CAGCCTGCGTGCCGAAGATACCGCCGTGTATTATTGTGCCCGCCAGCTGTATGG

CAACAGCTTCATGGATTATTGGGGCCAAGGCACCCTGGTTACCGTTAGCAGC
```

Combined (SEQ ID NOS: 51 and 52):
```
atgggtcgcctgaccagtagctttctgctgctgattgtgcctgcctatgtgttaagccag
 M  G  R  L  T  S  S  F  L  L  L  I  V  P  A  Y  V  L  S  Q ctgaccctgaaggagagcggcccgggtattctgaaacctagccagaccctgagcctgacc
 L  T  L  K  E  S  G  P  G  I  L  K  P  S  Q  T  L  S  L  T tgcagcctgagcggttttagcctgagtaccagcggtgtgggcgttggttggttccgccag
 C  S  L  S  G  F  S  L  S  T  S  G  V  G  V  G  W  F  R  Q ccgagcggtaaaggtctggaatggctggccctgatttggtgggatgatgataaatactac
 P  S  G  K  G  L  E  W  L  A  L  I  W  D  D  D  K  Y  Y aacccgagcctgaaaagccagctgagcattagcaaagattttagccgcaatcaggttttc
 N  P  S  L  K  S  Q  L  S  I  S  K  D  F  S  R  N  Q  V  F ctgaaaatcagcaacgtggacattgccgacaccgccacctactattgcgcccgccgcgac
 L  K  I  S  N  V  D  I  A  D  T  A  T  Y  Y  C  A  R  R  D ccgtttggctatgataacgccatgggctactggggccagggtaccagcgttaccgttagc
 P  F  G  Y  D  N  A  M  G  Y  W  G  Q  G  T  S  V  T  V  S agcgccagcaccaaaggcccggaagrgcagctggttgaaagcggtggtggtctggttcag
 S  A  S  T  K  G  P  E  V  Q  L  V  E  S  G  G  G  L  V  Q ccgggtggtagtctgcgtctgagttgcgccgccagcggctttgccttcaattattatgat
 P  G  G  S  L  R  L  S  C  A  A  S  G  F  A  F  N  Y  Y  D atccattgggttcgccaggcaccgggtaagggcctggaatgggtggcatacattaatccg
 I  H  W  V  R  Q  A  P  G  K  G  L  E  W  V  A  Y  I  N  P ggtggcggtaacacctactatgccgacagcgtgaaaggtcgcttcaccatcagcgccgat
 G  G  G  N  T  Y  Y  A  D  S  V  K  G  R  F  T  I  S  A  D accagcaagaacaccgcctatctgcagatgaacagcctgcgtgccgaagataccgccgtg
 T  S  K  N  T  A  Y  L  Q  M  N  S  L  R  A  E  D  T  A  V tattattgtgcccgccagctgtatggcaacagcttcatggattattggggccaaggcacc
 Y  Y  C  A  R  Q  L  Y  G  N  S  F  M  D  Y  W  G  Q  G  T ctggttaccgttagcagc
 L  V  T  V  S  S E10-13C6 LC DVD Fusion sequence-Amino Acid (SEQ ID NO: 53):
MGIKMKSQTQAFVFAFLWLSGVDGDIVMTQSQKFMSTSVGDRVSLTCK

ASQNVGTAVAWYQQKPGQSPKLLIYSASNRYTGVPDRFTGSGSGTDFTLTISNMQS

EDLADYFCQQYSSYPLTFGAGTKLELRRTVAAPDIQMTQSPSSLSASVGDRVTITCR

ASQDVTTAVAWYQQKPGKAPKLLIYWASRLHNGVPSRFSGSGSGTDFTLTISSLQP

EDFATYYCQQHYSTPLTFGQGTKVEIK
```

Underlined bold region is amino acid linker sequence.

```
Nucleotide (SEQ ID NO: 54):
ATGGGCATCAAAATGAAGAGCCAGACCCAGGCCTTTGTGTTTGCCTT

TCTGTGGCTGAGTGGCGTGGATGGCGATATCGTGATGACCCAGAGCCAAAAGTT

CATGAGCACCAGCGTGGGCGATCGCGTGAGCCTGACCTGCAAAGCCAGCCAGA

ACGTGGGCACCGCAGTGGCATGGTACCAGCAGAAACCGGGCCAGAGCCCGAAA

CTGCTGATCTACAGCGCAAGCAATCGCTATACCGGTGTTCCGGATCGCTTTACA

GGCAGCGGCAGCGGCACCGACTTTACCCTGACCATTAGCAACATGCAGAGCGA

AGACCTGGCCGACTATTTTTGCCAGCAGTACAGCAGCTATCCGCTGACCTTTGG

CGCCGGCACCAAATTAGAACTGCGCCGTACCGTTGCCGCCCCGGATATTCAGAT

GACCCAAAGCCCGAGTAGCCTGAGCGCAAGCGTGGGCGACCGTGTGACCATTA

CCTGTCGCGCCAGCCAGGACGTTACCACCGCAGTTGCCTGGTATCAGCAAAAAC

CGGGCAAAGCCCCGAAGCTGCTGATCTATTGGGCAAGTCGTCTGCATAACGGC
```

-continued

```
GTTCCGAGCCGCTTTAGCGGCAGTGGTAGCGGCACCGATTTCACCCTGACCATC

ACACCGCTGACCTTCGGCCAGGGCACCAAGGTGGAAATTAAA

Combined (SEQ ID NOS: 53 and 54):
atgggcatcaaaatgaagagccagacccaggcctttgtgtttgcctttctgtggctgagt
 M  G  I  K  M  K  S  Q  T  Q  A  F  V  F  A  F  L  W  L  S ggcgtggatggcgatatcgtgatgacccagagccaaaagttcatgagcaccagcgtgggc
 G  V  D  G  D  I  V  M  T  Q  S  Q  K  F  M  S  T  S  V  G gatcgcgtgagcctgacctgcaaagccagccagaacgtgggcaccgcagtggcatggtac
 D  R  V  S  L  T  C  K  A  S  Q  N  V  G  T  A  V  A  W  Y cagcagaaacccgggccagagcccgaaactgctgatctacagcgcaagcaatcgctatacc
 Q  Q  K  P  G  Q  S  P  K  L  L  I  Y  S  A  S  N  R  Y  T ggtgttccggatcgctttacaggcagcggcagcggcaccgactttaccctgaccattagc
 G  V  P  D  R  F  T  G  S  G  S  G  T  D  F  T  L  T  I  S aacatgcagagcgaagacctggccgactcttttttgccagcagtacagcagctatccgctg
 N  M  Q  S  E  D  L  A  D  Y  F  C  Q  Q  Y  S  S  Y  P  L acctttggcgccggcaccaaattagaactgcgccgtaccgttgccgccccggatattcag
 T  F  G  A  G  T  K  L  E  L  R  R  T  V  A  A  P  D  I  Q atgacccaaagcccgagtagcctgagcgcaagcgtgggcgaccgtgtgaccattacctgt
 M  T  Q  S  P  S  S  L  S  A  S  V  G  D  R  V  T  I  T  C cgcgccagccaggacgttaccaccgcagttgcctggtatcagcaaaaaccgggcaaagcc
 R  A  S  Q  D  V  T  T  A  V  A  W  Y  Q  Q  K  P  G  K  A ccgaagctgctgatctattgggcaagtcgtctgcataacggcgttccgagccgctttagc
 P  K  L  L  I  Y  W  A  S  R  L  H  N  G  V  P  S  R  F  S ggcagtggtagcggcaccgatttcaccctgaccatcagcagcctgcagccggaggattttt
 G  S  G  S  G  T  D  F  T  L  T  I  S  S  L  Q  P  E  D  F gccacctactactgtcagcagcactacagcacaccgctgaccttcggccagggcaccaag
 A  T  Y  Y  C  Q  Q  H  Y  S  T  P  L  T  F  G  Q  G  T  K gtggaaattaaa
 V  E  I  K F4-13C6 HC DVD Fusion sequence-Amino Acid (SEQ ID NO: 55):
MGRLTSSFLLLIVPAYYLSQLTLKBSGPGILKPSQTLSLTCSLSGFSLSTSG

VGVGWFRQPSGKGLEWLALIWWDDDKYYNPSLKSQLSISKDFSRNQVFLKISNVDI

ADTATYYCARRDPFGYDNAMGYWGQGTSVTVSSASTKGPEVQLVESGGGLVQPG

GSLRLSCAASGFAFNYYDMFWVRQAPGKGLEWVAYIKPGGGNTYYADSVKGRFTI

SADTSKNTAYLQMNSLRAEDTAVYYCARQLYGNSFFDYWGQGTLVTVSS
```

Underlined bold region is amino acid linker sequence.

```
Nucleotide (SEQ ID NO: 56):
ATGGGTCGCCTGACCAGTAGCTTTCTGCTGCTGATTGTGCCTGCCTAT

GTGTTAAGCCAGCTGACCCTGAAGGAGAGCGGCCCGGGTATTCTGAAACCTAG

CCAGACCCTGAGCCTGACCTGCAGCCTGAGCGGTTTTAGCCTGAGTACCAGCGG

TGTGGGCGTTGGTTGGTTCCGCCAGCCGAGCGGTAAAGGTCTGGAATGGCTGGC

CCTGATTTGGTGGGATGATGATAAATACTACAACCCGAGCCTGAAAAGCCAGCT

GAGCATTAGCAAAGATTTTAGCCGCAATCAGGTTTTVVTGAAAATCAGCAACGT

GGACATTGCCGACACCGCCACCTACTATTGCGCCCGCCGCGACCCGTTTGGCTA

TGATAACGCCATGGGCTACTGGGGCCAGGGTACCAGCGTTACCGTTAGCAGCG

CCAGCACCAAAGGCCCGGAAGTGCAGCTGGTTGAAAGCGGTGGTGGTCTHGYT

CAGCCGGGTGGTAGTCTGCGTCTGAGTTGCGCCGCCAGCGGCTTTGCCTTCAAT
```

-continued

```
TATTATGATATGTTTTGGGTTCGCCAGGCACCGGGTAAGGGCCTGGAATGGGTG

GCATACATTAAACCGGGTGGCGGTAACACCTACTATGCCGACAGCGTGAAAGG

TCGCTTCACCATCAGCGCCGATACCAGCAAGAACACCGCCTATCTGCAGATGAA

CAGCCTGCGTGCCGAAGATACCGCCGTGTATTATTGTGCCCGCCAGCTGTATGG

CAACAGCTTCTTTGATTATTGGGGCCAAGGCACCCTGGTTACCGTTAGCAGC

Combined (SEQ ID NOS: 55 and 56):
atgggtcgcctgaccagtagctttctgctgctgattgtgcctgcctatgtgttaagccag
M   G   R   L   T   S   S   F   L   L   L   I   V   P   A   Y   V   L   S   Q ctgaccctgaaggagagcggcccgggtattctgaaacctagccagaccctgagcctgacc
L   T   L   K   E   S   G   P   G   I   L   K   P   S   Q   T   L   S   L   T tgcagcctgagcggttttagcctgagtaccagcggtgtgggcgttggttggttccgccag
C   S   L   S   G   F   S   L   S   T   S   G   V   G   V   G   W   F   R   G aacccgagcctgaaaagccagctgagcattagcaaagattttagccgcaatcaggttttc
P   S   G   K   G   L   E   W   L   A   L   I   W   D   D   D   K   Y   Y ctgaaaatcagcaacgtggacattgccgacaccgccacctactattgcgcccgccgcgac
N   P   S   L   K   S   Q   L   S   I   S   K   D   F   S   R   N   Q   V   F ctgaaaatcagcaacgtggacattgccgacaccgccacctactattgcgcccgccgcgac
L   K   I   S   N   V   D   I   A   D   T   A   T   Y   Y   C   A   R   R   D ccgtttggctatgataacgccatgggctactggggccagggtaccagcgttaccgttagc
P   F   G   Y   D   N   A   M   G   Y   W   G   Q   G   T   S   V   T   V   S agcgccagcaccaaaggcccggaagtgcagctggttgaaagcggtggtggtctggttcag
S   A   S   T   K   G   P   E   V   Q   L   V   E   S   G   G   G   L   V   Q ccgggtggtagtctgcgtctgagttgcgccgccagcggctttgccttcaattattatgat
P   G   G   S   L   R   L   S   C   A   A   S   G   F   A   F   N   Y   Y   D atgttttgggttcgccaggcacccgggtaagggcctggaatgggtggcatacattaaaccg
M   F   W   V   R   Q   A   P   G   K   G   L   E   W   V   A   Y   I   K   P ggtggcggtaacacctactatgccgacagcgtgaaaggtcgcttcaccatcagcgccgat
G   G   G   N   T   Y   Y   A   D   S   V   K   G   R   F   T   I   S   A   D accagcaagaacaccgcctatctgcagatgaacagcctgcgtgccgaagataccgccgtg
T   S   K   N   T   A   Y   L   Q   M   N   S   L   R   A   E   D   T   A   V tattattgtgcccgccagctgtatggcaacagcttctttgattattggggccaaggcacc
Y   Y   C   A   R   Q   L   Y   G   N   S   F   F   D   Y   W   G   Q   G   T ctggttaccgttagcagc
L   V   T   V   S   S F4-13C6 LC DVD Fusion sequence-Amino Acid (SEQ ID NO: 57):
MGIKMKSQTQAFVFAFLWLSGVDGDIVMTQSQKFMSTSVGDRVSLCK

ASQNVGTAVAWYQQKPGQSPKLLIYSASNRYTGVPDRFTGSGSGTDFTLTISNMQS

EDLADYFCQQYSSYPLTFGAGTKLELRRTVAAPDIQMTQSPSSLSASVGDRVTITCK

ASQDVTTAVAWYQQKPGKAPKLLIYWASTRHTGVPSRFSGSGSGTDFTLTISSLQP

EDFATYYCQQHYSTPLTFGQGTKVEIK
```

Underlined bold region is amino acid linker sequence.

```
Nucleotide (SEQ ID NO: 58):
ATGGGCATCAAAATGAAGAGCCAGACCCAGGCCTTTGTGTTTGCCTT

TCTGTGGCTGAGTGGCGTGGATGGCGATATCGTGATGACCCAGAGCCAAAAGTT

CATGAGCACCAGCGTGGGCGATCGCGTGAGCCTGACCTGCAAAGCCAGCCAGA

ACGTGGGCACCGCAGTGGCATGGTACCADCAGAAACCGGGCCAGAGCCCGAAA

CTGCTGATCTACAGCGCAAGCAATCGCTATACCGGTGTTCCGGATCGCTTTACA

GGCAGCGGCAGCGGCACCGACTTTACCCTGACCATTAGCAACATGCAGAGCGA
```

```
AGACCTGGCCGACTATTTTTGCCAGCAGTACAGCAGCTATCCGCTGACCTTTGG

CGCCGGCACCAAATTAGAACTGCGCCGTACCGTTGCCGCCCCGGATATTCAGAT

GACCCAAAGCCCGAGTAGCCTGAGCGCAAGCGTGGGCGACCGTGTGACCATTA

CCTGTAAAGCCAGCCAGGACGTTACCACCGCAGTTGCCTGGTATCAGCAAAAA

CCGGGCAAAGCCCCGAAGCTGCTGATCTATTGGGCAAGTACCCTCATACCGGC

GTTCCGAGCCGCTTTAGCGGCAGTGGTAGCGGCACCGATTTCACCCTGACCATC

AGCAGCCTGCAGCCGGAGGATTTTGCCACCTACTACTGTCAGCAGCACTACAGC

ACACCGCTGACCTTCGGCCAGGGCACCAAGGTGGAAATTAAA

Nucleotide (SEQ ID NO: 57 and 58):
atgggcatcaaaatgaagagccagacccaggcctttgtgtttgcctttctgtggctgagt
 M   G   I   K   M   K   S   Q   Q   T   A   F   V   F   A   F   L   W   L   S ggcgtggatggcgatatcgtgatgacccagagccaaaagttcatgagcaccagcgtgggc
 G   V   D   G   D   I   V   M   T   Q   S   Q   K   F   M   S   R   S   V   G gatcgcgtgagcctgacctgcaaafccagccagaacgtgggcaccgcagtggcatggtac
 D   R   V   S   L   T   C   K   A   S   Q   N   V   G   T   A   V   A   W   Y cagcagaaaccgggccagagcccgaaactgctgatctacagcgcaagcaatcgctatacc
 Q   Q   K   P   G   Q   S   P   K   L   L   I   Y   S   A   S   N   R   Y   T ggtgttccggatcgctttacaggcagcggcagcggcaccgactttaccctgaccattagc
 G   V   P   D   R   F   T   G   S   G   S   G   T   D   F   T   L   T   I   S aacatgcagagcgaagacctggccgactattttgccagcagtacagcagctatccgctg
 N   M   Q   S   E   D   L   A   D   Y   F   C   Q   Q   Y   S   S   Y   P   L acctttggcgccggcaccaaattagaactgcgccgtaccgttgccgccccggatattcag
 T   F   G   A   G   T   K   L   E   L   R   R   T   V   A   A   P   D   I   Q atgacccaaagcccgagtagcctgagcgcaagcgtgggcgaccgtgtgaccattacctgt
 M   T   Q   S   P   S   S   L   S   A   S   V   G   D   R   V   T   I   T   C aaagccagccaggacgttaccaccgcagttgcctggtatcagcaaaaaccgggcaaagcc
 K   A   S   Q   D   V   T   T   A   V   A   W   Y   Q   Q   K   P   G   K   A ccgaagctgctgatctattgggcaagtacccgtcataccggcgttccgagccgctttagc
 P   K   L   L   I   Y   W   A   S   T   R   H   T   G   V   P   S   R   F   S ggcagtggtagcggcaccgatttcaccctgaccatcagcagcctgcagccggaggatttt
 G   S   G   S   G   T   D   F   T   L   T   I   S   S   L   Q   P   E   D   F gccacctactactgtcagcagcactacagcacaccgctgaccttcggccagggcaccaag
 A   T   Y   Y   C   Q   Q   H   Y   S   T   P   L   T   F   G   Q   G   T   K gtggaaattaaa
 V   E   I   K
```

In an embodiment of any of the antibodies and/or scFv described herein (of the compositions described herein), the antibody and/or scFv is a neutralizing antibody/scFv with respect to the relevant Ebola virus.

In an embodiment, the antibody or scFv binds the relevant Ebola virus glycoprotein pre-fusion core, which is a heterohexamer of three copies of the GP1 and 3 copies of the GP2.

In an embodiment, the antibody comprises an Fc region having a sequence identical to a human Fc region.

In an embodiment, the Fc region of the antibody is glycosylated.

A "humanized" antibody as used herein, unless otherwise indicated, is a chimeric antibody that contains minimal sequence (CDRs) derived from non-human immunoglobulin (e.g. such as a mouse immunoglobulin). In one embodiment, a humanized antibody is an antibody having a sequence of a human immunoglobulin (recipient antibody) in which CDR residues of a hypervariable region (HVR) of the recipient are replaced by CDR residues from a non-human species (donor antibody) such as a mouse having the desired specificity. In some instances, FR residues of the human immunoglobulin variable domain are replaced by corresponding non-human residues, for example by a backmutation. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. Other techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety. The framework regions of the antibodies of the invention having a sequence identical to a human framework region may include amino acid residues not encoded by human germline sequences (e.g., mutations introduced by random or site-specific mutagenesis). In an embodiment, the isolated antibody or antigen-binding antibody fragment comprises a variable domain framework sequence having a sequence identical to a human variable domain framework sequence FR1, FR2, FR3 or FR4. In an embodiment, the isolated antibody or antigen-binding antibody fragment comprises a variable domain framework sequence having a sequence identical to at least two of human variable domain framework sequences FR1, FR2, FR3 or FR4. In an embodiment, the isolated antibody or antigen-binding antibody fragment comprises a variable domain framework sequence having a sequence identical to at least three of human variable domain framework sequences FR1, FR2, FR3 or FR4. In an embodiment, the isolated antibody or antigen-binding antibody fragment comprises a variable domain framework sequence having a sequence identical to all four of human variable domain framework sequences FR1, FR2, FR3 and FR4.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine.

In an embodiment, the antibodies of the invention described herein comprise a human Fc region or a variant human Fc region. A variant human Fc region comprises an amino acid sequence which differs from that of a native sequence Fc region by virtue of at least one amino acid modification, yet retains at least one effector function of the native sequence human Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

In an embodiment, the scFv is a variable domain light chain (VL) and a variable domain heavy chain (VH) which are linked N—C or C—N, respectively, via a peptide linker. In an embodiment the linker of the scFv is 5-30 amino acids in length. In an embodiment the linker of the scFv is 10-25 amino acids in length. In an embodiment the peptide linker comprises glycine, serine and/or threonine residues. For example, see Bird et al., Science, 242:423-426 (1988) and Huston et al., Proc. Natl. Acad. Sci. USA, 85:5879-5883 (1988), each of which are hereby incorporated by reference in their entirety.

In an embodiment, the antibody and or scFv(s) of the composition of the invention do not recognize an Ebola GP1 mucin-like domain. In an embodiment, the antibody and or scFv(s) of the composition of the invention do not recognize an Ebola GP1 variable glycan cap.

For trispecific constructs, which target three different Filovirus strains and/or species, an IgG directed at the prefusion glycoprotein core for one strain is fused two different scFvs (each directed at a prefusion glycoprotein core for two other strains, respectively). The scFvs are fused to the IgG at two different positions, with the two scFv having specificity for the different viruses. In a non-limiting example, an SUDV-specific IgG with EBOV-specific scFv as light chain N-terminal fusion and a MARV-specific scFv as a heavy chain C-terminal fusion.

The phrase "and/or" as used herein, with option A and/or option B for example, encompasses the embodiments of (i) option A, (ii) option B, and (iii) option A plus option B.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group subjectly and all possible subgroups of the main group, but also the main group absent one or more of the group members. The present invention also envisages the explicit exclusion of one or more of any of the group members in the claimed invention.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Ebola virus pathogenesis and cell entry: The infectious agents Ebola virus and Marburg virus (MARV) are the two major species of the Filoviridae family of enveloped negative-sense RNA viruses (1-4). Based on nucleotide sequence and outbreak location, isolates of Ebola virus are classified into five species: *Zaire* (EBOV), Tai Forest (TAFV), *Sudan* (SUDV), Reston (RESTV), and Bundibugyo (BDBV). There are two MARV variants (Marburg and Ravn). Severe human disease and deaths (30-90% case fatality rates in large outbreaks) are associated with EBOV, SUDV, BDBV, and MARV (2). Although the ecology of these agents remains incompletely understood, several species of African fruit bats appear to be reservoirs for Ebola virus and MARV (5). EBOV and SUDV are the most pathogenic among the ebolaviruses, and both have been associated with recurring outbreaks (6). Among the 13 documented EBOV outbreaks and the six SUDV outbreaks from 1976-2012, the average human case fatality rates are 70% and 52%, respectively. Together, EBOV and SUDV account for over 95% of Ebola virus-related deaths (6); these statistics do not include the ongoing EBOV outbreak in West Africa that is of unprecedented scope and geographic distribution. Therefore, a therapeutic agent that is effective against both EBOV and SUDV would greatly reduce the threat of an Ebola virus pandemic.

All human outbreaks occur as a result of direct contact with infected wildlife, with subsequent person-to-person transmission, mostly through the mucosa or contaminated needles. Uncontrolled viral replication is central to filovirus-induced disease, both because it is cytopathic and because it induces dysregulation of the host immune system (2, 7, 8). Therefore, antiviral therapies that reduce viral load are expected to increase patient survival, in part, by allowing time to mount an effective immune response. While many cell types can be infected with filovirus in vitro and in vivo, antigen-presenting cells (macrophages and dendritic cells) appear to be early and sustained targets of infection in vivo. Infected macrophages are unable to stimulate a robust immune response, and cause a "cytokine storm" that is proposed to be the primary cause of the blood clotting abnormalities and vascular leakage characteristic of filovirus hemorrhagic fever (9). Damage to other tissues (e.g., liver, kidneys, vascular endothelia) is thought to contribute to the above and to late-stage multi-organ failure. Death typically occurs 8-15 days after infection (10). Because of their high mortality rate, rapid proliferation, and potential for aerosolization, Ebola virus and Marburg virus are classified as Category A biodefense pathogens. There are currently no FDA-approved treatments for these infections.

The filovirus genome is a ~19 kb single-strand negative-sense RNA genome that encodes seven genes arranged in a linear fashion (1-4). In mature viral particles and infected cells, the genome is intimately associated with four viral proteins: the nucleocapsid protein NP, the polymerase L, the polymerase accessory protein VP35, and the transcriptional activator protein VP30. This nucleocapsid structure is in turn encapsidated in a viral matrix, comprising proteins VP40 and VP24. The host-derived viral membrane bilayer surrounds, and is peripherally associated with, the matrix. Embedded in the viral membrane are trimers of the viral glycoprotein, GP, which mediates the first step in infection: delivery of the viral nucleocapsid "payload" into the cytoplasm of the host cell. GP is the target of virus-directed antibodies that neutralize extracellular filovirus particles (4, 11-14).

Figures 1A, 1B:
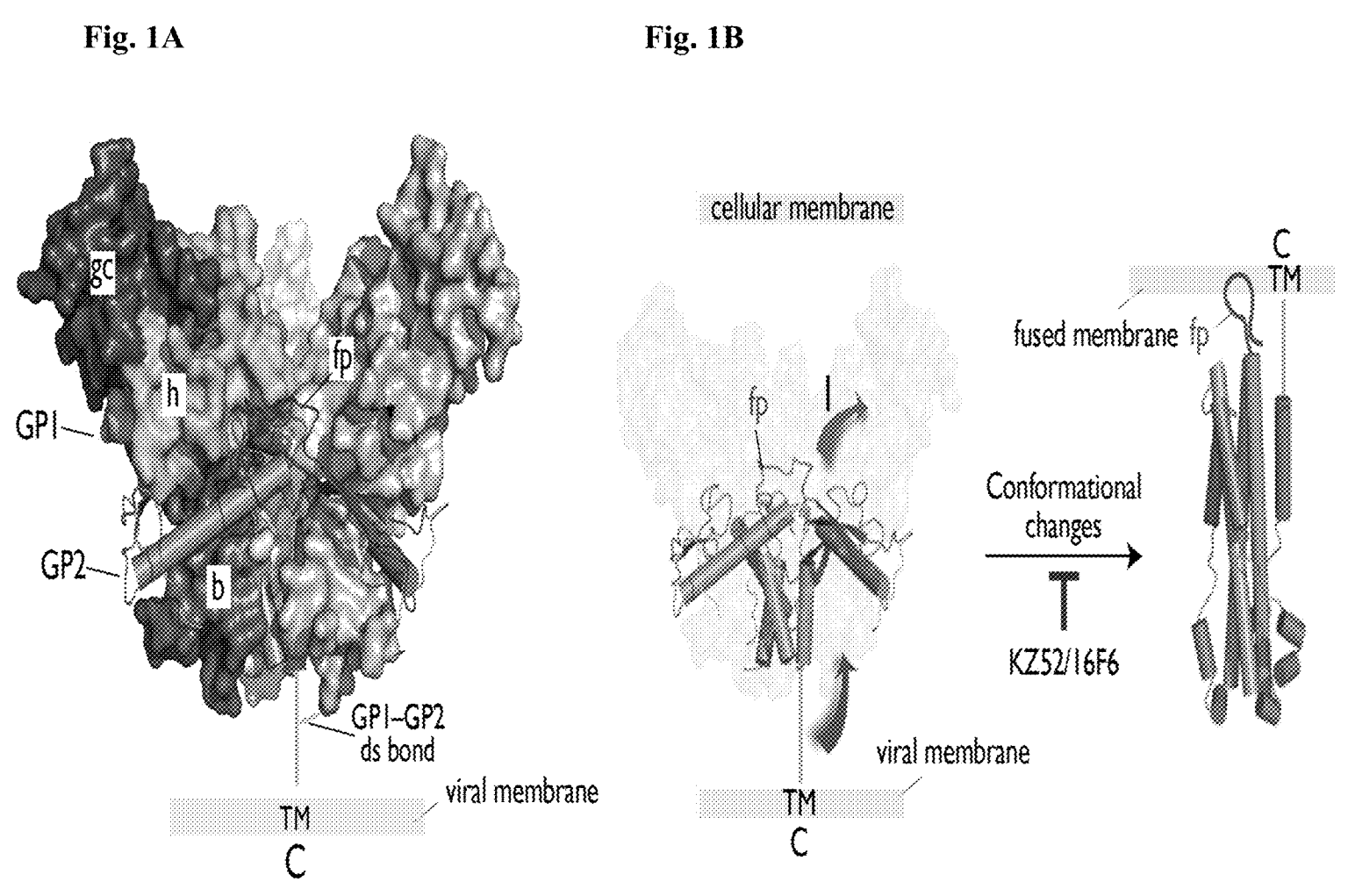

The mature filovirus GP spike is a trimer of three disulfide-linked GP1-GP2 heterodimers, generated by endoproteolytic cleavage of the GP0 precursor polypeptide by furin during virus assembly (4, 13-15). GP1 mediates viral adhesion to host cells and regulates the activity of the transmembrane subunit GP2, which mediates fusion of viral and cellular membranes during cell entry. The prefusion GP1-GP2 spike has a "chalice-and-bowl" morphology—the three GP2 subunits form the chalice within which the bowl, comprised of the three GP1 subunits, rests (FIG. 1A) (13-15). This trimeric assembly is stabilized mainly by GP1-GP2 and GP2-GP2 contacts. The GP1 subunit is organized into three subdomains. The base ('b', light blue) interacts extensively with GP2 and clamps it in its prefusion conformation. The head ('h', green) contains a putative receptor-binding sequence. Together with GP2, the base and head subdomains of GP1 form the conserved structural core of the GP1-GP2 spike. In contrast to the GP1-GP2 core, the most external subdomains of GP1—the glycan cap ('gc', dark blue) and the mucin-like domain (not shown)—are extensively glycosylated and display a high degree of sequence variation among filovirus isolates. Therefore, antibodies with broadly cross-neutralizing activity must recognize the conserved GP1-GP2 core and not the variable glycan cap or mucin-like domain. In response to a fusion trigger within host cell endosomes, GP2 disengages from GP1 and undergoes a series of large-scale conformational changes that drive coalescence of viral and cellular membrane bilayers (FIG. 1B) (4, 16-19). The result of viral membrane fusion is cytoplasmic release of the viral nucleocapsid. KZ52 and 16F6 likely function by inhibiting these fusion-associated conformational changes (4, 13, 14).

Figure 2:
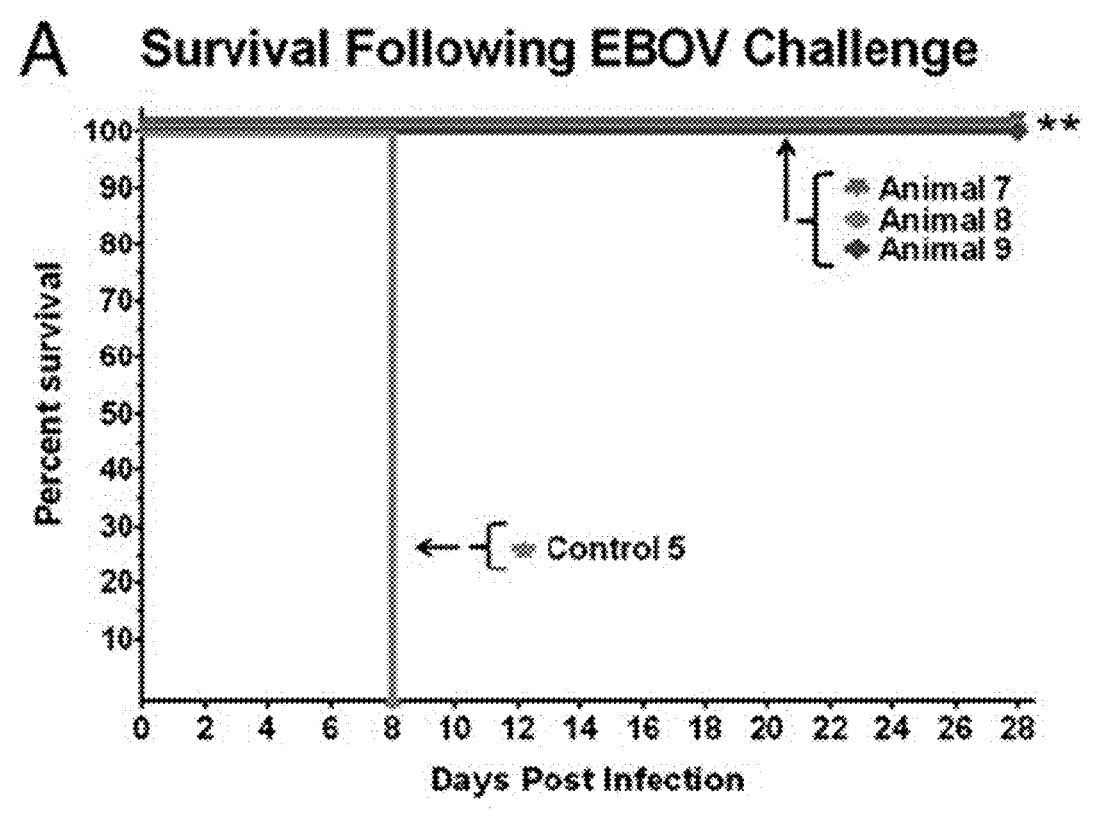

Immunotherapy is a tractable approach to filovirus treatment pre- and post-exposure. Until recently, it has been unclear if passive immunotherapy would be effective for treatment or prophylaxis of filovirus infection (20). However, recent studies using non-human primate (NHP) models have provided convincing evidence that immunotherapy can and should be pursued (21, 22). Dr. Dye's laboratory reported that rhesus macaques can be protected up to 48 hours post-exposure from EBOV or MARV infection by passive transfer of fractionated EBOV- or MARV-specific IgG isolated from convalescent animals (same species) (21). In this study, two of the three NHPs that were challenged with EBOV, and then administered serum IgG, had no clinical signs of illness; the third developed mild, delayed signs of the disease but fully recovered (FIG. 2). The control animal died eight days post exposure, as is typical for untreated infection. Similar results were obtained with MARV-challenged animals, suggesting that filovirus infection in general can be treated with antibodies. This protection required only three total administrations of the serum IgG (48 hours post exposure, then again at four and eight days). Therefore, antibody-based filovirus therapy is feasible, protective, and can be administered post-exposure. In 2012, three groups (Kobinger, Zeitlin/Olinger and Takada/Feldmann) independently reported that cocktails of mAbs could protect NHPs against EBOV challenge (22-24). The Kobinger study involved a cocktail of three GP-specific murine monoclonal antibodies (mAbs) that were administered at intervals of 3 days beginning 24 or 48 hours post-exposure. Initiation of the treatment at 24 hours conferred complete survival (4/4 macaques) and initiation of treatment 48 hours post-exposure conferred partial protection (2/4 macaques fully recovered) (22). The Olinger/Zeitlin study demonstrated that a cocktail of three mouse/human chimeric mAbs (known as 'MB-003') produced in whole plant cells provided full protection when administered 1 hour post-exposure, and partial protection when administered 24 or 48 hours post-exposure (23). The Takada/Feldmann study demonstrated that a combination of two human-mouse chimeric mAbs could partially protect NHPs against EBOV challenge (24). Three NHPs were administered a cocktail of the two mAbs 24 hours preceding challenge with EBOV, then again 24- and 48-hours post-exposure. One of the three animals survived, one had delayed onset of hemorrhagic fever and was ultimately euthanized, and the other was similar to the control. It was concluded that the protection could be improved if serum half-life of the mAbs were optimized, or if the mAbs were used in combination with other mAbs or therapies. Enhanced neutralization potency would also likely improve protection. More recent studies have shown that an optimized cocktail of three monoclonal antibodies (ZMapp) can provide protection in non-human primates up to six days post-exposure.

There is a gap in treatment of filovirus infection. Only a handful of animal challenge studies have been performed with mAb therapies, in part because few mAbs that target GP (the primary neutralization target) exist. Most antibodies elicited in natural infection react preferentially with a secreted, dimeric version of the glycoprotein known as sGP and do not neutralize the fusion-relevant GP spike (4, 25, 26). Wilson et al. first demonstrated that GP-specific neutralizing antibodies (nAbs) could protect mice from EBOV challenge (27). However, three of five protective antibodies recognize highly variable sequences within the GP1 mucin-like domain, rendering them unlikely candidates for development of cross-neutralizing mAbs. Antibodies KZ52 and 16F6 are among the few well-characterized nAbs and both bind to the GP prefusion core (13, 14). KZ52 was identified by phage-based panning of a B-cell antibody library isolated from a human survivor of EBOV infection (28). Initial experiments in rodent protection studies were promising, but KZ52 failed to protect in macaques when administered on days −1 and +4 at 50 mg/kg (12, 20). 16F6, a mouse mAb, was identified recently by Dr. Dye's group by vaccination with vector-based vaccine expressing SUDV GP (14).

mAb 16F6 is much more potent than is KZ52 against the corresponding virus species, but its murine scaffold limits therapeutic utility at this point. Fully humanized 16F6 variants have been developed (U.S. patent application Ser. No. 14/291,608, filed May 30, 2014, hereby incorporated by reference). Head-to-head comparison in neutralization assays using a vesicular stomatitis virus pseudotyped with GP (VSV-GP) with KZ52 (against EBOV GP, GPEBOV) and 16F6 (against SUDV GP, GPSUDV) indicates that 16F6 can reduce infectivity by ~100-fold more than KZ52 at high antibody concentrations (FIG. 3). Both KZ52 and 16F6 are narrowly strain specific (KZ52 for EBOV and 16F6 for SUDV), and therefore have limited potential as immunotherapeutics because they cannot cross-neutralize (13, 14).

Several candidate therapies and vaccines are under exploration for filovirus infection (27-33). Multiple promising vaccine candidates are able to protect NHPs from lethal challenge, including adenovirus-vectored, VSV-vectored, and virus-like particle-based vaccines (29-32). While any safe and effective EBOV vaccine will be useful for populations or workers that are at high risk for exposure, it is unlikely that vaccination against EBOV will be practical on a general population level. Therefore, there is still a need for an EBOV therapy that can be used to treat acute exposure or infection. Other biologics are under evaluation, including an antisense therapy undergoing clinical trials, and a promising RNAi therapy (33, 34). However, the use of nucleic acids as therapeutic agents in general is in its infancy and therefore there is a high barrier to FDA approval for such biologics. Furthermore, these therapeutic nucleic acids are strain-specific. Some small molecules against EBOV or host targets are also being explored, but studies are largely limited to early proof-of-concept stage (35-37).

Figures 9A, 9B:
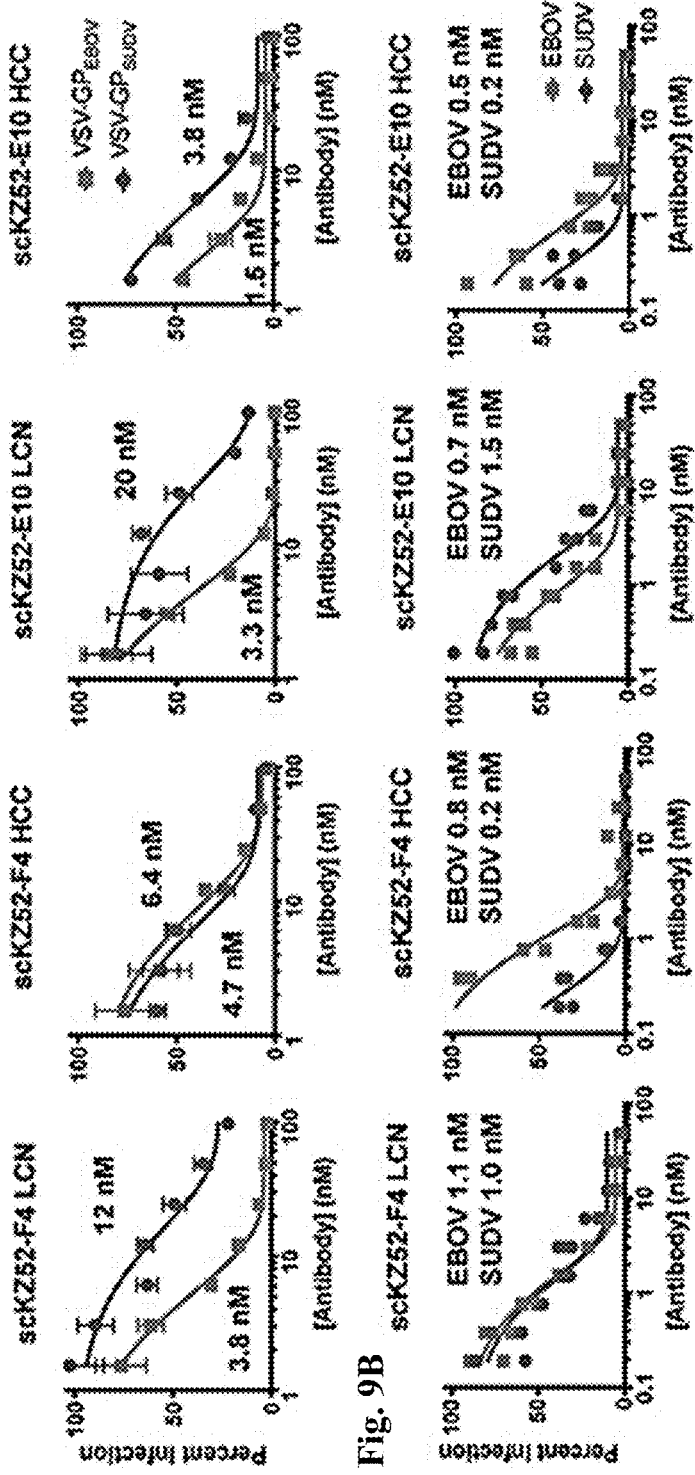
FIG. 9A-9B. Virus neutralization. (A) Dose-dependent neutralization of VSV-GPEBOV and VSV-GPSUDV by scKZ52-F4 LCN, scKZ52-F4 HCC, scKZ52-E10 LCN, and scKZ52-E10 HCC. Calculated IC50 values are listed next to each curve. (B) Neutralization of authentic viruses by PRNT assay, with IC50 values listed.

Based on favorable expression and stability profiles, Bis-mAbs scKZ52-F4 LCN, scKZ52-F4 HCC, scKZ52-E10 LCN, and scKZ52-E10 HCC were chosen for additional analysis. These four Bis-mAbs showed dose-dependent neutralization of both VSV-GP pseudotyped viruses, although the $IC_{50}$ values were in general higher for VSV-$GP_{SUDV}$ than VSV-$GP_{EBOV}$ for the "LCN" constructs (FIG. 9A). For both "HCC" constructs the relative IC50 values for the two pseudotyped viruses were approximately the same. In all cases, the highest levels (≥95%) of neutralization were achieved at 100 nM Bis-mAb concentration against both pseudotyped viruses. The four Bis-mAbs were also tested for their capacity to neutralize authentic EBOV (Kikwit-1995) and SUDV (Boniface-2000) under BioSafety Level 4 (BSL4) conditions using a plaque reduction neutralization test (PRNT) (FIG. 9B). For all Bis-mAbs, potent neutralization of both EBOV and SUDV were observed in both assays, with low- or sub-nanomolar IC50 values in the PRNT assay for both viruses.

In Vivo Efficacy. To explore the protective potential of a single cross-binding monoclonal antibody reagent, scKZ52-F4 LCN and scKZ52-F4 HCC were evaluated for their ability to confer protection of mice in two separate mouse models with post-exposure dosing (FIG. 10). For EBOV, a well-established mouse challenge model was employed with mouse-adapted (ma) EBOV (Mayinga) and WT C57BL/6 mice (40). For SUDV, this laboratory has previously reported a model for pathogenicity that utilizes type I interferon α/β receptor knockout mice infected at 4 weeks old with human lethal SUDV (Boniface) (41, 39). For maEBOV, a single Bis-mAb dose (200 µg) was provided 24 hours post-challenge and for SUDV, two doses (500 µg each) were provided at one and four days post-exposure. The SUDV model, which involves immunocompromised mice infected at 4 weeks of age, provides a more stringent requirement for protection, and thus higher antibody doses are required than that used for the maEBOV model. Monospecific mAbs Z.6D8 (EBOV) and F4 (SUDV) were included as controls as they have previously shown excellent protection against their respective viruses (41).

Both Bis-mAb treatments resulted in high (>70%) protection in both models, with scKZ52-F4 HCC conferring 100% protection against both viruses. As expected, Z.6D8 as a treatment was not protective against SUDV but was 100% protective against EBOV. SUDV monospecific mAb F4 provided 100% protection against SUDV, as we have previously reported (41) and afforded partial (30%) protection against maEBOV. However, the level of protection for F4 against maEBOV is not statistically distinguishable from a PBS control group, in which all mice succumbed to disease by day 7 (p=0.13). Murine 16F6 afforded no protection against maEBOV in a group size of n=5 challenge experiment. The 100% protection from maEBOV observed for scKZ52-F4 HCC was statistically distinguishable from both PBS and F4 controls in this experiment, whereas 70% protection of scKZ52-F4 LCN was distinguishable only from the PBS. These results indicate that both scKZ52-F4 HCC and scKZ52-F4 LCN provide statistically significant protection relative to a PBS control group. For SUDV, both Bis-mAbs and F4 were significantly protective relative to the Z.6D8 negative control treatment group.

Aggregate weight loss was observed in the Bis-mAb- and F4-treated group during the course of the SUDV challenge, a phenomenon we have previously reported for post-exposure dosing of protective SUDV mAbs (41,39). However, the surviving Bis-mAb or mAb-treated population continued to gain weight (on average) after day 8. For maEBOV, mean weight loss was observed during the initial infection period for scKZ52-F4 LCN- and F4-treated mice, as some mice became sick, but this trend was not observed with either Z.6D8 or scKZ52-F4 HCC mice. All mice from the Z.6D8- and scKZ52-F4 HCC-treated groups survived the infection.

Figure 10C:
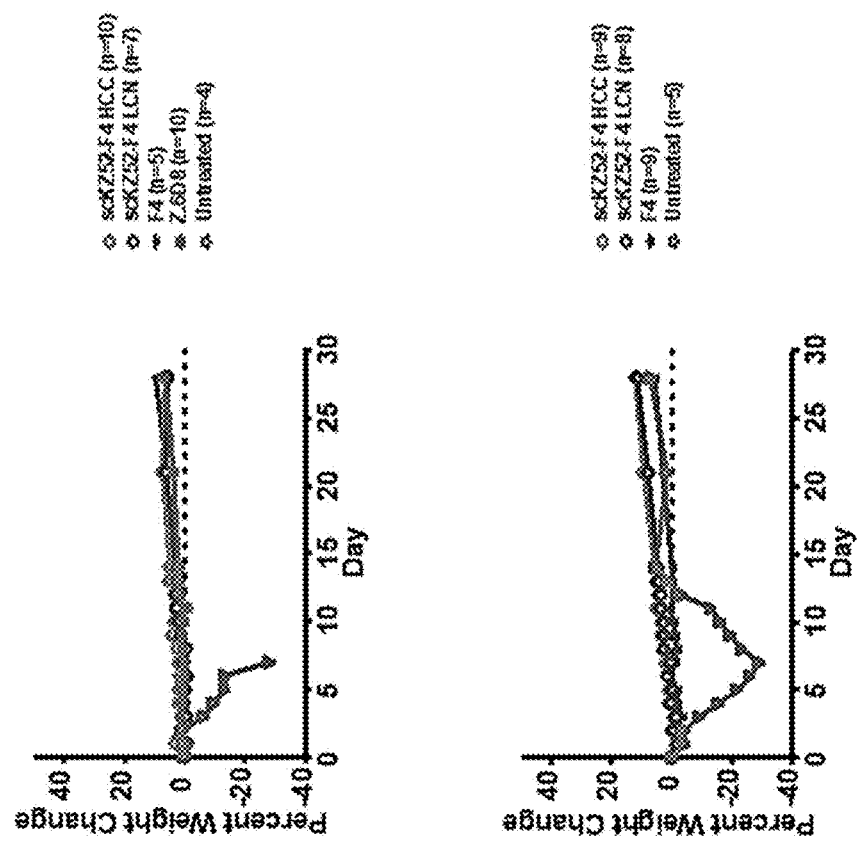
Figure 10C:
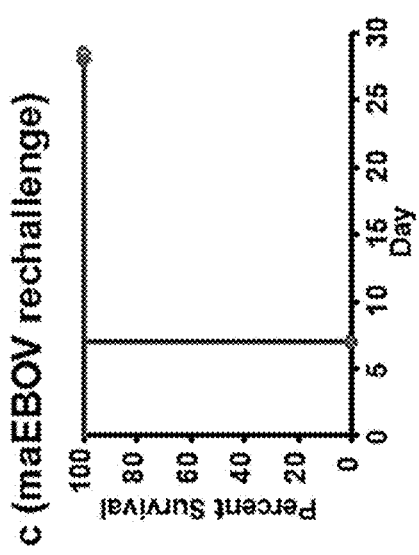
Figure 10D:
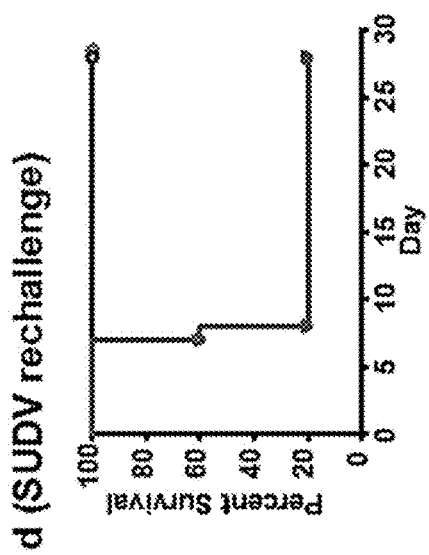

To examine the capacity for memory immunity in Bis-mAb and mAb-treated mice, the surviving cohort of both EBOV and SUDV challenges were subjected to rechallenge (with the same isolate of virus) without mAb treatment 35 days after the initial challenge (FIGS. 10C and 10D). For both EBOV and SUDV, Bis-mAb or mAb treated mice were completely protected against viral rechallenge with no observable aggregate weightloss, indicating memory immunity had been established. In both cases, an untreated negative control group was also included to confirm lethality of the virus.

Materials and Methods

Bispecific construct cloning using pMAZ-IgH and pMAZ-IgL vectors from Mazor et al. (38):

Constructs: KZ52 scFv was linked via a flexible peptide linker to either full length E10 or F4 IgG at the N- or C-terminus of the heavy chain (HC) and light chain (LC) (total of 8 constructs) were ordered from Genewiz, South Plainfield, NJ. The nucleotide sequence was optimized for *E. coli*. The constructs were re-suspended in MilliQ™ water to a final concentration of 100 ng/µL.

Cloning: KZ52-E10 and KZ52-F4 N-terminal HC fusions: pMAZ-IgH and the constructs were digested using BssHII and NheI in a final volume of 50 µL for 3 hours. Digests were purified using the Qiagen Gel Extraction Kit. The antibody inserts were ligated into the digested IgH vector using the Quick Ligase kit from NEB. The ligation product was then transformed into Top10 cells and plated onto LB/Carb plates. Sequences were verified via Sanger Sequencing by Genewiz.

KZ52-E10 and KZ52-F4 N-terminal LC fusions: pMAZ-IgL and the constructs were digested using BssHII and BsiWI in a final volume of 50 µL for 3 hours. Subsequent steps were performed as above.

KZ52-F4 C-terminal HC and LC fusions: pMAZ-IgH, pMAZ-IgL and the constructs were digested with BssHII and XbaI ina final volume of 50 µL for 3 hours. Subsequent steps were performed as above.

KZ52-E10 C-terminal HC and LC fusions: A BamHI restriction site was engineered into the flexible peptide linker for the KZ52-F4 C-terminal HC and LC fusions. To produce KZ52-E10 C-terminal HC and LC fusions, the F4-KZ52 C-terminal HC and LC (in pMAZ vectors) were digested with BssHII and BamHI in a final volume of 50 µL for 3 hours. Subsequent steps were performed as above.

After sequences were verified, all 8 constructs were maxiprepped using the Macherey-Nagel maxiprep kit. Additionally, the wildtype (WT) E10 and F4 IgH and IgL DNA was also maxiprepped.

Transfections: Transfections were carried out at the AECOM protein production facility using HEK293F cells in 600 mL cultures as follows:

For each bispecific construct, the WT E10 or F4 IgH or IgL was paired with the corresponding bispecific DNA (example: E10-KZ52 N-terminal HC-IgH is paired with the E10 IgL WT). Both plasmids were co-transfected into 293F cells at a final amount of 201 µg using 1.2 mg of PEI transfection reagent in 50 mL PBS. Cells were incubated for 6 days at 37° C., 5% $CO_2$, and 110 rpm.

Antibody purification: Cells were spun down at 4000 rpm, 4° C., for 15 minutes. The supernatant was brought to a pH of 8.0 using diluted NaOH. Protein A agarose beads (ThermoScientific) were washed in 10 mL Gentle Antibody Binding Buffer (ThermoScientific). Washed beads were then incubated with antibody containing supernatants for approximately 2 hours at 4° C. The flow through was collected. Beads were washed 2 times with 10 mL of Gentle Antibody Binding Buffer. Antibodies were eluted 5 times using 2.5 mL of Gentle Antibody Elution Buffer (ThermoScientific). Elutions were subsequently desalted into 150 mM HEPES/200 mM NaCl using PD-10 Desalting Columns (GE Healthcare). For verification of purity, SDS-PAGE (10-15%) were run and stained with Coomassie Blue dye.

Results

Figure 4:
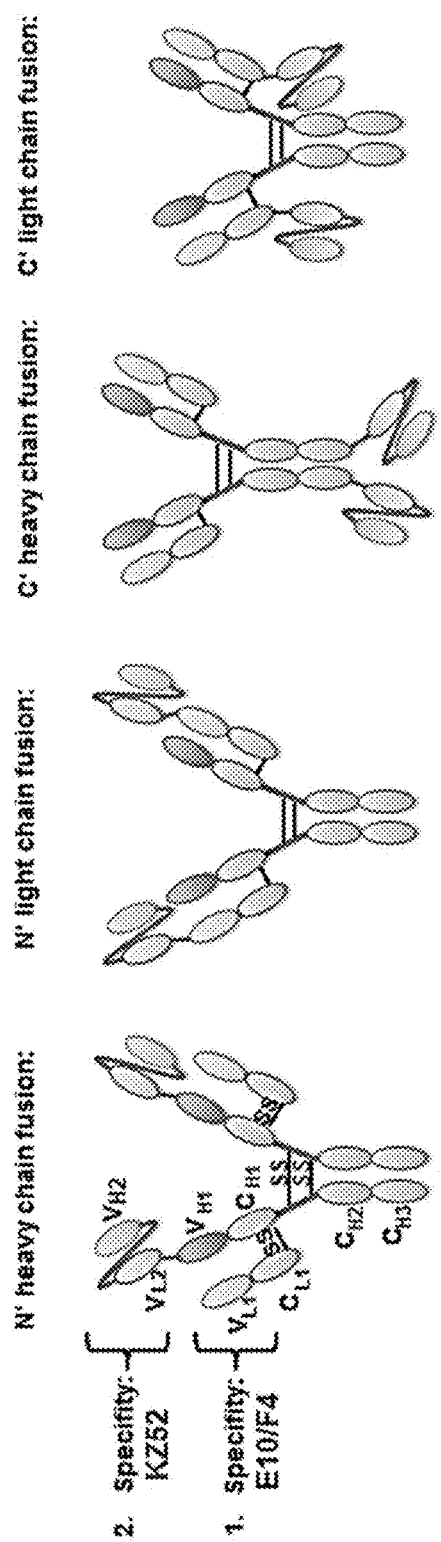
FIG. 4. Exemplary Bispecific (E10 & F4 IgG+KZ52 scFv) designs.
Figure 5:
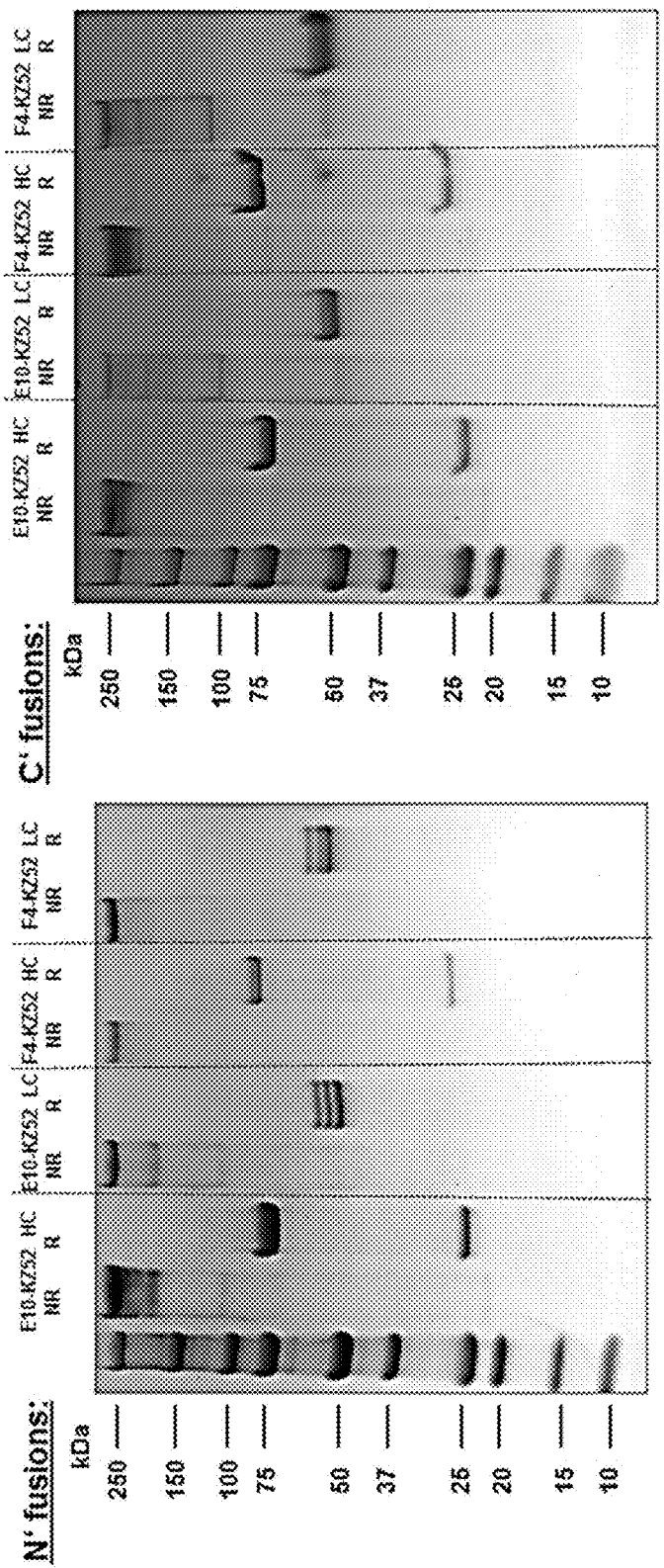
FIG. 5. Bispecifics (E10 & F4 IgG+KZ52 scFv) SDS PAGE.
Figure 6:
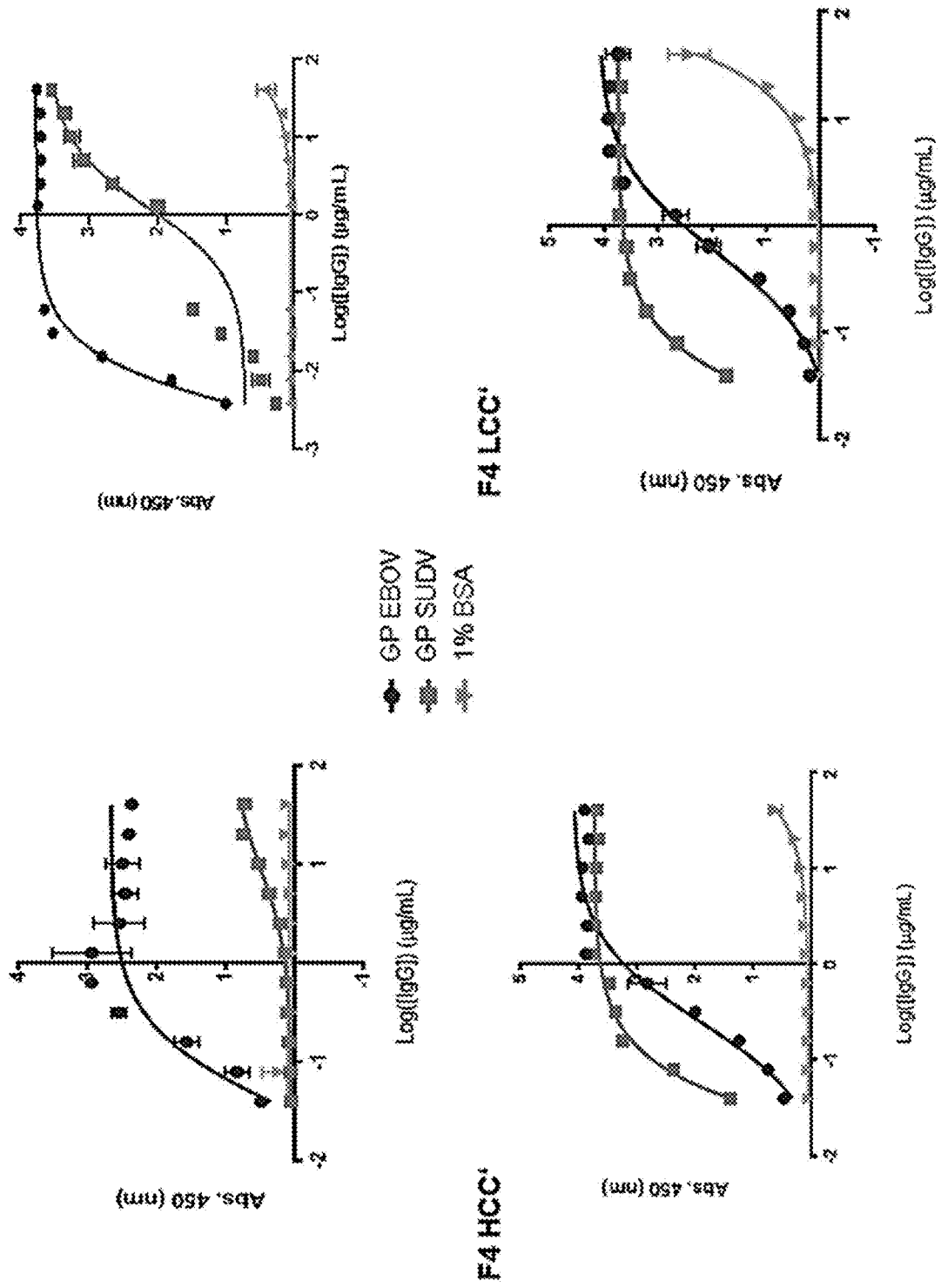
FIG. 6. Bispecifics (F4 IgG+KZ52 scFv) binding data.
Figure 7:
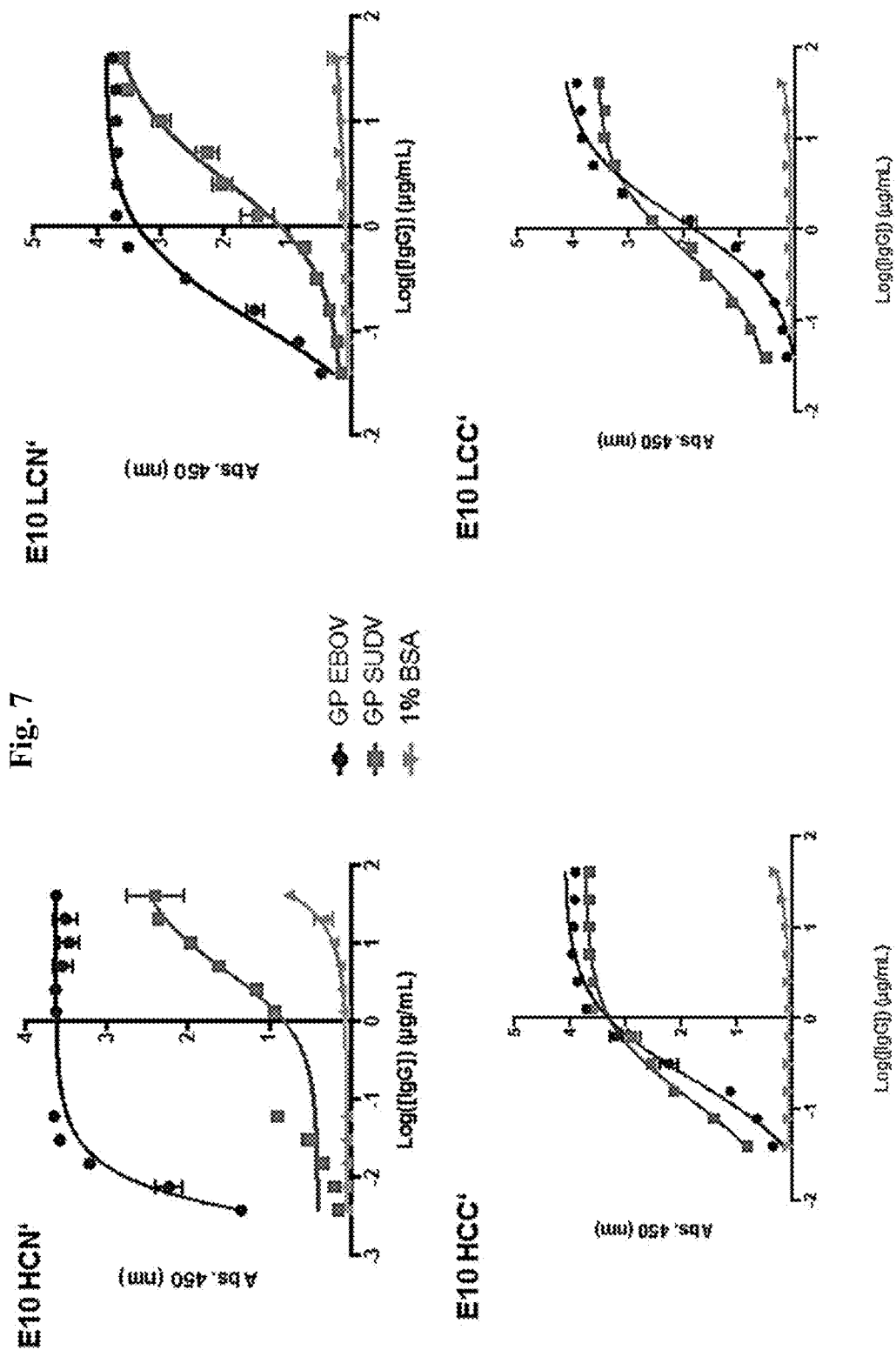
FIG. 7. Bispecifics (E10 IgG+KZ52 scFv) binding data.

Multi-specific antibody-based structures are disclosed herein, including the exemplified bispecific antibodies (Bis-mAbs) comprising a genetic fusion of a single chain Fv (scFv) and an IgG, each harboring two separate specificities. In one embodiment, EBOV/SUDV Bis-mAbs were created by fusing the scFv of EBOV-specific mAb KZ52 and the IgG of SUDV specific mAbs E10 or F4. Several formats for the fusion are available, with the scFv as an N-terminal fusion to the IgG heavy chain (N' heavy chain or HCN'), the IgG light chain (N' light chain or LCN'); or as a C-terminal fusion to the IgG heavy and light chains (C' heavy chain or HCC', and C' light chain or LCC') (see FIG. 4). KZ52 (EBOV-specific) is a human antibody, and E10 and F4 (SUDV-specific) are fully humanized versions of the mouse antibody 16F6 recently reported. All together, a total of eight Bis-mAbs were produced, and could be purified from HEK293F cells in varying yield and stability (see FIG. 5). The binding of all eight for the envelope glycoprotein (GP) from EBOV or SUDV was demonstrated (see FIGS. 5 and 7).

Figure 8:
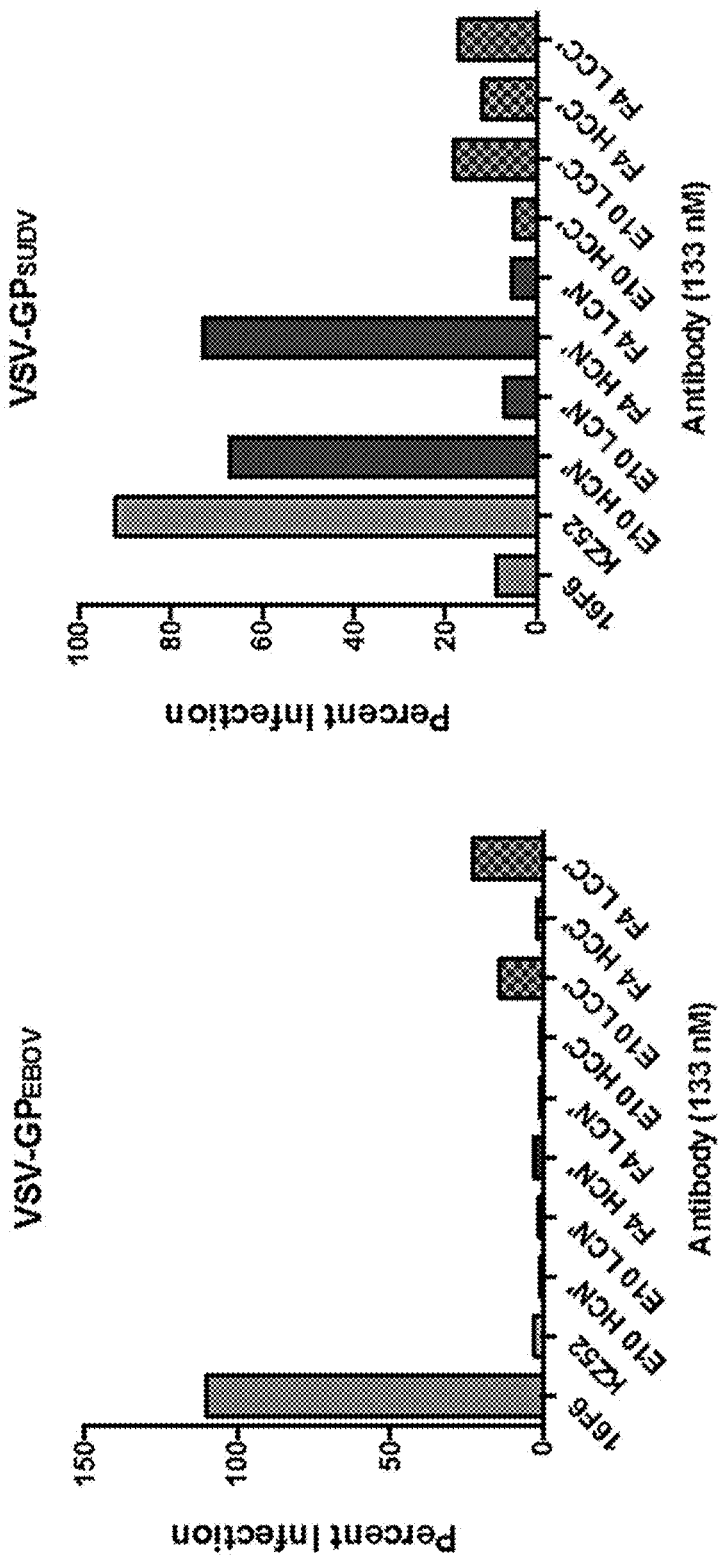
FIG. 8. Bispecific antibodies neutralization assay results.

Finally, in a pseudotyped virus infection model, where vesicular stomatitis virus displaying the EBOV or SUDV GP was used as the infecting virus, it was found that all eight Bis-mAbs could neutralize GP-mediated cell entry for both EBOV and SUDV GP at 133 nM (see FIG. 8). Testing of the bispecific antibody compositions under BSL4 conditions is performed against authentic pathogens.

REFERENCES

1. Kuhn, J. H., Becker, S., Ebihara, H., Geisbert, T. W., Johnson, K. M., Kawaoka, Y., Lipkin, W. I., Negredo, A. I., Netesov, S. V., Nichol, S. T., Palacios, G., Peters, C. J., Tenorio, A., Volchkov, V. E., and Jahrling, P. B. (2010) Proposal for a revised taxonomy of the family Filoviridae: classification, names of taxa and viruses, and virus abbreviations. Arch. Virol. 155, 2083-2103.
2. Feldmann, H., and Gesibert, T. W. (2011) Ebola haemorrhagic fever. Lancet 9768, 849-862.
3. Miller, E. H., and Chandran, K. (2012) Filovirus entry into cells-new insights. Curr. Opin. Virol. 2, 206-214.
4. Lee, J. E., and Saphire, E. O. (2009) Neutralizing ebolavirus: structural insights into the envelope glycoprotein and antibodies targeted against it. Curr. Opin. Struct. Biol. 19, 408-417.
5. Leroy, E. M., Kumulungui, B., Pourrut, X., Rouquet, P., Hassanin, A., Yaba, P., Delicat, A., Paweska, J. T., Gonzalez, J. P., and Swanepoel, R. (2005) Fruit bats as reservoirs of Ebola virus. Nature 438, 575-576.
6. http://www.cdc.gov/ncidod/dvrd/spb/mnpages/dispages/ebola.htm
7. Bradfute, S. B., Warfield, K. L., and Bavari, S. (2008) Functional CD8+ T cell responses in lethal Ebola virus infection. J. Immunol. 180, 4058-4066.
8. Zampieri, C. A., Sullivan, N. J., and Nabel, G. J. (2007) Immunopathology of highly virulent pathogens: insights from Ebola virus. Nat. Immunol. 8, 1159-1164.
9. Geisbert, T. W., Hensley, L. E., Larsen, T., Young, H. A., Reed, D. S., Geisbert, J. B., Scott, D. P., Kagan, E., Jahrling, P. B., and Davis, K. J. (2003) Pathogenesis of Ebola hemorrhagic fever in cynomolgus macaques: evidence that dendritic cells are early and sustained targets of infection. Am. J. Pathol. 163, 2347-2370.

10. Hensley, L. E., Jones, S. M., Feldmann, H., Jahrling, P. B., and Geisbert, T. W. (2005) Ebola and Marburg viruses: pathogenesis and development of countermeasures. Curr. Mol. Med. 5, 761-772.
11. Wilson, J. A., and Hart, M. K. (2001) Protection from Ebola virus mediated by cytotoxic T lymphocytes specific for the viral nucleoprotein. J. Virol. 75, 2660-2664.
12. Parren, P. W., Geisbert, T. W., Maruyama, T., Jahrling, P. B., and Burton, D. R. (2002) Pre- and post exposure prophylaxis of Ebola virus infection in an animal model by passive transfer of a neutralizing human antibody. J. Virol. 76, 6408-6412.
13. Lee, J. E., Fusco, M. L., Hessell, A. J., Oswald, W. B., Burton, D. R., and Saphire, E. O. (2008) Structure of the Ebola virus glycoprotein bound to an antibody from a human survivor. Nature 454, 177-182.
14. Dias, J. M., Kuehne, A. I., Abelson, D. M., Bale, S., Wong, A. C., Halfmann, P., Muhammad, M. A., Fusco, M. L., Zak, S. E., Kang, E., Kawaoka, Y., Chandran, K., Dye, J. M., and Saphire, E. O. (2011) A shared structural solution for neutralizing ebolaviruses. Nat. Struct. Mol. Biol. 18, 1424-1427.
15. Lee, J. E., and Saphire, E. O. (2009) Ebolavirus glycoprotein structure and mechanism of entry. Future Virol. 4, 621-635.
16. Weissenhorn, W., Carfi, A., Lee, K.-H., Skehel, J. J., and Wiley, D. C. (1998) Crystal structure of the Ebola virus membrane fusion subunit, GP2, from the envelope glycoprotein ectodomain. Mol. Cell 2, 605-616.
17. Malashkevich, V. N., Schneider, B. J., McNally, M. L., Milhollen, M. A., Pang, J. X., and Kim, P. S. (1999) Core structure of the envelope glycoprotein GP2 from Ebola virus at 1.9-Å resolution. Proc. Natl. Acad. Sci. USA 96, 2662-2667.
18. Koellhoffer, J. F., Malashkevich, V. N., Harrison, J. S., Toro, R., Bhosle, R. C., Chandran, K., Almo, S. C., Lai, J. R. (2012) Crystal structure of the Marburg virus GP2 core domain in its postfusion conformation. Biochemistry 51, 7665-7675.
19. Harrison, J. S., Koellhoffer, J. F., Chandran, K., and Lai, J. R. (2012) Marburg virus glycoprotein GP2: pH-dependent stability of the ectodomain α-helical bundle. Biochemistry 51, 2515-2525.
20. Oswald, W. B., Geisbert, T. W., Davis, K. J., Geisbert, J. B., Sullivan, N. J., Jahrling, P. B., Parren, P. W., and Burton, D. R. (2007) Neutralizing antibody fails to impact the course of Ebola virus infection in monkeys. PLOS Pathog. 3, e9.
21. Dye, J. M., Herbert, A. S., Kuehne, A. I., Barth, J. F., Muhammad, M. A., Zak, S. E., Ortiz, R. A., Prugar, L. I., and Pratt, W. D. (2012) Post exposure antibody prophylaxis protects nonhuman primates from filovirus disease. Proc. Natl. Acad. Sci. USA 109, 5034-5039.
22. Wong, G., Richardson, J. S., Pillet, S., Patel, A., Qiu, X., Alimonti, J., Hogan, J., Zhang, Y., Takada, A., Feldmann, H., Kobinger, G. P. (2012) Immune parameters correlate with protection against ebola virus infection in rodents and nonhuman primates. Sci. Transl. Med. 4, 158ra146.
23. Olinger, G. G. Jr., Pettitt, J., Kim, D., Working, C., Bohorov, O., Bratcher, B., Hiatt, E., Hume, S. D., Johnson, A. K., Morton, J., Pauly, M., Whaley, K. J., Lear, C. M., Biggins, J. E., Scully, C., Hensley, L., Zeitlin, L. (2012) Delayed treatment of Ebola virus infection with plant-derived monoclonal antibodies provides protection in rhesus macaques. Proc. Natl. Acad. Sci. USA 109, 18030-18035.
24. Marzi, A., Yoshida, R., Miyamoto, H., Ishijim, M., Suzuki, Y., Higuchi, M., Matsuyama, Y., Igarashi, M., Nakayama, E., Kuroda, M., Saijo, M., Feldmann, F., Brining, D., Feldmann, H., and Takada A. (2012) Protective efficacy of neutralizing monoclonal antibodies in a nonhuman primate model of Ebola hemorrhagic fever. PLOS One 7, e36192.
25. Wilson, J. A., Bosio, C. M., and Hart, M. K. (2001) Ebola virus: the search for vaccines and treatments. Cell Mol. Life Sci. 58, 1826-1841.
26. Sullivan, N. J., Martin, J. E., Graham, B. S., and Nabel, G. J. (2009) Correlates of protective immunity for Ebola vaccines: implications for regulatory approval by the animal rule. Nat. Rev. Microbiol. 7, 393-400.
27. Wilson, J. A., Hevey, M., Bakken, R., Guest, S., Bray, M., Schmaljohn, A. L., and Hart, M. K. (2000) Epitopes involved in antibody-mediated protection from Ebola virus. Science 287, 1664-1666.
28. Maruyama, T., Rodriguez, L. L., Jahrling, P. B., Sanchez, A., Khan, A. S., Nichol, S. T., Peters, C. J., Parren, P. W., and Burton, D. R. (1999) Ebola virus can be effectively neutralized by antibody produced in natural human infection. J. Virol. 73, 6024-6030.
29. Shurtleff, A. C., Warren, T. K., and Bavari, S. (2011) Non-human primates as models for the discovery and development of ebolavirus therapeutics. Expert Opin. Drug Discov. 6, 233-250.
30. Warfield, K. L., and Aman, M. J. (2011) Advances in virus-like particle vaccines for filoviruses. J. Infect. Dis. 204 Suppl 3, S1053-1059.
31. Fausther-Bovendo, H., Mulangu, S., and Sullivan, N. J. (2012) Ebolavirus vaccines for humans and apes. Curr. Opin. Virol. [Epub ahead of print] (May 3, PMID: 22560007)
32. Hoenen, T., Grosth, A., and Feldmann, H. (2012) Current ebola vaccines. Expert Opin. Biol. Ther. [Epub ahead of print] (May 5, PMID: 22559078)
33. Warren, T. K., Warfield, K. L., Wells, J., Swenson, D. L., Donner, K. S., Van Tongeren, S. A., Garza, N. L., Dong, L., Mourich, D. V., Crumley, S., Nichols, D. K., Iversen, P. L., and Bavari, S. (2010) Advanced antisense therapies for postexposure protection against lethal filovirus infections. Nat. Med. 16, 991-994.
34. Geisbert, T. W., Lee, A. C., Robbins, M., Geisbert, J. B., Honko, A. N., Sood, V., Johnson, J. C., de Jong, S., Tavakoli, I., Judge, A., Hensley, L. E., and Maclachlan, I. (2010) Post exposure protection of non-human primates against a lethal Ebola virus challenge with RNA interference: a proof-of-concept study. Lancet 375, 1896-1905.
35. Panchal, R. G., Reid, S. P., Tran, J. P., Bergeron, A. A., Wells, J., Kota, K. P., Aman, J., and Bavari, S. (2012) Identification of an antioxidant small-molecule with broad-spectrum antiviral activity. Antiviral Res. 93, 23-29.
36. Côté, M., Misasi, J., Ren, T., Bruchez, A., Lee, K., Filone, C. M., Hensley, L., Li, Q., Ory, D., Chandran, K., and Cunningham, J. (2011) Small molecule inhibitors reveal Niemann-Pick C1 is essential for Ebola virus infection. Nature 477, 344-348.
37. Basu, A., Li, B., Mills, D. M., Panchal, R. G., Cardinale, S. C., Butler, M. M., Peet, N. P., Majgier-Baranowska, H., Williams, J. D., Patel, I., Moir, D. T., Bavari, S., Ray, R., Farzan, M. R., Rong, L., and Bowlin, T. L. (2011) Identification of a small-molecule entry inhibitor for filoviruses. J. Virol. 85, 3106-3119.

38. Mazor, Y., Barnea, I., Keydar, I., and Benhar, I. (2007) Antibody internalization studied using a novel IgG binding toxin fusion. Journal of Immunological Methods, 321, (1), 41-59.
39. Brannan, J. M. et al. Interferon alpha/beta Receptor-Deficient Mice as a Model for Ebola Virus Disease. The Journal of infectious diseases 212 Suppl 2, S282-294, doi: 10.1093/infdis/jiv215 (2015).
40. Bray, M., Davis, K., Geisbert, T., Schmaljohn, C. & Huggins, J. A mouse model for evaluation of prophylaxis and therapy of Ebola hemorrhagic fever. The Journal of infectious diseases 178, 651-661 (1998).
41. Chen, G. et al. Synthetic Antibodies with a Human Framework That Protect Mice from Lethal *Sudan Ebolavirus* Challenge. ACS Chemical Biology 9, 2263-2273, doi: 10.1021/cb5006454 (2014).

The invention claimed is:

1. A recombinant dual-variable-domain antibody comprising:
   (1) a heavy chain amino acid sequence comprising in N terminal to C terminal order (i) a first $V_H$ amino acid sequence comprising at least one CDR directed to a membrane glycoprotein pre-fusion core of a first species of filovirus, (ii) a 4, 5, 6, 7, or 8 amino acid first linker sequence, (iii) a second $V_H$ amino acid sequence comprising at least one CDR directed to a membrane glycoprotein pre-fusion core of a second species of filovirus, (iv) an immunoglobulin G $C_H1$ amino acid sequence, (v) an immunoglobulin G hinge amino acid sequence, (vi) an immunoglobulin G $C_H2$ amino acid sequence, (vii) an immunoglobulin G $C_H3$ amino acid sequence, which is bound via one or more inter-chain disulfide bond(s) to
   (2) a light chain amino acid sequence comprising in N terminal to C terminal order (i) a first $V_L$ amino acid sequence comprising at least one CDR directed to a membrane glycoprotein pre-fusion core of a first species of filovirus, (ii) a 4, 5, 6, 7, or 8 amino acid second linker sequence, (iii) a second $V_L$ amino acid sequence comprising at least one CDR directed to a membrane glycoprotein pre-fusion core of a second species of filovirus, (iv) an immunoglobulin G $C_L$ amino acid sequence, wherein the first species of filovirus and second species of filovirus are different species,
   wherein the heavy chain comprises an amino acid sequence selected from SEQ ID NO: 43, 47, 51, or 55; and the light chain comprises an amino acid sequence selected from SEQ ID NO: 45, 49, 53, or 57.

2. The recombinant dual-variable-domain antibody of claim 1, wherein (1) and (2) are bound via an inter-chain disulfide bond between the $C_H1$ amino acid sequence and the CL amino acid sequence.

3. A construct comprising two of the recombinant dual-variable-domain antibody of claim 1 joined together by one or more disulfide bonds between the heavy chain amino acid sequence of each.

4. The construct of claim 3, wherein the two recombinant dual-variable-domain antibodies are joined together by two disulfide bonds between the immunoglobulin G hinge amino acid sequences of each.

5. The recombinant dual-variable-domain antibody of claim 1, wherein the 4, 5, 6, 7, or 8 amino acid first linker sequence is a 6 amino acid first linker sequence.

6. The recombinant dual-variable-domain antibody of claim 5, wherein the 6 amino acid first linker sequence is ASTKGP (SEQ ID NO:41).

7. The recombinant dual-variable-domain antibody of claim 1, wherein the 4, 5, 6, 7, or 8 amino acid second linker sequence is 5 amino acid second linker sequence.

8. The recombinant dual-variable-domain antibody of claim 1, wherein the 5 amino acid second linker sequence is TVAAP (SEQ ID NO:42).

9. The recombinant dual-variable-domain antibody of claim 1, wherein the first $V_H$ amino acid sequence comprises three different heavy chain CDRs each of the three CDRs directed to the membrane glycoprotein pre-fusion core of the first species of filovirus.

10. The recombinant dual-variable-domain antibody of claim 1, wherein the first $V_L$ amino acid sequence comprises three different light chain CDRs each of the three CDRs directed to the membrane glycoprotein pre-fusion core of the first species of filovirus.

11. The recombinant dual-variable-domain antibody of claim 1, wherein the second $V_H$ amino acid sequence comprises three different heavy chain CDRs each of the three CDRs directed to the membrane glycoprotein pre-fusion core of the second species of filovirus.

12. The recombinant dual-variable-domain antibody of claim 1, wherein the second $V_L$ amino acid sequence comprises three different light chain CDRs each of the three CDRs directed to the membrane glycoprotein pre-fusion core of the second species of filovirus.

13. The recombinant dual-variable-domain antibody of claim 1, where in the first species of filovirus and the second species of filovirus are both Ebolavirus species.

14. The recombinant dual-variable-domain antibody of claim 13, wherein the Ebola virus species are *Zaire ebolavirus* and *Sudan ebolavirus*.

15. An isolated nucleic acid encoding the recombinant dual-variable-domain antibody of claim 1.

16. The recombinant dual-variable-domain antibody of claim 1, wherein the recombinant dual-variable-domain antibody comprises SEQ ID NO: 43 and SEQ ID NO: 45.

17. The recombinant dual-variable-domain antibody of claim 1, wherein the recombinant dual-variable-domain antibody comprises SEQ ID NO: 47 and SEQ ID NO: 49.

18. The recombinant dual-variable-domain antibody of claim 1, wherein the recombinant dual-variable-domain antibody comprises SEQ ID NO: 51 and SEQ ID NO: 53.

19. The recombinant dual-variable-domain antibody of claim 1, wherein the recombinant dual-variable-domain antibody comprises SEQ ID NO: 55 and SEQ ID NO: 57.

* * * * *